US008877466B2

(12) United States Patent
Scholten et al.

(10) Patent No.: US 8,877,466 B2
(45) Date of Patent: Nov. 4, 2014

(54) BACTERIAL CELLS HAVING A GLYOXYLATE SHUNT FOR THE MANUFACTURE OF SUCCINIC ACID

(75) Inventors: Edzard Scholten, Mannheim (DE); Stefan Haefner, Speyer (DE); Hartwig Schröder, Nußloch (DE)

(73) Assignee: BASF SE, Ludwigshafen (DE)

( * ) Notice: Subject to any disclaimer, the term of this patent is extended or adjusted under 35 U.S.C. 154(b) by 429 days.

(21) Appl. No.: 12/644,059

(22) Filed: Dec. 22, 2009

(65) Prior Publication Data

US 2010/0159543 A1 Jun. 24, 2010

(30) Foreign Application Priority Data

Dec. 23, 2008 (EP) .................................. 08172793

(51) Int. Cl.
| | |
|---|---|
| C12P 7/46 | (2006.01) |
| C12N 1/20 | (2006.01) |
| C12P 21/06 | (2006.01) |
| C12P 19/34 | (2006.01) |
| C12N 15/00 | (2006.01) |
| C07H 21/04 | (2006.01) |
| C12N 9/88 | (2006.01) |
| C12N 9/10 | (2006.01) |
| C12N 9/02 | (2006.01) |

(52) U.S. Cl.
CPC ................ C12N 9/88 (2013.01); C12N 9/1025 (2013.01); C12P 7/46 (2013.01); C12N 9/0008 (2013.01)
USPC ...... 435/145; 435/252.3; 435/69.1; 435/91.1; 435/320.1; 536/23.1; 536/23.2

(58) Field of Classification Search
USPC ................. 435/145, 252.3, 69.1, 91.1, 320.1; 536/23.1, 23.2
See application file for complete search history.

(56) References Cited

U.S. PATENT DOCUMENTS

| | | | |
|---|---|---|---|
| 4,550,185 A | 10/1985 | Mabry et al. | |
| 5,504,004 A | 4/1996 | Guettler et al. | |
| 5,573,931 A | 11/1996 | Guettler et al. | |
| 5,723,322 A | 3/1998 | Guettler et al. | |
| 6,596,521 B1 | 7/2003 | Chang et al. | |
| 7,063,968 B2 | 6/2006 | Lee et al. | |
| 7,192,761 B2 | 3/2007 | Zeikus et al. | |
| 7,241,594 B2* | 7/2007 | Lee et al. | 435/71.2 |
| 7,256,016 B2* | 8/2007 | San et al. | 435/69.1 |
| 7,262,046 B2* | 8/2007 | Ka-Yiu et al. | 435/252.33 |
| 7,470,531 B2 | 12/2008 | Rehberger et al. | |
| 2007/0042481 A1 | 2/2007 | Lee et al. | |
| 2008/0293101 A1* | 11/2008 | Peters et al. | 435/69.1 |
| 2009/0137825 A1 | 5/2009 | Bauduin et al. | |
| 2009/0155869 A1 | 6/2009 | Buelter et al. | |
| 2010/0044626 A1 | 2/2010 | Fischer et al. | |
| 2010/0159542 A1 | 6/2010 | Scholten et al. | |
| 2010/0324258 A1 | 12/2010 | Zelder et al. | |
| 2011/0008851 A1 | 1/2011 | Scholten et al. | |
| 2011/0300589 A1* | 12/2011 | Schroder et al. | 435/121 |

FOREIGN PATENT DOCUMENTS

| | | |
|---|---|---|
| EP | 0805208 | 5/1997 |
| EP | 1842843 A1 | 10/2007 |
| EP | 2202294 | 6/2010 |
| EP | 2204443 | 7/2010 |
| JP | 2008011714 | 1/2008 |
| WO | WO-02/00846 A1 | 1/2002 |
| WO | WO-03/040690 | 5/2003 |
| WO | WO-2005/052135 A1 | 6/2005 |
| WO | WO-2006/034156 | 3/2006 |
| WO | WO-2006/066839 A2 | 6/2006 |
| WO | WO-2008/013405 A1 | 1/2008 |
| WO | WO-2009/024294 | 2/2009 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kimchi-Sarfaty et al., A "Silent" polymorphism in the MDR1 gene changes substrate specificty. Science, 2007, vol. 315: 525-528.*
Kisselev L., Polypeptide release factors in prokaryotes and eukaryotes: same function, different structure. Structure, 2002, vol. 10: 8-9.*
Nackley et al., Human Caechol-O-Methytransferase haplotypes modulate protein expression by altering mRNA secondary structure. Science, 2006, vol. 314: 1930-1933.*
Sauna et al., Silent polymorhisms speak: How they affect pharmacogenomics and the treatment of cancer. Cancer Res., 2007, vol. 67(20): 9609-9612.*
Seffernick et al., Melamine deaminase and Atrazine chlorohydrolase: 98 percent identical but functionally different. J. Bacteriol., 2001, vol. 183 (8): 2405-2410.*

(Continued)

*Primary Examiner* — Ganapathirama Raghu
(74) *Attorney, Agent, or Firm* — Drinker Biddle & Reath LLP

(57) ABSTRACT

The present invention is concerned with bacteria for the production of succinic acid. Specifically, the invention relates to a bacterial cell of the genus *Pasteurella* comprising a heterologous polypeptide having isocitrate lyase activity and a heterologous polypeptide having malate synthase activity. Further, the present invention contemplates a polynucleotide comprising a nucleic acid encoding a polypeptide having isocitrate lyase activity and a nucleic acid encoding a polypeptide having malate synthase activity. Finally, the present invention relates to the use of a bacterial cell of the invention for the manufacture of succinic acid.

14 Claims, 34 Drawing Sheets

(56) References Cited

OTHER PUBLICATIONS

Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Guo et al., Protein tolerance to random amino acid change. PNAS., 2004, vol. 101 (25): 9205-9210.*
DataBase EBI Accession No. UniProt: A1JRX1, Feb. 6, 2007, Isocitrate lyase, XP-002576046.
DataBase EBI accession No. UniProt: A1JRX8, Feb. 6, 2007, Malate Synthase, XP-002576047.
Berrios-Rivera, S., et al., "The Effect of Increasing NADH Availability on the Redistribution of Metabolic Fluxes in *Escherichia coli* Chemostat Cultures", Metabolic Engineering, vol. 4, No. 3, (2002), pp. 230-237.
Dharmadi, Y, et al., "Anaerobic Fermentation of Glycerol by *Escherichia coli*: A New Platform for Metabolic Engineering", Biotech Bioeng., vol. 94, (2006), pp. 821-829.
Durchschlag, H., et al., "Large-Scale Purification and Some Properities of Malate Synthase from Baker's Yeast", Eur. J. biochem., vol. 114, (1981), pp. 114-255.
Eggerer, H., et al., "Über das Katalyseprinzip der Malat-Synthase", European J. Biochem., vol. 1, (1967), pp. 447-475.
European Search Report EP 09 17 8048 dated Mar. 31, 2010.
Feng, D.-F., et al., "Progressive Sequence Alignment as a Prerequisite to Correct Phylogenetic Trees", J. Mol. Evol., vol. 25, (1987), pp. 351-360.
Ferry, J. G., "Formate Dehydrogenase", FEMS Microbiology Reviews, vol. 87, (1990), pp. 377-382.
Frey, J., "Construction of a Broad Host Range Shuttle Vector for Gene Cloning and Expression in *Actinobacillus pleuropneumoniae* and Other *Pasteurellaceae*", Res. Microbial, vol. 143, (1992), pp. 263-269.
Higgins, D. G., et al., "Fast and Sensitive Multiple Sequence Alignments on a Microcomputer", vol. 5, No. 2, (1989), pp. 151-163.
Hoyt, J. C., et al., "*Escherichia coli* Isocitrate Lyase: Properties and Comparisons", Biochimica et Biophysica Acta, vol. 966, (1988), pp. 30-35.
Kim, J. M., et al., "Development of a Markerless Gene Knock-Out System for *Mannheimia succiniciproducens* Using a Temperature-Sensitive Plasmid", FEMS Microbiol Lett, vol. 278, (2008), pp. 78-85.
Kuhnert and Christensen, "Pasteurellaceae, Biology, Genomics, and Molecular Aspects", (2008), ISBN 978-1-904455-34-9.
Lee, S. Y., et al., "From Genome Sequence to Integrated Bioprocess for Succinic Acid Production by *Mannheimia succiniciproducens*", Applied Microbiology Biotechnology, vol. 79, No. 1, (2008), pp. 11-22.
Lee, P.C., et al., "Isolation and Characterization of a New Succinic Acid-Producing Bacterium, *Mannheimia succiniciproducens* MBEL55E, From Bovine Rumen", Appl. Microbiol Biotechnol., vol. 58, (2002), pp. 663-668.
Lee, et al., "Genome-Based Metabolic Engineering of *Mannheimia succiniciproducens* for Succinic Acid Production," *Applied and Environmental Microbiology* (Mar. 2006), vol. 72, No. 3, pp. 1939-1948.
Lee, S. Y., "BTEC 18Genome-Scale Metabolic engineering of *Mannheimia succiniciproducens* for Enhanced Succinic Acid Production", Genomic and Systems Approaches to Metabolic Engineering, The 229th ACS National Meeting in San Diego, CA., Mar. 13-17, 2005.
Lee, P. C., et al., "Succinic Acid Production with Reduced By-Product Formation in the Fermentation of *Anaerobiospirillum succiniciproducens* Using Glycerol as a Carbon Source", Biotech Bioeng., vol. 72, (2001), pp. 41-48.
Leenhouts, K. J., et al., "Campbell-Like Integration of Heterologous Plasmid DNA into the *Chromosome* of *Lactococcus lactis* subsp. *lactis*", Applied and Environmental Microbiology, vol. 55, (1989), pp. 394-400.
Mackintosh, C., et al., "Purification and Regulatory Properties of Isocitrate Lyase From *Escherichia coli* ML308", Biochem. J., vol. 250, (1988), pp. 25-31.
Müller, U., et al., "Formate Dehydrogenase from *Pseudomonas oxalaticus*", Eur. J. Biochem, vol. 83, (1978), pp. 485-498.
Needleman, S. B., et al., "A General Method Applicable to the Search for Similarities in the Amino Acid Sequence of Two Proteins", J. Mol. Biol., vol. 48, (1970), pp. 443-453.
Robertson, E. F., et al., "Purification and Characterization of Isocitrate Lyase from *Escherichia coli*", Current Microbiology, vol. 14, (1987), pp. 347-350.
Scholten, E., et al., "Succinic Acid Production by a Newly Isolated Bacterium", Biotechnology Letters, vol. 30, No. 12, (2008), pp. 2143-2146.
Smith, et al., "Identification of Common Molecular Subsequences," *J. Mol. Biol.* (1981), vol. 147, pp. 195-197.
Sundaram, T. K., et al, Monomeric Malate Synthase from a Thermophilic *Bacillus*, Archives of Biochemistry and Biophysics, vol. 199, No. 2, (1980), pp. 515-525.
Tishkov, V.I, et al., "Catalytic Mechanism and Application of Formate Dehydrogenase", Biochemistry (Moscow), vol. 69, No. 11, (2004), pp. 1252-1267.
Watanabe, S., et al., "Purification and Characterization of a Cold-Adapted Isocitrate Lyase and a Malate Synthase from *Colwellia maris*, a Psychrophilic Bacterium", Biosci. Biotechnol. Biochem., vol. 65, No. 5, (2001), pp. 1095-1103.
Patentability Opinion of EP Searching Authority—EP 09 178 048.6, Mar. 31, 2010.
"ybiW predicted pyruvate formate lyase [*Escherichia coli* str. K-12 substr. MG1655]", Database NCBI, Accession No. 945444, Feb. 28, 2011.
"pflB pyruvate formate lyase I [*Escherichia coli* str. K-12 substr. MG1655]", Database NCBI, Accession No. 945514, Feb. 28, 2011.
"ldhA fermentative D-lactate dehydrogenase, NAD-dependent [*Escherichia coli* str. K-12 substr. MG1655]" Database NCBI, Accession No. 946315, May 21, 2011.
"tdcE pyruvate formate-lyase 4/2-ketobutyrate formate-lyase [*Escherichia coli* str. K-12 substr. MG1655]", Database NCBI, Accession No. 947623, Feb. 28, 2011.
"pflD predicted formate acetyltransferase 2 (pyruvate formate lyase II) [*Escherichia coli* str. K-12 substr. MG1655]", Database NCBI, Accession No. 948454, Feb. 28, 2011.
"Pyruvate formate lyase-activating enzyme 1 [*Shigella boydii* CDC 3083-94]", Database NCBI, Accession No. YP_001880903.1, Jan. 5, 2011.
"Formate acetyltransferase 1", Database UniProtKB, Accession No. P09373, Feb. 8, 2011.
"Formate acetyltransferase 2", Database UniProtKB, Accession No. P32674, Feb. 8, 2011.
"Keto-acid formate acetyltransferase", Database UniProtKB, Accession No. P42632, Feb. 8, 2011.
"Putative formate acetyltransferase", Database UniProtKB, Accession No. P75793, Feb. 8, 2011.
"PflD protein", Database UniProtKB, Accession No. Q65VK2, Nov. 30, 2010.
Dousse, F., et al., "Routine phenotypic identification of bacterial species of the family Pasteurellaceae isolated from animals," J. Vet. Diagn. Invest., 2008, vol. 20, pp. 716-724.
Guettler, M.V. et al., "*Actinobacillus succinogenes* sp. nov., a novel succinic-acid-producing strain from the bovine rumen," Int'l. J. of Systematic Bacteriol., 1999, vol. 49, pp. 207-216.
Guo, H.H., et al., "Protein tolerance to random amino acid change", PNAS, 2004, vol. 101, No. 25, pp. 9205-9210.
Hong, S.H., et al., "Metabolic Flux Analysis for Succinic Acid Production by Recombinant *Escherichia coli* with Amplified Malic Enzyme Activity," Biotechnology and Bioengineering, 2001, vol. 74, No. 2, pp. 89-96.

(56) References Cited

OTHER PUBLICATIONS

Hong, S.H. et al.: "The genome sequence of the capnophilic rumen bacterium *Mannheimia succiniciproducens*", Nature Biotechnology, Oct. 2004, vol. 22, No. 10, pp. 1275-1281.

Janssen, P.H., "Characterization of a succinate-fermenting anaerobic bacterium isolated from a glycolate-degrading mixed culture", Arch. Microbiol., 1991, vol. 155, pp. 288-293.

Knappe, J., et al., "A radical-chemical route to acetyl-CoA: the anaerobically induced pyruvate formate-lyase system of *Escherichia coli*," FEMS Microbiology Reviews, 1990, vol. 75, pp. 383-398.

Knappe, J., et al., "Pyruvate formate-lyase mechanism involving the protein-based glycyl radical," Biochemical Society Transactions, 1993, vol. 21, pp. 731-734.

Lee J., "Biological conversion of lignocellulosic biomass to ethanol", 1997, J. Biotech., vol. 56, pp. 1-24.

Lin, H., et al., "Effect of *Sorghum vulgare* phosphoenolpyruvate carboxylase and *Lactococcus lactis* pyruvate carboxylase coexpression on succinate production in mutant strains of *Escherichia coli*," Appl. Microbiol. Biotechnol., 2005, vol. 67, pp. 515-523.

Maidak, B.L. et al., "A new version of the RDP (Ribosomal Database Project)", Nucl. Acids Res., 1999, vol. 27, No. 1, pp. 171-173.

McKinlay, J. et al., "Insights into *Actinobacillus succinogenes* fermentative metabolism in a chemically defined growth medium", Appl. and Environ. Microbiol., 2005, vol. 71, pp. 6651-6656.

Nili, N. et al., "A defined medium for rumen bacteria and identification of strains impaired in de novo biosynthesis of certain amino acids", Lett. Appl. Microbiol., 1995, vol. 21, pp. 69-74.

Pascal, M. C., et al., "Mutants of *Escherichia coli* K 12 with Defects in Anaerobic Pyruvate Metabolism," J. Gen. Microbiol., 1981, vol. 124, pp. 35-42.

Peters-Wendisch, P. G., et al., "C3-Carboxylation as an anaplerotic reaction in phosphoenolpyruvate carboxylase-deficient *Corynebacterium glutamicum*," Arch. Microbiol., 1996, vol. 165, pp. 387-396.

Rainey, F.A. et al., "The genus *Nocardiopsis* represents a phylogenetically coherent taxon and a distinct actinomycete lineage: Proposal of Nocardiopsaceae fam. nov.", 1996, Int. J. Syst. Bacteriol., vol. 46, pp. 1088-1092.

Redfield, R.J., et al., "Evolution of competence and DNA uptake specificity in the Pasteurellaceae", BMC Evolutionary Biology, 2006, vol. 6, No. 82, pp. 1-15.

Saitou, N. et al., "The neighbor-joining method: a new method for reconstructing phylogenetic trees", Mol. Biol. Evol., 1987, vol. 4, pp. 406-425.

Sanchez, A. M., et al., "Novel pathway engineering design of the anaerobic central metabolic pathway in *Escherichia coli* to increase succinate yield and productivity," Metabolic Engineering, 2005, vol. 7, pp. 229-239.

Scholten, E., et al., "Continuous Cultivation Approach for Fermentative Succinic Acid Production from Crude Glycerol by *Basfia succiniciproducens* DD1", Biotechnol Lett, vol. 31, (2009), pp. 1947-1951.

Song, H. et al., "Production of succinic acid by bacterial fermentation", Enzyme and Microbial Technology, 2006, vol. 39, pp. 352-361.

Song, H. et al., "Development of chemically defined medium for *Mannheimia succiniciproducens* based on its genome sequence", Appl. Microbiol. Biotechnol., 2008, vol. 79, pp. 263-272.

Thomson, N. R, et al. "The complete genome sequence and comparative genome analysis of the high pathogenicity *Yersinia enterocolitica* strain 8081", PLoS Genetics, 2006, vol. 2, No. 12, pp. 2039-2051.

Varenne, S., et al., "A Mutant of *Escherichia coli* Deficient in Pyruvate Formate Lyase," Molec. Gen. Genet., 1975, vol. 141, pp. 181-184.

Vlysidis, A., et al., "Experimental and Modelling Studies of the Bioconversion of Glycerol to Succinic Acid by *Actinobacillus succinogenes*", AIChe100 Annual Meeting, Fuels and Petrochemicals Division (202h), Nov. 18, 2008.

White, W. T., et al., "Species and size compositions and reproductive biology of rays (Chondrichthyes, Batoidea) caught in target and non-target fisheries in eastern Indonesia," J. Fish Biol., 2007, vol. 70, pp. 1809-1837.

Zeikus, J.G., et al., "Biotechnology of succinic acid production and markets for derived industrial products", Appl. Microbiol. Biotechnol. 1999, vol. 51, pp. 545-552.

Yazdani, S. S., et al., "Anaerobic fermentation of glycerol: a path to economic viability for the biofuels industry," Current Opinion in Biotechnology, 2007, vol. 18, pp. 213-219.

Zhang, X., et al., "Fermentation of Glycerol to Succinate by Metabolically Engineered Strains of *Escherichia coli*," Applied and Environmental Microbiology, 2010, vol. 76, No. 8, pp. 2397-2401.

Zhu, J., et al., "Effect of a single-gene knockout on the metabolic regulation in *Escherichia coli* for D-lactate production under microaerobic condition," Metab. Engineering, 2005, vol. 7, pp. 104-115.

International Preliminary Report on Patentability, PCT/EP2010/051798, issued May 12, 2011.

International Preliminary Report on Patentability, PCT/EP2008/006714, issued Feb. 24, 2010.

European Opinion EP 09 17 8050 dated Feb. 23, 2010.

European Search Report EP 09 17 8050 dated Feb. 23, 2010.

\* cited by examiner pJFF224 PEFTU- Glyox operon Y_molaretii

FIG. 11 (Continued)

| | | | |
|---|---|---|---|
| | | | TMTKPFLSAYSRLLIKTCHKRGALAMGGMAAFIPNKDPEKNALVLDKVRADKELEASNGHD GTWVAHPGLADTVMDVFNKVLGDRPNQLEVSRAQDKPITAAELLEPCTGERTEEGMRANI RVAVQYIEAWISGNGCVPIYGLMEDAATAEISRTSIWQWIHHQKSLSNGQTVTKELFRNMLS EEMQVVKLELGAERFDGGRFEEAARLMERITTQDELIDFLTLPGYALLA |
| 5 | 5 | Formate dehydrogenase DNA (fdh) from C. boidinii | ATGAAGATCGTTTTAGTCTTATATGATGCTGGTAAGCACGCTGCTGATGAAGAAAAATTA TATGGTTGTACTGAAAATAAATTAGGTATTGCTAATTGGTTAAAAGATCAAGGTCATGAA CTAATTACTACTTCTGATAAAGAAGGTGAAACAAGTGAATTGGATAAACATATCCCAGAT GCTGATATTATCATCACCACTCCTTTCCATCCTGCTTATATCACTAAGGAAAGACTTGAC AAGGCTAAGAACTTAAAATTAGTCGTTGTCGCTGGTGTTGGTTCTGATCACATTGATTTA GATTATATTAATCAAACAGGTAAGAAAATCTCAGTCTTGGAAGTTACAGGTTCTAATGTT GTCTCTGTTGCTGAACACGTTGTCATGACCATGCTTGTCTTGGTTAGAAATTTCGTTCCA GCACATGAACAAATTATTAACCACGATTGGGAGGTTGCTGCTATCGCTAAGGATGCTTA CGATATCGAAGGTAAAACTATTGCTACCATTGGTGCTGGTAGAATTGGTTACAGAGTCTT GGAAAGATTACTCCCTTTTAATCCAAAAGAATTATTATACTACGATTATCAAGCTTTACCA AAAGAAGCTGAAGAAAAGTTGGTGCTAGAAGAGTTGAAAATATTGAAGAATTAGTTGCT CAAGCTGATATCGTTACAGTTAATGCTCCATTACACGCAGGTACAAAAGGTTTAATTAAT AAGGAATTATTATCTAAATTTAAAAAAGGTGCTTGGTTAGTCAATACCGCAAGAGGTGCT ATTTGTGTTGCTGAAGATGTTGCAGCAGCTTTAGAATCTGGTCAATTAAGAGGTTACGGT GGTGATGTTTGGTTCCCACAACCAGCTCCAAAGGATCACCCATGGAGAGATATGAGAAA TAAATATGGTGCTGGTAATGCCATGACTCCTCACTACTCTGGTACTACTTTAGATGCTCA AACAAGATACGCTGAAGGTACTAAAAATATCTTGGAATCATTCTTTACTGGTAAATTTGAT TACAGACCCACAAGATATTATCTTATTAAATGGTGAATACGTTACTAAAGCTTACGGTAAA CACGATAAGAAA |
| 6 | 6 | Formate dehydrogenase Prot. (Fdh) from C. boidinii | MKIVLVLYDAGKHAADEEKLYGCTENKLGIANWLKDQGHELITTSDKEGETSELDKHIPDADI IITTPFHPAYITKERLDKAKNLKLVVVAGVGSDHIDLDYINQTGKKISVLEVTGSNVVSVAEHV VMTMLVLVRNFVPAHEQIINHDWEVAAIAKDAYDIEGKTIATIGAGRIGYRVLERLLPFNPKEL LYYDYQALPKEAEEKVGARRVENIEELVAQADIVTVNAPLHAGTKGLINKELLSKFKKGAWL VNTARGAICVAEDVAAALESGQLRGYGGDVWFPQPAPKDHPWRDMRNKYGAGNAMTPH YSGTTLDAQTRYAEGTKNILESFFTGKFDYRPQDIILLNGEYVTKAYGKHDKK |
| 7 | 7 | 16SrDNA | ATTGAAGAGTTTGATCATGGCTCAGATTGAACGCTGGCGGCAGGCTTAACACATGCAA GTCGAACGGTAGCGGGAGGAAAGCTTGCTTTCTTTGCCGACGAGTGGCGGACGGGTG AGTAATGCTTGGGGATCTGGCTTATGGAGGGGGATAACGACGGGAAACTGTCGCTAAT ACCGCGTAATATCTTCGGATTAAAGGGTGGGACTTTCGGGCCCACCCGCCATAAGATGA GCCCAAGTGGGATTAGGTAGTTGGTGGGGTAAAGGCCTACCAAGCCGACGATCTCTAG CTGGTCTGAGAGGATGACCAGCCACACTGGAACTGAGACACGGTCCAGACTCCTACG GGAGGCAGCAGTGGGGAATATTGCACAATGGGGGGAACCCTGATGCAGCCATGCCGC GTGAATGAAGAAGGCCTTCGGGTTGTAAAGTTCTTTGGTGACGAGGAAGGTGTTTGTT TTAATAGGACAAGCAATTGACGTTAATCACAGAAGAAGCACCGGCTAACTCCGTGCCAG CAGCCGCGGTAATACGGAGGGTGCGAGCGTTAATCGGAATAACTGGGCGTAAAGGGC ATGCAGGCGGACTTTTAAGTGAGATGTGAAAGCCCCGGGCTTAACCTGGGAATTGCAT TTCAGACTGGGAGTCTAGAGTACTTTAGGGAGGGGTAGAATTCCACGTGTAGCGGTGA AATGCGTAGAGATGTGGAGGAATACCGAAGGCGAAGGCAGCCCCTTGGGAAGATACT GACGCTCATATGCGAAAGCGTGGGGAGCAAACAGGATTAGATACCCTGGTAGTCCACG CGGTAAACGCTGTCGATTTGGGGATTGGGCTTTAGGCCTGGTGCTCGTAGCTAACGTG ATAAATCGACCGCCTGGGGAGTACGGCCGCAAGGTTAAAACTCAAATGAATTGACGGG GGCCCGCACAAGCGGTGGAGCATGTGGTTTAATTCGATGCAACGCGAAGAACCTTACC TACTCTTGACATCCAGAGAATCCTGTAGAGATACGGGAGTGCCTTCGGGAGCTCTGAG ACAGGTGCTGCATGGCTGTCGTCAGCTCGTGTTGTGAAATGTTGGGTTAAGTCCCGCA ACGAGCGCAACCCCTTATCCTTTGTTGCCAGCATGTAAAGATGGGAACTCAAAGGAGACT GCCGGTGACAAACCGGAGGAAGGTGGGGATGACGTCAAGTCATCATGGCCCTTACGA GTAGGGCTACACACGTGCTACAATGGTGCATACAGAGGGCGGCGATACCGCGAGGTA GAGCGAATCTCAGAAAGTGCATCGTAGTCCGGATTGGAGTCTGCAACTCGACTCCATG AAGTCGGAATCGCTAGTAATCGCAAATCAGAATGTTGCGGTGAATACGTTCCCGGGCC TTGTACACACCGCCCGTCACACCATGGGAGTGGGTTGTACCAGAAGTAGATAGCTTAA CCTTCGGGGGGCGTTTACCACGGTATGATTCATGACTGGGGTGAAGTCGTAACAAGGT AACCGTAGGGGAACCTGCGGTTGGATCACCTCCTTAC |
| 8 | 8 | 23SrDNA | GTTAAGTGACTAAGCGTACAAGGTGGATGCCTTGGCAATCAGAGGCGAAGAAGGACGT GCTAATCTGCGAAAAGCTTGGGTGAGTTGATAAGAAGCGTCTAACCCAAGATATCCGAA TGGGGCAACCCAGTAGATGAAGAATCTACTATCAATAACCGAATCCATAGGTTATTGAG GCAAACCGGGAGAACTGAAACATCTAAGTACCCCGAGGAAAAGAAATCAACCGAGATTA CGTCAGTAGCGGCGAGCGAAAGCGTAAGAGCCGGCAAGTGATAGCATGAGGATTAGA GGAATCGGCTGGGAAGCCGGGCGGCACAGGGTGATAGCCCCGTACTTGAAAATCATT GTGTGGTACTGAGCTTGCGAGAAGTAGGGCGGGACAGGAAATCCTGTTTGAAGAAG GGGGGACCATCCTCCAAGGCTAAATACTCCTGATTGACCGATAGTGAANAGTACTGTGA AGGAAAGGCGAAAAGAACCCCGGTGAGGGGAGTGAAATAGAACCTGAAACCTTGTACG TACAAGCAGTGGGAGCCCGCGAGGGTGACTGCGTACCTTTTGTATAATGGGTCAGCGA CTTATATTATGTAGCGAGGTTAACCGAATAGGGGAGCCGAAGGGAAACCGAGTCTTAAC TGGGCGTCGAGTTGCATGATATAGACCCGAAACCCGGTGATCTAGCCATGGGCAGGTT GAAGGTTGGGTAACACTAACTGGAGGACCGAACCGACTAATGTTGAAAAATTAGCGGAT GACCTGTGGCTGGGGGTGAAAGGCCAATCAAACCGGGAGATAGCTGGTTCTCCCCGAA |

FIG. 11 (Continued)

| | | | |
|---|---|---|---|
| | | | ATCTATTTAGGTAGAGCCTTATGTGAATACCTTCGGGGGTAGAGCACTGTTTCGGCTAG<br>GGGGCCATCCCGGCTTACCAACCCGATGCAAACTGCGAATACCGAAGAGTAATGCATA<br>GGAGACACACGGCGGGTGCTAACGTTCGTCGTGGAGAGGGAAACAACCCAGACCGCC<br>AGCTAAGGTCCCAAAGTTTATATTAAGTGGGAAACGAAGTGGGAAGGCTTAGACAGCTA<br>GGATGTTGGCTTAGAAGCAGCCATCATTTAAAGAAAGCGTAATAGCTCACTAGTCGAGT<br>CGGCCTGCGCGGAAGATGTAACGGGGCTCAAATATAGCACCGAAGCTGCGGCATCAG<br>GCGTAAGCCTGTTGGGTAGGGGAGCGTCGTGTAAGCGGAAGAAGGTGGTTCGAGAGG<br>GCTGCTGGACGTATCACGAGTGCGAATGCTGACATAAGTAACGATAAAACGGGTGAAA<br>AACCCGTTCGCCGGAAGACCAAGGGTTCCTGTCCAACGTTAATCGGGGCAGGGTGAGT<br>CGGCCCCTAAGGCGAGGCTGAAGAGCGTAGTCGATGGGAAACGGGTTAATATTCCCGT<br>ACTTGTTATAATTGCGATGTGGGGACGGAGTAGGTTAGGTTATCGACCTGTTGGAAAAG<br>GTCGTTTAAGTTGGTAGGTGGAGCGTTTAGGCAAATCCGGACGCTTATCAACACCGAGA<br>GATGATGACGAGGCGCTAAGGTGCCGAAGTAACCGATACCACACTTCCAGGAAAAGCC<br>ACTAAGCGTCAGATTATAATAAACCGTACTATAAACCGACACAGGTGGTCAGGTAGAGA<br>ATACTCAGGCGCTTGAGAGAACTCGGGTGAAGGAACTAGGCAAAATAGCACCGTAACT<br>TCGGGAGAAGGTGCGCCGGCGTAGATTGTAGAGGTATACCCTTGAAGGTTGAACCGGT<br>CGAAGTGACCCGCTGGCTGCAACTGTTTATTAAAAACACAGCACTCTGCAAACACGAAA<br>GTGGACGTATAGGGTGTGATGCCTGCCCGGTGCTGGAAGGTTAATTGATGGCGTTATC<br>GCAAGAGAAGCGCCTGATCGAAGCCCCAGTAAACGGCGGCCGTAACTATAACGGTCCT<br>AAGGTAGCGAAATTCCTTGTCGGGTAAGTTCCGACCTGCACGAATGGCATAATGATGGC<br>CAGGCTGTCTCCACCCGAGACTCAGTGAAATTGAAATCGCCGTGAAGATGCGGTGTAC<br>CCGCGGCTAGACGGAAAGACCCCGTGAACCTTTACTATAGCTTGACACTGAACCTTGAA<br>TTTTGATGTGTAGGATAGGTGGGAGGCTTTGAAGCGGTAACGCCAGTTATCGTGGAGC<br>CATCCTTGAAATACCACCCTTTAACGTTTGATGTTCTAACGAAGTGCCCGGAACGGGTA<br>CTCGGACAGTGTCTGGTGGGTAGTTTGACTGGGGCGGTCTCCTCCCAAAGAGTAACGG<br>AGGAGCACGAAGGTTTGCTAATGACGGTCGGACATCGTCAGGTTAGTGCAATGGTATA<br>AGCAAGCTTAACTGCGAGACGGACAAGTCGAGCAGGTGCGAAAGCAGGTCATAGTGAT<br>CCGGTGGTTCTGAATGGAAGGGCCATCGCTCAACGGATAAAAGGTACTCCGGGGATAA<br>CAGGCTGATACCGCCCAAGAGTTCATATCGACGGCCGGTGTTTGGCACCTCGATGTCGG<br>CTCATCACATCCTGGGGCTGAAGTAGGTCCCAAGGGTATGGCTGTTCGCCATTTAAAGT<br>GGTACGCGAGCTGGGTTTAAAACGTCGTGAGACAGTTTGGTCCCTATCTGCCGTGGGC<br>GTTGGAGAATTGAGAGGGGCTGCTCCTAGTACGAGAGGACCGGAGTGGACGCATCACT<br>GGTGTTCCGGTTGTGTCGCCAGACGCATTGCCGGGTAGCTACATGCGGAAGAGATAAG<br>TGCTGAAAGCATCTAAGCACGAAACTTGCCTCGAGATGAGTTCTCCCAGTATTTAATACT<br>GTAAGGGTTGTTGGAGACGACGACGTAGATAGGCCGGGTGTGTAAGCGTTGCGAGAC<br>GTTGAGCTAACCGGTACTAATTGCCCGAGAGGCTTA |
| 9 | 9 | pSacB | TCGAGAGGCCTGACGTCGGGCCCGGTACCACGCGTCATATGACTAGTTCGGACCTAGG<br>GATATCGTCGACATCGATGCTCTTCTGCGTTAATTAACAATTGGGATCCTCTAGACTCCA<br>TAGGCCGCTTTCCTGGCTTTGCTTCCAGATGTATGCTCTCCTCCGGAGAGTACCGTGAC<br>TTTATTTTCGGCACAAATACAGGGGTCGATGGATAAATACGGCGATAGTTTCCTGACGG<br>ATGATCCGTATGTACCGGCGGAAGACAAGCTGCAAACCTGTCAGATGGAGATTGATTTA<br>ATGGCGGATGTGCTGAGAGCACCGCCCCGTGAATCCGCAGAACTGATCCGCTATGTGT<br>TGCGGATGATTGGCCGGAATAAATAAAGCCGGGCTTAATACAGATTAAGCCCGTATAG<br>GGTATTATTACTGAATACCAAACAGCTTACGGAGGACGGAATGTTACCCATTGAGACAA<br>CCAGACTGCCTTCTGATTATTAATATTTTTCACTATTAATCAGAAGGAATAACCATGAATT<br>TTACCCGGATTGACCTGAATACCTGGAATCGCAGGGAACACTTTGCCCTTTATCGTCAG<br>CAGATTAAATGCGGATTCAGCCTGACCACCAAACTCGATATTACCGCTTTGCGTACCGC<br>ACTGGCGGAGACAGGTTATAAGTTTTATCCGCTGATGATTTACCTGATCTCCCGGGCTG<br>TTAATCAGTTTCCGGAGTTCCGGATGGCACTGAAAGACAATGAACTTATTTACTGGGAC<br>CAGTCAGACCCGGTCTTTACTGTCTTTCATAAAGAAACCGAAACATTCTCTGCACTGTCC<br>TGCCGTTATTTTCCGGATCTCAGTGAGTTTATGGCAGGTTATAATGCGGTAACGGCAGA<br>ATATCAGCATGATACCAGATTGTTTCCGCAGGGAAATTTACCGGAGAATCACCTGAATAT<br>ATCATCATTACCGTGGGTGAGTTTTGACGGGATTTAACCTGAACATCACCGGAAATGAT<br>GATTATTTTGCCCCGGTTTTTACGATGGCAAAGTTTCAGCAGGAAGGTGACCGCGTATT<br>ATTACCTGTTTCTGTACAGGTTCATCATGCAGTCTGTGATGGCTTTCATGCAGCACGGTT<br>TATTAATACACTTCAGCTGATGTGTGATAACATACTGAAATAAATTAATTAATTCTGTATTT<br>AAGCCACCGTATCCGGCAGGAATGGTGGCTTTTTTTTTATATTTTAACCGTAATCTGTAA<br>TTTCGTTTCAGACTGGTTCAGGATGAGCTCGCTTGGACTCCTGTTGATAGATCCAGTAA<br>TGACCTCAGAACTCCATCTGGATTTGTTCAGAACGCTCGGTTGCCGCCGGGCGTTTTTT<br>ATTGGTGAGAATCCAAGCACTAGCGGCGCGCCGGCCGGCCCGGTGTGAAATACCGCA<br>CAGATGCGTAAGGAGAAAATACCGCATCAGGCGCTCTTCCGCTTCCTCGCTCACTGACT<br>CGCTGCGCTCGGTCGTTCGGCTGCGGCGAGCGGTATCAGCTCACTCAAAGGCGGTAA<br>TACGGTTATCCACAGAATCAGGGGATAACGCAGGAAAGAACATGTGAGCAAAAGGCCA<br>GCAAAAGGCCAGGAACCGTAAAAAGGCCGCGTTGCTGGCGTTTTTCCATAGGCTCCGC<br>CCCCCTGACGAGCATCACAAAAATCGACGCTCAAGTCAGAGGTGGCGAAACCCGACAG<br>GACTATAAAGATACCAGGCGTTTCCCCCTGGAAGCTCCCTCGTGCGCTCTCCTGTTCCG<br>ACCCTGCCGCTTACCGGATACCTGTCCGCCTTTCTCCCTTCGGGAAGCGTGGCGCTTT<br>CTCATAGCTCACGCTGTAGGTATCTCAGTTCGGTGTAGGTCGTTCGCTCCAAGCTGGG<br>CTGTGTGCACGAACCCCCCGTTCAGCCCGACCGCTGCGCCTTATCCGGTAACTATCGT<br>CTTGAGTCCAACCCGGTAAGACACGACTTATCGCCACTGGCAGCAGCCACTGGTAACA<br>GGATTAGCAGAGCGAGGTATGTAGGCGGTGCTACAGAGTTCTTGAAGTGGTGGCCTAA<br>CTACGGCTACACTAGAAGGACAGTATTTGGTATCTGCGCTCTGCTGAAGCCAGTTACCT<br>TCGGAAAAAGAGTTGGTAGCTCTTGATCCGGCAAACAAACCACCGCTGGTAGCGGTGG<br>TTTTTTTGTTTGCAAGCAGCAGATTACGCGCAGAAAAAAAGGATCTCAAGAAGATCCTTT |

FIG. 11 (Continued)

| | | | |
|---|---|---|---|
| | | | GATCTTTTCTACGGGGTCTGACGCTCAGTGGAACGAAAACTCACGTTAAGGGATTTTGG<br>TCATGAGATTATCAAAAAGGATCTTCACCTAGATCCTTTTAAAGGCCGGCCGCGGCCGC<br>CATCGGCATTTTCTTTTGCGTTTTTATTTGTTAACTGTTAATTGTCCTTGTTCAAGGATGC<br>TGTCTTTGACAACAGATGTTTTCTTGCCTTTGATGTTCAGCAGGAAGCTCGGCGCAAAC<br>GTTGATTGTTTGTCTGCGTAGAATCCTCTGTTTGTCATATAGCTTGTAATCACGACATTG<br>TTTCCTTTCGCTTGAGGTACAGCGAAGTGTGAGTAAGTAAAGGTTACATCGTTAGGATC<br>AAGATCCATTTTTAACACAAGGCCAGTTTTGTTCAGCGGCTTGTATGGGCCAGTTAAAG<br>AATTAGAAACATAACCAAGCATGTAAATATCGTTAGACGTAATGCCGTCAATCGTCATTT<br>TTGATCCGCGGGAGTCAGTGAACAGGTACCATTTGCCGTTCATTTTAAAGACGTTCGCG<br>CGTTCAATTTCATCTGTTACTGTGTTAGATGCAATCAGCGGTTTCATCACTTTTTTCAGTG<br>TGTAATCATCGTTTAGCTCAATCATACCGAGAGCGCCGTTTGCTAACTCAGCCGTGCGT<br>TTTTTATCGCTTTGCAGAAGTTTTTGACTTTCTTGACGGAAGAATGATGTGCTTTTGCCAT<br>AGTATGCTTTGTTAAATAAAGATTCTTCGCCTTGGTAGCCATCTTCAGTTCCAGTGTTTG<br>CTTCAAATACTAAGTATTTGTGGCCTTTATCTTCTACGTAGTGAGGATCTCTCAGCGTAT<br>GGTTGTCGCCTGAGCTGTAGTTGCCTTCATCGATGAACTGCTGTACATTTTGATACGTTT<br>TTCCGTCACCGTCAAAGATTGATTTATAATCCTCTACACCGTTGATGTTCAAAGAGCTGT<br>CTGATGCTGATACGTTAACTTGTGCAGTTGTCAGTGTTTGTTTGCCGTAATGTTTACCGG<br>AGAAATCAGTGTAGAATAAACGGATTTTTCCGTCAGATGTAAATGTGGCTGAACCTGAC<br>CATTCTTGTGTTTGGTCTTTTAGGATAGAATCATTTGCATCGAATTTGTCGCTGTCTTTAA<br>AGACGCGGCCAGCGTTTTTCCAGCTGTCAATAGAAGTTTCGCCGACTTTTTGATAGAAC<br>ATGTAAATCGATGTGTCATCCGCATTTTTAGGATCTCCGGCTAATGCAAAGACGATGTG<br>GTAGCCGTGATAGTTTGCGACAGTGCCGTCAGCGTTTTGTAATGGCCAGCTGTCCCAAA<br>CGTCCAGGCCTTTTGCAGAAGAGATATTTTTAATTGTGGACGAATCAAATTCAGAAACTT<br>GATATTTTTCATTTTTTTGCTGTTCAGGGATTTGCAGCATATCATGGCGTGTAATATGGG<br>AAATGCCGTATGTTTCCTTATATGGCTTTTGGTTCGTTTCTTCGCAAACGCTTGAGTTG<br>CGCCTCCTGCCAGCAGTGCGGTAGTAAAGGTTAATACTGTTGCTTGTTTTGCAAACTTTT<br>TGATGTTCATCGTTCATGTCTCCTTTTTTATGTACTGTGTTAGCGGTCTGCTTCTTCCAG<br>CCCTCCTGTTTGAAGATGGCAAGTTAGTTACGCACAATAAAAAAAGACCTAAAATATGTA<br>AGGGGTGACGCCAAAGTATACACTTTGCCCTTTACACATTTTAGGTCTTGCCTGCTTTAT<br>CAGTAACAAACCCGCGCGATTTACTTTTCGACCTCATTCTATTAGACTCTCGTTTGGATT<br>GCAACTGGTCTATTTTCCTCTTTTGTTTGATAGAAAATCATAAAAGGATTTGCAGACTAC<br>GGGCCTAAAGAACTAAAAAATCTATCTGTTTCTTTTCATTCTCTGTATTTTTTATAGTTTCT<br>GTTGCATGGGCATAAAGTTGCCTTTTTAATCACAATTCAGAAAATATCATAATATCTCATT<br>TCACTAAATAATAGTGAACGGCAGGTATATGTGATGGGTTAAAAAGGATCGGCGGCCGC<br>TCGATTTAAATC |
| 10 | 10 | pSacB<br>(delta ldh) | TCGAGAGGCCTGACGTCGGGCCCGGTACCACGCGTCATATGACTAGTTCGGACCTAGG<br>GATATCGTCGACATCGATGCTCTTCTGCGTTAATTAACAATTGGGATCCTCTAGACCCG<br>GGGATTCCAACCTGAAGACTGGCTCGGTATGACCGAACCCGTCAATATTCCGGGAACC<br>AGCACTCAATATGCTAACTGGCGGCGCCGTTTAACCGCAAATATAGAGGATATTTTTGC<br>CGATACGGATATTCAACATCTGTTAAAAGAGGTGAATGCTATTCGTAAGGAATAATTTTG<br>TTGCGAACGCAATGTGATTTTAACGGGTGCCGGATATGGCACCCTTATCAAAACGACGA<br>ATATTATAGACCTCTTACGATGACGCATCTTTCCCCAGATACGCAGGATTAGACGGATG<br>ATGTTACGGAATATCCCGTCCCTGTGCGGCAACATAAACCTTAATCCATTCTTCCTCAGT<br>GAAGGAAATTCGTAACGCATCCGCCGCGCTTTTTACCCGTTCAATTTTACCGGACCCCA<br>TAACCGGCATAATTTTTGCCGGATGCGCCAATAACCAGGCATAAGCCAATGTATCTAAA<br>CGGGTTTCTCCTTTCGTTTCACCGATTTCGAGTAATGTTTTTTGCACCGCCCGACTGTTC<br>TCATCCTGATTGAATAAACGACCGCCGGCAAGTGGCGACCATGCCATCGGTTGAATAC<br>GTTTTTCCAGTAAAAAATCCAGGGTACCGTCATCAAAAGCCTGACGATGAAGAGGCGAA<br>ATCTCAATTTGATTAGTGATTAACGGCTGATTCACATAAGATTGCAACATGGCGAACTTA<br>GCCGGCGTATAGTTAGATACCCCGAAATAACGTACTTTYCCGGTTTGATAAAGTTCATCA<br>AAAGCCCGCGCGATTTGTTCGGGATCCGCACAGGGAGAAAGWCGGTGAATCAGCAAT<br>ACATCTAAATAGTCGCATTGCAGTTTTTCAATGGAACGTTGCGCCGACCACATAATATGG<br>CGGTAGCTGTTGTCATAGTGATGGGATTTTATATCGGGTAATTCTTCATTAGGATACAAA<br>ATCCCGCATTTGGTCACCAAAGTAAGCTGTGCGCGCAAGGATTTATCCAGCGCCAGCG<br>CCCGTCCGAATTCCGCCTCGGAAGTAAAAGCCCCGTAACAAGCGGCATGATCCAGCGT<br>ATCAACGCCTAATTCTAATCCTTGCTTAACGAATGTAAGCAATTCCTGCGGCGCGATTTCCG<br>CCAGCTTTTTAACCGCCAGAATCCTTGAATTAAGCGACTGAATGTTAAATCGGGAGCCA<br>GTTGAATGTGTTGCATAAAACCTCCAAATAAATTGAATCAAACAGACTTAAGTATAAATCT<br>TTAAAGAAAAAGTGCGGTAGAAAAAATATGGATTTTCCGCATAAAAAAAGCGTACCCGATT<br>AGGTACGCTATTAAAAATATAAGCGGCGCTATTCTACTCTCTTATGGATCTCAGTCAAGA<br>AAGGATCCGGCAACCRCCCGAACAAATGGAGRCGAARAAATTGAAAAGACGAGGAAATC<br>AGCGCGTTAAAAATTCCCGAAAACCCACCGCACTTTTTATTGGAATTTGCTAACCTTAAA<br>AGTGCGGTCAAAAAGTTAAAAATTTTAAGATTGCAATTCCAACGGATTCTTACCCGCTTT<br>ACGCAAAGCCTGATGTTCTTTAATAATCGCCATAAAAGGCTGTCCGAAGCGCTGCCATT<br>TGATGGCGCCGACACCGTTGATTTGCAGCATTTCCACTTTGCTGGTCGGCTGATACAAC<br>GACATTTCCTGCAAGGTCGCGTCACTGAACACAATATAAGGCGGAATGTTTTCTTTGTC<br>GGCAATCTGTTTGCGCAGGAAACGCAGGCGGGCAAATAAATCTTTGTCGTAGTTGGTTA<br>CCGCATTGCGTTGCGGAGCCTGTACCATGGTAATGGAAGATAATCTCGGCATGGCCAG<br>TTCCAAAGACACTTCGCCGCGCAGCACGGGACGGCGCCTTTCGGTGAGCTGTAATCTG<br>GTCCCCATGCCGAAATCGCTGATGATTGTTGCACAAAGCCCAAATGAATCAGCTGACG<br>AATTACCGATTGCCAGTATTCTTTGCTTTTATCTTTGCCAATTCCGTAGACTTTCAACTCA<br>TCATGTTGATTTTCTTTTATTTTCTGATTCTGCAAACCGCGCATTACGCCGATTACGTATT<br>GCGTGCCGAAACGTTGCCCGGTGCGATAAATGGTCGAAAGGATTTTCTGCGCGTCTAA<br>TAATCCGTCATATTTTTTCGGCGGATCGAGGCAGATATCACAGTTATTACATGGCGTTTG |

FIG. 11 (Continued)

```
GCGGTTTTCGCCGAAATAATTTAACAGCACTAAACGACGGCAGGTCTGGCTTTCGGCAA
ATTCGCCGATGGCTTCCAGCTTATGCCGTTTAATATCCCGTTGCGGGCTTTCCGGCTCT
TCCAATAAAATTTTATGCAACCAGGCATAATCCGCCGGCTCGTAAAACAGTACCGCTTC
CGCCGGCAGGTCGTCCCGCCCCGCGCGCCCGGTTTCCTGATAATACGCCTCAATGCT
GCGAGATAAATCAAAATGCGCCACAAAACGCACATTAGATTTGTTGATCCCCATACCAA
AAGCAATGGTCGCCACCACCACTTGAATATTATCCCGTTGAAACGCCTGTTGCACCGCT
TCCCGCTGCGACGGCTCCATGCCCGCATGATAAGCGGCTGCGGAAATGCCTCTTTTCT
TCAGGGCTTCCGCAATGCGCTCCACTTTGCTACGGCTGTTGCAATAGACGATACCGCTT
TTACCTTTTTGCGCCGCCACAAAATTGTATAATTGCTCCATCGGTTTGAATTTTTCCACC
AAGGTATAACGAATATTCGGGCGGTCAAAACTACCTACATACAAGTGCGGTTCGTTCAG
GCTGACCCGGGATTTAAATCGCTAGCGGGCTGCTAAAGGAAGCGGAACACGTAGAAAG
CCAGTCCGCAGAAACGGTGCTGACCCCGGATGAATGTCAGCTACTGGGCTATCTGGAC
AAGGGAAAACGCAAGCGCAAAGAGAAAGCAGGTAGCTTGCAGTGGGCTTACATGGCGA
TAGCTAGACTGGGCGGTTTTATGGACAGCAAGCGAACCGGAATTGCCAGCTGGGGCGC
CCTCTGGTAAGGTTGGGAAGCCCTGCAAAGTAAACTGGATGGCTTTCTTGCCGCCAAG
GATCTGATGGCGCAGGGGATCAAGATCTGATCAAGAGACAGGATGAGGATCGTTTCGC
ATGATTGAACAAGATGGATTGCACGCAGGTTCTCCGGCCGCTTGGGTGGAGAGGCTAT
TCGGCTATGACTGGGCACAACAGACAATCGGCTGCTCTGATGCCGCCGTGTTCCGGCT
GTCAGCGCAGGGGCGCCCGGTTCTTTTTGTCAAGACCGACCTGTCCGGTGCCCTGAAT
GAACTGCAGGACGAGGCAGCGCGGCTATCGTGGCTGGCCACGACGGGCGTTCCTTGC
GCAGCTGTGCTCGACGTTGTCACTGAAGCGGGAAGGGACTGGCTGCTATTGGGCGAA
GTGCCGGGGCAGGATCTCCTGTCATCTCACCTTGCTCCTGCCGAGAAAGTATCCATCAT
GGCTGATGCAATGCGGCGGCTGCATACGCTTGATCCGGCTACCTGCCCATTCGACCAC
CAAGCGAAACATCGCATCGAGCGAGCACGTACTCGGATGGAAGCCGGTCTTGTCGATC
AGGATGATCTGGACGAAGAGCATCAGGGGCTCGCGCCAGCCGAACTGTTCGCCAGGC
TCAAGGCGCGCATGCCCGACGGCGAGGATCTCGTCGTGACCCATGGCGATGCCTGCT
TGCCGAATATCATGGTGGAAAATGGCCGCTTTTCTGGATTCATCGACTGTGGCCGGCTG
GGTGTGGCGGACCGCTATCAGGACATAGCGTTGGCTACCCGTGATATTGCTGAAGAGC
TTGGCGGCGAATGGGCTGACCGCTTCCTCGTGCTTTACGGTATCGCCGCTCCCGATTC
GCAGCGCATCGCCTTCTATCGCCTTCTTGACGAGTTCTTCTGAGCGGGACTCTGGGGT
TCGAAATGACCGACCAAGCGACGCCCAACCTGCCATCACGAGATTTCGATTCCACCGC
CGCCTTCTATGAAAGGTTGGGCTTCGGAATCGTTTTCCGGGACGCCGGCTGGATGATC
CTCCAGCGCGGGGATCTCATGCTGGAGTTCTTCGCCCACGCTAGCGGCGGCGGCGGCC
GGCCCGGTGTGAAATACCGCACAGATGCGTAAGGAGAAAATACCGCATCAGGCGCTCT
TCCGCTTCCTCGCTCACTGACTCGCTGCGCTCGGTCGTTCGGCTGCGGCGAGCGGTAT
CAGCTCACTCAAAGGCGGTAATACGGTTATCCACAGAATCAGGGGATAACGCAGGAAA
GAACATGTGAGCAAAAGGCCAGCAAAAGGCCAGGAACCGTAAAAAGGCCGCGTTGCTG
GCGTTTTTCCATAGGCTCCGCCCCCTGACGAGCATCACAAAAATCGACGCTCAAGTCA
GAGGTGGCGAAACCCGACAGGACTATAAAGATACCAGGCGTTTCCCCCTGGAAGCTCC
CTCGTGCGCTCTCCTGTTCCGACCCTGCCGCTTACCGGATACCTGTCCGCCTTTCTCCC
TTCGGGAAGCGTGGCGCTTTCTCATAGCTCACGCTGTAGGTATCTCAGTTCGGTGTAG
GTCGTTCGCTCCAAGCTGGGCTGTGTGCACGAACCCCCCGTTCAGCCCGACCGCTGC
GCCTTATCCGGTAACTATCGTCTTGAGTCCAACCCGGTAAGACACGACTTATCGCCACT
GGCAGCAGCCACTGGTAACAGGATTAGCAGAGCGAGGTATGTAGGCGGTGCTACAGA
GTTCTTGAAGTGGTGGCCTAACTACGGCTACACTAGAAGGACAGTATTTGGTATCTGCG
CTCTGCTGAAGCCAGTTACCTTCGGAAAAAGAGTTGGTAGCTCTTGATCCGGCAAACAA
ACCACCGCTGGTAGCGGTGGTTTTTTTGTTTGCAAGCAGCAGATTACGCGCAGAAAAAA
AGGATCTCAAGAAGATCCTTTGATCTTTTCTACGGGGTCTGACGCTCAGTGGAACGAAA
ACTCACGTTAAGGGATTTTGGTCATGAGATTATCAAAAAGGATCTTCACCTAGATCCTTT
TAAAGGCCGGCCGCGGCCGCCATCGGCATTTTCTTTTGCGTTTTTATTTGTTAACTGTTA
ATTGTCCTTGTTCAAGGATGCTGTCTTTGACAACAGATGTTTTCTTGCCTTTGATGTTCA
GCAGGAAGCTCGGCGCAAACGTTGATTGTTTGTCTGCGTAGAATCCTCTGTTTGTCATA
TAGCTTGTAATCACGACATTGTTTCCTTTCGCTTGAGGTACAGCGAAGTGTGAGTAAGTA
AAGGTTACATCGTTAGGATCAAGATCCATTTTTAACACAAGGCCAGTTTTGTTCAGCGGC
TTGTATGGGCCAGTTAAAGAATTAGAAACATAACCAAGCATGTAAATATCGTTAGACGTA
ATGCCGTCAATCGTCATTTTTGATCCGCGGGAGTCAGTGAACAGGTACCATTTGCCGTT
CATTTTAAAGACGTTCGCGCGTTCAATTTCATCTGTTACTGTGTTAGATGCAATCAGCGG
TTTCATCACTTTTTTCAGTGTGTAATCATCGTTTAGCTCAATCATACCGAGAGCGCCGTT
TGCTAACTCAGCCGTGCGTTTTTTATCGCTTTGCAGAAGTTTTTGACTTTCTTGACGGAA
GAATGATGTGCTTTTGCCATAGTATGCTTTGTTAAATAAAGATTCTTCGCCTTGGTAGCC
ATCTTCAGTTCCAGTGTTTGCTTCAAATACTAAGTATTTGTGGCCTTTATCTTCTACGTAG
TGAGGATCTCTCAGCGTATGGTTGTCGCCTGAGCTGTAGTTGCCTTCATCGATGAACTG
CTGTACATTTTGATACGTTTTTCCGTCACCGTCAAAGATTGATTTATAATCCTCTACACCG
TTGATGTTCAAAGAGCTGTCTGATGCTGATACGTTAACTTGTGCAGTTGTCAGTGTTTGT
TTGCCGTAATGTTTACCGGAGAAATCAGTGTAGAATAAACGGATTTTTCCGTCAGATGTA
AATGTGGCTGAACCTGACCATTCTTGTGTTTGGTCTTTTAGGATAGAATCATTTGCATCG
AATTTGTCGCTGTCTTTAAAGACGCGGCCAGCGTTTTTCCAGCTGTCAATAGAAGTTTC
GCCGACTTTTTGATAGAACATGTAAATCGATGTGTCATCCGCATTTTTAGGATCTCCGGC
TAATGCAAAGACGATGTGGTAGCCGTGATAGTTTGCGACAGTGCCGTCAGCGTTTTGTA
ATGGCCAGCTGTCCCAAACGTCCAGGCCTTTTGCAGAAGAGATATTTTAATTGTGGAC
GAATCAAATTCAGAAACTTGATATTTTTCATTTTTTTGCTGTTCAGGGATTTGCAGCATAT
CATGGCGTGTAATATGGGAAATGCCGTATGTTTCCTTATATGGCTTTTGGTTCGTTTCTT
TCGCAAACGCTTGAGTTGCGCCTCCTGCCAGCAGTGCGGTAGTAAAGGTTAATACTGTT
GCTTGTTTTGCAAACTTTTTGATGTTCATCGTTCATGTCTCCTTTTTTATGTACTGTGTTA
```

FIG. 11 (Continued)

| | | | |
|---|---|---|---|
| | | | GCGGTCTGCTTCTTCCAGCCCTCCTGTTTGAAGATGGCAAGTTAGTTACGCACAATAAA
AAAAGACCTAAAATATGTAAGGGGTGACGCCAAAGTATACACTTTGCCCTTTACACATTT
TAGGTCTTGCCTGCTTTATCAGTAACAAACCCGCGCGATTTACTTTTCGACCTCATTCTA
TTAGACTCTCGTTTGGATTGCAACTGGTCTATTTTCCTCTTTTGTTTGATAGAAAATCATA
AAAGGATTTGCAGACTACGGGCCTAAAGAACTAAAAAATCTATCTGTTTCTTTTCATTCT
CTGTATTTTTTATAGTTTCTGTTGCATGGGCATAAAGTTGCCTTTTTAATCACAATTCAGA
AAATATCATAATATCTCATTTCACTAAATAATAGTGAACGGCAGGTATATGTGATGGGTT
AAAAAGGATCGGCGGCCGCTCGATTTAAATC |
| 11 | 11 | pSacB
(delta pflD) | TCGAGAGGCCTGACGTCGGGCCCGGTACCACGCGTCATATGACTAGTTCGGACCTAGG
GATGGGATCGAGCTCTTTTCCTTGCCGACAAGGCGGAAGCTTTAGGGGAAATTCCCGT
AGGTGCCGTATTGGTGGATGAACGGGGCAATATCATTGGTGAAGGCTGGAACCTCTCT
ATTGTGAACTCGGATCCCACCGCCCATGCCGAAATTATTGCGTTGCGTAACGCCGCGC
AGAAAATCCAAAATTACCGCCTGCTCAATACCACTTTATACGTGACTTTAGAACCCTGCA
CCATGTGCGCCGGCGCGATTTTACACAGCCGAATCAAACGCTTGGTATTCGGGGCGTC
CGATTACAAAACCGGTGCGGTGGGTTCCAGATTTCATTTTTTTGAGGATTATAAAATGAA
TCATGGGGTTGAGATCACAAGCGGTGTCTTATAGGATCAATGCAGTCAGAAGTTAAGCC
GCTTTTTCCAAAAGCGCAGGGAACAGAAAAAACAACAAAAAAGCTACCGCACTTTTACAA
CACCCCCGGCTTAACTCCTCTGAAAAATAGTGACAAAAAAACCGTCATAATGTTTACGAC
GGTTTTTTTATTTCTTCTAATATGTCACATTAAGCCCGTAGCCTGCAAGCAACCCCTTAA
CATGCTCCATTAATTCTTTTGTCGGCGGTTTTACATCTTCAAGCTCGTATTTATCGCCGA
GTACTTCCCATTTATGGCGCCTAGACGGTGATAAGGTAATAATTCCACTTTTTCGATAT
TCTTCATATCTTTAATGAAATTCCCCAGCATGTGCAAATCTTCGTCACTATCTGTATAACC
CGGCACTACAACATGGCGGATCCAGGTACGCTGATTTCGATCCGCTAAATATTTTGCGA
ATTCGAGCACTCTTTTATTCGGCACGCCAATCAGGCTTTCGTGAACCCGTTCATTCATTT
CTTTCAGGTCAAGCAACACAAGATCCGTGTCATCAATCAATTCATCAATAATATGATCAT
GATGACGGACGAAACCGTTGGTATCCAAGCAAGTATTAATTCCTTCTTTATGGCAGGCT
CTGAACCAGTCCCGTACAAATTCCCGCCTGTAAAATAGCTTCACCGCCGGAAGCGGTAAC
TCCGCCGCCCGAGGCGTTCATAAAATGGCGATAGGTCACCACTTCTTTCATTAATTCTT
CAACGGAAATTTCTTTACCGCCGTGCAAATCCCAGGTGTCTCTGTTATGGCAATATTTAC
AACGCATTAAGCAGCCTTGTAAAAATAAAATAAAGCGGATTCCCGGCCCGTCAACTGTC
CCGCAGGTTTCAAATGAATGAATTCGTCCTAAAACCGACATAATATGCCCTTAAATAATC
AACAAAATATAGCAAGAAGATTATAGCAAAGAATTTCGTTTTTTTCAGAGAATAGTCAAAT
CTTCGCAAAAAACTACCGCACTTTTATCCGCTTTAATCAGGGGAATTAAAACAAAAAAAT
TCCGCCTATTGAGGCGGAATTTATTAAGCAATAAGACAAACTCTCAATTTTAATACTTCC
TTCTTTTCTAGTATTGATAAGATTGAAACCTTGCAAGGATGACGGCGGATTTGCCGTCAC
TCTCACCCAACTAATGTGGACGACTGGTAAACCATTGCATTAGACCAATGCAAACACCA
CCACCGACGATGTTACCTAAAGTAACAGGAATTAAATTTTTAATTACTAAATGGTACATAT
CTAAATTTGCAAACTGCTCGGCATTTAAACCCGTTGCCTGCCAGAATTCCGGCGATGCG
AAATTTGCAATTACCATGCCCATAGGGATCATAAACATATTTGCTACGCAGTGTTCAAAG
CCTGAAGCGACAAAYAACCCGATCGGCAGGATCATAATAAAAGCTTTATCCGTTAGAGT
YTTGCCGGCATAGGCCATCCAAACGGCAATACATACCATAATGTTGCAAAGAATACCTA
AACAGAAGGCTTCAAYCCAGGTATGTTCTATTTTATGTTGTGCCGTATTTAAAATGGTTA
ATCCCCACTGACCGTTTGCCGCCATGATCTGACCGGAAAACCAAATTAATGCAACAATA
AATAAACCGCCGACAAAATTACCGAARTAAACCCACAATCCAGTTACGTAACATCTGAATT
GTTGTAATTTTACTCTCAAAGCGGGCAATAGTCGATAAAGTTGATGAAGTAAATAGTTCA
CAGCCGCAAACCGCCACCATAATTACCCCGAGAGAGAACACCAAACCGCCGACCAGTT
TAGTTAATCCCCAAGGCGCTCCCGCACAGAGGCTGTTTGAGTTGTTGTATAAAAAACGAAT
GCAAGAGCAATAAACATACCGGCAGAGATCGCCGATAAAAATGAATAGGCTTGTTTTTT
CGTAGCTTTATAAACGCCGACGTCTAACCCGGTTTGAGCCATCTCGGTTGGCGAAGCC
ATCCAAGCCAATTTAAAATCTTCCGATTTCATTGAGCTTTCCTTAGTAATAAAACTACTCG
GAAATGAGTAGAACTGCCCTTAAAGCATAAATGATAGATTAAAAAAATCCAAAATTGTTGAA
TATTATTTAACGGGGGGATTATAAAAGATTCATAAATTAGATAATAGCTAATTTGAGTGAT
CCATATCACCTTTTACAGATTTTTTGACCTAAATCAAAATTACCCAAATAGAGTAATAATA
CCATTATAAAGGGTGTGGATTTATTCCTTTGGTTTACGAGATAAATTGCTATTTAAGCTG
ATTTCTGATAAAAAGTGCGGTAGATTTTTCCCAAAAAATAAGGAAACACAAAATGGCAGAA
GAAACAATTTTCAGTAAAATTATTCGTAAAGAAATTCCCGCCGACATTATATATCAAGAC
GATCTTGTCACCGCATTTCGCGATATTGCGCCGCAGGCAAAAACTCATATTTTAATTATT
CCGAATAAATTGATTCCGACAGTAAACGACGTAACCGCCCATCGTCGACATCGATGCTC
TTCTGCGTTAATTAACAATTGGGATCCTCTAGACTTTGCTTCCAGATGTATGCTCTCCTC
CGGGAGAGTACCGTGACTTTATTTTCGGCACAAATACAGGGCGTCGATGGATAAATACGGC
GATAGTTTCCTGACGGATGATCCGTATGTACCGGCGGAAGACAAGCTGCAAACCTGTC
AGATGGAGATTGATTTAATGGCGGATGTGCTGAGAGCACCGCCCCGTGAATCCGCAGA
ACTGATCCGCTATGTGTTTGCGGATGATTGGCCGGAATAAATAAAGCCGGGCTTAATAC
AGATTAAGCCCGTATAGGGTATTATTACTGAATACCAAACAGCTTACGGAGGACGGAAT
GTTACCCATTGAGACAACCAGACTGCCTTCTGATTATTAATATTTTTCACTATTAATCAGA
AGGAATAACCATGAATTTTACCCGGATTGACCTGAATACCTGGAATCGCAGGGAACACT
TTGCCCTTTATCGTCAGCAGATTAAATGCGGATTCAGCCTGACCACCAAACTCGATATTA
CCGCTTTGCGTACCGCACTGGCGGAGACAGGTTATAAGTTTTATCCGCTGATGATTTAC
CTGATCTCCCGGGCTGTTAATCAGTTTCGGGAGTTCCGGATGGCACTGAAAGACAATGA
ACTTATTTACTGGGACCAGTCAGACCCGGTCTTTACTGTCTTTCATAAAGAAACCGAAAC
ATTCTCTGCACTGTCCTGCCGTTATTTTCCGGATCTCAGTGAGTTTATGGCAGGTTATAA
TGCGGTAACGGCAGAATATCAGCATGATACCAGATTGTTTCCGCAGGGAAATTTACCGG
AGAATCACCTGAATATATCATCATTACCGTGGGTGAGTTTTGACGGGATTTAACCTGAAC
ATCACCGGAAATGATGATTATTTTGCCCCGGTTTTTACGATGGCAAAGTTTCAGCAGGA |

FIG. 11 (Continued)

| | | | |
|---|---|---|---|
| | | | AGGTGACCGCGTATTATTACCTGTTTCTGTACAGGTTCATCATGCAGTCTGTGATGGCTT
TCATGCAGCACGGTTTATTAATACACTTCAGCTGATGTGTGATAACATACTGAAATAAAT
TAATTAATTCTGTATTTAAGCCACCGTATCCGGCAGGAATGGTGGCTTTTTTTTATATTT
TAACCGTAATCTGTAATTTCGTTTCAGACTGGTTCAGGATGAGCTCGCTTGGACTCCTGT
TGATAGATCCAGTAATGACCTCAGAACTCCATCTGGATTTGTTCAGAACGCTCGGTTGC
CGCCGGGCGTTTTTTATTGGTGAGAATCCAAGCACTAGCGGCGCGCCGGCCGGCCCG
GTGTGAAATACCGCACAGATGCGTAAGGAGAAAATACCGCATCAGGCGCTCTTCCGCT
TCCTCGCTCACTGACTCGCTGCGCTCGGTCGTTCGGCTGCGGCGAGCGGTATCAGCTC
ACTCAAAGGCGGTAATACGGTTATCCACAGAATCAGGGGATAACGCAGGAAAGAACAT
GTGAGCAAAAGGCCAGCAAAAGGCCAGGAACCGTAAAAAGGCCGCGTTGCTGGCGTTT
TTCCATAGGCTCCGCCCCCCTGACGAGCATCACAAAAATCGACGCTCAAGTCAGAGGT
GGCGAAACCCGACAGGACTATAAAGATACCAGGCGTTTCCCCCTGGAAGCTCCCTCGT
GCGCTCTCCTGTTCCGACCCTGCCGCTTACCGGATACCTGTCCGCCTTTCTCCCTTCG
GGAAGCGTGGCGCTTTCTCATAGCTCACGCTGTAGGTATCTCAGTTCGGTGTAGGTCG
TTCGCTCCAAGCTGGGCTGTGTGCACGAACCCCCCGTTCAGCCCGACCGCTGCGCCTT
ATCCGGTAACTATCGTCTTGAGTCCAACCCGGTAAGACACGACTTATCGCCACTGGCAG
CAGCCACTGGTAACAGGATTAGCAGAGCGAGGTATGTAGGCGGTGCTACAGAGTTCTT
GAAGTGGTGGCCTAACTACGGCTACACTAGAAGGACAGTATTTGGTATCTGCGCTCTGC
TGAAGCCAGTTACCTTCGGAAAAAGAGTTGGTAGCTCTTGATCCGGCAAACAAACCACC
GCTGGTAGCGGTGGTTTTTTTGTTTGCAAGCAGCAGATTACGCGCAGAAAAAAAGGATC
TCAAGAAGATCCTTTGATCTTTCTACGGGGTCTGACGCTCAGTGGAACGAAAACTCAC
GTTAAGGGATTTTGGTCATGAGATTATCAAAAAGGATCTTCACCTAGATCCTTTTAAAGG
CCGGCCGCGGCCGCCATCGGCATTTTCTTTTGCGTTTTTATTTGTTAACTGTTAATTGTC
CTTGTTCAAGGATGCTGTCTTTGACAACAGATGTTTTCTTGCCTTTGATGTTCAGCAGGA
AGCTCGGCGCAAACGTTGATTGTTTGTCTGCGTAGAATCCTCTGTTTGTCATATAGCTTG
TAATCACGACATTGTTTCCTTTCGCTTGAGGTACAGCGAAGTGTGAGTAAGTAAAGGTTA
CATCGTTAGGATCAAGATCCATTTTTAACACAAGGCCAGTTTTGTTCAGCGGCTTGTATG
GGCCAGTTAAAGAATTAGAAACATAACCAAGCATGTAAATATCGTTAGACGTAATGCCGT
CAATCGTCATTTTTGATCCGCGGGAGTCAGTGAACAGGTACCATTTGCCGTTCATTTTAA
AGACGTTCGGCGCGTTCAATTTCATCTGTTACTGTGTTAGATGCAATCAGCGGTTTCATCA
CTTTTTTCAGTGTGTAATCATCGTTTAGCTCAATCATACCGAGAGCGCCGTTTGCTAACT
CAGCCGTGCGTTTTTTATCGCTTTGCAGAAGTTTTTGACTTTCTTGACGGAAGAATGATG
TGCTTTTGCCATAGTATGCTTTGTTAAATAAAGATTCTTCGCCTTGGTAGCCATCTTCAG
TTCCAGTGTTTGCTTCAAATACTAAGTATTTGTGGCCTTTATCTTCTACGTAGTGAGGAT
CTCTCAGCGTATGGTTGTCGCCTGAGCTGTAGTTGCCTTCATCGATGAACTGCTGTACA
TTTTGATACGTTTTTCCGTCACCGTCAAAGATTGATTTATAATCCTCTACACCGTTGATGT
TCAAAGAGCTGTCTGATGCTGATACGTTAACTTGTGCAGTTGTCAGTGTTTGTTTGCCGT
AATGTTTACCGGAGAAATCAGTGTAGAATAAACGGATTTTTCCGTCAGATGTAAATGTGG
CTGAACCTGACCATTCTTGTGTTTGGTCTTTTAGGATAGAATCATTTGCATCGAATTTGT
CGCTGTCTTTAAAGACGCGGCCAGCGTTTTTCCAGCTGTCAATAGAAGTTTCGCCGACT
TTTTGATAGAACATGTAAATCGATGTGTCATCCGCATTTTTAGGATCTCCGGCTAATGCA
AAGACGATGTGGTAGCCGTGATAGTTTGCGACAGTGCCGTCAGCGTTTTGTAATGGCC
AGCTGTCCCAAACGTCCAGGCCTTTTGCAGAAGAGATATTTTTAATTGTGGACGAATCA
AATTCAGAAACTTGATATTTTTCATTTTTTTGCTGTTCAGGGATTTGCAGCATATCATGGC
GTGTAATATGGGAAATGCCGTATGTTTCCTTATATGGCTTTTGGTTCGTTTCTTTCGCAA
ACGCTTGAGTTGCGCCTCCTGCCAGCAGTGCGGTAGTAAAGGTTAATACTGTTGCTTGT
TTTGCAAACTTTTTGATGTTCATCGTTCATGTCTCCTTTTTTATGTACTGTGTTAGCGGTC
TGCTTCTTCCAGCCCTCCTGTTTGAAGATGGCAAGTTAGTTACGCACAATAAAAAAAGAC
CTAAAATATGTAAGGGGTGACGCCAAAGTATACACTTTGCCCTTTACACATTTTAGGTCT
TGCCTGCTTTATCAGTAACAAACCCGCGCGATTTACTTTTCGACCTCATTCTATTAGACT
CTCGTTTGGATTGCAACTGGTCTATTTTCCTCTTTTTGTTTGATAGAAATCATAAAAGGAT
TTGCAGACTACGGGCCTAAAGAACTAAAAAATCTATCTGTTTCTTTTCATTCTCTGTATTT
TTTATAGTTTCTGTTGCATGGGCATAAAGTTGCCTTTTTAATCACAATTCAGAAAATATCA
TAATATCTCATTTCACTAAATAATAGTGAACGGCAGGTATATGTGATGGGTTAAAAAGGA
TCGGCGGCCGCTCGATTTAAATC |
| 12 | 12 | pJFF224 (icl ms Y.m.) | GATCCCCAGTAGATTTACGTTTAAACATTTTTATTTCCTTTTTAATTTAATTTAATTAACAG
TTGGTGCTATGACACTTTACCTCATAGCTGGCATAATTCGCAATACTCTGGGTCTTCGAG
AGGTATCCAACCTGAGTTGAAATACTTTACCATCGATTTAGCAGTTGTATCAGTTATATTT
ATATTACCTTTAACTCTTCGCCATCCAGGAGTTTTACCGTACAGATTAGAGGATAATAAT
AACACATAATTCTCGTAAGCAATATGAGATAATTTCCAAGACTCTATATTAGCTCGTGAT
GTTTTCCAAGGTCTAAAATCGTCACGGTTCATATAATTAGCCAATCTCATATGCTCTCTA
ACTTCCGATGATAAGCTGTCAAACATGAGAATTAACGATCTGATAGAGAAGGGTTTGCT
CGGGTCGGTGGCTCTGGTAACGACCAGTATCCCGATCCCGGCTGGCCGTCCTGGCCG
CCACATGAGGCATGTTCCGCGTCCTTGCAATACTGTGTTTACATACAGTCTATCGCTTA
GCGGAAAGTTCTTTTACCCTCAGCCGAAATGCCTGCCGTTGCTAGACATTGCCAGCCAG
TGCCCGTCACTCCCGTACTAACTGTCACGAACCCCTGCAATAACTGTCACGCCCCCTG
CAATAACTGTCACGAACCCCTGCAATAACTGTCACGCCCCCAAACCTGCAAACCCAGCA
GGGGCGGGGCTGGCGGGGTGTTGGAAAAATCCATCCATGATTATCTAAGAATAATCC
ACTAGGCGCGGTTATCAGCGCCCTTGTGGGGCGCTGCTGCCCTTGCCCAATATGCCCG
GCCAGAGGCCGGATAGCTGGTCTATTCGCTGCGCTAGGCTACACACCGCCCCACCGCT
GCGCGGCAGGGGGAAAGGCGGGCAAAGCCCGCTAAACCCCACACCAAACCCCGCAGA
AATACGCTGGGAGCGCTTTTAGCCGCTTTAGCGGCCTTTCCCCCTACCCGAAGGGTGG
GGGCGCGTGTGCAGCCCCGCAGGGCCTGTCTCGGTCGATCATTCAGCCCGGCTCATC
CTTCTGGCGTGGCGGCAGACCGAACAAGGCGCGGTCGTGGTCGCGTTCAAGGTACGC |

FIG. 11 (Continued)

```
ATCCATTGCCGCCATGAGCCGATCCTCCGGCCACTCGCTGCTGTTCACCTTGGCCAAA
ATCATGGCCCCCACCAGCACCTTGCGCCTTGTTTCGTTCTTGCGCTATTGCTGCTGTTC
CCTTGCCCGCACCCGCTGAATTTCGGCATTGATTCGCGCTCGTTGTTCTTCGAGCTTGG
CCAGCCGATCCGCCGCCTTGTTGCTCCCCTTAACCATCTTGACACCCCATTGTTAATGT
GCTGTCTCGTAGGCTATCATGGAGGCACAGCGGCGGCAATCCCGACCCTACTTTGTAG
GGGAGGGCCATTGCATGGAGCCGAAAAGCAAAAGCAACAGCGAGGCAGCATGGCGAT
TTATCACCTTACGGCGAAAACCGGCAGCAGGTCGGGCGGCCAATCGGCCAGGGCCAA
GGCCGACTACATCCAGCGCGAAGGCAAGTATGCCCGCGACATGGATGAAGTCTTGCAC
GCCGAATCCGGGCACATGCCGGAGTTCGTCGAGCGGCCCGCCGACTACTGGGATGCT
GCCGACCTGTATGAACGCGCCAATGGGCGGCTGTTCAAGGAGGTCGAATTTGCCCTGC
CGGTCGAGCTGACCCTCGACCAGCAGAAGGCGCTGGCGTCCGAGTTCGCCCAGCACC
TGACCGGTGCCGAGCGCCTGCCGTATACGCTGGCCATCCATGCCGGTGGCGGCGAGA
ACCCGCACTGCCACCTGATGATCTCCGAGCGGATCAATGACGGCATCGAGCGGCCCG
CCGCTCAGTGGTTCAAGCGGTACAACGGCAAGACCCCGGAGAAGGGCGGGGCACGA
AGACCGAAGCGCTCAAGCCCAAGGCATGGCTTGAGCAGACCCGCGAGGCATGGGCCG
ACCATGCCAACCGGGCATTAGAGCGGGCTGGCCACGACGCCCGCATTGACCACAGAA
CACTTGAGGCGCAGGGCATCGAGCGCCTGCCCGGTGTTCACCTGGGGCCGAACGTGG
TGGAGATGGAAGGCCGGGGCATCCGCACCGACCGGGCAGACGTGGCCCTGAACATCG
ACACCGCCAACGCCCAGATCATCGACTTACAGGAATACCGGGAGGCAATAGACCATGA
ACGCAATCGACAGAGTGAAGAAATCCAGAGGCATCAACGAGTTAGCGGAGCAGATCGA
ACCGCTGGCCCAGAGCATGGCGACACTGGCCGACGAAGCCCGGCAGGTCATGAGCCA
GACCCAGCAGGCCAGCGAGGCGCAGGCGGCGGAGTGGCTGAAAGCCCAGCGCCAGA
CAGGGGCGGCATGGGTGGAGCTGGCCAAAGAGTTGCGGGAGGTAGCCGCCGAGGTG
AGCAGCGCCGCGCAGAGCGCCCGGAGCGCGTCGCGGGGGTGGCACTGGAAGCTATG
GCTAACCGTGATGCTGGCTTCCATGATGCCTACGGTGGTGCTGCTGATCGCATCGTTG
CTCTTGCTCGACCTGACGCCACTGACAACCGAGGACGGCTCGATCTGGCTGCGCTTGG
TGGCCCGATGAAGAACGACAGGACTTTGCAGGCCATAGGCCGACAGCTCAAGGCCATG
GGCTGTGAGCGCTTCGATATCGGCGTCAGGGACGCCACCACCGGCCAGATGATGAAC
CGGGAATGGTCAGCCGCCGAAGTGCTCCAGAACACGCCATGGCTCAAGCGGATGAAT
GCCCAGGGCAATGACGTGTATATCAGGCCCGCCGAGCAGGACGGCGCCATGGTCTGGTG
CTGGTGGACGACCTCAGCGAGTTTGACCTGGATGACATGAAAGCCGAGGGCCGGGAG
CCTGCCCTGGTAGTGGAAACCAGCCCGAAGAACTATCAGGCATGGGTCAAGGTGGCC
GACGCCGCAGGCGGTGAACTTCGGGGGCAGATTGCCCGGACGCTGGCCAGCGAGTAC
GACGCCGACCCGGCCAGCGCCGACAGCCGCCACTATGGCCGCTTGGCGGGCTTCACC
AACCGCAAGGACAAGCACACCACCCGCGCCGGTTATCAGCCGTGGGTGCTGCTGCGT
GAATCCAAGGGCAAGACCGCCACCGCTGGCCCGGCGCTGGTGCAGCAGGCTGGCCA
GCAGATCGAGCAGGCCCAGCGGCAGCAGGAGAAGGGCCGCAGGCTGGCCAGCCTCG
AACTGCCCGAGCGGCAGCTTAGCCGCCACCGGCGCACGGCGCTGGACGAGTACCGCA
GCGAGATGGCCGGGCTGGTCAAGCGCTTCGGTGATGACCTCAGCAAGTGCGACTTTAT
CGCCGCGCAGAAGCTGGCCAGCCGGGGCCGCAGTGCCGAGGAAATCGGCAAGGCCA
TGGCCGAGGCCAAGCCCAGCGCTGGCAGAGCGCAAGCCCGGCCACGAAGCGGATTACA
TCGAGCGCACCGTCAGCAAGGTCATGGGTCTGCCCAGCGTCCAGCTTGCGCGGGCCG
AGCTGGCACGGGCACCGGCACCCCGCCAGCGAGGCATGGACAGGGGCGGGCCAGAT
TCAGCATGTAGTGCTTGCGTTGGTACTCACGCCTGTTATACTATGAGTACTCACGCAC
AGAAGGGGGTTTTATGGAATACGAAAAAAGCGCTTCAGGGTCGGTCTACCTGATCAAAA
GTGACAAGGGCTATTGGTTGCCCGGTGGCTTTGGTTATACGTCAAACAAGGCCGAGGC
TGGCCGCTTTTCAGTCGCTGATATGGCCAGCCTTAACCTTGACGGCTGCACCTTGTCCT
TGTTCCGCGAAGACAAGCCTTTCGGCCCCGGCAAGTTTCTCGGTGACTGATATGAAAG
ACCAAAAGGACAAGCAGACCGGCGACCTGCTGGCCAGCCCTGACGCTGTACGCCAAG
CGCGATATGCCGAGCGCATGAAGGCCAAAGGGATGCGTCAGCGCAAGTTCTGGCTGA
CCGACGACGAATACGAGGCGCTGCGCGAGTGCCTGGAAGAACTCAGAGCGGCGCAGG
GCGGGGGTAGTGACCCCGCCAGCGCCTAACCACCAACTGCCTGCAAAGGAGGCAATC
AATGGCTACCCATAAGCCTATCAATATTCTGGAGGCGTTCGCAGCAGCGCCGCCACCG
CTGGACTACGTTTTGCCCAACATGGTGGCCGGTACGGTCGGGGCGCTGGTGTCGCCC
GGTGGTGCCGGTAAATCCATGCTGGCCCTGCAACTGGCCGCACAGATTGCAGGCGGG
CCGGATCTGCTGGAGGTGGGCGAACTGCCCCACCGGCCCGGTGATCTACCTGCCCGCC
GAAGACCCGCCCACCGCCATTCATCACCGCCTGCACGCCCTTGGGGCGCACCTCAGC
GCCGAGGAACGGCAAGCCGTGGCTGACGGCCTGCTGATCCAGCCGCTGATCGGCAGC
CTGCCCAACATCATGGCCCCGGAGTGGTTCGACGGCCTCAAGCGCGCCGCCGAGGGC
CGCCGCCTGATGGTGCTGGACACGCTGCGCCGGTTCCACATCGAGGAAGAAAACGCC
AGCGGCCCCATGGCCCAGGTCATCGGTCGCATGGAGGCCATCGCCGCCGATACCGGG
TGCTCTATCGTGTTCCTGCACCATGCCAGCAAGGGCGCGGCCATGATGGGCGCAGGC
GACCAGCAGCAGGCCAGCCGGGGCAGCTCGGTACTGGTCGATAACATCCGCTGGCAG
TCCTACCTGTCGAGCATGACCAGCGCCGAGGCCGAGGAATGGGGTGTGGACGACGAC
CAGCGCCGGTTCTTCGTCCGCTTCGGTGTGAGCAAGGCCAACTATGGCGCACCGTTCG
CTGATCGGTGGTTCAGGCGGCATGACGGCGGGGTGCTCAAGCCCGCCGTGCTGGAGA
GGCAGCGCAAGAGCAAGGGGGTGCCCCGTGGTGAAGCCTAAGAACAAGCACAGCCTC
AGCCACGTCCGGCACGACCCGGCGCACTGTCTGGCCCCCGGCCTGTTCCGTGCCCTC
AAGCGGGGCGAGCGCAAGCGCAGCAAGCTGGACGTGACGTATGACTACGGCGACGGC
AAGCGGATCGAGTTCAGCGGCCCGGAGCCGCTGGGCGCTGATGATCTGCGCATCCTG
CAAGGGCTGGTGGCCATGGCTGGGCCTAATGGCCTAGTGCTTGGCCCGGAACCCAAG
ACCGAAGGCGGACGGCAGCTCCGGCTGTTCCTGGAACCCAAGTGGGAGGCCGTCACC
GCTGATGCCATGGTGGTCAAAGGTAGCTATCGGGCGCTGGCAAAGGAAATCGGGGCA
GAGGTCGATAGTGGTGGGGCGCTCAAGCACATACAGGACTGCATCGAGCGCCTTTGGA
```

FIG. 11 (Continued)

```
AGGTATCCATCATCGCCCAGAATGGCCGCAAGCGGCAGGGGTTTCGGCTGCTGTCGG
AGTACGCCAGCGACGAGGCGGACGGGCGCCTGTACGTGGCCCTGAACCCCTTGATCG
CGCAGGCCGTCATGGGTGGCGGCCAGCATGTGCGCATCAGCATGGACGAGGTGCGG
GCGCTGGACAGCGAAACCGCCCGCCTGCTGCACCAGCGGCTGTGTGGCTGGATCGAC
CCCGGCAAAACCGGCAAGGCTTCCATAGATACCTTGTGCGGCTATGTCTGGCCGTCAG
AGGCCAGTGGTTCGACCATGCGCAAGCGCCGCCAGCGGGTGCGCGAGGCGTTGCCG
GAGCTGGTCGCGCTGGGCTGGACGGTAACCGAGTTCGCGGCGGGCAAGTACGACATC
ACCCGGCCCAAGGCGGCAGGCTGACCCCCCCCACTCTATTGTAAACAAGACATTTTTTA
TCTTTTATATTCAATGGCTTATTTTCCTGCTAATTGGTAATACCATGAAAAATACCATGCT
CAGAAAAGGCTTAACAATATTTTGAAAAATTGCCTACTGAGCGCTGCCGCACAGCTCCA
TAGGCCGCTTTCCTGGCTTTGCTTCCAGATGTATGCTCTCCTCCGGAGAGTACCGTGAC
TTTATTTTCGGCACAAATACAGGGGTCGATGGATAAATACGGCGATAGTTTCCTGACGG
ATGATCCGTATGTACCGGCGGAAGACAAGCTGCAAACCTGTCAGATGGAGATTGATTTA
ATGGCGGATGTGCTGAGAGCACCGCCCCGTGAATCCGCAGAACTGATCCGCTATGTGT
TTGCGGATGATTGGCCGGAATAAATAAAGCCGGGCTTAATACAGATTAAGCCCGTATAG
GGTATTATTACTGAATACCAAACAGCTTACGGAGGACGGAAGTGTTACCCATTGAGACAA
CCAGACTGCCTTCTGATTATTAATATTTTTCACTATTAATCAGAAGGAATAACCATGAATT
TTACCCGGATTGACCTGAATACCTGGAATCGCAGGGAACACTTTGCCCTTTATCGTCAG
CAGATTAAATGCGGATTCAGCCTGACCACCAAACTCGATATTACCGCTTTGCGTACCGC
ACTGGCGGAGACAGGTTATAAGTTTTATCCGCTGATGATTTACCTGATCTCCCGGGCTG
TTAATCAGTTTCCGGAGTTCCGGATGGCACTGAAAGACAATGAACTTATTTACTGGGAC
CAGTCAGACCCGGTCTTTACTGTCTTTCATAAAGAAACCGAAACATTCTCTGCACTGTCC
TGCCGTTATTTTCCGGATCTCAGTGAGTTTATGGCAGGTTATAATGCGGTAACGGCAGA
ATATCAGCATGATACCAGATTGTTTCCGCAGGGAAATTTACCGGAGAATCACCTGAATAT
ATCATCATTACCGTGGGTGAGTTTTGACGGGATTTAACCTGAACATCACCGGAAATGAT
GATTATTTTGCCCCGGTTTTTACGATGGCAAAGTTTCAGCAGGAAGGTGACCGCGTATT
ATTACCTGTTTCTGTACAGGTTCATCATGCAGTCTGTGATGGCTTTCATGCAGCACGGTT
TATTAATACACTTCAGCTGATGTGTGATAACATACTGAAATAAATTAATTAATTCTGTATTT
AAGCCACCGTATCCGGCAGGAATGGTGGCTTTTTTTTTATATTTTAACCGTAATCTGTAA
TTTCGTTTCAGACTGGTTCAGGATCACTGTACGATAATGCCCCCGCAGTTTGGTAATAC
CCTTAATAAAAAGAAACAGCAAAGACTGACAGCAATAATAATAAAGTAAGCAGTAACAA
TAATATTAACAACACCAGATGCAGTTATAATAATAGTATTTAAGACACCAGAAAGACTGC
TGCGACAGTCATTTTGAACAACACCAAAATGCCGTAAAGGCAGTAGTAACAACACCAGT
GAAAACATCACGATAGCATAGTGATATGCCTGAGTGTGTGTAATTAAACAATAAATAAAC
CGCCATATATAACAGAAGATAGTATTCTGAATGGCATGCTTTTCTGTTCAGTATAAACAT
ATCATCCCGGTTGGTATAAGGATGATATATAATAAGTTAAGCTGAACACATATTTATTTTG
GTTTTATTTTACAAATAAAGTAAGACGATCCGTTAAGTCAAAGCGGGGTATATTTATTATA
CCCTGCTTTTTTATTTGTCCGCCGGGCGCGGATAATGGATCAGATTATGCAGTGTCACA
ATGGCCTTACCGGGATTGGCGTAAGCGTGCGGGATATCCGCATGGAAGCGCAGGGATT
CCCCGGCAGAAACGGTGTGCCACTCATCCCCCAGCCGCAGTTGTAATGCGCCTTCCAG
TACAATGACATGTTCTCTGGTTCTGAAATCCATCCCTGTCGGTGTTGCTTATGCAGTCTG
GTCGGGACTCGGCGTCGTCATAATTACAGCCATTGCCTGGTTGCTTCATGGGCAAAAG
CTTTATGCTTGTAAACCGTTTTGTGAAAAAATTTTTAAAATAAAAAAGGGGACCTCTAGG
GTCCCCAATTAATTAGTAATATAATCTATTAAAGGTCATTCAAAAGGTCATCCACCGGAT
CCGGGCCCCCCCTCGAGGTCGACGGTATCGATAAGCTTGATATCGAATTCCCATATTGT
GCATCGAATCCCTGCAAAATTGTCTGAGCGATTAATTGTTCTAATTTTACCGCCATGCTC
ACCCCCCGCCATACGGAACAGAGCCTGCATCAGCAGGCTCCAGATAAAACATAAACTC
ATTAATCAGTGGCTTAGAACTGCTGCTCTTCCGTCGAGCCAGTCAGTGCAGTGACTGAT
GACTCGCCGCCCTGAATGATATTGGTGACTTTATCAAAATAGCCCGTGCCCACTTCTTG
TTGATGGGAAGCAAAGGTGTAGCCGCGTTCAACGGAGGCAAATTCTGGCTGCTGCACT
TTCTCAACATAGTGCTTCATGCCCTCGCCTTGCGCGTAAGCATGGGCCAAGTCGAACAT
GTTGAACCACATACTGTGGATGCCCGCCAAGGTAATAAATTGATATTTGTAGCCCATCG
CGGAGAGGTCATCTTGGAAGCTGGCGATCTGCTGGTCAGTCAGGTTCTTTTTCCAGTTA
AATGATGGCGAACAGTTATAAGCCAATAATTTACCGGGGAATTTAGCGTGAACCGCATC
TGCAAAGCGTTTAGCCAGCGCCAGATCTGGCGTCGAGGTTTCACACCACACCAAGTCG
GCGTAAGGGCATAGGCCAGACCACGGCTGATGGCTTGCTCAATGCCCGCGTGAGTG
CGGAAGAAGCCCTCAGCAGTACGATCACCAGCAATAAATTCGCTGTCATAAGGGTCGC
AATCAGAGGTCAGCAAATCCGCAGCATCAGCATCAGTGCGCGCAATCAGCAGTGTTGG
CACGCCAAGAACGTCAGCGGCTAAGCGGGCAGCAACCAGCTTCTGAATCGCTTCTTGT
GTTGGCACCAAAACTTTGCCGCCCATATGGCCGCATTTCTTCACCGCCGCCAATTGATC
TTCAAAGTGAACGCCCGCAGCACCGGCTTCAATCATGGCTTTCATCAATTCAAACGCAT
TCAATACGCCGCCAAAACCCGCTTCGGCATCCGCCACAATCGGCAGGAAATAGTCGGT
ATAGCCTTTGCTGCCCGGCTCAATATTATTCGACCACTGAATCTGATCTGCACGGCGGA
AGCTGTTATTAATACGCTTAACCACGGCCGGAACAGAGTCGACCGGGTAAAGAGATTGA
TCGGGATACATGCTGGAGGCGGTATTGGCATCGGCGGCGACCTGCCAACCCGACAGA
TAAATCGCTTCAACACCGGCCTTTGCCTGTTGCAATGCCTGACCGCCTGTTAGCGCCCC
CAGACAGTTGATGTAGCCTTTACGCGATTCGCCGTGCAGCAACTCCCACAATCTTTTCG
CGCCGTGCTGTGCCAGCGTACATTCTGGGTTAACGGAACCGCGCAGTTTGATCACTTC
TTCGGCGCTATAGGGGCGGGTGATGCCCTTCCAGCGCGGTGATTTCCATTCCTGTTCC
AACTGCTGAATTTGTTGAGTACGAGAGGTTGTCATGGCGATATTCCTTATTACTTATTTTT
GTAGGGTTAAATAACTGGCCTAGGCGAGTAATGCGTAGCCCGGCAACGTCAGAAAGTC
GATAAGCTCGTCTTGTGTTGTAATCCGCTCCATCAGACGTGCGGCTTCTTCAAACCGCC
CGCCATCAAAACGCTCTGCGCCAAGTTCAAGTTTCACGACCTGCATTTCTTCACTCAAC
ATGTTACGGAACAGCTCTTTGGTCACCGTCTGACCATTGCTCAGGCTTTTCTGGTGATG
```

FIG. 11 (Continued)

| | | | |
|---|---|---|---|
| | | | TATCCATTGCCAGATAGAAGTACGGGAAATCTCAGCCGTCGCGGCATCTTCCATCAGGC
CATAAATCGGTACACAGCCATTGCCCGATATCCATGCTTCGATGTATTGCACTGCGACC
CGGATATTGGCCCGCATCCCCTCTTCGGTGCGCTCACCCGTGCAAGGCTCTAGCAACT
CAGCGGCAGTGATTGGTTTATCTTGCGCGCGACTCACCTCTAATTGGTTTGGACGATCG
CCCAGTACTTTGTTGAAAACGTCCATCACGGTATCGGCCAGACCGGGGTGTGCGACCC
ATGTACCATCGTGGCCGTTGCTGGCTTCCAGCTCTTTGTCAGCGCGAACTTTATCTAAG
ACCAGCGCATTTTTTTCTGGATCTTTGTTCGGGATAAAGGCCGCCATGCCGCCCATCGC
CAAGGCACCGCGCTTATGGCAGGTTTTGATCAGTAAACGAGAGTAGGCACTCAGGAAG
GGTTTCGTCATCGTGACCGACTGGCGATCGGGCAGCACGCGATCGCTGTGATTTTTCA
GCGTTTTGATATAGCTGAAAATGTAGTCCCAACGGCCACAATTCAGGGCAACAATGTGA
TGGCGCAGATGGTAGAGGATCTCATCCATCTGGAATACCGCAGGCAATGTCTCGATTAA
TACTGTGGCCTTAATGGTGCCTTGCGGCAGATCGAAACGCTGCTCGGTAAAGCTGAAA
ACATCACTCCACCAAGCCGCTTCCTGATAAGACTGCATCTTGGGTAGATAGAAATAGGG
GCCGCTGCCATTGGCAAGCAGTAACTTATAGTTATGGTAGAAATACAACGCGAAATCGA
ATAAGCCACCGGGGATATCCTCCCCCTGCCACTTCACGTGTTTTTCTGGCAAGTGCAGA
CCACGCACCCGAGCAATCAACACCGCTGGATTGGGTTTTAGCTGATAAATCTTACCGGA
TTCATTCGCGTAAGAGATTGTGCCTTTGACCGCATCGTGCAAATTAATCTGACCTTCGAT
AACCTTATCCCAACTGGGTGCCAGCGAATCCTCAAAGTCAGCCATAAAGACTTTCACAT
TCGCATTGAGGGCATTAATCACCATTTTGCGCTCAACCGGCCCGGTGATCTCGACGCG
ACGATCACGTAAATCCGCAGGAATACTTTGAATTTTCCAGTCACCATTACGAATGGAATT
GGTTTCCGAAATGAAATCAGGCAATGCGCCTTGGTCAATGGCCTGTTGCCAAGCGGCC
CGTGCAGCAAGGAGTTTGCTACGCGGCTCTGCAAATTTCGCCACCAATTCTGCCAAAAA
TTCGATGGCCTCATCGGGCAAAACCTGCCGCTCAGCAGCATTAAAATGCTGGGTGAAA
ACTAACTCCGTGCCGACTATCTGTTGTGTCATTCCCTTCCCCTTCCCCTTCCCCATCTCTCGAC
GATCATTTTTCAGTTTCCTTTTGTTATTCCCCAAAAGTGCGGTGCAAATTTGGGGAGTTT
TAGTTAATTAAAAAAATTATTTTTTACGAGCTTCGATTACTGCAGCAGCAACACTTGTTGG
CGCTTCAGCATATTTTAACGGTTCCATTGAGTATGATGCTCTAGAGCGGCCGCCACCGC
GGTGG |
| 13 | 13 | pJFF224
(icl ms S.t.) | GATCCCACCGCGGTGGCGGCCGCTCTAGAGGGTTCCCTCATCCGGCACCACGTCATG
CCGGATGGCGCGTTCGCTTATCCGGCCTACGCTATCTGTAGGCCCGGTAAGCGCAGC
GCCACCGGGCATCAATCAAAACTGCGCTTCTTCGGTGGAACCCGTTAACGCGGTAACG
GATGACGCGCCGCCCTGAATAATGGTGGTGACTTTGTCGAAGTAACCAGTACCCACTTC
CTGCTGGTGGGAAACAAAGGTGTAGCCATCTTTCGCCGCGGCGAACTCGGGTTGTTGA
ACCTTCTCAACATAGTGCTTCATGCCCTCGCCCTGCGCGTATGCATGCGCCAGGTCGA
ACATGTTGAACCACATGCTGTGGATGCCCGCCAGGGTAATAAACTGGTATTTGTAACCC
ATGTCCGACAACTGCTGCTGGAAGCTGGCAATGGTCTTGTCGTCCAGATTCTTCTGCCA
GTTGAAGGATGGTGAACAGTTATAGGCCAGCAGTTTGCCCGGATACTTCGCGTGGATA
GCATCGGCAAAACGACGCGCCAGTTCGAGATCCGGCGTAGAGGTTTCGCACCATACCA
GATCGGCATACGGGGCATACGCCAGACCGCGGCTGATCGCCTGCTCAATGCCCGCAT
GGGTGCGGTAGAAACCTTCGCTGGTGCGTTCGCCGGTAATAAAACCGCTGTCATAGGG
ATCGCAGTCGGAGGTGATCAGATCTGCCGCATCCGCATCGGTACGGCAATCACCAGC
GTCGGGACGCCCATCACATCAGCGGCCAGACGCAGCAACCAGTTTCTGAATCGCCT
CCTGCGTGGGGACCAGCACCTTGCCGCCCATATGGCCGCATTTCTTCACCGACGCCAG
CTGATCTTCGAAGTGAACGGCCGCTGCACCGGCTTCAATCATCGATTTCATCAGTTCGA
AGGCATTCAGAACGCCGCCAAAACCGGCTTCCGCATCAGCAACGATCGGCAGGAAGTA
ATCCACATAGCGCGGATCGTTGGGTTCAATACCGGATGCCCACTGGATCTGATCTGCA
CGACGAAAAGTGTTGTTGATCCGATCCACTACCGCCGGAACAGAGTTTGCCGGGTACA
ACGATTGATCCGGATACATGCTGGATGCCAGGTTGGCATCTGCCGCCACCTGCCAGCC
TGAAAGATAAATCGCCTCAATACCGGCTTTCGCCTGCTGCAACGCCTGACCGCCGGTC
AGCGCGCCAAGGCTGTTGATATAGCCTTTTTTCGCTTCACCGTGCAACAGCCGCCACAT
TTTCGCGGCGCCGAGCTGCGCCAGCGTGCATTCCGGGTTAACCGAGCCGCGTAATTTC
ACCACCTCCTCCGCGCTGTACGGGCGGGTGATGCCTTCCCAGCGCGGTTGTGTCCACT
CTTTCTGTAATTCTTCGATTTGTTGAGTACGGGTTTTCATGTGCAGATGCTCCATATTGTT
ATGTGGTGAATTAAGCCAGTAAGCGATAGCCCCGGCAGGGTGAGGAAGTCGATTAAGTC
ATCTGAGGTGGTGATTTGCTCCATCAGACGTGCGGCATCGTCGAAGCGCCCGCTGCTG
TAGCGGTGCTCGCCCAGTTCGTCCTGGATTACCCGCATCTCTTCCGCCAACATTTCGCG
GAAAAGCGTTTTCGTTACGGGTTTTCCATTGCTCAGTGTTTTCTCATGGTGAATCCACTG
CCAGATAGAGGTTCGTGAGATTTCCGCCGTCGCGGCATCCTCCATCAGACCGTAAATC
GGTACACAGCCATTGCCGGAGATCCACGCTTCAATGTACTGCACTGCCACGCGAATATT
GGCGCGCATTCCCGCTTCTGTGCGTTCGCCTTCACATGGCTCCAGTAACTGTTCAGCG
GTAATCGGCGCATCTTCATCACGGGTAATGAACAGCCTGATTTTTGTGCTCGCCCAGTAC
CTCGTTAAAGACGGCCATTGCGGTATCCGCCAACCCAGGATGCGCAATCCACGTGCCG
TCGTGGCCGTTGTTCGCTTCCAGCGCTTTATCCGCTTTCACTTTGGCAAGGACCTGATT
GTTGCGTTCAACGTCTTTGCTCGGGATAAACGCCGCCATACCGCCCATCGCGAACGCG
CCGCGCTTGTGGCAGGTTTTGATCAGCAGGCGCGAGTAGGCGCTCAGAAACGGTTTGT
CCATCGTTACCACCTGCCTGTCCGGCAAAACGCGATCCGGGTGATTTTTCAACGTTTTG
ATATAGCTGAAAATATAATCCCAGCGACCACAGTTGAGACCGACGATATGATCACGCAG
CGCATGAAGAATCTCATCCATCTGGAAAACAGCCGGCAGCGTTTCAATCAACAGGGTC
GCTTTGATCGTACCGCGCGGCAGGTTAAAGCGGTCTTCGGCGTAGCTGAACACTTCGC
TCCACCAGGCTGCCTCCTGCCAGGCTTGCGTTTTCGGCAGGTAAAAATACGGGCCGCT
ACCTTTAGCGAGCAGCGCTTTATAGTTGTGGAAAAAGTACAGAGCAAAATCAAACAGGC
TGCCGGGAATGGCTTCCCCCCCGCCAGGTAACATGTTTTTCTGGCAGATGTAGACCACG
TACACGACAAATCAATACGGCCGGATCGGGCTTGAGCTGATAGATTTTCCGGCTTCGT
TGGTATAGCTAATGGTGCCGTTCACCGCATCACGCAGGTTGATTTGACCATCAATAACT |

FIG. 11 (Continued)

```
TTATTCCAGTCCGGCGCCAGCGAGTCTTCAAAATCCGCCATAAACACTTTCACATTTGC
GTTCAGGGCATTAATCACCATTTTACGTTCAACCGGCCCGGTAATTTCTACTCGGCGAT
CCTGTAAATCCGCCGGAATACCACGAATCTGCCAATTACTTTCTCTAATGGAAGTGGTTT
CCGAAATAAAATCAGGCAACTTACCGTTATCAATATCCTGCTGTTGCTGGATACGGGCA
GCCAGGAGTTTATTGCGTTTTGGCGTAAAACGGGTGACTAACTCCGTCAAAAACTCGAC
TGCTTCAGCCGGTCAGGACTTGCTTTTCCAGCTCGCCTTGCGGGCCTGGTAAAGGTTAATT
CATCAGTTGTGGTTGCCTGTGGATTCATCATGCAGCTCCTCGTTGTTGATCCAGATACA
TCCCCAATGCGAACGAAGGATCACTGTGCACTTTTCGTTCAACACAACTAAGACTACTC
AATTAAATTTCAAAATCAAAAACAATTTCCATTTTTAATTTAATTATGCATTAACCTATTGA
TAACAATATAAATTAAATTTAATTACATGATGAGGTGCGTTTCGGAAAGACGTCAGGCCT
CTCGAGGGGGGGCCCGGATCCCCAGTAGATTTACGTTTAAACATTTTTATTTCCTTTTTA
ATTTAATTTAATTAACAGTTGGTGCTATGACACTTTACCTCATAGCTGGCATAATTCGCAA
TACTCTGGGTCTTCGAGAGGTATCCAACCTGAGTTGAAATACTTTACCATCGATTTAGCA
GTTGTATCAGTTATATTTATATTACCTTTAACTCTTCGCCATCCAGGAGTTTTACCGTACA
GATTAGAGGATAATAATAACACATAATTCTCGTAAGCAATATGAGATAATTTCCAAGACT
CTATATTAGCTCGTGATGTTTTCCAAGGTCTAAAATCGTCACGGTTCATATAATTAGCCA
ATCTCATATGCTCTCTAACTTCCGATGATAAGCTGTCAAACATGAGAATTAACGATCTGA
TAGAGAAGGGTTTGCTCGGGTCGGTGGCTCTGGTAACGACCAGTATCCCGATCCCGGC
TGGCCGTCCTGGCCGCCACATGAGGCATGTTCCGCGTCCTTGCAATACTGTGTTTACAT
ACAGTCTATCGCTTAGCGGAAAGTTCTTTTACCCTCAGCCGAAATGCCTGCCGTTGCTA
GACATTGCCAGCCAGTGCCCGTCACTCCCGTACTAACTGTCACGAACCCCTGCAATAAC
TGTCACGCCCCCCTGCAATAACTGTCACGAACCCCTGCAATAACTGTCACGCCCCCAAA
CCTGCAAACCCAGCAGGGGCGGGGGCTGGCGGGGTGTTGGAAAAATCCATCCATGAT
TATCTAAGAATAATCCACTAGGCGCGGTTATCAGCGCCCTTGTGGGGCGCTGCTGCCC
TTGCCCAATATGCCCGGCCAGAGGCCGGATAGCTGGTCTATTCGCTGCGCTAGGCTAC
ACACCGCCCCACCGCTGCGCGGCAGGGGGAAAGGCGGGCAAAGCCCGCTAAACCCC
ACACCAAACCCCGCAGAAATACGCTGGGAGCGCTTTTAGCCGCTTTAGCGGCCTTTCC
CCCTACCCGAAGGGTGGGGGCGCGTGTGCAGCCCCGCAGGGCCTGTCTCGGTCGATC
ATTCAGCCCGGCTCATCCTTCTGGCGTGGCGGCAGACCGAACAAGGCGCGGTCGTGG
TCGCGTTCAAGGTACGCATCCATTGCCGCCCATGAGCCGATCCTCCGGCCACTCGCTGC
TGTTCACCTTGGCCAAAATCATGGCCCCCACCAGCACCTTGCGCCTTGTTTCGTTCTTG
CGCTATTGCTGCTGTTCCCTTGCCCGCACCCGCTGAATTTCGGCATTGATTCGCGCTCG
TTGTTCTTCGAGCTTGGCCAGCCGATCCGCCGCCTTGTTGCTCCCCTTAACCATCTTGA
CACCCCATTGTTAATGTGCTGTCTCGTAGGCTATCATGGAGGCACAGCGGCGGCAATC
CCGACCCTACTTTGTAGGGGAGGGCCATTGCATGGAGCCGAAAAGCAAAAGCAACAGC
GAGGCAGCATGGCGATTTATCACCTTACGGCGAAAACCGGCAGCAGGTCGGGCGGCC
AATCGGCCAGGGCCAAGGCCGACTACATCCAGCGCGAAGGCAAGTATGCCCGCGACA
TGGATGAAGTCTTGCACGCCCGAATCCGGGCACATGCCGGAGTTCGTCGAGCGGCCCG
CCGACTACTGGGATGCTGCCGACCTGTATGAACGCGCCAATGGGCGGCTGTTCAAGGA
GGTCGAATTTGCCCTGCCGGTCGAGCTGACCCTCGACCAGCAGAAGGCGCTGGCGTC
CGAGTTCGCCCAGCACCTGACCGGTGCCGAGCGCCTGCCGTATACGCTGGCCATCCA
TGCCGGTGGCGGCGAGAACCCGCACTGCCACCTGATGATCTCCGAGCGGATCAATGA
CGGCATCGAGCGGCCCGCCGCTCAGTGGTTCAAGCGGTACAACGGCAAGACCCCGGA
GAAGGGCGGGGCACAGAAGACCGAAGCGCTCAAGCCCAAGGCATGGCTTGAGCAGAC
CCGCGAGGCATGGGCCGACCATGCCAACCGGGCATTAGAGCGGGCTGGCCACGACG
CCCGCATTGACCACAGAACACTTGAGGCGCAGGGCATCGAGCGCCTGCCCGGTGTTC
ACCTGGGGCCGAACGTGGTGGAGATGGAAGGCCGGGGCATCCGCACCGACCGGGCA
GACGTGGCCCTGAACATCGACACCGCCAACGCCCAGATCATCGACTTACAGGAATACC
GGGAGGCAATAGACCATGAACGCAATCGACAGAGTGAAGAAATCCAGAGGCATCAACG
AGTTAGCGGAGCAGATCGAACCGCTGGCCCAGAGCATGGCGACACTGGCCGACGAAG
CCCGGCAGGTCATGAGCCAGACCCAGCAGGCCAGCAGGGCGCAGGCGGCGGAGTGG
CTGAAAGCCCAGCGCCAGACAGGGGCGGCATGGGTGGAGCTGGCCAAAGAGTTGCGG
GAGGTAGCCGCCGAGGTGAGCAGCGCCGCGCAGAGCGCCCGGAGCGCGTCGCGGG
GGTGCACTGGAAGCTATGGCTAACCGTGATGCTGGCTTCCATGATGCCTACGGTGGT
GCTGCTGATCGCATCGTTGCTCTTGCTCGACCTGACGCCACTGACAACCGAGGACGGC
TCGATCTGGCTGCGCTTGGTGGCCCGATGAAGAACGACAGGACTTTGCAGGCCATAGG
CCGACAGCTCAAGGCCATGGGCTGTGAGCGCTTCGATATCGGCGTCAGGGACGCCAC
CACCGGCCAGATGATGAACCGGGAATGGTCAGCCGCCGAAGTGCTCCAGAACACGCC
ATGGCTCAAGCGGATGAATGCCCAGGGCAATGACGTGTATATCAGGCCCGCCGAGCAG
GAGCGGCATGGTCTGGTGCTGGTGGACGACCTCAGCGAGTTTGACCTGGATGACATGA
AAGCCGAGGGCCGGGAGCCTGCCCTGGTAGTGGAAACCAGCCCGAAGAACTATCAGG
CATGGGTCAAGGTGGCCGACGCCGCAGGCGGTGAACTTCGGGGGCAGATTGCCCGGA
CGCTGGCCAGCGAGTACGACGCCGACCCGGCCAGCGCCGACAGCCGCCACTATGGC
CGCTTGGCGGGCTTCACCAACCGCAAGGACAAGCACACCACCCGCGCCGGTTATCAG
CCGTGGGTGCTGCTGCGTGAATCCAAGGGCAAGACCGCCACCGCTGGCCCGGCGCTG
GTGCAGCAGGCTGGCCAGCAGATCGAGCAGGCCCAGCGGCAGCAGGAGAAGGCCCG
CAGGCTGGCCAGCCTCGAACTGCCCGAGCGGCAGCTTAGCCGCCACCGGCGCACGG
CGCTGGACGAGTACCGCAGCGAGATGGCCGGGCTGGTCAAGCGCTTCGGTGATGACC
TCAGCAAGTGCGACTTTATCGCCGCGCAGAAGCTGGCCAGCCGGGGCCGCAGTGCCG
AGGAAATCGGCAAGGCCATGGCCGAGGCCAGCCCAGCGCTGGCAGAGCGCAAGCCC
GGCCACGAAGCGGATTACATCGAGCGCACCGTCAGCAAGGTCATGGGTCTGCCCAGC
GTCCAGCTTGCGCGGGCCGAGCTGCACGGGCACCGGCACCCCGCCAGCGAGGCAT
GGACAGGGGCGGGCCAGATTTCAGCATGTAGTGCTTGCGTTGGTACTCACGCCTGTTA
TACTATGAGTACTCACGCACAGAAGGGGGTTTTATGGAATACGAAAAAAGCGCTTCAGG
```

FIG. 11 (Continued)

```
GTCGGTCTACCTGATCAAAAGTGACAAGGGCTATTGGTTGCCCGGTGGCTTTGGTTATA
CGTCAAACAAGGCCGAGGCTGGCCGCTTTTCAGTCGCTGATATGGCCAGCCTTAACCT
TGACGGCTGCACCTTGTCCTTGTTCCGCGAAGACAAGCCTTTCGGCCCCGGCAAGTTT
CTCGGTGACTGATATGAAAGACCAAAAGGACAAGCAGACCGGCGACCTGCTGGCCAGC
CCTGACGCTGTACGCCAAGCGCGATATGCCGAGCGCATGAAGGCCAAAGGGATGCGT
CAGCGCAAGTTCTGGCTGACCGACGACGAATACGAGGCGCTGCGCGAGTGCCTGGAA
GAACTCAGAGCGGCGCAGGGCGGGGGTAGTGACCCCGCCAGCGCCTAACCACCAACT
GCCTGCAAAGGAGGCAATCAATGGCTACCCATAAGCCTATCAATATTCTGGAGGCGTTC
GCAGCAGCGCCGCCACCGCTGGACTACGTTTTGCCCAACATGGTGGCCGGTACGGTC
GGGGCGCTGGTGTCGCCCGGTGGTGCCGGTAAATCCATGCTGGCCCTGCAACTGGCC
GCACAGATTGCAGGCGGGCCGGATCTGCTGGAGGTGGGCGAACTGCCCACCGGCCC
GGTGATCTACCTGCCCGCCGAAGACCCGCCCACCGCCATTCATCACCGCCTGCACGCC
CTTGGGGCGCACCTCAGCGCCGAGGAACGGCAAGCCGTGGCTGACGGCCTGCTGATC
CAGCCGCTGATCGGCAGCCTGCCCAACATCATGGCCCCGGAGTGGTTCGACGGCCTC
AAGCGCGCCGCCGAGGGCCGCCGCCTGATGGTGCTGGACACGCTGCGCCGGTTCCA
CATCGAGGAAGAAAACGCCAGCGGCCCCATGGCCCAGGTCATCGGTCGCATGGAGGC
CATCGCCGCCGATACCGGGTGCTCTATCGTGTTCCTGCACCATGCCAGCAAGGGCGCG
GCCATGATGGGCGCAGGCGACCAGCAGCAGGCCAGCCGGGGCAGCTCGGTACTGGT
CGATAACATCCGCTGGCAGTCCTACCTGTCGAGCATGACCAGCGCCGAGGCCGAGGA
ATGGGGTGTGGACGACGACCAGCGCCGGTTCTTCGTCCGCTTCGGTGTGAGCAAGGC
CAACTATGGCGCACCGTTCGCTGATCGGTGGTTCAGGCGGCATGACGGCGGGGTGCT
CAAGCCCGCCGTGCTGGAGAGGCAGCGCAAGAGCAAGGGGGTGCCCCGTGGTGAAG
CCTAAGAACAAGCACAGCCTCAGCCACGTCCGGCACGACCCGGCCGCACTGTCTGGCC
CCCGGCCTGTTCCGTGCCCTCAAGCGGGGCGAGCGCAAGCGCAGCAAGCTGGACGTG
ACGTATGACTACGGCGACGGCAAGCGGATCGAGTTCAGCGGCCCGGAGCCGCTGGGC
GCTGATGATCTGCGCATCCTGCAAGGGCTGGTGGCCATGGCTGGGCCTAATGGCCTAG
TGCTTGGCCCGGAACCCAAGACCGAAGGCGGACGGCAGCTCCGGCTGTTCCTGGAAC
CCAAGTGGGAGGCCGTCACCGCTGATGCCATGGTGGTCAAAGGTAGCTATCGGGCGC
TGGCAAAGGAAATCGGGGCAGAGGTCGATAGTGGTGGGGCGCTCAAGCACATACAGG
ACTGCATCGAGCGCCTTTGGAAGGTATCCATCATCGCCCAGAATGGCCGCAAGCGGCA
GGGGTTTCGGCTGCTGTCGGAGTACGCCAGCGACGAGGCGGACGGGCGCCTGTACGT
GGCCCTGAACCCCTTGATCGCGCAGGCCGTCATGGGTGGCGGCCAGCATGTGCGCAT
CAGCATGGACGAGGTGCGGGCGCTGGACAGCGAAACCGCCCGCCTGCTGCACCAGC
GGCTGTGTGGCTGGATCGACCCCGGCAAAACCGGCAAGGCTTCCATAGATACCTTGTG
CGGCTATGTCTGGCCGTCAGAGGCCAGTGGTTCGACCATGCGCAAGCGCCGCCAGCG
GGTGCGCGAGGCGTTGCCGGAGCTGGTCGCGCTGGGCTGGACGGTAACCGAGTTCG
CGGCGGGCAAGTACGACATCACCCGGCCCAAGGCGGCAGGCTGACCCCCCCCACTCT
ATTGTAAACAAGACATTTTTTATCTTTTATATTCAATGGCTTATTTTCCTGCTAATTGGTAA
TACCATGAAAAATACCATGCTCAGAAAAGGCTTAACAATATTTTGAAAAATTGCCTACTG
AGCGCTGCCGCACAGCTCCATAGGCCGCTTTCCTGGCTTTGCTTCCAGATGTATGCTCT
CCTCCGGAGAGTACCGTGACTTTATTTTCGGCACAAATACAGGGGTCGATGGATAAATA
CGGCGATAGTTTCCTGACGGATGATCCGTATGTACCGGCGGAAGACAAGCTGCAAACC
TGTCAGATGGAGATTGATTTAATGGCGGATGTGCTGAGAGCACCGCCCCGTGAATCCG
CAGAACTGATCCGCTATGTGTTTGCGGATGATTGGCCGGAATAAATAAAGCCGGGCTTA
ATACAGATTAAGCCCGTATAGGGTATTATTACTGAATACCAAACAGCTTACGGAGGACG
GAATGTTACCCATTGAGACAACCAGACTGCCTTCTGATTATTAATATTTTTCACTATTAAT
CAGAAGGAATAACCATGAATTTTACCCGGATTGACCTGAATACCTGGAATCGCAGGGAA
CACTTTGCCCTTTATCGTCAGCAGATTAAATGCGGATTCAGCCTGACCACCAAACTCGA
TATTACCGCTTTGCGTACCGCACTGGCGGAGACAGGTTATAAGTTTTATCCGCTGATGA
TTTACCTGATCTCCCGGGCTGTTAATCAGTTTCCGGAGTTCCGGATGGCACTGAAAGAC
AATGAACTTATTTACTGGGACCAGTCAGACCCGGTCTTTACTGTCTTTCATAAAGAAACC
GAAACATTCTCTGCACTGTCCTGCCGTTATTTTCCGGATCTCAGTGAGTTTATGGCAGG
TTATAATGCGGTAACGGCAGAATATCAGCATGATACCAGATTGTTTCCGCAGGGAAATT
TACCGGAGAATCACCTGAATATATCATCATTACCGTGGGTGAGTTTTGACGGGATTTAA
CCTGAACATCACCGGAAATGATGATTATTTTGCCCCGGTTTTTACGATGGCAAAGTTTCA
GCAGGAAGGTGACCGCGTATTATTACCTGTTTCTGTACAGGTTCATCATGCAGTCTGTG
ATGGCTTTCATGCAGCACGGTTTATTAATACACTTCAGCTGATGTGTGATAACATACTGA
AATAAAATTAATTAATTCTGTATTTAAGCCACCGTATCCGGCAGGAATGGTGGCTTTTTTTT
TATATTTTAACCGTAATCTGTAATTTCGTTTCAGACTGGTTCAGGATCACTGTACGATAAT
GCCCCCGCAGTTTGGTAATACCCTTAATAAAAAAGAAACAGCAAAGACTGACAGCAATA
ATAATAAAGTAAGCAGTAACAATAATATTAACAACACCAGATGCAGTTATAATAATAGTAT
TTAAGACACCAGAAAGACTGCTGCGACAGTCATTTTGAACAACACCAAAATGCCGTAAA
GGCAGTAGTAACAACACCAGTGAAAACATCACGATAGCATAGTGATATGCCTGAGTGTG
TGTAATTAAACAATAAATAAACCGCCATATATAACAGAAGATAGTATTCTGAATGGCATG
CTTTTCTGTTCAGTATAAACATATCATCCCGGTTGGTATAAGGATGATATATAATAAGTTA
AGCTGAACACATATTTATTTTGGTTTTATTTTACAAATAAAGTAAGACGATCCGTTAAGTC
AAAGCGGGGTATATTTATTATACCCTGCTTTTTTATTTGTCCGCCGGGCGCGGATAATG
GATCAGATTATGCAGTGTCACAATGGCCTTACCGGGATTGGCGTAAGCGTGCGGGATA
TCCGCATGGAAGCGCAGGGATTCCCCGGCAGAAACGGTGTGCCACTCATCCCCCAGC
CGCAGTTGTAATGCGCCTTCCAGTACAATGACATGTTCTCTGGTTCTGAAATCCATCCCT
GTCGGTGTTGCTTATGCAGTCTGGTCGGGACTCGGCGTCGTCATAATTACAGCCATTGC
CTGGTTGCTTCATGGGCAAAAGCTTTATGCTTGTAAACCGTTTTGTGAAAAAATTTTTAA
AATAAAAAAGGGGACCTCTAGGGTCCCCAATTAATTAGTAATATAATCTATTAAAGGTCA
TTCAAAAGGTCATCCACCG
```

FIG. 11 (Continued)

| 14 | 14 | pJFF224 (PpckA fdh C.b.) | CTAGTTCTAGAGCGGCCGCCACCGCGGTGGATCCCCAGTAGATTTACGTTTAAACATTT<br>TTATTTCCTTTTTAATTTAATTTAATTAACAGTTGGTGCTATGACACTTTACCTCATAGCTG<br>GCATAATTCGCAATACTCTGGGTCTTCGAGAGGTATCCAACCTGAGTTGAAATACTTTAC<br>CATCGATTTAGCAGTTGTATCAGTTATATTTATATTACCTTTAACTCTTCGCCATCCAGGA<br>GTTTTACCGTACAGATTAGAGGATAATAATAACACATAATTCTCGTAAGCAATATGAGAT<br>AATTTCCAAGACTCTATATTAGCTCGTGATGTTTTCCAAGGTCTAAAATCGTCACGGTTC<br>ATATAATTAGCCAATCTCATATGCTCTCTAACTTCCGATGATAAGCTGTCAAACATGAGA<br>ATTAACGATCTGATAGAGAAGGGTTTGCTCGGGTCGGTGGCTCTGGTAACGACCAGTAT<br>CCCGATCCCGGCTGGCCGTCCTGGCCGCCACATGAGGCATGTTCCGCGTCCTTGCAAT<br>ACTGTGTTTACATACAGTCTATCGCTTAGCGGAAAGTTCTTTTACCCTCAGCCGAAATGC<br>CTGCCGTTGCTAGACATTGCCAGCCAGTGCCCGTCACTCCCGTACTAACTGTCACGAA<br>CCCCTGCAATAACTGTCACGCCCCCTGCAATAACTGTCACGAACCCCTGCAATAACTG<br>TCACGCCCCCAAACCTGCAAACCCAGCAGGGGCGGGGGCTGGCGGGGTGTTGGAAAA<br>ATCCATCCATGATTATCTAAGAATAATCCACTAGGCGCGGTTATCAGCGCCCTTGTGGG<br>GCGCTGCTGCCCTTGCCCAATATGCCCGGCCAGAGGCCGGATAGCTGGTCTATTCGCT<br>GCGCTAGGCTACACACCGCCCCACCGCTGCGCGGCAGGGGGAAAGGCGGGCAAAGC<br>CCGCTAAACCCCACACCAAACCCCGCAGAAATACGCTGGGAGCGCTTTTAGCCGCTTT<br>AGCGGCCTTTCCCCCTACCCGAAGGGTGGGGGCCGCGTGTGCAGCCCCGCAGGGCCT<br>GTCTCGGTCGATCATTCAGCCCGGCTCATCCTTCTGGCGTGGCGGCAGACCGAACAAG<br>GCGCGGTCGTGGTCGCGTTCAAGGTACGCATCCATTGCCGCCATGAGCCGATCCTCCG<br>GCCACTCGCTGCTGTTCACCTTGGCCAAAATCATGGCCCCCACCAGCACCTTGCGCCT<br>TGTTTCGTTCTTGCGCTATTGCTGCTGTTCCCTTGCCCGCACCCGCTGAATTTCGGCAT<br>TGATTCGCGCTCGTTGTTCTTCGAGCTTGGCCAGCCGATCCGCCGCCTTGTTGCTCCC<br>CTTAACCATCTTGACACCCCATTGTTAATGTGCTGTCTCGTAGGCTATCATGGAGGCAC<br>AGCGGCGGCAATCCCGACCCTACTTTGTAGGGGAGGGCCATTGCATGGAGCCGAAAA<br>GCAAAAGCAACAGCGAGGCAGCATGGCGATTTATCACCTTACGGCGAAAACCGGCAGC<br>AGGTCGGGCGGCCAATCGGCCAGGGCCAAGGCCGACTACATCCAGCGCGAAGGCAAG<br>TATGCCCGCGACATGGATGAAGTCTTGCACGCCGAATCCGGGCACATGCCGGAGTTCG<br>TCGAGCGGCCCGCCGACTACTGGGATGCTGCCGACCTGTATGAACGCGCCAATGGGC<br>GGCTGTTCAAGGAGGTCGAATTTGCCCTGCCGGTCGAGCTGACCCTCGACCAGCAGAA<br>GGCGCTGGCGTCCGAGTTCGCCCAGCACCTGACCGGTGCCGAGCGCCTGCCGTATAC<br>GCTGGCCATCCATGCCGGTGGCGGCGAGAACCCGCACTGCCACCTGATGATCTCCGA<br>GCGGATCAATGACGGCATCGAGCGGCCCGCCGCTCAGTGGTTCAAGCGGTACAACGG<br>CAAGACCCCGGAGAAGGGCGGGGCACAGAAGACCGAAGCGCTCAAGCCCAAGGCATG<br>GCTTGAGCAGACCCGCGAGGCATGGGCCGACCATGCCAACCGGGCATTAGAGCGGGC<br>TGGCCACGACGCCCGCATTGACCACAGAACACTTGAGGCGCAGGGCATCGAGCGCCT<br>GCCCGGTGTTCACCTGGGGCCGAACGTGGTGGAGATGGAAGGCCGGGGCATCCGCAC<br>CGACCGGGCAGACGTGGCCCTGAACATCGACACCGCCAACGCCCAGATCATCGACTTA<br>CAGGAATACCGGGAGGCAATAGACCATGAACGCAATCGACAGAGTGAAGAAATCCAGA<br>GGCATCAACGAGTTAGCGGAGCAGATCGAACCGCTGGCCCAGAGCATGGCGACACTG<br>GCCGACGAAGCCCGGCAGGTCATGAGCCAGACCCAGCAGGCCAGCGAGGCGCAGGC<br>GGCGGAGTGGCTGAAAGCCCAGCGCCAGACAGGGGCGGCATGGGTGGAGCTGGCCA<br>AAGAGTTGCGGGAGGTAGCCGCCGAGGTGAGCAGCGCCGCGCAGAGCGCCCGGAGC<br>GCGTCGCGGGGGTGGCACTGGAAGCTATGGCTAACCGTGATGCTGGCTTCCATGATG<br>CCTACGGTGGTGCTGCTGATCGCATCGTTGCTCTTGCTCGACCTGACGCCACTGACAA<br>CCGAGGACGGCTCGATCTGGCTGCGCTTGGTGGCCCGATGAAGAACGACAGGACTTT<br>GCAGGCCATAGGCCGACAGCTCAAGGCCATGGGCTGTGAGCGCTTCGATATCGGCGT<br>CAGGGACGCCACCACCGGCCAGATGATGAACCGGGAATGGTCAGCCGCCGAAGTGCT<br>CCAGAACACGCCATGGCTCAAGCGGATGAATGCCCAGGGCAATGACGTGTATATCAGG<br>CCCGCCGAGCAGGAGCGGCATGGTCTGGTGCTGGTGGACGACCTCAGCGAGTTTGAC<br>CTGGATGACATGAAAGCCGAGGGCCGGGAGCCTGCCCTGGTAGTGGAAACCAGCCCG<br>AAGAACTATCAGGCATGGGTCAAGGTGGCCGACGCCGCAGGCGGTGAACTTCGGGGG<br>CAGATTGCCCGGACGCTGGCCAGCGAGTACGACGCCGACCCGGCCAGCGCCGACAG<br>CCGCCACTATGGCCGCTTGGCGGGCTTCACCAACCGCAAGGACAAGCACACCACCCG<br>CGCCGGTTATCAGCCGTGGGTGCTGCTGCGTGAATCCAAGGGCAAGACCGCCACCGC<br>TGGCCCGGCGCTGGTGCAGCAGGCTGGCCAGCAGATCGAGCAGGCCCAGCGGCAGC<br>AGGAGAAGGCCCGCAGGCTGGCCAGCCTCGAACTGCCCGAGCGGCAGCTTAGCCGCC<br>ACCGGCGCACGGCGCTGGACGAGTACCGCAGCGAGATGGCCGGGCTGGTCAAGCGC<br>TTCGGTGATGACCTCAGCAAGTGCGACTTTATCGCCGCGGCCAGAAGCTGGCCAGCCGGG<br>GCCGCAGTGCCGAGGAAATCGGCAAGGCCATGGCCGAGGCCAGCCCAGCGCTGGCA<br>GAGCGCAAGCCCGGCCACGAAGCGGATTACATCGAGCGCACCGTCAGCAAGGTCATG<br>GGTCTGCCCAGCGTCCAGCTTGCGCGGGCCGAGCTGGCACGGGCACCGGCACCCCG<br>CCAGCGAGGCATGGACAGGGGCGGGCCAGATTTCAGCATGTAGTGCTTGCGTTGGTA<br>CTCACGCCTGTTATACTATGAGTACTCACGCACAGAAGGGGGTTTTATGGAATACGAAA<br>AAAGCGCTTCAGGGTCGGTCTACCTGATCAAAAGTGACAAGGGCTATTGGTTGCCCGG<br>TGGCTTTGGTTATACGTCAAACAAGGCCGAGGCTGGCCGCTTTTCAGTCGCTGATATGG<br>CCAGCCTTAACCTTGACGGCTGCACCTTGTCCTTGTTCCGCGAAGACAAGCCTTTCGGC<br>CCCGGCAAGTTTCTCGGTGACTGATATGAAAGACCAAAAGGACAAGCAGACCGGCGAC<br>CTGCTGGCCAGCCCTGACGCTGTACGCCAAGCGCGATATGCCGAGCGCATGAAGGCC<br>AAAGGGATGCGTCAGCGCAAGTTCTGGCTGACCGACGACGAATACGAGGCGCTGCGC<br>GAGTGCCTGGAAGAACTCAGAGCGGCGCAGGGCGGGGGTAGTGACCCCGCCAGCGC<br>CTAACCACCAACTGCCTGCAAAGGAGGCAATCAATGGCTACCCATAAGCCTATCAATAT<br>TCTGGAGGCGTTCGCAGCAGCGCCGCCACCGCTGGACTACGTTTGCCCAACATGGTG<br>GCCGGTACGGTCGGGGCGCTGGTGTCGCCCGGTGGTGCCGGTAAATCCATGCTGGCC |

FIG. 11 (Continued)

```
CTGCAACTGGCCGCACAGATTGCAGGCGGGCCGGATCTGCTGGAGGTGGGCGAACTG
CCCACCGGCCCGGTGATCTACCTGCCCGCCGAAGACCCGCCCCACCGCCATTCATCAC
CGCCTGCACGCCCTTGGGGCGCACCTCAGCGCCGAGGAACGGCAAGCCGTGGCTGAC
GGCCTGCTGATCCAGCCGCTGATCGGCAGCCTGCCCAACATCATGGCCCCGGAGTGG
TTCGACGGCCTCAAGCGCGCCGCCGAGGGCCGCCCGCCTGATGGTGCTGGACACGCTG
CGCCGGTTCCACATCGAGGAAGAAAACGCCAGCGGCCCCATGGCCCAGGTCATCGGT
CGCATGGAGGCCATCGCCGCCGATACCGGGTGCTCTATCGTGTTCCTGCACCATGCCA
GCAAGGGCGCGGCCATGATGGGCGCAGGCGACCAGCAGCAGGCCAGCCGGGGCAGC
TCGGTACTGGTCGATAACATCCGCTGGCAGTCCTACCTGTCGAGCATGACCAGCGCCG
AGGCCGAGGAATGGGGTGTGGACGACGACCAGCGCCGGTTCTTCGTCCGCTTCGGTG
TGAGCAAGGCCAACTATGGCGCACCGTTCGCTGATCGGTGGTTCAGGCGGCATGACG
GCGGGGTGCTCAAGCCCGCCGTGCTGGAGAGGCAGCGCAAGAGCAAGGGGGTGCCC
CGTGGTGAAGCCTAAGAACAAGCACAGCCTCAGCCACGTCCGGCACGACCCGGCGCA
CTGTCTGGCCCCCGGCCTGTTCCGTGCCCTCAAGCGGGGCGAGCGCAAGCGCAGCAA
GCTGGACGTGACGTATGACTACGGCGACGGCAAGCGGATCGAGTTCAGCGGCCCGGA
GCCGCTGGGCGCTGATGATCTGCGCATCCTGCAAGGGCTGGTGGCCATGGCTGGGCC
TAATGGCCTAGTGCTTGGCCCGGAACCCAAGACCGAAGGCGGACGGCAGCTCCGGCT
GTTCCTGGAACCCAAGTGGGAGGCCGTCACCGCTGATGCCATGGTGGTCAAAGGTAGC
TATCGGGCGCTGGCAAAGGAAATCGGGGCAGAGGTCGATAGTGGTGGGGCGCTCAAG
CACATACAGGACTGCATCGAGCGCCTTTGGAAGGTATCCATCATCGCCCAGAATGGCC
GCAAGCGGCAGGGGTTTCGGCTGCTGTCGGAGTACGCCAGCGACGAGGCGGACGGG
CGCCTGTACGTGGCCCTGAACCCCTTGATCGCGCAGGCCGTCATGGGTGGCGGCCAG
CATGTGCGCATCAGCATGGACGAGGTGCGGGCGCTGGACAGCGAAACCGCCCGCCTG
CTGCACCAGCGGCTGTGTGGCTGGATCGACCCCGGCAAAACCGGCAAGGCTTCCATA
GATACCTTGTGCGGCTATGTCTGGCCGTCAGAGGCCCAGTGGTTCGACCATGCGCAAGC
GCCGCCAGCGGGTGCGCGAGGCGTTGCCGGAGCTGGTCGCGCTGGGCTGGACGGTA
ACCGAGTTCGCGGCGGGCAAGTACGACATCACCCGGCCCAAGGCGGCAGGCTGACCC
CCCCCACTCTATTGTAAACAAGACATTTTTTATCTTTTATATTCAATGGCTTATTTTCCTG
CTAATTGGTAATACCATGAAAAATACCATGCTCAGAAAAGGCTTAACAATATTTTGAAAA
ATTGCCTACTGAGCGCTGCCGCACAGCTCCATAGGCCGCTTTCCTGGCTTTGCTTCCA
GATGTATGCTCTCCTCCGGAGAGTACCGTGACTTTATTTTCGGCACAAATACAGGGGTC
GATGGATAAATACGGCGATAGTTTCCTGACGGATGATCCGTATGTACCGGCGGAAGAC
AAGCTGCAAACCTGTCAGATGGAGATTGATTTAATGGCGGATGTGCTGAGAGCACCGC
CCCGTGAATCCGCAGAACTGATCCGCTATGTGTTTGCGGATGATTGGCCGGAATAAATA
AAGCCGGGCTTAATACAGATTAAGCCCGTATAGGGTATTATTACTGAATACCAAACAGC
TTACGGAGGACGGAATGTTACCCATTGAGACAACCAGACTGCCTTCTGATTATTAATATT
TTTCACTATTAATCAGAAGGAATAACCATGAATTTTACCCGGATTGACCTGAATACCTGG
AATCGCAGGGAACACTTTGCCCTTTATCGTCAGCAGATTAAATGCGGATTCAGCCTGAC
CACCAAACTCGATATTACCGCTTTGCGTACCGCACTGGCGGAGACAGGTTATAAGTTTT
ATCCGCTGATGATTTACCTGATCTCCCGGGCTGTTAATCAGTTTCCGGAGTTCCGGATG
GCACTGAAAGACAATGAACTTATTTACTGGGACCAGTCAGACCCGGTCTTTACTGTCTTT
CATAAAGAAACCGAAACATTCTCTGCACTGTCCTGCCGTTATTTTCCGGATCTCAGTGA
GTTTATGGCAGGTTATAATGCGGTAACGGCAGAATATCAGCATGATACCAGATTGTTTC
CGCAGGGAAATTTACCGGAGAATCACCTGAATATATCATCATTACCGTGGGTGAGTTTT
GACGGGATTTAACCTGAACATCACCGGAAATGATGATTATTTTGCCCCGGTTTTTACGAT
GGCAAAGTTTCAGCAGGAAGGTGACCGCGTATTATTACCTGTTTCTGTACAGGTTCATC
ATGCAGTCTGTGATGGCTTTCATGCAGCACGGTTTATTAATACACTTCAGCTGATGTGTG
ATAACATACTGAAATAAATTAATTAATTCTGTATTTAAGCCACCGTATCCGGCAGGAATG
GTGGCTTTTTTTTTATATTTTAACCGTAATCTGTAATTTCGTTTCAGACTGGTTCAGGATC
ACTGTACGATAATGCCCCCGCAGTTTGGTAATACCCTTAATAAAAAAGAAACAGCAAAG
ACTGACAGCAATAATAATAAAGTAAGCAGTAACAATAATATTAACAACACCAGATGCAGT
TATAATAATAGTATTTAAGACACCAGAAAGACTGCTGCGACAGTCATTTTGAACAACACC
AAAATGCCGTAAAGGCAGTAGTAACAACACCAGTGAAAACATCACGATAGCATAGTGAT
ATGCCTGAGTGTGTGTAATTAAACAATAAATAAACCGCCATATATAACAGAAGATAGTAT
TCTGAATGGCATGCTTTTCTGTTCAGTATAAACATATCATCCCGGTTGGTATAAGGATGA
TATATAATAAGTTAAGCTGAACACATATTTATTTTGGTTTTATTTTACAAATAAAGTAAGAC
GATCCGTTAAGTCAAAGCGGGGTATATTTATTATACCCTGCTTTTTTATTTGTCCGCCGG
GCGCGGATAATGGATCAGATTATGCAGTGTCACAATGGCCTTACCGGGATTGGCGTAA
GCGTGCGGGATATCCGCATGGAAGCGCAGGGATTTCCCCGGCAGAAACGGTGTGCCAC
TCATCCCCCAGCCGCAGTTGTAATGCGCCTTCCAGTACAATGACATGTTCTCTGGTTCT
GAAATCCATCCCTGTCGGTGTTGCTTATGCAGTCTGGTCGGGACTCGGCGTCGTCATAA
TTACAGCCATTGCCTGGTTGCTTCATGGGCAAAAGCTTTATGCTTGTAAACCGTTTTGTG
AAAAAATTTTTAAAATAAAAAAGGGGACCTCTAGGGTCCCAATTAATTAGTAATATAATC
TATTAAAGGTCATTCAAAAGGTCATCCACCGGGGGCCCCCCCTCGAGAGGCCTGACGT
CGGGCCCGGTACCACGCGTTTATTTCTTATCGTGTTTACCGTAAGCTTTAGTAACGTATT
CACCATTTAATAAGATAATATCTTGTGGTCTGTAATCAAATTTACCAGTAAAGAATGATTC
CAAGATATTTTTAGTACCTTCAGCGTATCTTGTTTGAGCATCTAAAGTAGTACCAGAGTA
GTGAGGAGTCATGGCATTACCAGCACCATATTTATTTCTCATATCTCTCCATGGGTGATC
CTTTGGAGCTGGTTGTGGGAACCAAACATCACCACCGTAACCTCTTAATTGACCAGATT
CTAAAGCTGCTGCAACATCTTCAGCAACACAAATAGCACCTCTTGCGGTATTGACTAAC
CAAGCACCTTTTTTAAATTTAGATAATAATTCCTTATTAATTAAACCTTTTGTACCTGCGT
GTAATGGAGCATTAACTGTAACGATATCAGCTTGAGCAACTAATTCTTCAATATTTTCAA
CTCTTCTAGCACCAACTTTTTCTTCAGCTTCTTTTGGTAAAGCTTGATAATCGTAGTATAA
TAATTCTTTTGGATTAAAAGGGAGTAATCTTTCCAAGACTCTGTAACCAATTCTACCAGC
```

FIG. 11 (Continued)

| | | | |
|---|---|---|---|
| | | | ACCAATGGTAGCAATAGTTTTACCTTCGATATCGTAAGCATCCTTAGCGATAGCAGCAAC<br>CTCCCAATCGTGGTTAATAATTTGTTCATGTGCTGGAACGAAATTTCTAACCAAGACAAG<br>CATGGTCATGACAACGTGTTCAGCAACAGAGACAACATTAGAACCTGTAACTTCCAAGA<br>CTGAGATTTTCTTACCTGTTTGATTAATATAATCTAAATCAATGTGATCAGAACCAACACC<br>AGCGACAACGACTAATTTTAAGTTCTTAGCCTTGTCAAGTCTTTCCTTAGTGATATAAGC<br>AGGATGGAAAGGAGTGGTGATGATAATATCAGCATCTGGGATATGTTTATCCAATTCAC<br>TTGTTTCACCTTCTTTATCAGAAGTAGTAATTAGTTCATGACCTTGATCTTTTAACCAATT<br>AGCAATACCTAATTTATTTTCAGTACAACCATATAATTTTTCTTCATCAGCAGCGTGCTTA<br>CCAGCATCATATAAGACTAAAACGATCTTCATACATCACCTCATAAAATAAATTAAAAAT<br>AATAAAAACTAATGTTTCGCATTATAGGACAAAAGATACCTAAAAAATGTTATCTAGATCA<br>AATTATTGGAAAATATATGAAAATAATTTTTGTTTAAAAAGCGAACGACATTAGTATTTTTC<br>ATAAAAATACGTACATTGTTATCCGTCGCTATTTAA |
| 15 | 14a | pJFF224<br>PEFTU<br>Glyoxylate<br>operon<br>Yersinia<br>molaretii | GATCCCCAGTAGATTTACGTTTAAACATTTTTATTTCCTTTTTAATTTAATTTAATTAACAG<br>TTGGTGCTATGACACTTTACCTCATAGCTGGCATAATTCGCAATACTCTGGGTCTTCGAG<br>AGGTATCCAACCTGAGTTGAAATACTTTACCATCGATTTAGCAGTTGTATCAGTTATATTT<br>ATATTACCTTTAACTCTTCGCCATCCAGGAGTTTTACCGTACAGATTAGAGGATAATAAT<br>AACACATAATTCTCGTAAGCAATATGAGATAATTTCCAAGACTCTATATTAGCTCGTGAT<br>GTTTTCCAAGGTCTAAAATCGTCACGGTTCATATAATTAGCCAATCTCATATGCTCTCTA<br>ACTTCCGATGATAAGCTGTCAAACATGAGAATTAACGATCTGATAGAGAAGGGTTTGCT<br>CGGGTCGGTGGCTCTGGTAACGACCAGTATCCCGATCCCGGCTGGCCGTCCTGGCCG<br>CCACATGAGGCATGTTCCGCGTCCTTGCAATACTGTGTTTACATACAGTCTATCGCTTA<br>GCGGAAAGTTCTTTTACCCTCAGCCGAAATGCCTGCCGTTGCTAGACATTGCCAGCCAG<br>TGCCCGTCACTCCCGTACTAACTGTCACGAACCCCTGCAATAACTGTCACGCCCCCCTG<br>CAATAACTGTCACGAACCCCTGCAATAACTGTCACGCCCCCAAACCTGCAAACCCAGCA<br>GGGGCGGGGGCTGGCGGGGTGTTGGAAAAATCCATCCATGATTATCTAAGAATAATCC<br>ACTAGGCGCGGTTATCAGCGCCCTTGTGGGGCGCTGCTGCCCTTGCCCAATATGCCCG<br>GCCAGAGGCCGGATAGCTGGTCTATTCGCTGCGCTAGGCTACACACCGCCCCACCGCT<br>GCGCGGCAGGGGGAAAGGCGGGCAAAGCCCGCTAAACCCCACACCAAACCCCGCAGA<br>AATACGCTGGGAGCGCTTTTAGCCGCTTTAGCGGCCTTTCCCCCTACCCGAAGGGTGG<br>GGGCGCGTGTGCAGCCCCGCAGGGCCTGTCTCGGTCGATCATTCAGCCCGGCTCATC<br>CTTCTGGCGTGGCGGCAGACCGAACAAGGCGCGGTCGTGGTCGCGTTCAAGGTACGC<br>ATCCATTGCCGCCATGAGCCGATCCTCCGGCCACTCGCTGCTGTTCACCTTGGCCAAA<br>ATCATGGCCCCCACCAGCACCTTGCGCCTTGTTTCGTTCTTGCGCTATTGCTGCTGTTC<br>CCTTGCCCGCACCCGCTGAATTTCGGCATTGATTCGCGCTCGTTGTTCTTCGAGCTTGG<br>CCAGCCGATCCGCCGCCTTGTTGCTCCCCTTAACCATCTTGACACCCCATTGTTAATGT<br>GCTGTCTCGTAGGCTATCATGGAGGCACAGCGGCGGCAATCCCGACCCTACTTTGTAG<br>GGGAGGGCCATTGCATGGAGCCGAAAAGCAAAAGCAACAGCGAGGCAGCATGGCGAT<br>TTATCACCTTACGGCGAAAACCGGCAGCAGGTCGGGCGGCCAATCGGCCAGGGCCAA<br>GGCCGACTACATCCAGCGCGAAGGCAAGTATGCCCGCGACATGGATGAAGTCTTGCAC<br>GCCGAATCCGGGCACATGCCGGAGTTCGTCGAGCGGCCCGCCGACTACTGGGATGCT<br>GCCGACCTGTATGAACGCGCCAATGGGCGGCTGTTCAAGGAGGTCGAATTTGCCCTGC<br>CGGTCGAGCTGACCCTCGACCAGCAGAAGGCGCTGGCGTCCGAGTTCGCCCAGCACC<br>TGACCGGTGCCGAGCGCCTGCCGTATACGCTGGCCATCCATGCCGGTGGCGGCGAGA<br>ACCCGCACTGCCACCTGATGATCTCCGAGCGGATCAATGACGGCATCGAGCGGCCCG<br>CCGCTCAGTGGTTCAAGCGGTACAACGGCAAGACCCCGGAGAAGGGCGGGGCACAGA<br>AGACCGAAGCGCTCAAGCCCAAGGCATGGCTTGAGCAGACCCGCGAGGCATGGGCCG<br>ACCATGCCAACCGGGCATTAGAGCGGGCTGGCCACGACGCCCGCATTGACCACAGAA<br>CACTTGAGGCGCAGGGCATCGAGCGCCTGCCCGGTGTTCACCTGGGGCCGAACGTGG<br>TGGAGATGGAAGGCCGGGGCATCCGCACCGACCGGGCAGACGTGGCCCTGAACATCG<br>ACACCGCCAACGCCCAGATCATCGACTTACAGGAATACCGGGAGGCAATAGACCATGA<br>ACGCAATCGACAGAGTGAAGAAATCCAGAGGCATCAACGAGTTAGCGGAGCAGATCGA<br>ACCGCTGGCCCAGAGCATGGCGACACTGGCCGACGAAGCCCGGCAGGTCATGAGCCA<br>GACCCAGCAGGCCAGCGAGGCGCAGGCGGCGGAGTGGCTGAAAGCCCAGCGCCAGA<br>CAGGGGCGGCATGGGTGGAGCTGGCCAAAGAGTTGCGGGAGGTAGCCGCCGAGGTG<br>AGCAGCGCCGCGCAGAGCGCCCGGAGCGCGTCGCGGGGGTGGCACTGGAAGCTATG<br>GCTAACCGTGATGCTGGCTTCCATGATGCCTACGGTGGTGCTGCTGATCGCATCGTTG<br>CTCTTGCTCGACCTGACGCCACTGACAACCGAGGACGGCTCGATCTGGCTGCGCTTGG<br>TGGCCCGATGAAGAACGACAGGACTTTGCAGGCCATAGGCCGACAGCTCAAGGCCATG<br>GGCTGTGAGCGCTTCGATATCGGCGTCAGGGACGCCACCACCGGCCAGATGATGAAC<br>CGGGAATGGTCAGCCGCCGAAGTGCTCCAGAACACGCCATGGCTCAAGCGGATGAAT<br>GCCCAGGGCAATGACGTGTATATCAGGCCCGCCGAGCAGGAGCGGCATGGTCTGGTG<br>CTGGTGGACGACCTCAGCGAGTTTGACCTGGATGACATGAAAGCCGAGGGCCGGGAG<br>CCTGCCCTGGTAGTGGAAACCAGCCCGAAGAACTATCAGGCATGGGTCAAGGTGGCC<br>GACGCCGCAGGCGGTGAACTTCGGGGGCAGATTGCCCGGACGCTGGCCAGCGAGTAC<br>GACGCCGACCCGGCCAGCGCCGACAGCCGCCACTATGGCCGCTTGGCGGGCTTCACC<br>AACCGCAAGGACAAGCACACCACCCGCGCCGGTTATCAGCCGTGGGTGCTGCTGCGT<br>GAATCCAAGGGCAAGACCGCCACCGCTGGCCCGGCGCTGGTGCAGCAGGCTGGCCA<br>GCAGATCGAGCAGGCCCAGCGGCAGCAGGAGAAGGCCCGCAGGCTGGCCAGCCTCG<br>AACTGCCCGAGCGGCAGCTTAGCCGCCACCGGCGCACGGCGCTGGACGAGTACCGCA<br>GCGAGATGGCCGGGCTGGTCAAGCGCTTCGGTGATGACCTCAGCAAGTGCGACTTTAT<br>CGCCGCGCAGAAGCTGGCCAGCCGGGGCCGCAGTGCCGAGGAAATCGGCAAGGCCA<br>TGGCCGAGGCCAGCCCAGCGCTGGCAGAGCGCAAGCCCGGCCACGAAGCGGATTACA<br>TCGAGCGCACCGTCAGCAAGGTCATGGGTCTGCCCAGCGTCCAGCTTGCGCGGGCCG<br>AGCTGGCACGGGCACCGGCACCCCGCCAGCGAGGCATGGACAGGGGCGGGCCAGAT |

FIG. 11 (Continued)

```
TTCAGCATGTAGTGCTTGCGTTGGTACTCACGCCTGTTATACTATGAGTACTCACGCAC
AGAAGGGGGTTTTATGGAATACGAAAAAAGCGCTTCAGGGTCGGTCTACCTGATCAAAA
GTGACAAGGGCTATTGGTTGCCCGGTGGCTTTGGTTATACGTCAAACAAGGCCGAGGC
TGGCCGCTTTTCAGTCGCTGATATGGCCAGCCTTAACCTTGACGGCTGCACCTTGTCCT
TGTTCCGCGAAGACAAGCCTTTCGGCCCCGGCAAGTTTCTCGGTGACTGATATGAAAG
ACCAAAAGGACAAGCAGACCGGCGACCTGCTGGCCAGCCCTGACGCTGTACGCCAAG
CGCGATATGCCGAGCGCATGAAGGCCAAAGGGATGCGTCAGCGCAAGTTCTGGCTGA
CCGACGACGAATACGAGGCGCTGCGCGAGTGCCTGGAAGAACTCAGAGCGGCGCAGG
GCGGGGGTAGTGACCCCGCCAGCGCCTAACCACCAACTGCCTGCAAAGGAGGCAATC
AATGGCTACCCATAAGCCTATCAATATTCTGGAGGCGTTCGCAGCAGCGCCGCCACCG
CTGGACTACGTTTTGCCCAACATGGTGGCCGGTACGGTCGGGGCGCTGGTGTCGCCC
GGTGGTGCCGGTAAATCCATGCTGGCCCTGCAACTGGCCGCACAGATTGCAGGCGGG
CCGGATCTGCTGGAGGTGGGCGAACTGCCCACCGGCCCGGTGATCTACCTGCCCGCC
GAAGACCCGCCCACCGCCATTCATCACCGCCTGCACGCCCTTGGGGCGCACCTCAGC
GCCGAGGAACGGCAAGCCGTGGCTGACGGCCTGCTGATCCAGCCGCTGATCGGCAGC
CTGCCCAACATCATGGCCCCGGAGTGGTTCGACGGCCTCAAGCGCGCCGCCGAGGGC
CGCCGCCTGATGGTGCTGGACACGCTGCGCCGGTTCCACATCGAGGAAGAAAACGCC
AGCGGCCCCATGGCCCAGGTCATCGGTCGCATGGAGGCCATCGCCGCCGATACCGGG
TGCTCTATCGTGTTCCTGCACCATGCCAGCAAGGGCGCGGCCATGATGGGCGCAGGC
GACCAGCAGCAGGCCAGCCGGGGCAGCTCGGTACTGGTCGATAACATCCGCTGGCAG
TCCTACCTGTCGAGCATGACCAGCGCCGAGGCCGAGGAATGGGGTGTGGACGACGAC
CAGCGCCGGTTCTTCGTCCGCTTCGGTGTGAGCAAGGCCAACTATGGCGCACCGTTCG
CTGATCGGTGGTTCAGGCGGCATGACGGCGGGGTGCTCAAGCCCGCCGTGCTGGAGA
GGCAGCGCAAGAGCAAGGGGGTGCCCCGTGGTGAAGCCTAAGAACAAGCACAGCCTC
AGCCACGTCCGGCACGACCCGGCGCACTGTCTGGCCCCCGGCCTGTTCCGTGCCCTC
AAGCGGGGCGAGCGCAAGCGCAGCAAGCTGGACGTGACGTATGACTACGGCGACGGC
AAGCGGATCGAGTTCAGCGGCCCGGAGCCGCTGGGCGCTGATGATCTGCGCATCCTG
CAAGGGCTGGTGGCCATGGCTGGGCCTAATGGCCTAGTGCTTGGCCCGGAACCCAAG
ACCGAAGGCGGACGGCAGCTCCGGCTGTTCCTGGAACCCAAGTGGGAGGCCGTCACC
GCTGATGCCATGGTGGTCAAAGGTAGCTATCGGCGCTGGCAAAGGAAATCGGGGCA
GAGGTCGATAGTGGTGGGGCGCTCAAGCACATACAGGACTGCATCGAGCGCCTTTGGA
AGGTATCCATCATCGCCCAGAATGGCCGCAAGCGGCAGGGGTTTCGGCTGCTGTCGG
AGTACGCCAGCGACGAGGCGGACGGGCGCCTGTACGTGGCCCTGAACCCCTTGATCG
CGCAGGCCGTCATGGGTGGCGGCCAGCATGTGCGCATCAGCATGGACGAGGTGCGG
GCGCTGGACAGCGAAACCGCCCGCCTGCTGCACCAGCGGCTGTGTGGCTGGATCGAC
CCCGGCAAAACCGGCAAGGCTTCCATAGATACCTTGTGCGGCTATGTCTGGCCGTCAG
AGGCCAGTGGTTCGACCATGCGCAAGCGCCGCCAGCGGGTGCGCGAGGCGTTGCCG
GAGCTGGTCGCGCTGGGCTGGACGGTAACCGAGTTCGCGGCGGGCAAGTACGACATC
ACCCGGCCCAAGGCGGCAGGCTGACCCCCCCCACTCTATTGTAAACAAGACATTTTTTA
TCTTTTATATTCAATGGCTTATTTTCCTGCTAATTGGTAATACCATGAAAAATACCATGCT
CAGAAAAGGCTTAACAATATTTTGAAAAATTGCCTACTGAGCGCTGCCGCACAGCTCCA
TAGGCCGCTTCCTGGCTTTGCTTCCAGATGTATGCTCTCCTCCGGAGAGTACCGTGAC
TTTATTTTCGGCACAAATACAGGGGTCGATGGATAAATACGGCGATAGTTTCCTGACGG
ATGATCCGTATGTACCGGCGGAAGACAAGCTGCAAACCTGTCAGATGGAGATTGATTTA
ATGGCGGATGTGCTGAGAGCACCGCCCCGTGAATCCGCAGAACTGATCCGCTATGTGT
TTGCGGATGATTGGCCGGAATAAATAAAGCCGGGCTTAATACAGATTAAGCCCGTATAG
GGTATTATTACTGAATACCAAACAGCTTACGGAGGACGGAATGTTACCCATTGAGACAA
CCAGACTGCCTTCTGATTATTAATATTTTTCACTATTAATCAGAAGGAATAACCATGAATT
TTACCCCGGATTGACCTGAATACCTGGAATCGCAGGGAACACTTTGCCCTTTATCGTCAG
CAGATTAAATGCGGATTCAGCCTGACCACCCAAACTCGATATTACCGCTTTGCGTACCGC
ACTGGCGGAGACAGGTTATAAGTTTTATCCGCTGATGATTTACCTGATCTCCCGGGCTG
TTAATCAGTTTCCGGAGTTCCGGATGGCACTGAAAGACAATGAACTTATTTACTGGGAC
CAGTCAGACCCGGTCTTTACTGTCTTTCATAAAGAAACCGAAACATTCTCTGCACTGTCC
TGCCGTTATTTTCCGGATCTCAGTGAGTTTATGGCAGGTTATAATGCGGTAACGGCAGA
ATATCAGCATGATACCAGATTGTTTCCGCAGGGAAATTTACCGGAGAATCACCTGAATAT
ATCATCATTACCGTGGGTGAGTTTTGACGGGATTTAACCTGAACATCACCGGAAATGAT
GATTATTTTGCCCCGGTTTTTACGATGGCAAAGTTTCAGCAGGAAGGTGACCGCGTATT
ATTACCTGTTTCTGTACAGGTTCATCATGCAGTCTGTGATGGCTTTCATGCAGCACGGTT
TATTAATACACTTCAGCTGATGTGTGATAACATACTGAAATAAATTAATTAATTCTGTATTT
AAGCCACCGTATCCGGCCAGGAATGGTGGCTTTTTTTTTATATTTTAACCGTAATCTGTAA
TTTCGTTTCAGACTGGTTCAGGATCACTGTACGATAATGCCCCCGCAGTTTGGTAATAC
CCTTAATAAAAAAGAAACAGCAAAGACTGACAGCAATAATAATAAAGTAAGCAGTAACAA
TAATATTAACAACACCAGATGCAGTTATAATAATAGTATTTAAGACACCAGAAAGACTGC
TGCGACAGTCATTTTGAACAACACCAAAATGCCGTAAAGGCAGTAGTAACAACACCAGT
GAAAACATCACGATAGCATAGTGATATGCCTGAGTGTGTGTAATTAAACAATAAATAAAC
CGCCATATATAACAGAAGATAGTATTCTGAATGGCATGCTTTTCTGTTCAGTATAAACAT
ATCATCCCGGTTGGTATAAGGATGATATATAATAAGTTAAGCTGAACACATATTTATTTTG
GTTTTATTTTACAAATAAAGTAAGACGATCCGTTAAGTCAAAGCGGGGTATATTTATTATA
CCCTGCTTTTTTATTTGTCCGCCGGGCGCGGATAATGGATCAGATTATGCAGTGTCACA
ATGGCCTTACCGGGATTGGCGTAAGCGTGCGGGATATCCGCATGGAAGCGCAGGGATT
CCCCGGCAGAAACGGTGTGCCACTCATCCCCCAGCCGCAGTTGTAATGCGCCTTCCAG
TACAATGACATGTTCTCTGGTTCTGAAATCCATCCCTGTCGGTGTTGCTTATGCAGTCTG
GTCGGGACTCGGCGTCGTCATAATTACAGCCATTGCCTGGTTGCTTCATGGGCAAAAG
CTTTATGCTTGTAAACCGTTTTGTGAAAAAATTTTTAAAATAAAAAAGGGGACCTCTAGG
```

FIG. 11 (Continued)

| | | | |
|---|---|---|---|
| | | | GTCCCCAATTAATTAGTAATATAATCTATTAAAGGTCATTCAAAAGGTCATCCACCGGAT
CCGGGCCCCCCCTCGAGGTCGACGGTATCGATAAGCTTGATATCGAATTCCCATATTGT
GCATCGAATCCCTGCAAATTGTCTGAGCGATTAATTGTTCTAATTTTACCGCCATGCTC
ACCCCCCGCCTACGGAACAGAGCCTGCATCAGCAGGCTCCAGATAAAACATAAACTC
ATTAATCAGTGGCTTAGAACTGCTGCTCTTCCGTCGAGCCAGTCAGTGCAGTGACTGAT
GACTCGCCGCCCTGAATGATATTGGTGACTTTATCAAAATAGCCCGTGCCCACTTCTTG
TTGATGGGAAGCAAAGGTGTAGCCGCGTTCAACGGAGGCAAATTCTGGCTGCTGCACT
TTCTCAACATAGTGCTTCATGCCCTCGCCTTGCGCGTAAGCATGGGCCAAGTCGAACAT
GTTGAACCACATACTGTGGATGCCCGCCAAGGTAATAAATTGATATTTGTAGCCCATCG
CGGAGAGGTCATCTTGGAAGCTGGCGATCTGCTGGTCAGTCAGGTTCTTTTTCCAGTTA
AATGATGGCGAACAGTTATAAGCCAATAATTTACCGGGGAATTTAGCGTGAACCGCATC
TGCAAAGCGTTTAGCCAGCGCCAGATCTGGCGTCGAGGTTTCACACCACACCAAGTCG
GCGTAAGGGGCATAGGCCAGACCACGGCTGATGGCTTGCTCAATGCCCGCGTGAGTG
CGGAAGAAGCCCTCAGCAGTACGATCACCAGCAATAAATTCGCTGTCATAAGGGTCGC
AATCAGAGGTCAGCAAATCCGCAGCATCAGTGCGCGCAATCAGCAGTGTTGG
CACGCCAAGAACGTCAGCGGCTAAGCGGGCAGCAACCAGCTTCTGAATCGCTTCTTGT
GTTGGCACCAAAACTTTGCCGCCCATATGGCCGCATTTCTTCACCGCCGCCAATTGATC
TTCAAAGTGAACGCCCGCAGCACCGGCTTCAATCATGGCTTTCATCAATTCAAACGCAT
TCAATACGCCGCCAAAACCCGCTTCGGCATCCGCCACAATCGGCAGGAAATAGTCGGT
ATAGCCTTTGCTGCCCGGCTCAATATTATTCGACCACTGAATCTGATCTGCACGGCGGA
AGCTGTTATTAATACGCTTAACCACGGCCGGAACAGAGTCGACCGGGTAAAGAGATTGA
TCGGGATACATGCTGGAGGCGGTATTGGCATCGGCGGCGACCTGCCAACCCGACAGA
TAAATCGCTTCAACACCGGCCTTTGCCTGTTGCAATGCCTGACCGCCTGTTAGCGCCCC
CAGACAGTTGATGTAGCCTTTACGCGATTCGCCGTGCAGCAACTCCCACAATCTTTTCG
CGCCGTGCTGTGCCAGCGTACATTCTGGGTTAACGGAACCGCGCAGTTTGATCACTTC
TTCGGCGCTATAGGGGCGGGTGATGCCCTTCCAGCGCGGTGATTTCCATTCCTGTTCC
AACTGCTGAATTTGTTGAGTACGAGAGGTTGTCATGGCGATATTCCTTATTACTTATTTTT
GTAGGGTTAAATAACTGGCCTAGGCGAGTAATGCGTAGCCCGGCAACGTCAGAAAGTC
GATAAGCTCGTCTTGTGTTGTAATCCGCTCCATCAGACGTGCGGCTTCTTCAAACCGCC
CGCCATCAAAACGCTCTGCGCCAAGTTCAAGTTTCACGACCTGCATTTCTTCACTCAAC
ATGTTACGGAACAGCTCTTTGGTCACCGTCTGACCATTGCTCAGGCTTTTCTGGTGATG
TATCCATTGCCAGATAGAAGTACGGGAAATCTCAGCCGTCGCGGCATCTTCCATCAGGC
CATAAATCGGTACACAGCCATTGCCCGATATCCATGCTTCGATGTATTGCACTGCGACC
CGGATATTGGCCCGCATCCCCTCTTCGGTGCGCTCACCCGTGCAAGGCTCTAGCAACT
CAGCGGCAGTGATTGGTTTATCTTGCGCGCGACTCACCTCTAATTGGTTTGGACGATCG
CCCAGTACTTTGTTGAAAACGTCCATCACGGTATCGGCCAGACCGGGGGTGTGCGACCC
ATGTACCATCGTGGCCGTTGCTGGCTTCCAGCTCTTTGTCAGCGCGAACTTTATCTAAG
ACCAGCGCATTTTTTCTGGATCTTTGTTCGGGATAAAGGCCGCCATGCCGCCCATCGC
CAAGGCACCGCGCTTATGGCAGGTTTTGATCAGTAAACGAGAGTAGGCACTCAGGAAG
GGTTTCGTCATCGTGACCGACTGGCGATCGGGCAGCACGCGATCGCTGTGATTTTTCA
GCGTTTTGATATAGCTGAAAATGTAGTCCCAACGGCCACAATTCAGGGCAACAATGTGA
TGGCGCAGATGGTAGAGGATCTCATCCATCTGGAATACCGCAGGCAATGTCTCGATTAA
TACTGTGGCCTTAATGGTGCCTTGCGGCAGATCGAAACGCTGCTCGGTAAAGCTGAAA
ACATCACTCCACCAAGCCGCTTCCTGATAAGACTGCATCTTGGGTAGATAGAAATAGGG
GCCGCTGCCATTGGCAAGCAGTAACTTATAGTTATGGTAGAAATACAACGCGAAATCGA
ATAAGCCACCGGGGATATCCTCCCCCTGCCACTTCACGTGTTTTTCTGGCAAGTGCAGA
CCACGCACCCGAGCAATCAACACCGCTGGATTGGGTTTTAGCTGATAAATCTTACCGGA
TTCATTCGCGTAAGAGATTGTGCCTTTGACCGCATCGTGCAAATTAATCTGACCTTCGAT
AACCTTATCCCAACTGGGTGCCAGCGAATCCTCAAAGTCAGCCATAAAGACTTTCACAT
TCGCATTGAGGGCATTAATCACCATTTTGCGCTCAACCGGCCCGGTGATCTCGACGCG
ACGATCACGTAAATCCGCAGGAATACTTTGAATTTTCCAGTCACCATTACGAATGGAATT
GGTTTCCGAAATGAAATCAGGCAATGCGCCTTGGTCAATGGCCTGTTGCCAAGCGGCC
CGTGCAGCAAGGAGTTTGCTACGCGGCTCTGCAAATTTCGCCACCAATTCTGCCAAAAA
TTCGATGGCCTCATCGGGCAAAACCTGCCGCTCAGCAGCATTAAAATGCTGGGTGAAA
ACTAACTCCGTGCCGACTATCTGTTGTGTCATTCCCCTTCCCCTTCCCCATCTCTCGAC
GATCATTTTTCAGTTTCCTTTTGTTATTCCCCAAAAGTGCGGTGCAAATTTGGGGAGTTT
TAGTTAATTAAAAAAAATTATTTTTTACGAGCTTCGATTACTGCAGCAGCAACACTTGTTGG
CGCTTCAGCATATTTTAACGGTTCCATTGAGTATGATGCTCTAGAGCGGCCGCCACCGC
GGTGG |
| 16 | 15 | Alcohol dehydrogenase DNA (adhE) from DD1 | ATGATTATGAGTAACGCTGTTGAAAACACAGTAAGCCCCGCTCAAGCGGAGGTGAACTC
ACTGGTTGAGAAAGGTTTAGTGGCACTGGAGCAATTCCGCCAACTAAATCAGGAACAG
GTGGACTACATTGTAGCGAAAGCTTCTGTTGCCGCTTTAGACCAACATGGAGCATTGGC
GCTACATGCGTTAGAGGAAACCGGGCGCGGCGTGTTCGAGGACAAAGCCACTAAAAAC
CTGTTTGCCTGCGAACATGTAGTGAACAAAATGCGACATTGGAAAACCGCCGGGATTAT
CAGTGACGACGATGTCACAGGTATCACCGAAATTGCCGATCCGGTGGGAGTGGTCTGC
GGCATTACACCTACCACTAATCCTACTTCCACGGCTATCTTCAAATCACTGATCGCTTTA
AAAACCCGCAATCCTATTGTTTTCGCTTTCCACCCTTCCGCCCAACAGTCTTCCGCTCAT
GCCGCACAAATTGTGCGCGATGCCGCGGTAGCCGCCGGTGCGCCGGAAAACTGTATT
CAATGGATTGCACAACCCTCTATGGAAGGAACTAATGCGTTAATGAACCATCCGGGTAT
TGCCACCATTCTGGCTACCGGCGGTAACGCTATGGTGCAGGCCGCTTATTCATGCGGC
AAGCCGGCGTTGGGAGTCGGTGCCGGAAATGTACCCGCTTATGTGGAAAAATCCGCCG
ATATTAAACAGGCAACTCACGATATCGTGATGTCGAAATCCTTTGATAACGGTATGGTAT
GCGCTTCAGAGCAAGCCGCTATTGCCGATCGGAAATTTATGACGAATTCGTCAACGAA
TTAAAATCCTACGGTGTGTATTTCGTCAATAAAAAAAGAAAAAAACTTTATTGGAAGAATTTA |

FIG. 11 (Continued)

| | | | |
|---|---|---|---|
| | | | TGTTCGGTGTAAAAGCTAACGGTGCAAATTGCGCCGGTGCGAAACTAAACGCCGACGT GGTAGGTAAATCCGCATACTGGATTGCTCAACAAGCGGGCTTTGAAGTGCCGAAAAAAA CCAATATTCTTGCCGCAGAATGTAAAGAAGTCAGCCCGAAAGAACCTTTAACCCGGGAA AAATTATCACCGGTGCTTGCCGTTTTAAAATCCCGTTCTACCGAAGAGGGATTAACGCTT GCCGAAGCCATGGTGGAATTTAACGGTTTAGGACACTCCGCGGCAATTCACACCAAAG ATGCGGCGCTTGCCAAACGCTTCGGCGAGCGCGTTAAAGCCATTCGCGTTATCTGGAA TTCGCCTTCTACCTTCGGCGGTATCGGCGACGTTTATAACGCTTTCCTGCCTTCATTAAC CCTGGGTTGCGGTTCTTACGGCAAAAATTCCGTCAGCAACAATGTCAGCGCCATGAACT TAGTAAATATCAAACGTGTGGGAAGACGGAGAAATAATATGCAATGGTTTAAAGTACCTT CAAAAATCTATTTTGAACGGGATTCAATTCAATATTTACAATCCGTACCGGATATGCGAC GAGTAGTTATCGTAACCGACCGCACTATGGTGGATCTTGGGTTTGTACAAAAAATCGCC CATCAGTTGGAATCCCGTCGCGATCCGGTTTCTTACCAGTTATTTGCCGATGTAGAACC GGATCCGAGTATTCAAACCGTGCGCCGCGGTGTGGATTTAATCCGTAATTTCAAACCGG ACACTATTATCGCGCTTGGCGGCGGTTCCGCCATGGATGCGGCAAAAGTGATGTGGTT ATTCTATGAACAACCGGAAATTGACTTCCGTGATTTGGTTCAAAAATTCATGGATATTCG TAAACGTGCCTTTAAATTTCCATCATTGGGAAAAAAAGCCCGCTATATCGGCATTCCGAC CACATCCGGTACGGGTTCGGAAGTGACCCCGTTTGCGGTGATTACCGAAGGTAACAAA AAATATCCGATTGCGGACTATTCGCTAACGCCGACTATCGCTTTAGTGGATCCGGCATT AGTTATGACGGTACCCGCCCATGTAGCGGCGGATACGGGATTAGACGTATTAACTCAT GCCACCGAAGCTTATGTTTCCGTACTGGCCAACGATTATACCGACGGTCTTGCTTTACA GGCGATTAAACTGGTATTCCGGTATTTGGAAAAATCCGTAAAAGAAAATGATCCGGAGG CAAGAGAAAAGATGCATAATGCGTCCACCATTGCGGGTATGGCGTTTGCCAATGCATTC TTAGGTATGAATCATTCCCTTGCGCATAAACTTGGCGGCCATTTCCATACGCCTCACGG GCGCACTAATGCGATCTTAATGCCGCACGTGATCCGTTATAACGGTACTAAACCGACGA AAACCGCCACATGGCCGAAATACAACTATTACAAAGCGGACGAAAAATATCAGGATATC GCCCGTTTATTAGGCTTACCTGCGGCGACCCCGGAAGAGGGCGTGAAATCTTATGCCA AAGCGGTTTACGATTTAGCGGTACGTTGCCGTGATTAAAATGTCCTTCAAAGAACAGGGA CTGGAAGAACAGGCCTGGATGGACGCCCGCCATGAAATTGCATTGCTTGCCTATGAAG ACCAATGTTCGCCGGCAAATCCGCGATTACCGATTGTGGCGGACATGGAAGAAATTCTC ACTAACGCCTACTATGGTTATGACGAAAGCAAATAC |
| 17 | 16 | Alcohol dehydrogen ase DNA (adhE) from DD1 | MIMSNAVENTVSPAQAEVNSLVEKGLVALEQFRQLNQEQVDYI VAKASVAALDQHGALALHALEETGRGVFEDKATKNLFACEHVV NKMRHWKTAGIISDDDVTGITEIADPVGVVCGITPTTNPTSTAIF KSLIALKTRNPIVFAFHPSAQQSSAHAAQIVRDAAVAAGAPENC IQWIAQPSMEGTNALMNHPGIATILATGGNAMVQAAYSCGKPA LGVGAGNVPAYVEKSADIKQATHDIVMSKSFDNGMVCASEQAA IADAEIYDEFVNELKSYGVYFVNKKEKTLLEEFMFGVKANGANC AGAKLNADVVGKSAYWIAQQAGFEVPKKTNILAAECKEVSPKE PLTREKLSPVLAVLKSRSTEEGLTLAEAMVEFNGLGHSAAIHTK DAALAKRFGERVKAIRVIWNSPSTFGGIGDVYNAFLPSLTLGCG SYGKNSVSNNVSAMNLVNIKRVGRRRNNMQWFKVPSKIYFERD SIQYLQSVPDMRRVVIVTDRTMVDLGFVQKIAHQLESRRDPVSY QLFADVEPDPSIQTVRRGVDLIRNFKPDTIIALGGGSAMDAAKV MWLFYEQPEIDFRDLVQKFMDIRKRAFKFPSLGKKARYIGIPTT SGTGSEVTPFAVITEGNKKYPIADYSLTPTIALVDPALVMTVPAH VAADTGLDVLTHATEAYVSVLANDYTDGLALQAIKLVFRYLEKS VKENDPEAREKMHNASTIAGMAFANAFLGMNHSLAHKLGGHFH TPHGRTNAILMPHVIRYNGTKPTKTATWPKYNYYKADEKYQDIA RLLGLPAATPEEGVKSYAKAVYDLAVRCGIKMSFKEQGLEEQA WMDARHEIALLAYEDQCSPANPRLPIVADMEEILTNAYYGYDES KY |
| 18 | 17 | pSacB (delta adhE) | TCGAGATAAATTCGCGGAACCGGCGCAGGCTCACCTGGCTGTTGCGATCGATAGGTAC GTTGATTATGGTGTTGATTACATCTCTTGTACCTGGCACATTTGCCGTTTTATCAATTTCA CTGCTCACCTCGTTTTGTGCGTTCACGTTGATTACAATGATGTTTTTTAATTGATTCTTTA CCGCTTCCTGATACATACCTTCCTGACCCGCAACATCATAAATATCAATTAAGCCGGACA GTCCTAAATTATCCGTTAAACCGCCGTCCACCAAATGAATAAAAGGGCGTTCTTTGCTGT TTTGATATAAAGACAAGGTATTTTTTAATTCTTCCAGATTTTTTGATTTTTGCGCATCATTG CTGATATTTTGGCTGATTTGAATTAATTCCGGTATATCGAAATGGCAGTTGCCGCCGTTG TTGTTTAAAGTCAACGGGCTGAACAGCAACGGTACCGAACTTGATGCGGCGACGGCAC GGGAAATTTCCATTTTACTTAAGTCAATACAAAGACCGTCGAAAAATTCTTGCGTAAAGG TTATTTTTTGTCCTAAATTCATATCCGTCGCACTCACTACGACAAACGGTCCTTTACGTTT TCGCTCAAGATCACCGAAGGTAGCGCCTTTGTATAATGTTTGATCCAGCTGTTCCTGTA ATAAGTCGCCGCGACCGAATTGAGGGGAGGTTATTCGCGGTAAATTGGAAAGGGATAA AACCTGACTGATAATTTCCCGCTGGAAATTTTTTTTTAGGAAGTTTTCTTCAAATTTAGGC ACCGCATCCCGCCCGTATAGGGAATAATAAGTGGCTAAAACGGATCCGCCGGATACGC CGTATACCAAATCCACATTATCAATTAGGGTTGTACCTTTTGCCGTCGGGCGCACGGCG GCGTTTTTAAATTCCTCTAACACGCCGTAGCCCAAACTTGCCGCCCGGCTGCCGCCGC CCGAAAACATTAAAATAATCAAATTGCCGTCGGGTTGCTGAATGGCATTTCTCATTCGAT ACCCTTGCTTAGCGTTCACATGGCTGATGGTATCAACGGGCTGATAAGTCACTAAGGTA CAAGCTGACAACAACAAAACAGTCAAACCGGCGAAATATTTTTTAGCATCATAGTTGTA ACGGATAAATCTAAATTTTTATTTATAGAAAAAGAAAATAATATGCTACATCGTACTATATT AATTTTTATCCTGCGTTCATATCTTATCAGAAGGCAAACCGCTTTTTCTATGCAAGGAAAA TTTTATAAATGACTAATGTACTCAAATAATGAAGAAAGATAAACAAACATTTTTTCATGAG AAAATTCTTATGAATTCTAAGCCTCGGTAATTCCTATTGGTATTTTATTTTTGAAACCGATT |

FIG. 11 (Continued)

```
ACCTTTTAAATTAAAATTTTTTATTTGATTTAAATCAATTTAATCGCATTATTAATCCCATTT
CATAACTCCAAAGTAGTAAAATTCGCACCAGTAACCAAATTTAAATATTAAACAACTTTAG
GAGAATAATTTGTAAAATTCTTAAAAATCGTACCGCACTTTTTCTAAAAGTGCGGTATTTT
TTTGATTGTTTTTATCCGTCTAAAGGGTAAAATCAACGGGATTTATTGATATTAAAGGAAA
CAATTATGGCAACAACTATTCATACAGAAAACGCGCCCGCAGCAATCGGTCCTTATGTT
CAAGCGGTAGATTTAGGCAATTTAGTGCTGACTTCGGGGCAAATTCCGGTGAATCCGG
CAACCGGCGAAGTGCCGGCGGATATTAGCGCACAAGCCCGCCAATCTTTAGAAAACGT
TAAAGCGATTATCGAACAGGCAGGGTTAACCGTGGCGGATATTGTAAAAACTACGGTTT
TTGTTAAGGATTTAAACGATTTTGCCACCGTAAATGCGGAATACGAACGTTTTTTCAAAG
AGAATGACCATCCGAATTTCCCTGCTCGCTCATGCGTTGAAGTGGCGCGTTTACCGAAA
GACGTCGGCTTGGAAATTGAAGCTATTGCGGTGCGCAAATAAGGCTGGGTTAAGCGCT
TATTTATACAAAAGTGCGGTCAAAAAATCCGTTTTTTGTAAAAGAAAAGGCATAGTTTTAT
TGACCGTGCCTTTTTGCTATTTGATGATTTATTTGCGCAACTTCACTTCTTGTACCGCAT
GGTCGGCACCTTTGCGTAAAATTAAATTTGCCCGTTCACGGGTCGGCAAAATATTTTGC
CGTAAATTTAAGCCGTTAATAGTATTCCAAATATTAGCGGCGGTTTCAACCGCTTCTTCT
TTAGAGAGTTTTGCATAATCTTTAAAATAGGAATTCGGATCGGTAAACGCGCTTTCACGG
AATTTCAAAAAGCGGCGAATATACCATTCCTTTAATAAGGCTTCATCGGCGTCCACATAA
ACGGAAAAATCAACAAAATCGGAGACAAAAGTCTGTTCCGCTTTGCGCGAACCGGTTTG
TAATACGTTTAAACCTTCCAATATAAGAATATCCGGGCGATCTACCTTGTTAAATTTATCG
GGGATAATATCATAGGTCAAATGCGAATAAATCGGCGCCGACACGTTCGGTTTGCCGG
ATTTTACGTCCGCCAGAAATTTGATTAATTTGGGCGTATCGTAAGAGACGGGGAAGCCT
TTTTTATGCAATAAATTTTCTTTTTTTAATTTTTCTAAAGGATAGAGAAAACCGTCGGTGG
TAATCAAATCCACTTTGCGATTTTCAGGCCAGTTAGACAGTAAAGACTGCAAAATACGCG
CGGAAGTGCTTTTCCCGACCGAAACGCTGCCGGCAATACTGATAATATAAGGTACATTG
GCGTTGGTATTGCCGAGAAAACGGTTCATTACGGTCTGGCGACGTAAATTTTCTTCAAT
ATAATAATTAATTAAACGCGCAAGAGGCAGGTAAATGGTGCTGACTTCTTCCAACGATAA
TTCTTCGTTAAAACCGAGTAAAGGCTTTAAATCTTGTTCTGTCAGTTTTAAAGGCACGGA
TTTCCGCAATTCCGCCCATTGTTTACGGGTAAATGTCAAAAACGGGCTGAATTTCTCTGA
AACTGACGATTGGCTTTCTATGTTCACGGCTCATTCTAATGTTAAGAAAGTAAAAATCTA
GACTCCATAGGCCGCTTTCCTGGCTTTGCTTCCAGATGTATGCTCTCCTCCGGAGAGTA
CCGTGACTTTATTTTCGGCACAAATACAGGGGTCGATGGATAAATACGGCGATAGTTTC
CTGACGGATGATCCGTATGTACCGGCGGAAGACAAGCTGCAAACCTGTCAGATGGAGA
TTGATTTAATGGCGGATGTGCTGAGAGCACCGCCCCGTGAATCCGCAGAACTGATCCG
CTATGTGTTTGCGGATGATTGGCCGGAATAAATAAAGCCGGGCTTAATACAGATTAAGC
CCGTATAGGGTATTATTACTGAATACCAAACAGCTTACGGAGGACGGAATGTTACCCAT
TGAGACAACCAGACTGCCTTCTGATTATTAATATTTTTCACTATTAATCAGAAGGAATAAC
CATGAATTTTACCCGGATTGACCTGAATACCTGGAATCGCAGGGAACACTTTGCCCTTT
ATCGTCAGCAGATTAAATGCGGATTCAGCCTGACCACCAAACTCGATATTACCGCTTTG
CGTACCGCACTGCCGGAGACAGGTTATAAGTTTTATCCGCTGATGATTTACCTGATCTC
CCGGGCTGTTAATCAGTTTCCGGAGTTCCGGATGGCACTGAAAGACAATGAACTTATTT
ACTGGGACCAGTCAGACCCGGTCTTTACTGTCTTTCATAAAGAAACCGAAACATTCTCT
GCACTGTCCTGCCGTTATTTTCCGGATCTCAGTGAGTTTATGGCAGGTTATAATGCGGT
AACGGCAGAATATCAGCATGATACCAGATTGTTTCCGCAGGGAAATTTACCGGAGAATC
ACCTGAATATATCATCATTACCGTGGGTGAGTTTTGACGGGATTTAACCTGAACATCACC
GGAAATGATGATTATTTTGCCCCGGTTTTTACGATGGCAAAGTTTCAGCAGGAAGGTGA
CCGCGTATTATTACCTGTTTCTGTACAGGTTCATCATGCAGTCTGTGATGGCTTTCATGC
AGCACGGTTTATTAATACACTTCAGCTGATGTGTGATAACATACTGAAATAAATTAATTAA
TTCTGTATTTAAGCCACCGTATCCGGCAGGAATGGTGGCTTTTTTTTTATATTTTAACCG
TAATCTGTAATTTCGTTTCAGACTGGTTCAGGATGAGCTCGCTTGGACTCCTGTTGATAG
ATCCAGTAATGACCTCAGAACTCCATCTGGATTTGTTCAGAACGCTCGGTTGCCGCCGG
GCGTTTTTTATTGGTGAGAATCCAAGCACTAGCGGCGCGCCGGCCGGCCCGGTGTGAA
ATACCGCACAGATGCGTAAGGAGAAAATACCGCATCAGGCGCTCTTCCGCTTCCTCGC
TCACTGACTCGCTGCGCTCGGTCGTTCGGCTGCGGCGAGCGGTATCAGCTCACTCAAA
GGCGGTAATACGGTTATCCACAGAATCAGGGGATAACGCAGGAAAGAACATGTGAGCA
AAAGGCCAGCAAAAGGCCAGGAACCGTAAAAAGGCCGCGTTGCTGGCGTTTTTCCATA
GGCTCCGCCCCCTGACGAGCATCACAAAAATCGACGCTCAAGTCAGAGGTGGCGAAA
CCCGACAGGACTATAAAGATACCAGGCGTTTCCCCCTGGAAGCTCCCTCGTGCGCTCT
CCTGTTCCGACCCTGCCGCTTACCGGATACCTGTCCGCCTTTCTCCCTTCGGGAAGCG
TGGCGCTTTCTCATAGCTCACGCTGTAGGTATCTCAGTTCGGTGTAGGTCGTTCGCTCC
AAGCTGGGCTGTGTGCACGAACCCCCCGTTCAGCCCGACCGCTGCGCCTTATCCGGTA
ACTATCGTCTTGAGTCCAACCCGGTAAGACACGACTTATCGCCACTGGCAGCAGCCACT
GGTAACAGGATTAGCAGAGCGAGGTATGTAGGCGGTGCTACAGAGTTCTTGAAGTGGT
GGCCTAACTACGGCTACACTAGAAGGACAGTATTTGGTATCTGCGCTCTGCTGAAGCCA
GTTACCTTCGGAAAAAGAGTTGGTAGCTCTTGATCCGGCAAACAAACCACCGCTGGTAG
CGGTGGTTTTTTTGTTTGCAAGCAGCAGATTACGCGCAGAAAAAAAGGATCTCAAGAAG
ATCCTTTGATCTTTTCTACGGGGTCTGACGCTCAGTGGAACGAAAACTCACGTTAAGGG
ATTTTGGTCATGAGATTATCAAAAAGGATCTTCACCTAGATCCTTTTAAAGGCCGGCCGC
GGCCGCCATCGGCATTTTCTTTTGCGTTTTTATTTGTTAACTGTTAATTGTCCTTGTTCAA
GGATGCTGTCTTTGACAACAGATGTTTTCTTGCCTTTGATGTTCAGCAGGAAGCTCGGC
GCAAACGTTGATTGTTTGTCTGCGTAGAATCCTCTGTTTTGTCATATAGCTTGTAATCACG
ACATTGTTTCCTTTCGCTTGAGGTACAGCGAAGTGTGAGTAAGTAAAGGTTACATCGTTA
GGATCAAGATCCATTTTTAACACAAGGCCAGTTTTGTTCAGCGGCTTGTATGGGCCAGT
TAAAGAATTAGAAACATAACCAAGCATGTAAATATCGTTAGACGTAATGCCGTCAATCGT
CATTTTTGATCCGCGGGAGTCAGTGAACAGGTACCATTTGCCGTTCATTTTAAAGACGTT
```

FIG. 11 (Continued)

| | | | |
|---|---|---|---|
| | | | CGCGCGTTCAATTTCATCTGTTACTGTGTTAGATGCAATCAGCGGTTTCATCACTTTTTT<br>CAGTGTGTAATCATCGTTTAGCTCAATCATACCGAGAGCGCCGTTTGCTAACTCAGCCG<br>TGCGTTTTTTATCGCTTTGCAGAAGTTTTTGACTTTCTTGACGGAAGAATGATGTGCTTTT<br>GCCATAGTATGCTTTGTTAAATAAAGATTCTTCGCCTTGGTAGCCATCTTCAGTTCCAGT<br>GTTTGCTTCAAATACTAAGTATTTGTGGCCTTTATCTTCTACGTAGTGAGGATCTCTCAG<br>CGTATGGTTGTCGCCTGAGCTGTAGTTGCCTTCATCGATGAACTGCTGTACATTTTGATA<br>CGTTTTTCCGTCACCGTCAAAGATTGATTTATAATCCTCTACACCGTTGATGTTCAAAGA<br>GCTGTCTGATGCTGATACGTTAACTTGTGCAGTTGTCAGTGTTTGTTTGCCGTAATGTTT<br>ACCGGAGAAATCAGTGTAGAATAAACGGATTTTTCCGTCAGATGTAAATGTGGCTGAAC<br>CTGACCATTCTTGTGTTTGGTCTTTTAGGATAGAATCATTTGCATCGAATTTGTCGCTGT<br>CTTTAAAGACGCGGCCAGCGTTTTTCCAGCTGTCAATAGAAGTTTCGCCGACTTTTTGAT<br>AGAACATGTAAATCGATGTGTCATCCGCATTTTTAGGATCTCCGGCTAATGCAAAGACG<br>ATGTGGTAGCCGTGATAGTTTGCGACAGTGCCGTCAGCGTTTTGTAATGGCCAGCTGTC<br>CCAAACGTCCAGGCCTTTTGCAGAAGAGATATTTTTAATTGTGGACGAATCAAATTCAGA<br>AACTTGATATTTTTCATTTTTTTGCTGTTCAGGGATTTGCAGCATATCATGGCGTGTAATA<br>TGGGAAATGCCGTATGTTTCCTTATATGGCTTTTGGTTCGTTTCTTTCGCAAACGCTTGA<br>GTTGCGCCTCCTGCCAGCAGTGCGGTAGTAAAGGTTAATACTGTTGCTTGTTTTGCAAA<br>CTTTTTGATGTTCATCGTTCATGTCTCCTTTTTTATGTACTGTGTTAGCGGTCTGCTTCT<br>CCAGCCCTCCTGTTTGAAGATGGCAAGTTAGTTACGCACAATAAAAAAGACCTAAAATA<br>TGTAAGGGGTGACGCCAAAGTATACACTTTGCCCTTTACACATTTTAGGTCTTGCCTGCT<br>TTATCAGTAACAAACCCGCGCGATTTACTTTTCGACCTCATTCTATTAGACTCTCGTTTG<br>GATTGCAACTGGTCTATTTTCCTCTTTTGTTTGATAGAAAATCATAAAAGGATTTGCAGAC<br>TACGGGCCTAAAGAACTAAAAAATCTATCTGTTTCTTTTCATTCTCTGTATTTTTTATAGTT<br>TCTGTTGCATGGGCATAAAGTTGCCTTTTTAATCACAATTCAGAAAATATCATAATATCTC<br>ATTTCACTAAATAATAGTGAACGGCAGGTATATGTGATGGGTTAAAAAGGATCGGCGGC<br>CGCTCGATTTAAATC |
| 19 | 18 | Formate dehydrogenase DNA (fdh) from Wolinella succinogenes | ATGAGTGAAGCGTTAAGCGGACGCGGGAACGATCGAAGAAAGTTCCTAAAGATGTCGG<br>CTTTAGCAGGAGTCGCAGGCGTGAGTCAAGCGGTTGGCTCCGACCAAAGCAAAGTGCT<br>TAGACCTGCAACAAAACAAGAGTTAATCGAAAAATACCCAGTGTCCAAAAAGGTAAAAA<br>CGATTTGCACCTATTGCTCGGTCGGATGTGGAATTATAGCGGAAGTGGTCGATGGTGTA<br>TGGGTACGCCAAGAGGTCGCTCAAGATCACCCCATTAGTCAAGGGGGTCACTGCTGCA<br>AGGGCGCCGATATGATTGATAAGGCTCGAAGCGAAACAAGACTTCGATACCCCATTGA<br>GAAAGTTGGCGGAAAATGGCGTAAAACTTCATGGGATAGCGCCATGGATAAGATTGCC<br>AAGCAGCTTCAGGATCTCACCCAAAAATATGGCCCTGATAGCGTCATGTTCATTGGCGG<br>CTCCAAGTGTTCGATTGAACAATCCTATTATTTTAGAAAGTTTGCCGCCTTTTTTGGCAC<br>CAACAATCTCGATACCATCGCACGAATCTGCCATGCCCCAACAGTTGCTGGAGTCTCCA<br>ATACCCTTGGATATGGCGGTATGACCAATCACTTGGCAGACATGATGCACTCCAAGGCG<br>ATTTTTATCATTGGTGGAAATCCCGCAGTGAATCACCCTGTAGGCATGGTGCATATCTTG<br>CGCGCTAAAGAGGCAGGAGCAAAAATCATCGTTGTGGATCCCCACTTCAGTCGAACAG<br>CAACTAAAGCCGATCACTATGTGAGATTGCGCAATGGCACGGATGTCGCCTTCATGTAT<br>GGGATGATTCGCCATATTGTAAAAAATGGACTAGAAGATAAAGAATTTATTCGACAACGC<br>CTATTTGGCTACGAAGAGATTCTTAAAGAGTGCGAACAGTACACCCCTGAAGTGGTCGA<br>AGAGGTCACAGGCGTGCCCGCCCAACAACTTATTGAGATCACGGAGATCTTCGCTAAA<br>GCCAAGCCTGCTTCACTGATCTGGGGGATGGGTCTCACCCAGCACACCACAGGTACAA<br>GCAACACTCGTTTGGCCCCTATTTTACAGATGATTCTTGGAAACATTGGCAAACGAGGT<br>GGAGGCACTAACGTTTTACGAGGTCATGACAATGTCCAAGGCGCGACGGACATGGGCA<br>ACCTAGCCGACAGTCTTCCTGGCTATATGGGTTAGACAAAAATGCATGGAATCACTTC<br>TGTGGAATCTGGAAAGTGGATTTCGAAGCAATGCAAAAACGCTTTAAGACCCCTGATAT<br>GATGCATAAAAAAGGTTTCAGTGTATCCACATGGAGATATGGGGTGACTGAAGAGGAGA<br>ACATCCCCCACAATGCAGGCACTAAACTTCGATCCTTGATTGTCGTGGGAAGCGGAATC<br>TCTACGATCGCACGCGTGGATACCACCAAAGACGCTCTAGACAAGATGGATTTAGTCGT<br>CTTTTTTGATCCCTATTTCAATGATGCAGCCGCCCTCACCAACCGAAAAGATAATCTCTA<br>TATCCTTCCTGCCGCCACACAGATGGAGACCAGCGGAAGAGTCGCAGCGGACGAATCGA<br>AGCTATCAGTGGCGATCCATGGTTATGAAGCCACTCTTTGAGTGTCGACCTGACGAAGA<br>GATTCTCTTTGATTTAGCTAAGCGACTTGGATTCTATGAGGAGTACACTCGCTCTTTGGG<br>GGATGGCAAAGGAAACTTTGTATGGCCCGATGATGCGACTAGAGAGGTGGCCAAGGCT<br>ATACGAACTGTCGGCTTCCAAGGCAGAACTCCAGAACGACTCAAGGCTCATGCAGAAA<br>ACTGGCATATGTTTGATAAGTTCACCCTCAGAGGAAAGGGCGGCCCCGTCAAAGGCGA<br>ATACTATGGTCTTCCTTGGCCTTGCTGGAGCGAAAAGCATCCTGGAACACCAAATCTAT<br>GGGATGACAGCATCCCTGTAATGGATGGAGGTCTTGGCTTTAGGGTTCGATGGGGTGA<br>TGTGTCACCCACAGGAGAAAGTTTGTTGGCCAGCCAGGACAGCTCTTTGCCCGGCTCA<br>AAATTCAAGGGCGGTCATAGCATGATCACCGATAAAAATGTCGAAGCTATCACTGGAAT<br>CGCCCTCACCGAAGAGGAAAAAGCCAAAGTGGCAGGCAAGACATGGGCGACTGACAC<br>CACCAATATCTTGGTTGAAAAAGCACTCGCCGCAGGTCTCTCCCCTATGGGTAATGGTA<br>GAGCTAGAGCGATTGTTTGGGAGTGGACGGATCAGATTCCTAAACACCGTGAACCCAT<br>CTACACAATTCGACACGATCTCATTAGCCAATATCCAACCTTCAAAGACAAGCCCAACCA<br>CTTTAGGGCAAATATTCGCTATGAGAGCCGCCAAAAAGAGAAAGATTGGACCAAAGAGT<br>TCCCGCTTAATATGCTTTCTGGACGACTAGTAGCACAGTTTGGCACAGGCACAGAGACA<br>AGATCAGCTCATTACCTCGCCGAGGTTCAGCCTGAGATGTTTGTGGAGATTCATCCCGA<br>AACAGCCACGGATTTAGGCGTGAAGCATGGTGACATGGTTTGGGTGCACGGCACCAAT<br>GGGGCAAAGATTCTCGTGAAAGCGAGACATAGCTACAAGGTCAACAAAACAAGTGTTTT<br>CCTCCCCCAGAATTTCGGAGGAATGTATCAAGGAGAGTCACTGGTTCCGTATCATATTG<br>CAGGCACAGAGCCTTATGTTATTGGTGAATCATGCAATACCATCACAAGTGATGCATAC<br>GACATCAACACCAGTACTCCTGAAACCAAGTGCGGCCTCTGCCGCATCGAAAAAGCGT |

FIG. 11 (Continued)

| | | | |
|---|---|---|---|
| | | | AGGGGGTGAAGCATGGAAAGTCAAGCTAGAGTCAAGTTCTATTGTGATGAGGCTAGAT GTATTGATTGTCATGGATGTGATGTGGCTTGTAAAGAGGCCCATCACCTTCCTGTGGGA GTCAACCGAAGAAGAGTGGTGACCCTCAATGAAGGTCTTGTAGGCAAAGAGAAATCCC TCTCTATTGCCTGCATGCACTGCTCTGATGCCCCTTGTGCTCAGGTCTGCCCAGTGGAC TGCTTCTATGTTCGAGCCGATGGGATTGTATTGCATGACAAAGAGAAGTGCATTGGATG CGGTTACTGCCTCTATGCCTGCCCCTTTGGTGCTCCTCAATTCCCCAAGAGTGGAATCT TTGGTTCAAGAGGACCTATGGATAAGTGCACCTTCTGTGCTGGAGGTCCTGAAGAGACT CACAGCGAGAAGGAGTATAAGCTCTATGGACAGAATCGTATCGCTGAGGGCAAAGTCC CTGTATGTGCAGCGATGTGCTCCACCAAGGCACTCCTAGCAGGAGATTCTGATAGCATC TCGCTCATCATTCGTGAGAGAGTGCTCAAGCGAGGCAGTGGAACAGCCAGTGTTCCTT ACACCTGGTCACAAGCCTACAAGGATTAAGAATGAAAAAGCCTCTATTGCCCCTCCTCT CCCTTCTGGGAGCCTTGGGGCACAAGCTTCTGAGAATCTCAAGGAGCCCTTGGATTT CAGCTACAACACCCAAATCTATGGAAAGCCCATGATTGAGGCAATCCCCACTTGGGGAA GTGGAGGGATTCTAGGTCTTGGAGAGATTGGAGGAATAGGAGGATTAGGAGAGCTCTT CACCTTCTTGCAAAGTGGTTACTTTGCTCTTATCTTCCTAGCGATCATCATCGCTATCCC TTTGGTCTTCCTAGGTCACTATATGGTGATTGGACCCAAGCGATTCTCTCATGAGGGGA AGAAGATCAAGGTCTTTAACACCTTCAACATCATGGTGCACTGGATTGCAGGGATTCCC TTTGTGCTTCTTTGCATCACAGGACTTCTGATGGTCTTTGGAGATGCCCTAGGGGGTGG AGCTTTTATTCGATTCGCTAGAGATGTGCATGGATTAGCCACGATCATCTTTGCGATCTT TGGTCCCCTCATGTTCATCATGTGGGTGAAGCACGCTCTCTTTAAGATGTATGACATCG ACTGGATGCTCATTCTTGGAGGGTATCTAAGCAAGGTGAAGAGACCTATTCCTGCAGGC AAATTCAATGCGGGTCAGAAGATGTGGTTCTGGGTCTGCACGATGGGAGGATTCTTCAT GGTCTATAGTGGCTATGTGATGTTCTTCCAAGAGGGCAATATTGAGACCCTAAGACTCA TGGCGATCTTGCACAATGTAGTGGGGTTTGCTGTGGTGGCTCTCCTTATGACTCACATC TATATGGCAGCCTTTGCGATTGAGGGTGCATTGCACTCCATCCTAGATGGTCATATGGG TGAAGAGGAGGTAGCGATTCTTCATAGTTTCTACTATAAAGAGTTGCAGGCGGAGGGGA AAGTATGAGACACACCGATAGATTTGTTAAAAAGGTGGTGATTGAACGAATCGGCGATC AGAGAGTGCTCGCCGAGGAGGAAGATGTGGTGATCAAAGAGGAGGAGAATCTCTCTCTA TCTTAATGGCACCAAGCTTATGTCCATGATGTCTCTTCCTTCCGATCAAGATGCTCATGC GGTGGGCTTCTTGATGAGTGAGGGGGTGATTGAGAAGATCGAAGACTTAAAGAGTGTT CAAATCTCTTCTGATGGGAGCTCTGTCTATGTAGAGGCTCTCATCAACCATGAGAACAT CACCAATCTCTTCAAAGAGAAGACACTCACTTCAGGTTGTTGTGTCGGAGTGACGGGGA ATCTTGAAGGCAATGTCCTAAGAAAGTTCATCGCTACTCCCATGCAGATTTCTTTGGAGA GAATCTGGGAAGGGATGGAAGAGTTTGAGATGAGCAGCCATCTCTTTCATGAGACAGG CTGCGTTCATAAAGCCTCCCTTCTCTTAGAAGATGGAAGCAAGATCACGGCTGAGGATA TTGGTCGTCATAATGCAATTGATAAGGTGATGGGTAAAGCCAGGCTAGGGAGAATAGAT ACAGAGAAGGCTGTGCTAGTGGTGAGCGGAAGACTCTCCATGGAGATGGTGGTTAAAG CTGTCATGCACAACATTCCCATGATTGTCTCTAGGGCAGCAGCAACCTTTCTTGGAATC AAGACAGCCCAAGAGCTAGGGGTGACTCTAGTGGGCTTTGCTAGAGGGGGAGAAGATGA ATATCTACACCCATTCTGGTCGAGTGGACTTGAGGGCTTGCAAGAGGAAAAGAGGGGT GACTCTTCACGCTCCAAATCAATCTAGCTCTCTTCTTCGT |
| 20 | 19 | pJFF224 (idh W.s.) | TCGAGGGGGGGGCCCGGATCCCCAGTAGATTTACGTTTAAACATTTTTATTTCCTTTTTAA TTTAATTTAATTAACAGTTGGTGCTATGACACTTTACCTCATAGCTGGCATAATTCGCAAT ACTCTGGGTCTTCGAGAGGTATCCAACCTGAGTTGAAATACTTTACCATCGATTTAGCA GTTGTATCAGTTATATTTATATTACCTTTAACTCTTCGCCATCCAGGAGTTTTACCGTACA GATTAGAGGATAATAATAACACATAATTCTCGTAAGCAATATGAGATAATTTCCAAGACT CTATATTAGCTCGTGATGTTTTCCAAGGTCTAAAATCGTCACGGTTCATATAATTAGCCA ATCTCATATGCTCTCTAACTTCCGATGATAAGCTGTCAAACATGAGAATTAACGATCTGA TAGAGAAGGGTTTGCTCGGGTCGGTGGCTCTGGTAACGACCAGTATCCCGATCCCGGC TGGCCGTCCTGGCCGCCACATGAGGCATGTTCCGCGTCCTTGCAATACTGTGTTTACAT ACAGTCTATCGCTTAGCGGAAAGTTCTTTTACCCTCAGCCGAAATGCCTGCCGTTGCTA GACATTGCCAGCCAGTGCCCGTCACTCCCGTACTAACTGTCACGAACCCCTGCAATAAC TGTCACGCCCCCTGCAATAACTGTCACGAACCCCTGCAATAACTGTCACGCCCCCAAA CCTGCAAACCCAGCAGGGGCGGGGGCTGGCGGGGTGTTGGAAAAATCCATCCATGAT TATCTAAGAATAATCCACTAGGCGCGGTTATCAGCGCCCTTGTGGGGCGCTGCTGCCC TTGCCCAATATGCCCGGCCAGAGGCCGGATAGCTGGTCTATTCGCTGCGCTAGGCTAC ACACCGCCCCACCGCTGCGCGGCAGGGGAAAGGCGGGCAAAGCCCGCTAAACCCC ACACCAAACCCCGCAGAAATACGCTGGGAGCGCTTTTAGCCGCTTTAGCGGCCTTTCC CCCTACCCGAAGGGTGGGGCGCGTGTGCAGCCCCGCAGGGCCTGTCTCGGTCGATC ATTCAGCCCGGCTCATCCTTCTGGCGTGGCGGCAGACCGGAACAAGGCGCGGTCGTGG TCGCGTTCAAGGTACGCATCCATTGCCGCCATGAGCCGATCCTCCGGCCACTCGCTGC TGTTCACCTTGGCCAAAATCATGGCCCCACCAGCACCTTGCGCCTTGTTTCGTTCTTG CGCTATTGCTGCTGTTCCCTTGCCCGCACCCGCTGAAATTCGGCATTGATTCGCGCTCG TTGTTCTTCGAGCTTGGCCAGCCGATCCGCCGCCTTGTTGCTCCCCTTAACCATCTTGA CACCCCATTGTTAATGTGCTGTCTCGTAGGCTATCATGGAGGCACAGCGGCGGCAATC CCGACCCTACTTTGTAGGGGAGGGCCATTGCATGGAGCCGAAAAGCAAAAGCAACAGC GAGGCAGCATGGCGATTTATCACCTTACGGCGAAAACCGGCAGCAGGTCGGGCGGCC AATCGGCCAGGGCCAAGGCCGACTACATCCAGCGCGAAGGCAAGTATGCCCGCGACA TGGATGAAGTCTTGCACGCCGAATCCGGGCACATGCCGGAGTTCGTCGAGCGGCCCG CCGACTACTGGGATGCTGCCGACCTGTATGAACGCGCCAATGGGCGGCTGTTCAAGGA GGTCGAATTTGCCCTGCCGGTCGAGCTGACCCTCGACCAGCAGAAGGCGCTGGCGTC CGAGTTCGCCCAGCACCTGACCGGTGCCGAGCGCCTGCCGTATACGCTGGCCATCCA TGCCGGTGGCGGCGAGAACCCGCACTGCCACCTGATGATCTCCGAGCGGATCAATGA CGGCATCGAGCGGCCCGCCGCTCAGTGGTTCAAGCGGTACAACGGCAAGACCCCGGA |

FIG. 11 (Continued)

```
GAAGGGCGGGGCACAGAAGACCGAAGCGCTCAAGCCCAAGGCATGGCTTGAGCAGAC
CCGCGAGGCATGGGCCGACCATGCCAACCGGGCATTAGAGCGGGCTGGCCACGACG
CCCGCATTGACCACAGAACACTTGAGGCGCAGGGCATCGAGCGCCTGCCCGGTGTTC
ACCTGGGGCCGAACGTGGTGGAGATGGAAGGCCGGGGCATCCGCACCGACCGGGCA
GACGTGGCCCTGAACATCGACACCGCCAACGCCCAGATCATCGACTTACAGGAATACC
GGGAGGCAATAGACCATGAACGCAATCGACAGAGTGAAGAAATCCAGAGGCATCAACG
AGTTAGCGGAGCAGATCGAACCGCTGGCCCAGAGCATGGCGACACTGGCCGACGAAG
CCCGGCAGGTCATGAGCCAGACCCAGCAGGCCAGCGAGGCGCAGGCGGCGGAGTGG
CTGAAAGCCCAGCGCCAGACAGGGGCGGCATGGGTGGAGCTGGCCAAAGAGTTGCGG
GAGGTAGCCGCCGAGGTGAGCAGCGCCGCGCAGAGCGCCCGGAGCGCGTCGCGGG
GGTGGCACTGGAAGCTATGGCTAACCGTGATGCTGGCTTCCATGATGCCTACGGTGGT
GCTGCTGATCGCATCGTTGCTCTTGCTCGACCTGACGCCACTGACAACCGAGGACGGC
TCGATCTGGCTGCGCTTGGTGGCCCGATGAAGAACGACAGGACTTTGCAGGCCATAGG
CCGACAGCTCAAGGCCATGGGCTGTGAGCGCTTCGATATCGGCGTCAGGGACGCCAC
CACCGGCCAGATGATGAACCGGGAATGGTCAGCCGCCGAAGTGCTCCAGAACACGCC
ATGGCTCAAGCGGATGAATGCCCAGGGCAATGACGTGTATATCAGGCCCGCCGAGCAG
GAGCGGCATGGTCTGGTGCTGGTGGACGACCTCAGCGAGTTTGACCTGGATGACATGA
AAGCCGAGGGCCGGGAGCCTGCCCTGGTAGTGGAAACCAGCCCGAAGAACTATCAGG
CATGGGTCAAGGTGGCCGACGCCGCAGGCGGTGAACTTCGGGGGCAGATTGCCCGGA
CGCTGGCCAGCGAGTACGACGCCGACCCGGCCAGCGCCGACAGCCGCCACTATGGC
CGCTTGGCGGGCTTCACCAACCGCAAGGACAAGCACACCACCCGCGCCGGTTATCAG
CCGTGGGTGCTGCTGCGTGAATCCAAGGGCAAGACCGCCACCGCTGGCCCGGCGCTG
GTGCAGCAGGCTGGCCAGCAGATCGAGCAGGCCCAGCGGCAGCAGGAGAAGGCCCG
CAGGCTGGCCAGCCTCGAACTGCCCGAGCGGCAGCTTAGCCGCCACCGGCGCACGG
CGCTGGACGAGTACCGCAGCGAGATGGCCGGGCTGGTCAAGCGCTTCGGTGATGACC
TCAGCAAGTGCGACTTTATCGCCGCGCAGAAGCTGGCCAGCCGGGGCCGCAGTGCCG
AGGAAATCGGCAAGGCCATGGCCGAGGCCAGCCCAGCGCTGGCAGAGCGCAAGCCC
GGCCACGAAGCGGATTACATCGAGCGCACCGTCAGCAAGGTCATGGGTCTGCCCAGC
GTCCAGCTTGCGCGGGCCGAGCTGGCACGGGCACCGGCACCCCGCCAGCGAGGCAT
GGACAGGGGCGGGCCAGATTTCAGCATGTAGTGCTTGCGTTGGTACTCACGCCTGTTA
TACTATGAGTACTCACGCACAGAAGGGGGTTTTATGGAATACGAAAAAAGCGCTTCAGG
GTCGGTCTACCTGATCAAAAGTGACAAGGGCTATTGGTTGCCCGGTGGCTTTGGTTATA
CGTCAAACAAGGCCGAGGCTGGCCGCTTTTCAGTCGCTGATATGGCCAGCCTTAACCT
TGACGGCTGCACCTTGTCCTTGTTCCGCGAAGACAAGCCTTTCGGCCCCGGCAAGTTT
CTCGGTGACTGATATGAAAGACCAAAAGGACAAGCAGACCGGCGACCTGCTGGCCAGC
CCTGACGCTGTACGCCAAGCGCGATATGCCGAGCGCATGAAGGCCAAAGGGATGCGT
CAGCGCAAGTTCTGGCTGACCGACGACGAATACGAGGCGCTGCGCGAGTGCCTGGAA
GAACTCAGAGCGGCGCAGGGCGGGGGTAGTGACCCCGCCAGCGCCTAACCACCAACT
GCCTGCAAAGGAGGCAATCAATGGCTACCCATAAGCCTATCAATATTCTGGAGGCGTTC
GCAGCAGCGCCGCCACCGCTGGACTACGTTTTGCCCAACATGGTGGCCGGTACGGTC
GGGGCGCTGGTGTCGCCCGGTGGTGCCGGTAAATCCATGCTGGCCCTGCAACTGGCC
GCACAGATTGCAGGCGGGCCGGATCTGCTGGAGGTGGGCGAACTGCCCACCGGCCC
GGTGATCTACCTGCCCGCCGAAGACCCGCCCACCGCCATTCATCACCGCCTGCACGCC
CTTGGGGCGCACCTCAGCGCCGAGGAACGGCAAGCCGTGGCTGACGGCCTGCTGATC
CAGCCGCTGATCGGCAGCCTGCCCAACATCATGGCCCCGGAGTGGTTCGACGGCCTC
AAGCGCGCCGCCGAGGGCCGCCGCCTGATGGTGCTGGACACGCTGCGCCGGTTCCA
CATCGAGGAAGAAAACGGCCAGCGGCCCCATGGCCCAGGTCATCGGTCGCATGGAGGC
CATCGCCGCCGATACCGGGTGCTCTATCGTGTTCCTGCACCATGCCAGCAAGGGCGCG
GCCATGATGGGCGCAGGCGACCAGCAGCAGGCCAGCCGGGGCAGCTCGGTACTGGT
CGATAACATCCGCTGGCAGTCCTACCTGTCGAGCATGACCAGCGCCGAGGCCGAGGA
ATGGGGTGTGGACGACGACCAGCGCCGGTTCTTCGTCCGCTTCGGTGTGAGCAAGGC
CAACTATGGCGCACCGTTCGCTGATCGGTGGTTCAGGCGGCATGACGGCGGGGTGCT
CAAGCCCGCCGTGCTGGAGAGGCAGCGCAAGAGCAAGGGGGTGCCCCGTGGTGAAG
CCTAAGAACAAGCACAGCCTCAGCCACGTCCGGCACGACCCGGCGCACTGTCTGGCC
CCCGGCCTGTTCCGTGCCCTCAAGCGGGGCGAGCGCAAGCGCAGCAAGCTGGACGTG
ACGTATGACTACGGCGACGGCAAGCGGATCGAGTTCAGCGGCCCGGAGCCGCTGGGC
GCTGATGATCTGCGCATCCTGCAAGGGCTGGTGGCCATGGCTGGGCCTAATGGCCTAG
TGCTTGGCCCGGAACCCAAGACCGAAGGCGGACGGCAGCTCCGGCTGTTCCTGGAAC
CCAAGTGGGAGGCCGTCACCGCTGATGCCATGGTGGTCAAAGGTAGCTATCGGGCGC
TGGCAAAGGAAATCGGGGCAGAGGTCGATAGTGGTGGGGCGCTCAAGCACATACAGG
ACTGCATCGAGCGCCTTTGGAAGGTATCCATCATCGCCCAGAATGGCCGCAAGCGGCA
GGGGTTTCGGCTGCTGTCGGAGTACGCCAGCGACGAGGCGGACGGGCGCCTGTACGT
GGCCCTGAACCCCTTGATCGCGCAGGCCGTCATGGGTGGCGGCCAGCATGTGCGCAT
CAGCATGGACGAGGTGCGGGCGCTGGACAGCGAAACCGCCCGCCTGCTGCACCAGC
GGCTGTGTGGCTGGATCGACCCCGGCAAAACCGGCAAGGCTTCCATAGATACCTTGTG
CGGCTATGTCTGGCCGTCAGAGGCCAGTGGTTCGACCATGCGCAAGCGCCGCCAGCG
GGTGCGCGAGGCGTTGCCGGAGCTGGTCGCGCTGGGCTGGACGGTAACCGAGTTCG
CGGCGGGCAAGTACGACATCACCCGGCCCAAGGCGGCAGGCTGACCCCCCCCACTCT
ATTGTAAACAAGACATTTTTTATCTTTTATATTCAATGGCTTATTTTCCTGCTAATTGGTAA
TACCATGAAAAATACCATGCTCAGAAAAGGCTTAACAATATTTTGAAAAATTGCCTACTG
AGCGCTGCCGCACAGCTCCATAGGCCGCTTTCCTGGCTTTGCTTCCAGATGTATGCTCT
CCTCCGGAGAGTACCGTGACTTTATTTTCGGCACAAATACAGGGGTCGATGGATAAATA
CGGCGATAGTTTCCTGACGGATGATCCGTATGTACCGGCGGAAGACAAGCTGCAAACC
TGTCAGATGGAGATTGATTTAATGGCGGATGTGCTGAGAGCACCGCCCCGTGAATCCG
```

FIG. 11 (Continued)

```
CAGAACTGATCCGCTATGTGTTTGCGGATGATTGGCCGGAATAAATAAAGCCGGGCTTA
ATACAGATTAAGCCCGTATAGGGTATTATTACTGAATACCAAACAGCTTACGGAGGACG
GAATGTTACCCATTGAGACAACCAGACTGCCTTCTGATTATTAATATTTTTCACTATTAAT
CAGAAGGAATAACCATGAATTTTACCCGGATTGACCTGAATACCTGGAATCGCAGGGAA
CACTTTGCCCTTTATCGTCAGCAGATTAAATGCGGATTCAGCCTGACCACCAAACTCGA
TATTACCGCTTTGCGTACCGCACTGGCGGAGACAGGTTATAAGTTTTATCCGCTGATGA
TTTACCTGATCTCCCGGGCTGTTAATCAGTTTCCGGAGTTCCGGATGGCACTGAAAGAC
AATGAACTTATTTACTGGGACCAGTCAGACCCGGTCTTTACTGTCTTTCATAAAGAAACC
GAAACATTCTCTGCACTGTCCTGCCGTTATTTTCCGGATCTCAGTGAGTTTATGGCAGG
TTATAATGCGGTAACGGCAGAATATCAGCATGATACCAGATTGTTTCCGCAGGGAAATT
TACCGGAGAATCACCTGAATATATCATCATTACCGTGGGTGAGTTTTGACGGGATTTAA
CCTGAACATCACCGGAAATGATGATTATTTTGCCCCGGTTTTTACGATGGCAAAGTTTCA
GCAGGAAGGTGACCGCGTATTATTACCTGTTTCTGTACAGGTTCATCATGCAGTCTGTG
ATGGCTTTCATGCAGCACGGTTTATTAATACACTTCAGCTGATGTGTGATAACATACTGA
AATAAATTAATTAATTCTGTATTTAAGCCACCGTATCCGGCAGGAATGGTGGCTTTTTTTT
TATATTTTAACCGTAATCTGTAATTTCGTTTCAGACTGGTTCAGGATCACTGTACGATAAT
GCCCCCGCAGTTTGGTAATACCCTTAATAAAAAAGAAACAGCAAAGACTGACAGCAATA
ATAATAAAGTAAGCAGTAACAATAATATTAACAACACCAGATGCAGTTATAATAATAGTAT
TTAAGACACCAGAAAGACTGCTGCGACAGTCATTTTGAACAACACCAAAATGCCGTAAA
GGCAGTAGTAACAACACCAGTGAAAACATCACGATAGCATAGTGATATGCCTGAGTGTG
TGTAATTAAACAATAAATAAACCGCCATATATAACAGAAGATAGTATTCTGAATGGCATG
CTTTTCTGTTCAGTATAAACATATCATCCCGGTTGGTATAAGGATGATATATAATAAGTTA
AGCTGAACACATATTTATTTTGGTTTTATTTTACAAATAAAGTAAGACGATCCGTTAAGTC
AAAGCGGGGTATATTTATTATACCCTGCTTTTTTATTTGTCCGCCGGGCGCGGATAATG
GATCAGATTATGCAGTGTCACAATGGCCTTACCGGGATTGGCGTAAGCGTGCGGGATA
TCCGCATGGAAGCGCAGGGATTCCCCGGCAGAAACGGTGTGCCACTCATCCCCCAGC
CGCAGTTGTAATGCGCCTTCCAGTACAATGACATGTTCTCTGGTTCTGAAATCCATCCCT
GTCGGTGTTGCTTATGCAGTCTGGTCGGGACTCGGCGTCGTCATAATTACAGCCATTGC
CTGGTTGCTTCATGGGCAAAAGCTTTATGCTTGTAAACCGTTTTGTGAAAAAATTTTTAA
AATAAAAAAGGGGACCTCTAGGGTCCCCAATTAATTAGTAATATAATCTATTAAAGGTCA
TTCAAAAGGTCATCCACCGGATCCCACCGCGGTGGCGGCCGTCTAACGAAGAAGAGAG
CTAGATTGATTTGGAGCGTGAAGAGTCACCCCTCTTTTCCTCTTGCAAGCCCTCAAGTC
CACTCGACCAGAATGGGTGTAGATATTCATCTTCTCCCCTCTAGCAAAGCCCACTAGAG
TCACCCCTAGCTCTTGGGCTGTCTTGATTCCAAGAAAGGTTGCTGCTGCCCTAGAGACA
ATCATGGGAATGTTGTGCATGACAGCTTTAACCACCATCTCCATGGAGAGTCTTCCGCT
CACCACTAGCACAGCCTTCTCTGTATCTATTCTCCCTAGCCTGGCTTTACCCATCACCTT
ATCAATTGCATTATGACGACCAATATCCTCAGCCGTGATCTTGCTTCCATCTTCTAAGAG
AAGGGAGGCTTTATGAACGCAGCCTGTCTCATGAAAGAGATGGCTGCTCATCTCAAACT
CTTCCATCCCTTCCCAGATTCTCTCCAAAGAAATCTGCATGGGAGTAGCGATGAACTTT
CTTAGGACATTGCCTTCAAGATTCCCCGTCACTCCGACACAACAACCTGAAGTGAGTGT
CTTCTCTTTGAAGAGATTGGTGATGTTCTCATGGTTGATGAGAGCCTCTACATAGACAGA
GCTCCCATCAGAAGAGATTTGAACACTCTTTAAGTCTTCGATCTTCTCAATCACCCCCTC
ACTCATCAAGAAGCCCACCGCATGAGCATCTTGATCGGAAGGAAGAGAGACATCATGGAC
ATAAGCTTGGTGCCATTAAGATAGAGAGAGATTCTCTCCTCTTTGATCACCACATCTTCC
TCCTCGGCGAGCACTCTCTGATCGCCGATTCGTTCAATCACCACCTTTTTAACAAATCTA
TCGGTGTGTCTCATACTTTCCCCTCCGCCTGCAACTCTTTATAGTAGAAACTATGAAGAA
TCGCTACCTCCTCCTTCACCCATATGACCATCTAGGATGGAGTGCAATGCACCCTCAATC
GCAAAGGCTGCCATATAGATGTGAGTCATAAGGAGAGCCACCACAGCAAACCCCACTA
CATTGTGCAAGATCGCCATGAGTCTTAGGGTCTCAATATTGCCCTCTTGGAAGAACATC
ACATAGCCACTATAGACCATGAAGAATCCTCCCATCGTGCAGACCCAGAACCACATCTT
CTGACCCGCATTGAATTTGCCTGCAGGAATAGGTCTCTTCACCTTGCTTAGATACCCTC
CAAGAATGAGCATCCAGTCGATGTCATACATCTTAAAGAGAGCGTGCTTCACCCACATG
ATGAACATGAGGGGACCAAAGATCGCAAAGATGATCGTGGCTAATCCATGCACATCTCT
AGCGAATCGAATAAAAGCTCCACCCCCTAGGGCATCTCCAAAGACCATCAGAAGTCCTG
TGATGCAAAGAAGCACAAAGGGAATCCCTGCAATCCAGTGCACCATGATGTTGAAGGT
GTTAAAGACCTTGATCTTCTTCCCCTCATGAGAGAATCGCTTGGGTCCAATCACCATATA
GTGACCTAGGAAGACCAAAGGGATAGCGATGATGATCGCTAGGAAGATAAGAGCAAAG
TAACCACTTTGCAAGAAGGTGAAGAGCTCTCCTAATCCTCCTATTCCTCCAATCTCTCCA
AGACCTAGAATCCCTCCACTTCCCCAAGTGGGGATTGCCTCAATCATGGGCTTTCCATA
GATTTGGGTGTTGTAGCTGAAATCCAAGGGCTCCTTGAGATTCTCAGAAGCTTGTGCCC
CCAAGGCTCCCAGAAGGGAGAGGAGGGGCAATAGAGGCTTTTTCATTCTTAATCCTTGT
AGGCTTGTGACCAGGTGTAAGGAACACTGGCTGTTCCACTGCCTCGCTTGAGCACTCT
CTCACGAATGATGAGCGAGATGCTATCAGAATCTCCTGCTAGGAGTGCCTTGGTGGAG
CACATCGCTGCACATACAGGGACTTTGCCCTCAGCGATACGATTCTGTCCATAGAGCTT
ATACTCCTTCTCGCTGTGAGTCTCTTCAGGACCTCCAGCACAGAAGGTGCACTTATCCA
TAGGTCCTCTTGAACCAAAGATTCCACTCTTGGGGAATTGAGGAGCACCAAAGGGGCA
GGCATAGAGGCAGTAACCGCATCCAATGCACTTCTCTTTGTCATGCAATACAATCCCAT
CGGCTCGAACATAGAAGCAGTCCACTGGGCAGACCTGAGCACAAGGGGCATCAGAGC
AGTGCATGCAGGCAATAGAGAGGGATTTCTCTTTGCCTACAAGACCTTCATTGAGGGTC
ACCACTCTTCTTCGGTTGACTCCCACAGGAAGGTGATGGGCCTCTTTACAAGCCACATC
ACATCCATGACAATCAATACATCTAGCCTCATCACAATAGAACTTGACTCTAGCTTGACT
TTCCATGCTTCACCCCCTACGCTTTTTCGATGCGGCAGAGGCCGCACTTGGTTTCAGGA
GTACTGGTGTTGATGTCGTATGCATCACTTGTGATGGTATTGCATGATTCACCAATAACA
TAAGGCTCTGTGCCTGCAATATGATACGGAACCAGTGACTCTCCTTGATACATTCCTCC
```

FIG. 11 (Continued)

| | | | |
|---|---|---|---|
| | | | GAAATTCTGGGGGAGGAAAACACTTGTTTTGTTGACCTTGTAGCTATGTCTCGCTTTCAC |
| | | | GAGAATCTTTGCCCCATTGGTGCCGTGCACCCAAACCATGTCACCATGCTTCACGCCTA |
| | | | AATCCGTGGCTGTTTCGGGATGAATCTCCACAAACATCTCAGGCTGAACCTCGGCGAG |
| | | | GTAATGAGCTGATCTTGTCTCTGTGCCTGTGCCAAACTGTGCTACTAGTCGTCCAGAAA |
| | | | GCATATTAAGCGGGAACTCTTTGGTCCAATCTTTCTCTTTTTGGCGGCTCTCATAGCGAA |
| | | | TATTTGCCCTAAAGTGGTTGGGCTTGTCTTTGAAGGTTGGATATTGGCTAATGAGATCGT |
| | | | GTCGAATTGTGTAGATGGGTTCACGGTGTTTAGGAATCTGATCCGTCCACTCCCAAACA |
| | | | ATCGCTCTAGCTCTACCATTACCCATAGGGGAGAGACCTGCGGCGAGTGCTTTTTCAAC |
| | | | CAAGATATTGGTGGTGTCAGTCGCCCATGTCTTGCCTGCCACTTTGGCTTTTTCCTCTTC |
| | | | GGTGAGGGCGATTCCAGTGATAGCTTCGACATTTTTATCGGTGATCATGCTATGACCGC |
| | | | CCTTGAATTTTGAGCCGGGCAAAGAGCTGTCCTGGCTGGCCAACAAACTTTCTCCTGTG |
| | | | GGTGACACATCACCCCATCGAACCCTAAAGCCAAGACCTCCATCCATTACAGGGATGCT |
| | | | GTCATCCCATAGATTTGGTGTTCCAGGATGCTTTTCGCTCCAGCAAGGCCAAGGAAGAC |
| | | | CATAGTATTCGCCTTTGACGGGGCCGCCCTTTCCTCTGAGGGTGAACTTATCAAACATA |
| | | | TGCCAGTTTTCTGCATGAGCCTTGAGTCGTTCTGGAGTTCTGCCTTGGAAGCCGACAGT |
| | | | TCGTATAGCCTTGGCCACCTCTCTAGTCGCATCATCGGGCCATACAAAGTTTCCTTTGC |
| | | | CATCCCCCAAAGAGCGAGTGTACTCCTCATAGAATCCAAGTCGCTTAGCTAAATCAAAG |
| | | | AGAATCTCTTCGTCAGGTCGACACTCAAAGAGTGGCTTCATAACCATGGATCGCCACTG |
| | | | ATAGCTTCGATTCGTCGCTGCGACTCTTCCGCTGGTCTCCATCTGTGTGGCGGCAGGA |
| | | | AGGATATAGAGATTATCTTTTCGGTTGGTGAGGGCGGCTGCATCATTGAAATAGGGATC |
| | | | AAAAAAGACGACTAAATCCATCTTGTCTAGAGCGTCTTTGGTGGTATCCACGCGTGCGA |
| | | | TCGTAGAGATTCCGCTTCCCACGACAATCAAGGATCGAAGTTTAGTGCCTGCATTGTGG |
| | | | GGGATGTTCTCCTCTTCAGTCACCCCATATCTCCATGTGGATACACTGAAACCTTTTTA |
| | | | TGCATCATATCAGGGGTCTTAAAGCGTTTTTGCATTGCTTCGAAATCCACTTTCCAGATT |
| | | | CCACAGAAGTGATTCCATGCATTTTTGTCTAACCCATAATAGCCAGGAAGACTGTCGGC |
| | | | TAGGTTGCCCATGTCCGTCGCGCCTTGGACATTGTCATGACCTCGTAAAACGTTAGTGC |
| | | | CTCCACCTCGTTTGCCAATGTTTCCAAGAATCATCTGTAAAATAGGGGCCAAACGAGTG |
| | | | TTGCTTGTACCTGTGGTGTGCTGGGTGAGACCCATCCCCCAGATCAGTGAAGCAGGCT |
| | | | TGGCTTTAGCGAAGATCTCCGTGATCTCAATAAGTTGTTGGGCGGGCACGCCTGTGAC |
| | | | CTCTTCGACCACTTCAGGGGTGTACTGTTCGCACTCTTTAAGAATCTCTTCGTAGCCAAA |
| | | | TAGGCGTTGTCGAATAAATTCTTTATCTTCTAGTCCATTTTTTACAATATGGCGAATCATC |
| | | | CCATACATGAAGGCGACATCCGTGCCATTGCGCAATCTCACATAGTGATCGGCTTTAGT |
| | | | TGCTGTTCGACTGAAGTGGGGATCCACAACGATGATTTTTGCTCCTGCCTCTTTAGCGC |
| | | | GCAAGATATGCACCATGCCTACAGGGTGATTCACTGCGGGATTTCCACCAATGATAAAA |
| | | | ATCGCCTTGGAGTGCATCATGTCTGCCAAGTGATTGGTCATACCGCCATATCCAAGGGT |
| | | | ATTGGAGACTCCAGCAACTGTTGGGGCATGGCAGATTCGTGCGATGGTATCGAGATTG |
| | | | TTGGTGCCAAAAAAGGCGGCAAACTTTCTAAATAATAGGATTGTTCAATCGAACACTTG |
| | | | GAGCCGCCAATGAACATGACGCTATCAGGGCCCATATTTTTGGGTGAGATCCTGAAGCT |
| | | | GCTTGGCAATCTTATCCATGGCGCTATCCCATGAAGTTTTACGCCATTTTCCGCCAACTT |
| | | | TCTCAATGGGGTATCGAAGTCTTGTTTCGCTTCGAGCCTTATCAATCATATCGGCGCCC |
| | | | TTGCAGCAGTGACCCCCTTGACTAATGGGGTGATCTTGAGCGACCTCTTGGCGTACCC |
| | | | ATACACCATCGACCACTTCCGCTATAATTCCACATCCGACCGAGCAATAGGTGCAAATC |
| | | | GTTTTTACCTTTTTGGACACTGGGTATTTTTCGATTAACTCTTGTTTTGTTGCAGGTCTAA |
| | | | GCACTTTGCTTTGGTCGGAGCCAACCGCTTGACTCACGCCTGCGACTCCTGCTAAAGC |
| | | | CGACATCTTTAGGAACTTTCTTCGATCGTTCCCGCGTCCGCTTAACGCTTCACTCATACA |
| | | | TCACCTCATAAAATAAATTAAAAAATAATAAAAACTAATGTTTCGCATTATAGGACAAAAG |
| | | | ATACCTAAAAAATGTTATCTAGATCAAATTATTGGAAAATATATGAAAATAATTTTTGTTTA |
| | | | AAAAGCGAACGACATTAGTATTTTTCATAAAAATACGTACATTGTTATCCGTCGCTATTTA |
| | | | GGTACCGGGCCCGACGTCAGGCCTC |
| 21 | 20 | Lactate Dehydrogenase DNA (ldh) from DD1 | TTGACAAAATCAGTATGTTTAAATAAGGAGCTAACTATGAAAGTTGCCGTTTACAGTACT |
| | | | AAAAATTATGATCGCAAACATCTGGATTTGGCGAATAAAAAATTTAATTTTGAGCTTCATT |
| | | | TCTTTGATTTTTTACTTGATGAACAAACCGCGAAAATGGCGGAGGGCGCCGATGCCGTC |
| | | | TGTATTTTCGTCAATGATGATGCGAGCCGCCCGGTGTTAACAAAGTTGGCGCAAATCGG |
| | | | AGTGAAAATTATCGCTTTACGTTGTGCCGGTTTTAATAATGTGGATTTGGAGGCGGCAA |
| | | | AAGAGCTGGGATTAAAAGTCGTACGGGTGCCTGCGTATTCGCCGGAAGCCGTTGCCGA |
| | | | GCATGCGATCGGATTAATGCTGACTTTAAACCGCCGTATCCATAAGGCTTATCAGCGTA |
| | | | CCCGCGATGCGAATTTTTCTCTGGAAGGATTGGTCGGTTTTAATATGTTCGGCAAAACC |
| | | | GCCGGAGTGATTGGTACGGGAAAAATCGGCTTGGCGGCTATTCGCATTTTAAAAGGCTT |
| | | | CGGTATGGACGTTCTGGCGTTTGATCCTTTTAAAAATCCGGCCGGCGGAAGCGTTGGGC |
| | | | GCAAAATATGTCGGTTTAGACGAGCTTTATGCAAAATCCCATGTTATCACTTTGCATTGC |
| | | | CCGGCTACGGCGGATAATTATCATTTATTAAATGAAGCGGCTTTTAATAAAATGCGCGAC |
| | | | GGTGTAATGATTATTAATACCAGCCGCGGCGTTTTAATTGACAGCCGGCGGCAATCGA |
| | | | AGCGTTAAAACGGCAGAAAATCGGCGCTCTCGGTATGGATGTTTATGAAAATGAACGGG |
| | | | ATTTGTTTTTCGAGGATAAATCTAACGATGTTATTACGGATGATGTATTCCGTCGCCTTT |
| | | | CTTCCTGTCATAATGTGCTTTTTACCGGTCATCAGGCGTTTTAACGGAAGAAGCGCTG |
| | | | AATAATATCGCCGATGTGACTTTATCGAATATTCAGGCGGTTTCCAAAAATGCAACGTGC |
| | | | GAAAATAGCGTTGAAGGC |
| 22 | 21 | Lactate Dehydrogenase Prot. (Ldh) from DD1 | MTKSVCLNKELTMKVAVYSTKNYDRKHLDLANKKFNFELHFFDFLLDEQTAKMAEGADAVC IFVNDDASRPVLTKLAQIGVKIIALRCAGFNNVDLEAAKELGLKVVRVPAYSPEAVAEHAIGLM LTLNRRIHKAYQRTRDANFSLEGLVGFNMFGKTAGVIGTGKIGLAAIRILKGFGMDVLAFDPF KNPAAEALGAKYVGLDELYAKSHVITLHCPATADNYHLLNEAAFNKMRDGVMIINTSRGVLID SRAAIEALKRQKIGALGMDVYENERDLFFEDKSNDVITDDVFRRLSSCHNVLFTGHQAFLTE EALNNIADVTLSNIQAVSKNATCENSVEG* |

FIG. 11 (Continued)

| 23 | 22 | Pyruvate formate lyase DNA (pflD) from DD1 | ATGGCTGAATTAACAGAAGCTCAAAAAAAAGCATGGGAAGGATTCGTTCCCGGTGAATG<br>GCAAAACGGCGTAAATTTACGTGACTTTATCCAAAAAAACTATACTCCGTATGAAGGTGA<br>CGAATCATTCTTAGCTGATGCGACTCCTGCAACCAGCGAGTTGTGGAACAGCGTGATG<br>GAAGGCATCAAAATCGAAAACAAAACTCACGCACCTTTAGATTTCGACGAACATACTCC<br>GTCAACTATCACTTCTCACAAGCCTGGTTATATCAATAAAGATTTAGAAAAAATCGTTGG<br>TCTTCAAACAGACGCTCCGTTAAAACGTGCAATTATGCCGTACGGCGGTATCAAAATGA<br>TCAAAGGTTCTTGCGAAGTTTACGGTCGTAAATTAGATCCGCAAGTAGAATTTATTTTCA<br>CCGAATATCGTAAAACCCATAACCAAGGCGTATTCGACGTTTATACGCCGGATATTTAC<br>GCTGCCGTAAATCAGGCGTGTTAACCGGTTTACCGGATGCTTACGGTCGTGGTCGTATT<br>ATCGGTGACTACCGTCGTTTAGCGGTATACGGTATTGATTACCTGATGAAAGATAAAAAA<br>GCCCAATTCGATTCATTACAACCGCGTTTGGAAGCGGGCGAAGACATTCAGGCAACTAT<br>CCAATTACGTGAAGAAATTGCCGAACAACACCGCGCTTTAGGCAAAATCAAAGAAATGG<br>CGGCATCTTACGGTTACGACATTTCCGGCCCTGCGACAAACGCACAGGAAGCAATCCA<br>ATGGACATATTTTGCTTATCTGGCAGCGGTTAAATCACAAAACGGTGCGGCAATGTCAT<br>TCGGTCGTACGTCTACATTCTTAGATATCTATATCGAACGTGACTTAAAACGCGGTTTAA<br>TCACTGAACAACAGGCGCAGGAATTAATGGACCACTTAGTAATGAAATTACGTATGGTT<br>CGTTTCTTACGTACGCCGGAATACGATCAATTATTCTCAGGCGACCCGATGTGGGCAAC<br>CGAAACTATCGCCGGTATGGGCTTAGACGGTCGTCCGTTGGTAACTAAAAACAGCTTCC<br>GCGTATTACATACTTTATACACTATGGGTACTTCTCCGGAACCAAACTTAACTATTCTTTG<br>GTCCGAACAATTACCTGAAGCGTTCAAACGTTTCTGTGCGAAAGTATCTATTGATACTTC<br>CTCCGTACAATACGAAAATGATGACTTAATGCGTCCTGACTTCAACAACGATGACTATGC<br>AATCGCATGCTGCGTATCACCGATGGTCGTAGGTAAACAAATGCAATTCTTCGGTGCGC<br>GCGCAAACTTAGCTAAAACTATGTTATACGCAATTAACGGCGGTATCGATGAGAAAAAT<br>GGTATGCAAGTCGGTCCTAAAACTGCGCCGATTACAGACGAAGTATTGAATTTCGATAC<br>CGTAATCGAACGTATGGACAGTTTCATGGACTGGTTGGCGACTCAATATGTAACCGCAT<br>TGAACATCATCCACTTCATGCACGATAAATATGCATATGAAGCGGCATTGATGGCGTTC<br>CACGATCGCGACGTATTCCGTACAATGCTTGCGGTATCGCGGGTCTTTCCGTGGCTG<br>CGGACTCATTATCCGCAATCAAATATGCGAAAGTTAAACCGATTCGCGGCGACATCAAA<br>GATAAAGACGGTAATGTCGTGGCCTCGAATGTTGCTATCGACTTCGAAATTGAAGGCGA<br>ATATCCGCAATTCGGTAACAATGATCCGCGTGTTGATGATTTAGCGGTAGACTTAGTTG<br>AACGTTTCATGAAAAAAGTTCAAAAACACAAAACTTACCGCAACGCAACTCCGACACAAT<br>CTATCCTGACTATCACTTCTAACGTGGTATACGGTAAGAAAACCGGTAATACTCCGGAC<br>GGTCGTCGAGCAGGCGCGCCATTCGGACCGGGTGCAAACCCAATGCACGGTCGTGAC<br>CAAAAAGGTGCGGTTGCTTCACTTACTTCTGTGGCTAAACTTCCGTTCGCTTACGCGAA<br>AGACGGTATTTCATATACCTTCTCTATCGTACCGAACGCATTAGGTAAAGATGACGAAG<br>CGCAAAAACGCAACCTTGCCGGTTTAATGGACGGTTATTTCCATCATGAAGCGACAGTG<br>GAAGGCGGTCAACACTTGAATGTTAACGTTCTTAACCGTGAAATGTTGTTAGACGCGAT<br>GGAAAATCCGGAAAAATACCCGCAATTAACCATTCGTGTTTCAGGTTACGCGGTTCGTT<br>TCAACTCATTAACTAAAGAGCAACAACAAGACGTCATCACTCGTACGTTTACACAATCAA<br>TG |
| 24 | 23 | Pyruvate formate lyase Prot. (PflD) from DD1 | MAELTEAQKKAWEGFVPGEWQNGVNLRDFIQKNYTPYEGDESFLADATPATSELWNSVM<br>EGIKIENKTHAPLDFDEHTPSTITSHKPGYINKDLEKIVGLQTDAPLKRAIMPYGGIKMIKGSC<br>EVYGRKLDPQVEFIFTEYRKTHNQGVFDVYTPDILRCRKSGVLTGLPDAYGRGRIIGDYRRL<br>AVYGIDYLMKDKKAQFDSLQPRLEAGEDIQATIQLREEIAEQHRALGKIKEMAASYGYDISGP<br>ATNAQEAIQWTYFAYLAAVKSQNGAAMSFGRTSTFLDIYIERDLKRGLITEQQAQELMDHLV<br>MKLRMVRFLRTPEYDQLFSGDPMWATETIAGMLDGRPLVTKNSFRVLHTLYTMGTSPEP<br>NLTILWSEQLPEAFKRFCAKVSIDTSSVQYENDDLMRPDFNNDDYAIACCVSPMVVGKQMQ<br>FFGARANLAKTMLYAINGGIDEKNGMQVGPKTAPITDEVLNFDTVIERMDSFMDWLATQYVT<br>ALNIIHFMHDKYAYEAALMAFHDRDVFRTMACGIAGLSVAADSLSAIKYAKVKPIRGDIKDKD<br>GNVVASNVAIDFEIEGEYPQFGNNDPRVDDLAVDLVERFMKKVQKHKTYRNATPTQSILTIT<br>SNVVYGKKTGNTPDGRRAGAPFGPGANPMHGRDQKGAVASLTSVAKLPFAYAKDGISYTF<br>SIVPNALGKDDEAQKRNLAGLMDGYFHHEATVEGGQHLNVNVLNREMLLDAMENPEKYPQ<br>LTIRVSGYAVRFNSLTKEQQQDVITRTFTQSM |

US 8,877,466 B2

BACTERIAL CELLS HAVING A GLYOXYLATE SHUNT FOR THE MANUFACTURE OF SUCCINIC ACID

RELATED APPLICATIONS

This application claims benefit under 35 U.S.C. §119(a) of European application 08172793.5, filed Dec. 23, 2008.

SUBMISSION OF SEQUENCE LISTING

The Sequence Listing associated with this application is filed in electronic format via EFS-Web and hereby incorporated by reference into the specification in its entirety. The name of the text file containing the Sequence Listing is SEQUENCE_LISTING_13156_00312_ST25.txt. The size of the text file is 160 kb, and the text file was created on Dec. 21, 2009.

BACKGROUND OF THE INVENTION

Description of Related Art

The fermentative production of succinic acid (SA) from biomass has already drawn much attention because said acid represents an important constituent of synthetic resins or is a source of further valuable low-molecular chemical compounds, in particular tetrahydrofuran (THF), 1,4-butanediol (BDO), gamma-butyrolactone (GBL) and pyrrolidones (WO-A-2006/066839).

A SA-producing bacterium isolated from bovine rumen was described by Lee et al., 2002, Appl Microbiol Biotechnol 58, 663-668. The bacterium is a non-motile, non-spore-forming, mesophilic and capnophilic gram-negative rod or coccobacillus. Phylogenetic analysis based on the 16S rRNA sequence and physiological analysis indicated that the strain belongs to the genus *Mannheimia* as a novel species, and has been named *Mannheimia succiniciproducens* MBEL55E. Under 100% $CO_2$ conditions, it grows well in the pH range of 6.0-7.5 and produces SA, acetic acid and formic acid at a constant ratio of 2:1:1. When *M. succiniciproducens* MBEL55E was cultured anaerobically under $CO_2$-saturation with glucose as carbon source, 19.8 g/L of glucose were consumed and 13.3 g/L of SA were produced in 7.5 h of incubation.

A significant drawback of said organism is, however, its inability to metabolize glycerol, which, as a constituent of triacyl glycerols (TAGs), becomes readily available e. g. as byproduct in the transesterification reaction of Biodiesel production (Dharmadi et al., 2006, Biotech Bioeng 94: 821-829).

The fermentative production of SA from glycerol has been described in the scientific literature (Lee et al., 2001, Biotech Bioeng 72, 41-48; Dharmadi et al., 2006, Biotech Bioeng 94: 821-829) and with glycerol higher yields [mass of SA produced/mass of raw material consumed] than with common sugars like glucose were achieved (Lee et al., 2001, Biotech Bioeng 72, 41-48). However, the space time yield obtained with glycerol was substantially lower than with glucose (0.14 vs. 1.0 g SA/[L h]) and no crude glycerol was used.

Therefore, there is a need for further bacterial strains, which have the ability to produce organic acids, in particular SA, from glycerol. In particular, such strains should produce said acids with high productivity from glycerol, especially if crude glycerol e. g. from biodiesel production can be used without prior purification.

BRIEF SUMMARY OF THE INVENTION

The present invention is concerned with bacteria for the production of succinic acid. Specifically, it relates to a bacterial cell of the genus *Pasteurella* comprising a heterologous polypeptide having isocitrate lyase activity and a heterologous polypeptide having malate synthase activity. Further, the present invention contemplates a polynucleotide comprising a nucleic acid encoding a polypeptide having isocitrate lyase activity and a nucleic acid encoding a polypeptide having malate synthase activity. Finally, the present invention relates to the use of a bacterial cell of the invention for the manufacture of succinic acid.

The technical problem underlying this invention could be seen as the provision of means and methods for complying with the aforementioned needs. The technical problem is solved by the embodiments described in the claims and herein below.

BRIEF DESCRIPTION OF THE DRAWINGS

FIG. 11: The sequences of SEQ ID No: 1 to 21.

DETAILED DESCRIPTION OF THE INVENTION

Figure 1:
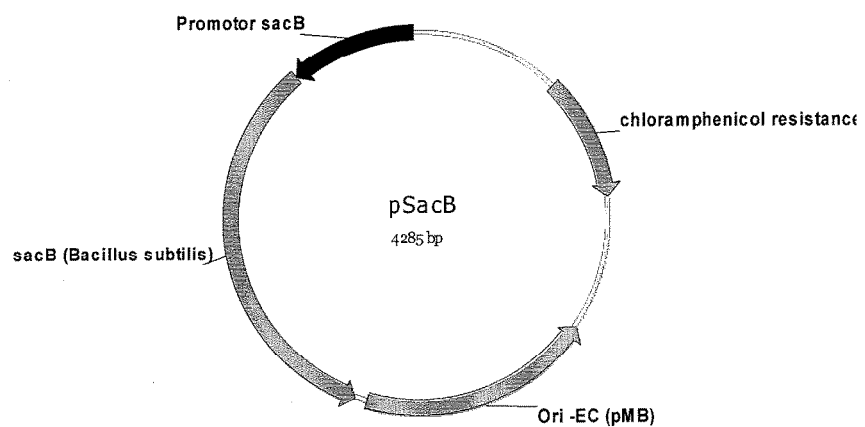
FIG. 1: A schematic map of plasmid pSacB.

The present invention, thus, relates to a bacterial cell of the genus *Pasteurella* comprising a heterologous polypeptide having isocitrate lyase activity and a heterologous polypeptide having malate synthase activity.

The term "bacterial cell" as used herein refers to a prokaryotic organism, i.e. a bacterium. Bacteria can be classified based on their biochemical and microbiological properties as well as their morphology. These classification criteria are well known in the art. The bacterial cell referred to in accordance with the present invention is from the genus of *Pasteurella*. The bacteria of the genus *Pasteurella* are gram-negative and facultative anaerobic. *Pasteurella* species are non-motile, pleimorphic and most often catalase- and oxidase-positive (Kuhnert and Christensen, 2008, ISBN 978-1-904455-34-9).

Preferably, the bacterial cell is a *Pasteurella* bacterial cell and, more preferably, a *Pasteurella* strain DD1 cell. Most preferably, the *Pasteurella* strain DD1 is the bacterial strain deposited under the Budapest Treaty with DSMZ (Deutsche Sammlung von Mikroorganismen and Zellkulturen, GmbH), Germany, having the deposit number DSM 18541.

*Pasteurella* bacteria can be isolated from the gastro-intestinal tract of animals and, preferably, mammals. The bacterial strain DD1, in particular, can be isolated from bovine rumen and is capable of utilizing glycerol (including crude glycerol) as a carbon source. Preferably, the said strain has the ability to produce SA from glycerol (including crude glycerol), in particular, under anaerobic conditions. Moreover, the *Pasteurella* strain DD1 exhibits at least one of the following additional metabolic characteristics:

a) production of SA from sucrose; in particular, under anaerobic conditions;
b) production of SA from D-fructose; in particular, under anaerobic conditions;
c) production of SA from D-galactose; in particular, under anaerobic conditions;
d) production of SA from D-mannose; in particular, under anaerobic conditions;
e) production of SA from D-glucose; in particular, under anaerobic conditions;
f) production of SA from D-xylose; in particular, under anaerobic conditions;
g) production of SA from L-arabinose; in particular, under anaerobic conditions;
h) no utilization of of xylitol, inositol and sorbitol;
i) growth both under aerobic and anaerobic conditions;
j) growth at initial glucose concentrations of 75 g/L or more;
k) ammonia tolerance.

In particular, said strain shows at least 2, 3, 4, 5, 6, 7, 8, 9, 10 or all of said metabolic characteristics.

Also preferably, the *Pasteurella* strain DD1 has a 16S rDNA having a nucleic acid sequence as shown in SEQ ID NO: 7 or a sequence which is at least 96, 97, 98, 99 or 99.9% identical thereto and/or a 23S rDNA having a nucleic acid sequence as shown in SEQ ID NO: 8 or a sequence which shows a sequence homology of at least 95, 96, 97, 98, 99 or 99.9% thereto.

The identity in percentage values referred to in connection with the various polypeptides or polynucleotides to be used for the bacterial cell of the present invention is, preferably, calculated as identity of the residues over the complete length of the aligned sequences, such as, for example, the identity calculated (for rather similar sequences) with the aid of the program needle from the bioinformatics software package EMBOSS (Version 5.0.0, emboss.sourceforge.net/what/) with the default parameters which are, i.e. gap open (penalty to open a gap): 10.0, gap extend (penalty to extend a gap): 0.5, and data file (scoring matrix file included in package): EDNAFUL.

The term "heterologous" as used herein refers to a polypeptide which does not naturally occur in the bacterial cell, i.e. which is not encoded by the endogenous bacterial genes or derived by posttranslational processing from a polypeptide precursor being encoded by the said bacterial genes. A heterologous polypeptide as referred to in accordance with the present invention, thus, can be exogenously introduced into the bacterial cell. Alternatively, the heterologous polypeptide is encoded by a heterologous polynucleotide which has been exogenously introduced into the bacterial cell. In this case, the heterologous polypeptide will be expressed from the heterologous polynucleotide. It will be understood that the heterologous polynucleotide, preferably, comprises in addition to an open reading frame nucleic acid sequence encoding the heterologous polypeptide further sequences which are required for gene expression in bacteria. Such sequences, preferably, include an expression control sequence, e.g., a promoter being active in *Pasteurella*, and a termination sequence. The heterologous polynucleotide encoding the heterologous polypeptide can be introduced episomally by transformation of an episomal plasmid comprising the heterologous polynucleotide or can be integrated into the bacterial genome by homologous recombination techniques. How to introduce and to achieve expression of heterologous polynucleotides in bacteria and, in particular, *Pasteurella* is well known to the person skilled in the art and described elsewhere in this specification in detail.

The bacterial cell of the present invention shall comprise a heterologous polypeptide having isocitrate lyase activity. Isocitrate lyase activity as meant herein refers to the capability of a polypeptide to convert isocitrate into succinate and glyoxylate. Polypeptides having isocitrate lyase activity are well known in the art (Robertson E F, 1987, Curr Microbiol 14, 347-350). The enzymatic activity can be determined, preferably, as described in Watanabe et al. (Watanabe et al., 2001, Biosci Biotechnol Biochem 65, 1095-1103) or in the accompanying examples.

Preferably, said heterologous polypeptide having isocitrate lyase activity is encoded by a polynucleotide comprising a nucleic acid selected from the group consisting of:

a) a nucleic acid having a nucleotide sequence as shown in SEQ ID NO: 1;
b) a nucleic acid encoding an amino acid sequence as shown in SEQ ID NO: 2;
c) a nucleic acid which is at least 70% identical to the nucleic acid of a) or b); and
d) a nucleic acid encoding an amino acid sequence which is at least 70% identical to the amino acid sequence encoded by the nucleic acid of a) or b).

The term "polynucleotide" as used in accordance with the present invention relates to a nucleic acid molecule which encodes a polypeptide having the aforementioned biological activity. A polynucleotide encoding a polypeptide having the aforementioned biological activity has been obtained in accordance with the present invention from *Salmonella typhimurium* or *Yersinia molaretii*. Thus, the polynucleotide, preferably, comprises the nucleic acid sequence shown in SEQ ID NO: encoding the polypeptide having an amino acid sequence as shown in SEQ ID NO: 2. It is to be understood that a polypeptide having an amino acid sequence as shown in SEQ ID NO: 2 may be also encoded due to the degenerated genetic code by other polynucleotides as well. Moreover, the term "polynucleotide" as used in accordance with the present invention further encompasses variants of the aforementioned specific polynucleotides. Said variants may represent orthologs, paralogs or other homologs of the polynucleotide of the present invention. The polynucleotide variants, preferably, comprise a nucleic acid sequence characterized in that the sequence can be derived from the aforementioned specific nucleic acid sequences shown in SEQ ID NO: 1 by at least one nucleotide substitution, addition and/or deletion whereby the variant nucleic acid sequence shall still encode a polypeptide having the activity as specified above. Variants also encompass polynucleotides comprising a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N.Y. (1989), 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA: DNA hybrids are preferably for example 0.1×SSC and 20° C. to 45° C., preferably between 30° C. and 45° C. The hybridization conditions for DNA: RNA hybrids are preferably, for example, 0.1×SSC and 30° C. to 55° C., preferably between 45° C. and 55° C. The abovementioned hybridization temperatures are determined for example for a nucleic acid with approximately 100 by (=base pairs) in length and a G+C content of 50% in the absence of formamide. The skilled worker knows how to determine the hybridization conditions required by referring to textbooks such as the textbook mentioned above, or the following textbooks: Sambrook et al., 1989, "Molecular Cloning", Cold Spring Harbor Laboratory; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, polynucleotide variants are obtainable by PCR-based techniques such as mixed oligonucleotide primer-based amplification of DNA, i.e. using degenerated primers against conserved domains of the polypeptides of the present invention. Conserved domains of the polypeptide of the present invention may be identified by a sequence comparison of the nucleic acid sequence of the polynucleotide or the amino acid sequence of the polypeptide of the present invention with sequences of other isocitrate lyases. Oligonucleotides suitable as PCR primers as well as suitable PCR conditions are described in the accompanying Examples. As a template, DNA or cDNA from bacteria, fungi, plants or animals may be used. Further, variants include polynucleotides comprising nucleic acid sequences which are at least 70%, at least 75%, at least 80%, at least 85%, at least 90%, at least 95%, at least 98% or at least 99% identical to the nucleic acid sequences shown in SEQ ID NO: 1. Moreover, also encompassed are polynucleotides which comprise nucleic acid sequences encoding amino acid sequences which are at least 70%, at least 75%, at least 80%, at least 85%, at least 90%, at least 95%, at least 98% or at least 99% identical to the amino acid sequences shown in SEQ ID NO: 2. The percent identity values are, preferably, calculated over the entire amino acid or nucleic acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (Feng & Doolittle, 1987, J Mol Evol 25, 351-360; Higgins & Sharp, 1989, Comput Appl Biosci 5, 151-153) or the programs Gap and BestFit (Needleman & Wunsch, 1970, J Mol Biol 48, 443-453; Smith & Waterman, 1981, J Mol Biol 147, 195-197), which are part of the GCG software packet [Genetics Computer Group, 575 Science Drive, Madison, Wis., USA 53711 (1991)], are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. It is to be understood that the aforementioned variant polynucleotides shall encode polypeptides having isocitrate lyase activity. A polynucleotide comprising a fragment of any of the aforementioned nucleic acid sequences is also encompassed as a polynucleotide of the present invention. The fragment shall encode a polypeptide which still has the activity as specified above. Accordingly, the polypeptide may comprise or consist of the domains of the polypeptide of the present invention conferring the said biological activity. A fragment as meant herein, preferably, comprises at least 50, at least 100, at least 250 or at least 500 consecutive nucleotides of any one of the aforementioned nucleic acid sequences or encodes an amino acid sequence comprising at least 20, at least 30, at least 50, at least 80, at least 100 or at least 150 consecutive amino acids of any one of the aforementioned amino acid sequences. The polynucleotides of the present invention either essentially consist of the aforementioned nucleic acid sequences or comprise the aforementioned nucleic acid sequences. Thus, they may contain further nucleic acid sequences as well. Specifically, the polynucleotides of the present invention may encode fusion proteins wherein one partner of the fusion protein is a polypeptide being encoded by a nucleic acid sequence recited above. Such fusion proteins may comprise as additional part so called "tags" which may serve as a detectable marker or as an auxiliary measure for purification purposes. Tags for the different purposes are well known in the art and comprise FLAG-tags, 6-histidine-tags, MYC-tags and the like. The polynucleotide, preferably, is DNA or RNA. The term encompasses single as well as double stranded polynucleotides. Moreover, comprised are also chemically modified polynucleotides including naturally occurring modified polynucleotides or artificial modified ones.

The bacterial cell of the present invention shall comprise a heterologous polypeptide having malate synthase activity. Malate synthase activity as meant herein refers to the capability of a polypeptide to convert glyoxylate into malate. This enzymatic reaction is dependent on acetyl-CoA. Polypeptides having malate synthase activity are well known in the art (Sundaram et al., 1980, Arch Biochem Biophys 199, 515-525). The enzymatic activity can be determined, preferably, as described in Eggerer & Klette, 1967, Eur J Biochem 1, 447-475 and in Durchschlag et al., 1981, Eur. J. Biochem 114, 255-262 or in the accompanying examples.

Preferably, said heterologous polypeptide having malate synthase activity is encoded by a polynucleotide comprising a nucleic acid selected from the group consisting of:
  a) a nucleic acid having a nucleotide sequence as shown in SEQ ID NO: 3;
  b) a nucleic acid encoding an amino acid sequence as shown in SEQ ID NO: 4;
  c) a nucleic acid which is at least 70% identical to the nucleic acid of a) or b); and
  d) a nucleic acid encoding an amino acid sequence which is at least 70% identical to the amino acid sequence encoded by the nucleic acid of a) or b).

The definitions of the term "polynucleotide" made above apply accordingly. Specifically, the polynucleotide shall comprise a nucleic acid sequence which encodes a polypeptide having the aforementioned biological activity. A polynucleotide encoding a polypeptide having the aforementioned biological activity has been obtained in accordance with the present invention from *Salmonella typhimurium* or *Yersinia molaretii*. Thus, the polynucleotide, preferably, comprises the nucleic acid sequence shown in SEQ ID NO: 3 encoding the polypeptide having an amino acid sequence as shown in SEQ ID NO: 4. It is to be understood that a polypeptide having an amino acid sequence as shown in SEQ ID NO: 4 may be also encoded due to the degenerated genetic code by other polynucleotides as well. The definitions of variant polynucleotides or polynucleotides comprising a fragment of the aforementioned polynucleotides made before apply accordingly to variant polynucleotides encoding a polypeptide having malate synthase activity.

The aforementioned heterologous polynucleotides may be introduced into the bacterial cell by transformation using a suitable vector. Suitable vectors, preferably, encompass phage or plasmid vectors as well artificial chromosomes, such as bacterial artificial chromosomes. Moreover, the term also relates to targeting constructs which allow for random or site-directed integration of the targeting construct into genomic DNA. Such target constructs, preferably, comprise DNA of sufficient length for either homologous or heterologous recombination with the bacterial genome. The vector, preferably, comprises at least one of the heterologous polynucleotides referred to herein above. It is to be understood that the vector may also comprise both heterologous polynucleotides referred to herein above and, more preferably, even a third polynucleotide as referred to herein below. Preferably, the vector further comprises selectable markers for propagation and/or selection in the bacterial cell. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerens. Alternatively, a vector may be introduced by heat shock or electroporation techniques. The vector, preferably, further comprises an expression control sequences allowing expression in the Pasteurella bacterial cells. Moreover, the vector, preferably, further comprise regulatory sequences ensuring initiation of transcription and, optionally, poly-A signals ensuring termination of transcription and stabilization of the transcript. Possible regulatory elements permitting expression in bacterial cells comprise, e.g., the lac, trp or tac promoters. Preferred vectors to be used for Pasteurella species are selected from the group consisting of: pSacB, pJFF224.

Pasteurella species and, in particular, strain DD1 naturally lack a glyoxylate metabolism. Advantageously, it has been found in the studies underlying the present invention that by introducing an isocitrate lyase in combination with a malate synthase, the production of SA can be significantly increased in a bacterial cell which naturally lacks these enzymes. Thus, by establishing a partial glyoxylate metabolism in such bacterial cells, a so called "glyoxylate shunt", the bacterial cells can significantly increase their SA production by converting acetyl-CoA into SA whereby losses due to $CO_2$ can be prevented. Such losses would normally occur within the citric acid cycle. In accordance with the present invention, it has been found that a bacterial cell as defined herein can be advantageously used for the manufacture of SA, preferably in an industrial scale.

In a preferred embodiment of the bacterial cell of the present invention, said bacterial cell further comprises a heterologous polypeptide having formate dehydrogenase activity.

The bacterial cell of the present invention shall comprise a heterologous polypeptide having formate dehydrogenase activity. Formate dehydrogenase activity as meant herein refers to the capability of a polypeptide to convert formate into $CO_2$. This enzymatic reaction yields redox-equivalents, i.e. NADH. Polypeptides having formate dehydrogenase activity are well known in the art (Ferry 1990, FEMS Microbiol Rev 7, 377-382). The enzymatic activity can be determined, preferably, as described in Müller et al., 1978, Eur J Biochem 83, 485-498 or in the accompanying Examples.

Preferably, said heterologous polypeptide having formate dehydrogenase activity is encoded by a polynucleotide comprising a nucleic acid selected from the group consisting of:

a) a nucleic acid having a nucleotide sequence as shown in SEQ ID NO: 5 or SEQ ID NO: 18;

b) a nucleic acid encoding an amino acid sequence as shown in SEQ ID NO: 6;

c) a nucleic acid which is at least 70% identical to the nucleic acid of a) or b); and d) a nucleic acid encoding an amino acid sequence which is at least 70% identical to the amino acid sequence encoded by the nucleic acid of a) or b).

The definitions of the term "polynucleotide" made above apply accordingly. Specifically, the polynucleotide shall comprise a nucleic acid sequence which encodes a polypeptide having the aforementioned biological activity. A polynucleotide encoding a polypeptide having the aforementioned biological activity has been obtained in accordance with the present invention from *Candida boidinii* or *Wolinella succinogenes*. Thus, the polynucleotide, preferably, comprises the nucleic acid sequence shown in SEQ ID NO: 5 encoding the polypeptide having an amino acid sequence as shown in SEQ ID NO: 6 or a polynucleotide as shown in SEQ ID NO: 18. It is to be understood that a polypeptide having an amino acid sequence as shown in SEQ ID NO: 6 may be also encoded due to the degenerated genetic code by other polynucleotides as well. The definitions of variant polynucleotides or polynucleotides comprising a fragment of the aforementioned polynucleotides made before apply accordingly to variant polynucleotides encoding a polypeptide having formate dehydrogenase activity.

It has been found in the studies underlying the present invention that the production of SA can even be more increased by further expressing a formate dehydrogenase in the bacterial cell.

In a further preferred embodiment of the bacterial cell of the present invention, said bacterial cell has reduced lactate dehydrogenase activity.

In yet a further preferred embodiment of the bacterial cell of the present invention, said bacterial cell has reduced lactate dehydrogenase and reduced pyruvate formate lyase activity.

The term "reduced lactate dehydrogenase activity" and "reduced lactate dehydrogenase and reduced pyruvate formate lyase activity" encompasses a modified bacterial cell which has no detectable lactate dehydrogenase activity or no detectable lactate dehydrogenase and no detectable pyruvate formate lyase activity. Moreover, the term encompasses a bacterial cell which has a significantly reduced lactate dehydrogenase activity or significantly reduced lactate dehydrogenase and reduced pyruvate lyase activity when compared to a bacterial cell exhibiting physiological lactate dehydrogenase activity levels or significantly reduced lactate dehydrogenase and pyruvate formate lyase activity levels when compared to a bacterial cell exhibiting physiological activity levels of said enzymes. Whether a reduction is significant can be determined by statistical methods well known to those skilled in the art. Bacterial cells being deficient in lactate dehydrogenase or being deficient in lactate dehydrogenase and pyruvate formate lyase activity may occur naturally, i.e. due to spontaneous mutations. A bacterial cell can be modified to lack or to have significantly reduced lactate dehydrogenase activity or significantly reduced lactate dehydrogenase and pyruvate formate lyase activity by various techniques. Preferably, such bacterial cells are obtainable by chemical treatment or radiation. To this end, bacterial cells will be treated by, e.g., a mutagenizing chemical agent, X-rays, or UV light. In a subsequent step, those bacterial cells which lack lactate dehydrogenase or lactate dehydrogenase and pyruvate formate lyase activity or which at least have a reduced lactate dehydrogenase or a reduced lactate dehydrogenase and pyruvate formate lyase activity activity will be selected. Bacterial cells are also obtainable by homologous recombination techniques which aim to mutate, disrupt or excise the lactate dehydrogenase gene or the lactate dehydrogenase and pyruvate formate lyase activity genes in the genome of the bacterial cell. In the following, a preferred technique for recombination, in particular for introducing mutations or for deleting sequences, is described.

This technique is also sometimes referred to as the "Campbell recombination" herein (Leenhouts et al., 1989, Appl Env Microbiol 55, 394-400). "Campbell in," as used herein, refers to a transformant of an original host cell in which an entire circular double stranded DNA molecule (for example a plasmid) has integrated into a chromosome by a single homologous recombination event (a cross in event), and that effectively results in the insertion of a linearized version of said circular DNA molecule into a first DNA sequence of the chromosome that is homologous to a first DNA sequence of the said circular DNA molecule. "Campbelled in" refers to the linearized DNA sequence that has been integrated into the chromosome of a "Campbell in" transformant. A "Campbell in" contains a duplication of the first homologous DNA sequence, each copy of which includes and surrounds a copy of the homologous recombination crossover point.

"Campbell out," as used herein, refers to a cell descending from a "Campbell in" transformant, in which a second homologous recombination event (a cross out event) has occurred between a second DNA sequence that is contained on the linearized inserted DNA of the "Campbelled in" DNA, and a second DNA sequence of chromosomal origin, which is homologous to the second DNA sequence of said linearized insert, the second recombination event resulting in the deletion (jettisoning) of a portion of the integrated DNA sequence, but, importantly, also resulting in a portion (this can be as little as a single base) of the integrated Campbelled in DNA remaining in the chromosome, such that compared to the original host cell, the "Campbell out" cell contains one or more intentional changes in the chromosome (for example, a single base substitution, multiple base substitutions, insertion of a heterologous gene or DNA sequence, insertion of an additional copy or copies of a homologous gene or a modified homologous gene, or insertion of a DNA sequence comprising more than one of these aforementioned examples listed above). A "Campbell out" cell is, preferably, obtained by a counter-selection against a gene that is contained in a portion (the portion that is desired to be jettisoned) of the "Campbelled in" DNA sequence, for example the *Bacillus subtilis* sacB gene, which is lethal when expressed in a cell that is grown in the presence of about 5% to 10% sucrose. Either with or without a counter-selection, a desired "Campbell out" cell can be obtained or identified by screening for the desired cell, using any screenable phenotype, such as, but not limited to, colony morphology, colony color, presence or absence of antibiotic resistance, presence or absence of a given DNA sequence by polymerase chain reaction, presence or absence of an auxotrophy, presence or absence of an enzyme, colony nucleic acid hybridization, antibody screening, etc. The term "Campbell in" and "Campbell out" can also be used as verbs in various tenses to refer to the method or process described above.

It is understood that the homologous recombination events that leads to a "Campbell in" or "Campbell out" can occur over a range of DNA bases within the homologous DNA sequence, and since the homologous sequences will be identical to each other for at least part of this range, it is not usually possible to specify exactly where the crossover event occurred. In other words, it is not possible to specify precisely which sequence was originally from the inserted DNA, and which was originally from the chromosomal DNA. Moreover, the first homologous DNA sequence and the second homologous DNA sequence are usually separated by a region of partial non-homology, and it is this region of non-homology that remains deposited in a chromosome of the "Campbell out" cell.

Preferably, first and second homologous DNA sequence are at least about 200 base pairs in length, and can be up to several thousand base pairs in length. However, the procedure can be made to work with shorter or longer sequences. For example, a length for the first and second homologous sequences can range from about 500 to 2000 bases, and the obtaining of a "Campbell out" from a "Campbell in" is facilitated by arranging the first and second homologous sequences to be approximately the same length, preferably with a difference of less than 200 base pairs and most preferably with the shorter of the two being at least 70% of the length of the longer in base pairs.

It has been found in the studies underlying the present invention that the production of SA is even more increased in bacterial cells lacking lactate dehydrogenase activity or lacking lactate dehydrogenase and pyruvate formate lyase activity.

A preferred lactate dehydrogenase as referred to in accordance with the present invention is encoded by a polynucleotide comprising a nucleic acid selected from the group consisting of:
  a) a nucleic acid having a nucleotide sequence as shown in SEQ ID NO: 20;
  b) a nucleic acid encoding an amino acid sequence as shown in SEQ ID NO: 21;
  c) a nucleic acid which is at least 70% identical to the nucleic acid of a) or b); and
  d) a nucleic acid encoding an amino acid sequence which is at least 70% identical to the amino acid sequence encoded by the nucleic acid of a) or b).

A preferred pyruvate formate lyase as referred to in accordance with the present invention is encoded by a polynucleotide comprising a nucleic acid selected from the group consisting of:
  a) a nucleic acid having a nucleotide sequence as shown in SEQ ID NO: 22;
  b) a nucleic acid encoding an amino acid sequence as shown in SEQ ID NO: 23;
  c) a nucleic acid which is at least 70% identical to the nucleic acid of a) or b); and
  d) a nucleic acid encoding an amino acid sequence which is at least 70% identical to the amino acid sequence encoded by the nucleic acid of a) or b).

The present invention also contemplates a polynucleotide comprising a nucleic acid encoding a polypeptide having isocitrate lyase activity as defined above and a nucleic acid encoding a polypeptide having malate synthase activity as defined above. Moreover, the aforementioned polynucleotide, preferably, also comprises a nucleic acid encoding a polypeptide having formate dehydrogenase activity. Said polynucleotide is, preferably, an isolated polynucleotide.

The term includes all entities of the two or three nucleic acids on a polynucleotide except where the nucleic acids are linked together in their natural context. Accordingly, even the said two or three nucleic acids appear as heterologous nucleic acids linked together in a genome would be regarded as an isolated polynucleotide according to the invention. Moreover, such a polynucleotide comprising a cluster of nucleic acids encoding the two or three enzymes can be incorporated into an bacterial expression vector and used for transformation of bacterial cells (sometimes also referred to as an operon). The advantage of such a polynucleotide or expression vector is that both polypeptides having the aforementioned enzymatic activities will be present in all transfected cells and can be expressed in an equal ratio. Thus, the efficacy for SA production of a bacterial cell can be further improved.

Finally, the present invention relates to a method for manufacturing SA comprising
i) cultivating a bacterial cell of the present invention under suitable culture conditions; and
ii) obtaining SA from the cultured bacterial cells.

The term "succinic acid" (SA) has to be understood in its broadest sense and also encompasses salts thereof, as for example alkali metal salts, like Na and K salts, or earth alkali salts, like Mg and Ca salts, or ammonium salts; or anhydrides of said acids.

Suitable culture conditions and techniques for obtaining the SA to be applied in the method of the invention, i.e. the fermentative process for the production of SA, are as follows:

The bacterial cell of the present invention is, preferably, incubated in a medium containing an carbon source which can be assimilated and cultivated at a temperature in the range of about 10 to 60 or 20 to 50 or 30 to 45° C. at a pH of 5.0 to 9.0 or 5.5 to 8.0 or 6.0 to 7.0 in the presence of carbon dioxide.

Preferably, SA is produced under anaerobic conditions. Anaerobic conditions may be established by means of conventional techniques, as for example by degassing the constituents of the reaction medium and maintaining anaerobic conditions by introducing carbon dioxide or nitrogen or mixtures thereof and optionally hydrogen at a flow rate of, for example, 0.1 to 1 or 0.2 to 0.5 vvm. Aerobic conditions may be established by means of conventional techniques, as for example by introducing air or oxygen at a flow rate of, for example, 0.1 to 1 or 0.2 to 0.5 vvm. If appropriate, a slight over pressure of 0.1 to 1.5 bar may be applied in the process.

The assimilable carbon source is preferably selected from glycerol, D-glucose, D-xylose, L-arabinose, D-galactose, D-mannose and mixtures thereof or compositions containing at least one of said compounds, or is selected from decomposition products of starch, cellulose, hemicellulose and/or lignocellulose.

The initial concentration of the assimilable carbon source is, preferably, adjusted to a value in a range of 5 to 100 g/l and may be maintained in said range during cultivation.

The pH of the reaction medium may be controlled by addition of suitable bases as for example, ammonium hydroxide in the form of an at least 5% (w/v) or more concentrated (up to saturation) aqueous solution or gaseous ammonia or other bases.
Particularly Preferred Conditions for Producing SA are:
Carbon source: Glucose or glycerol (including crude glycerol)
Temperature: 30 to 45° C.
pH: 5.5 to 7.0
supplied gas: $CO_2$ The term "crude glycerol" has to be understood as untreated glycerol-containing stream as it accrues in processes in which glycerol is a by product, as for example the production of bio diesel or bio ethanol. Unless otherwise stated the term "glycerol" as used herein also encompasses "crude glycerol".

Further preferred conditions will be derivable from the attached examples and figures.

Succinic acid and/or SA salts produced are, preferably, obtained by methods known in the art, as for example crystallization, filtration, electrodialysis, chromatography. For example, they may be isolated by precipitating as a calcium succinate product in the fermenter during the fermentation by using calcium hydroxide, -oxide, -carbonate or hydrogen carbonate for neutralization and filtration of the precipitate.

The desired SA product is recovered from the precipitated calcium or succinate by acidification of the succinate with sulfuric acid followed by filtration to remove the calcium sulfate (gypsum) or which precipitates. The resulting solution may be further purified by means of ion exchange chromatography in order to remove undesired residual ions.

Another embodiment of the invention relates to a process for the production of SA and/or SA salts, in particular ammonium salts, which method comprises the fermentative production of SA as defined above and controlling the pH with a suitable base, in particular inorganic base, like ammonia, or an aqueous solution thereof.

Another embodiment of the invention relates to a process for the production of tetrahydrofuran (THF) and/or 1,4-butanediol (BDO) and/or gamma-butyrolactone (GBL) which comprises
a) the fermentative production of SA and/or SA salts, e. g. ammonium salts as defined above, and
b1) either the direct catalytic hydrogenation of the obtained free acid to THF and/or BDO and/or GBL or
b2) the chemical esterification of obtained free SA and/or SA ammonium salts to its corresponding di-loweralkyl ester and subsequent catalytic hydrogenation of said ester to THF and/or BDO and/or GBL.

Lower alkyl preferably represent a straight chain or branched $C_1$-$C_6$-, preferably $C_1$-$C_4$-alkyl residue, in particular methyl, ethyl, n-propyl, isopropyl, n-butyl, sec-butyl, isobutyl, tert-butyl, as well as n-pentyl and n-nexyl and branched analogues thereof.

Another embodiment of the invention relates to a process for the production of pyrrolidones which comprises
a) the fermentative production of SA ammonium salts as defined above, and
b) the chemical conversion of SA ammonium salts to pyrrolidones in a manner known per se, for example as described in WO-A-2006/066839 (which document is herewith incorporated by reference).

In a preferred embodiment, said glycerol, which is used as assimilable carbon source, is crude glycerol.
More Details on Direct Hydrogenation of SA:

Suitable experimental conditions for performing direct catalytic hydrogenation are well known, and for example, described in U.S. Pat. No. 4,550,185, incorporated herewith by reference.

The SA is hydrogenated in a manner known per se using processes, apparatus and assistants, such as solvents, familiar to the person skilled in the art. In particular, a continuous or batch wise liquid phase hydrogenation is carried out in the presence of a heterogeneous catalyst suitable for the acid hydrogenation. The optimal process parameters can be established by the person skilled in the art without unacceptable effort. For example, the reaction temperature is in the range from about 100 to about 300° C., preferably in the range from about 130 to 285° C., and the pressure is from about 20 to 350 bar, for example from 100 to 250 bar. Catalysts usable for the hydrogenation reaction are known to the person skilled in the art. For example, various palladium/rhenium/carbon catalysts may be used. Solvents usable for the hydrogenation reaction are known to the person skilled in the art. For example, an aqueous solvent medium may be used.

More Details on Esterification of SA Followed by Hydrogenation:

Suitable experimental conditions for performing the chemical esterification, followed by direct catalytic hydrogenation are well known, and for example, described in European Patent application 06007118.0 incorporated herewith by reference.

a) Esterification process:

The esterification process which may comprise a reactive distillation can be performed using an apparatus known per se in various designs.

For example an esterification plant which is operated in continuous mode can be used which comprises a rectification column with an appropriate number of theoretical stages achieved by installation of trays or packings. The aqueous charge comprising the ammonium salt of SA is fed into the top of the column from a reservoir vessel as soon as a steady-state temperature profile has formed in the column as a result of feeding-in alkanol that is evaporated in the evaporator loop adherent to the sump of the column. The reaction forms a countercurrent flow of descending, ammonium salt-containing liquid and condensate, and ascending, alkanol-containing vapor phase. To catalyze the esterification reaction, a homogeneous catalyst may be added to the ammonium salt initial charge. Alternatively, heterogeneous catalysts may be provided in the column internals. The carboxylic ester formed is liquid under the process conditions and passes via the lower end of the column into the sump of the distillation column and is continuously withdrawn from the sump. Gaseous components, for example azeotropic mixtures comprising alkanol-water and/or ammonia, are removed from the reaction column and hence from the reaction equilibrium at the top of the column.

Further modifications of the above-described specific embodiments can be implemented by the person skilled in the art without unacceptable effort.

Suitable process parameter ranges for the esterification process according to the invention can be determined easily by the person skilled in the art depending on the configuration of the apparatus used, for example type of column internals used, type and amount of the reactants, type and amount of the catalyst used if appropriate. For instance, without being restrictive thereto, individual parameters may be set within the following parameter ranges:

Column temperature: 0-300° C., in particular 40-250° C., or 70-200° C.

Pressure: from 0.1 to 6 bar, in particular standard pressure

Residence time: a few seconds (for example from 1 to 60) up to days (for example from 1 to 5), in particular from a few minutes (for example from 1 to 60) to a few hours (for example from 1 to 15), more preferably from a few minutes (for example from 5 to 20) to 2 h.

b) Hydrogenation process

The SA esters prepared in accordance with the invention are hydrogenated in a manner known per se using processes, apparatus and assistants, such as catalysts, familiar to the person skilled in the art.

In particular, a continuous or batch wise gas phase hydrogenation is carried out in the presence of a heterogeneous catalyst suitable for the ester hydrogenation. The optimal process parameters can be established by the person skilled in the art for the particular ester without unacceptable effort. For example, the reaction temperature is in the range from about 100 to about 300° C., preferably in the range from about 200 to 280° C., and the pressure is from about 5 to 100 bar, for example from 10 to 50 bar. The molar ratio of reactant to hydrogen is set within the range from about 1:100 to about 1:2000, for example from 1:800 to 1:1500.

Catalysts usable for the inventive hydrogenation reaction are known to the person skilled in the art. For example, various copper catalysts may be used. The prior art describes, for example, the use of reduced copper chromite catalysts which are obtainable under the name 85/1 from Davy Process Technology Ltd., England. However, catalysts particularly suitable in accordance with the invention are supported copper oxide catalysts, the copper oxide being applied to alumina or silica support materials. The examples of the hydrogenation of succinic esters to BDO (1,4-Butanediol)/GBL (gamma-butyrlactone)/THF with copper catalysts are also well known in the art.

Fermentation as used according to the present invention can be performed in stirred fermenters, bubble columns and loop reactors. The possible method types including stirrer types and geometric designs are well known in the art and can be found in standard text books. In the process, typical variants available are the following variants known to those skilled in the art or explained, for example, in a standard textbook (Chmiel H, Hammes W P, Bailey J E, 1987, "Biochemical engineering. A challenge for interdisciplinary cooperation.", ISBN: 3-437-30574-3.), such as batch, fed batch, repeated fed batch or else continuous fermentation with and without recycling of the biomass. Depending on the production strain, sparging with air, oxygen, carbon dioxide, hydrogen, nitrogen or appropriate gas mixtures can/must be effected in order to achieve good yields.

Before the chemical conversion in the fermentation broth in the process according to the invention, the fermentation broth can be pretreated; for example, the biomass of the broth can be removed. Processes for removing the biomass are known to those skilled in the art, for example filtration, sedimentation and flotation. Consequently, the biomass can be removed, for example, with centrifuges, separators, decanters, filters or in flotation apparatus. For maximum recovery of the product of value, washing of the biomass is often advisable, for example in the form of a diafiltration. The selection of the method is dependent upon the biomass content in the fermenter broth and the properties of the biomass, and also the interaction of the biomass with the product of value. In one embodiment, the fermentation broth can be sterilized or pasteurized.

In a further embodiment, the fermentation broth is concentrated. Depending on the requirement, this concentration can be done batch wise or continuously. The pressure and temperature range should be selected such that firstly no product damage occurs, and secondly minimal use of apparatus and energy is necessary. The skillful selection of pressure and temperature levels for a multistage evaporation in particular enables saving of energy.

The term "fermentation broth" is understood to mean an aqueous solution which is based on a fermentative process and has not been worked up or has been worked up, for example, as described herein.

In apparatus terms, stirred tanks, falling-film evaporators, thin-film evaporators, forced-flash circulation evaporators and other evaporator types can be utilized in natural or forced circulation mode.

All references cited in this specification are herewith incorporated by reference with respect to their entire disclosure content and the disclosure content specifically mentioned in this specification.

The invention will be now described by the following examples which shall not be construed, whatsoever, as a limitation of its scope.

EXAMPLES

Example 1

Transformation of DD1

TABLE 1

Nomenclature of the DD1 wildtype and mutants referred to in the Examples.

| Strain | Description |
| --- | --- |
| LU13843 | Wildtype DD1 (deposit DSM18541) |
| LU15050 | DD1 delta ldh |
| LU15224 | DD1 delta ldh pflD |
| LU15224 pJFF224 (icl ms Y. m.) | DD1 delta ldh pflD pJFF224 (icl ms Y. m.) |
| LU15224 pJFF224 | DD1 delta ldh pflD pJFF224 |
| LU13843 pJFF224 | DD1 pJFF224 |
| LU13843 pJFF224 (icl ms S. t.) | DD1 pJFF224 (icl ms S. t.) |
| LU 15050 pJFF224 | DD1 delta ldh pJFF224 |
| LU15050 pJFF224 (icl ms S. t.) | DD1 delta ldh pJFF224 (icl ms S. t.) |
| LU 15050 pJFF224 (icl ms Y. m.) | DD1 delta ldh pJFF224 (icl ms Y. m.) |
| LU 13843 pJFF224 (PpckA fdh C. b.) | DD1 pJFF224 (PpckA fdh C. b.) |
| LU 15050 pJFF224 (PpckA fdh C. b.) | DD1 delta ldh pJFF224 (PpckA fdh C. b.) |
| LU 13843 pJFF224 (PpckA fdh C. b., PEFTU icl ms Y. m.) | DD1 pJFF224 (PpckA fdh C. b., PEFTU icl ms Y. m.) |
| LU15050 delta adhE. | DD1 delta ldh delta adhE |
| LU15050 delta adhE. pJFF224 (PpckA fdh C. b.) | DD1 delta ldh delta adhE pJFF224 (PpckA fdh C. b.) |
| LU 13843 pJFF224 (fdh W. s.) | DD1 pJFF224 (fdh W. s.) |
| LU 15050 pJFF224 (fdh W. s.) | DD1 delta ldh pJFF224 (fdh W. s.) |
| LU 15050 delta adhE pJFF224 (fdh W. s.) | DD1 delta ldh delta adhE pJFF224 (fdh W. s.) |

*Pasteurella* strain LU13843 was transformed with DNA by electroporation using the following protocol:

Pre-Culture:

LU 13843 was inoculated from a freshly grown BHI-Agar plate into 40 ml BHI (brain heart infusion, Difco) in 100 ml shake flask. Incubation was performed over night at 30° C.; 200 rpm.

Main-Culture:

50 ml BHI in 100 ml shake flask

Inoculated to a final OD(610) of 0.4

Incubation: approximately 1.5 h at 30° C., 200 rpm

The cells were harvested at an OD of approximately 1.3

Pellet washed once with 10% cold glycerol at 4° C.

Resuspended in 1.7 ml 10% glycerol (4° C.)

100 µl of competent cells were mixed with 5-10 µg DNA (10-20 µl) and kept on ice for 2 min in an electroporation cuvette with a width of 0.2 cm.

Electroporation conditions: 800 Ω; 25 µF; 2 kV (Gene Pulser, Bio-Rad)

Addition of 1 ml of BHI immediately after electroporation

Incubation for 2 h at 30° C.

Cells were plated on BHI with 5 mg/L chloramphenicol and incubated for 2-5 d at 30° C. until the colonies of the transformants were visible. Clones were isolated and restreaked onto BHI with 5 mg/L chloramphenicol until purity of clones was obtained.

Example 2

Generation of Deletion Constructs

Figure 2:
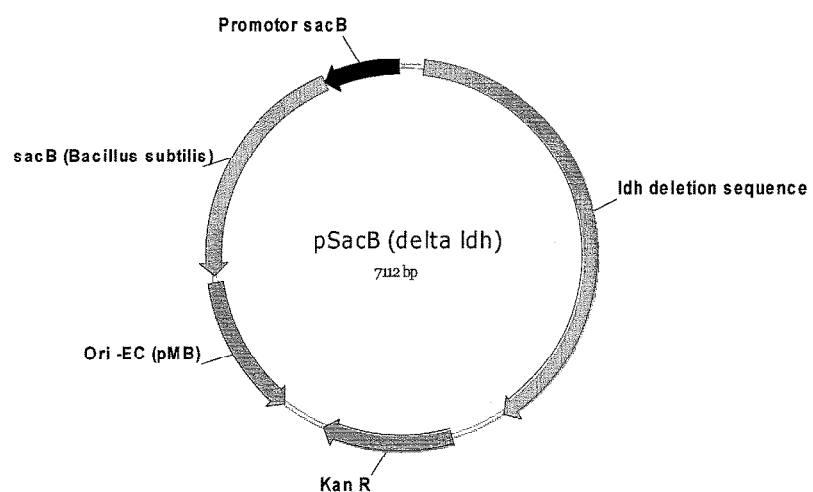
FIG. 2: A schematic map of plasmid pSacB (delta ldhA) (lactate dehydrogenase).
Figure 3:
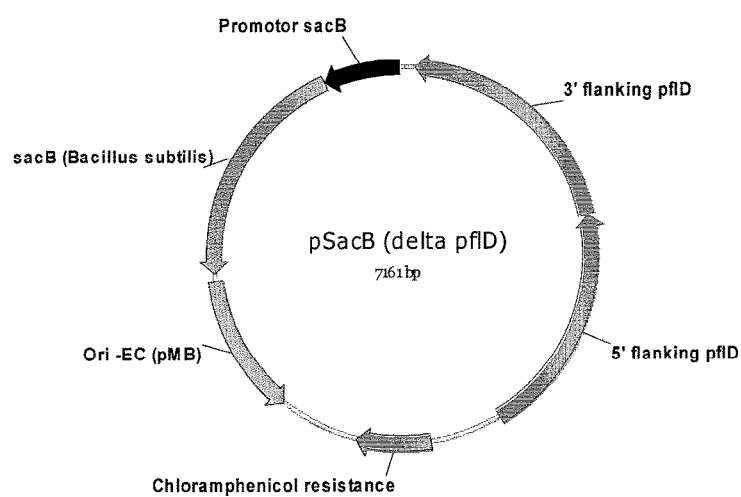
FIG. 3: A schematic map of plasmid pSacB (delta pflD) (pyruvate formate lyase).
Figure 4:
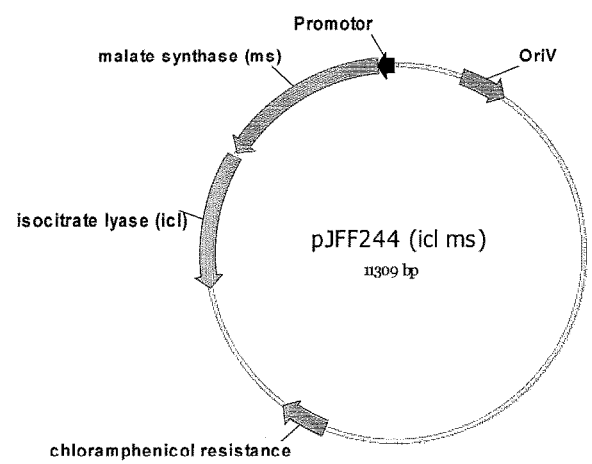
FIG. 4: A schematic map of an expression plasmid pJFF224 (icl ms Y.m.) for the expression of the glyoxylate shunt operon of *Yersinia molaretii* (isocitrate lyase (icl) and malate synthase (ms)).

Deletion plasmids were constructed based on the vector pSacB (SEQ ID NO 9). FIG. 1 shows a schematic map of plasmid pSacB. 5'- and 3'-flanking regions of the chromosomal fragment which should be deleted were amplified by PCR from chromosomal DNA of LU 13843 and introduced into the vector using standard techniques. Normally, at least 80% of the ORF were targeted for a deletion. In such a way, the deletion plasmids for lactate dehydrogenase ldhA, pSacB (delta ldhA), and for the pyruvate formate lyase pflD, pSacB (delta pflD) were constructed. FIGS. 2 and 3 show schematic maps of plasmid pSacB (delta ldhA) and pSacB (delta pflD).

Example 3

Generation of Improved Succinate Producing Strains

LU 13843 was transformed as described above with the pSacB (delta ldh) and "Campbelled in" to yield a "Campbell in" strain. Transformation and integration into the genome of LU 13843 was confirmed by PCR yielding bands for the integrational event of the plasmid into the genome of LU 13843. The "Campbell in" strain was then "Campbelled out" using agar plates containing sucrose as a counter selection medium, selecting for the loss (of function) of the sacB gene. Therefore, the "Campbell in" strains were incubated in 25-35 ml of non selective medium (BHI containing no antibiotic) at 37° C., 220 rpm over night. The overnight culture was then streaked onto freshly prepared BHI containing sucrose plates (10%, no antibiotics) and incubated overnight at 37° C. ("first sucrose transfer"). Single colony obtained from first transfer were again streaked onto freshly prepared BHI containing sucrose plates (10%) and incubated overnight at 37° C. ("second sucrose transfer"). This procedure was repeated until a minimal completion of five transfers ("third, forth, fifth sucrose transfer") in sucrose. The term "first to fifth sucrose transfer" refers to the transfer of a strain after chromosomal integration of a vector containing a sacB levansucrase gene onto sucrose and growth medium containing agar plates for the purpose of selecting for strains with the loss of the sacB gene and the surrounding plasmid sequences. Single colony from the fifth transfer plates were inoculated onto 25-35 ml of non selective medium (BHI containing no antibiotic) and incubated at 37° C., 220 rpm over night. The overnight culture was serially diluted and plated onto BHI plates to obtain isolated single colonies. The "Campbelled out" strains containing the deletion of the ldhA gene were confirmed by chloramphenicol sensitivity. The deletion mutants among these strains were identified and confirmed by PCR analysis. This led to the ldhA deletion mutant LU15050.

LU15050 was transformed with pSacB (delta pflD) as described above and "Campbelled in" to yield a "Campbell in" strain. Transformation and integration was confirmed by PCR. The "Campbell in" strain was then "Campbelled out" as described previously. The deletion mutants among these strains were identified and confirmed by PCR analysis. This led to the ldhA pflD double deletion mutant LU15224.

LU15224 was transformed with pJFF224 (icl ms Y.m.) expressing the gyloxylate shunt operon from *Yersinia molaretii* and pJFF224 as a vector control. Resulting transformants were used for further experiments. LU15050 was transformed with pJFF224 (icl ms S.t.) expressing the gyloxylate shunt operon from *Salmonella typhimurium*. Resulting transformants were used for further experiments.

Example 4

Cell Bank Preparation

1. Media Preparation

Composition of the cultivation media is described in table 3.

TABLE 3

Composition of solid and liquid media for the preparation of cell banks.

| Compound | Concentration [g/L] | Concentration of stock solution [g/L] |
| --- | --- | --- |
| Glucose | varying[a] | 650 |
| Bacto yeast extrakt (Becton Dickinson) | 5 | — |
| Bacto peptone (Becton Dickinson) | 5 | — |
| $(NH_4)_2SO_4$ | 1 | 500 |
| $CaCl_2*2H_2O$ | 0.2 | 20 |
| $MgCl_2*6H_2O$ | 0.2 | 20 |
| NaCl | 1 | 100 |
| $K_2HPO_4$ | 3 | 500 |
| $MgCO_3$ | varying[b] | — |
| Bacto-Agar (for solid media only) | 12 | |

[a]Glucose concentrations were 15 g/L (in plates) and 20 or 50 g/L (in liquid media).
[b]$MgCO_3$ (Riedel-de Haen, product number: 13117 by Sigma-Aldrich Laborchemikalien GmbH) concentrations were 5 g/L (in plates) and 0 or 30 g/L (in liquid media).

5 g yeast extract, 5 g peptone, MgCO3 and (for solid media) 12 g Bacto-Agar were mixed in 900 mL distilled water and autoclaved (20 min). After cooling down to about 65° C. the missing components were added as sterile stock solutions. Glucose, ammonium sulfate and K2HPO4 were all separately autoclaved. Ca-, Mg- and Na-chlorides were autoclaved together.

2. MCB Preparation

Two agar plates were freshly inoculated with the desired strain and incubated at 37° C. in an anaerobic jar (Anaerocult A, Merck) over night. The biomass was taken off the plates and resuspended in the MgCO3-free liquid medium with 20 g/L glucose to adjust OD600≈1.0. Inoculation was performed with 0.5 mL of this cell suspension. Cultivations were performed in 100 mL-serum bottles with gas tight butyl rubber stoppers (Ochs GmbH, Bovenden/Lenglern, Germany) containing 50 mL of the liquid medium with 20 g/L glucose and 30 g/L MgCO3 and a CO2-atmosphere with 0.8 bar overpressure. The serum bottles (in total 10) were incubated at 37° C., a rotary speed of 160 rpm and a shaking diameter of 2.5 cm.

To monitor glucose consumption the cultivation of one bottle was stopped and sampling and HPLC analysis were performed after 0, 3, 4, 5, 7, 8 and 8.5 h. After 8.5 h (the glucose concentration was 3.4 g/L) the cultivation was stopped. Aliquots of 0.5 mL cell suspension and 0.5 mL sterile glycerol were filled in cryovials, mixed and stored for 13 h at −20 and afterwards at −80° C. as MCB. The MCB was tested for purity by streaking a loop of the last cryovial on agar plates for contamination control and checking in liquid culture (media as described table 8) the product spectrum and for contamination (by microscopy).

Consumption of glucose and formation of SA and by-products were quantified via HPLC analyses of the undiluted cell free supernatants of the cultivation broth using RI-detection. Broth samples were taken with a sterile syringe through the butyl rubber plug, cell separation was performed by filtration (0.22 μm). A 300×7.8 mm I. D. Column Aminex HPX-87 H (Biorad) and 5 mm H2SO4 were used as stationary and mobile phase, respectively. The column temperature was 30° C., the flow rate was 0.5 mL min$^{-1}$.

3. WCB Preparation

One vial of the MCB was used to inoculate a 100 mL-serum bottle with gas tight butyl rubber stopper (see above) containing 50 mL of the liquid medium with 50 g/L glucose. Incubation was performed for 10 h at 37° C. in a shaking incubator (rotary speed: 180 rpm, shaking diameter: 2.5 cm). At the end of the cultivation the glucose concentration was 20 g/L and the pH around 6.5. Aliquots of 0.5 mL cell suspension and 0.5 mL sterile glycerol were filled in cryovials, mixed and stored at −80° C. as WCB. Purity checks were the same as for the MCB. HPLC conditions were the same as those described above.

Example 5

Fermentation of Mutant Strains LU15224 pJFF224 (icl ms Y.m.) and LU15224 pJFF224

The mutant strain of DD1 LU15224 pJFF224 (icl ms Y.m.), which is a double knockout for Δldh and ΔpflD and over-expresses the plasmid pJFF224 (icl ms Y.m.), containing the glyoxylate shunt operon genes, was analyzed by anaerobic fermentation experiments in comparison to the plasmid control strain LU15224 pJFF224, containing the same genetic background as LU15224 pJFF224 (icl ms Y.m.) but only an empty expression plasmid pJFF224. Mutant strains were generated as described in example 1 to 3.

1. Medium Preparation

The composition of the cultivation medium is described in the following table 4.

TABLE 4

Medium composition for batch cultivations of DD1-mutants with over-expression plasmids.

| Compound | Concentration [g/L] | Concentration of stock solution [g/L] |
| --- | --- | --- |
| Glucose-Monohydrat | 50 | 722 |
| Bacto yeast extrakt (Becton Dickinson) | 5 | 100 |
| $(NH_4)_2SO_4$ | 1 | 500 |
| $CaCl_2*2H_2O$ | 0.2 | 20 |
| $MgCl_2*6H_2O$ | 0.2 | 20 |
| NaCl | 1 | 100 |
| $K_2HPO_4$ | 3 | 500 |
| Chloramphenicol | 0.005 | 5 |
| $MgCO_3$[a] | 50 | — |

[a]$MgCO_3$ was used as buffering agent in serum bottle experiments only.

MgCO3 was supplemented with ddH2O and autoclaved in serum bottles. Yeast extract, glucose, ammonium sulfate and potassium phosphate were all separately autoclaved. Ca-, Mg- and Na-chlorides were autoclaved together. After cooling down the ddH2O autoclaved fermenters and serum bottles the missing components were added as sterile stock solutions. For the seed cultures the same medium was used.

2. Cultivations and Analytics

The seed culture was grown anaerobically in a 100 mL-serum bottle with gas tight butyl rubber stoppers containing 50 mL medium at 37° C. in a shaking incubator (rotary speed: 170 rpm, shaking diameter: 2.5 cm). Inoculation of the seed culture was performed with 1 mL of the WCB (as described in example 4) under sterile conditions. Immediately after the inoculation the aerobic gas atmosphere was substituted by pure CO2 with an overpressure of about 0.8 bar. After 11 h and 17 h of incubation for LU15224 pJFF224 (icl ms Y.m.) and LU15224 pJFF224, respectively, the fermenter was inoculated with 20 mL to start the cultivation in the 500 mL fermenter (Sixfors, Infors Switzerland) containing 380 mL of cultivation medium which had been gassed over night with $CO_2$ to ensure oxygen-free conditions. The cultivation temperature was maintained at 37° C. and the pH at 6.5 with 25% $NH_4OH$. The $CO_2$-gas stream was adjusted to 0.4 l*$min^{-1}$. The stirrer speed was adjusted to 500 rpm.

Consumption of glucose and formation of SA and by-products were quantified via HPLC as described in example 4.

3. Results

The results are summarized in table 5 showing values after glucose depletion.

Heterologous over-expression of the glyoxylate shunt genes lead to a significant increase of the succinate yield compared to the control strain LU15224 pJFF224. It is also detected that acetate is produced with a lower titer in LU15224 pJFF224 (icl ms Y.m.) compared to the control, hinting to an improved flux from pyruvate via acetyl-CoA, isocitrate, malate, fumarate to succinate introduced by the heterologous glyoxylate shunt operon.

TABLE 5

Production of succinate by the mutant LU15224 pJFF224 (icl ms *Y. m.*) and the plasmid control LU15224 pJFF224 after glucose depletion in a SixFors fermentation broth.

| Parameter | LU15224 pJFF224 (icl ms Y.m.) | LU15224 pJFF224 |
|---|---|---|
| Final volume of fermentation broth [ml] | 432 | 435 |
| consumed glucose [g] | 22.98 | 23.17 |
| produced succinate [g] | 20 | 19.16 |
| succinate yield [g/g] | 0.87 | 0.83 |
| produced lactate [g] | 0 | 0 |
| produced pyruvate [g] | 0 | 0 |
| produced acetate [g] | 3.12 | 3.26 |
| produced formate [g] | 0 | 0 |

Example 6

Cloning and Expression of the Glyoxylate Shunt Operon From *Salmonella typhimurium* LT2

Figure 5:
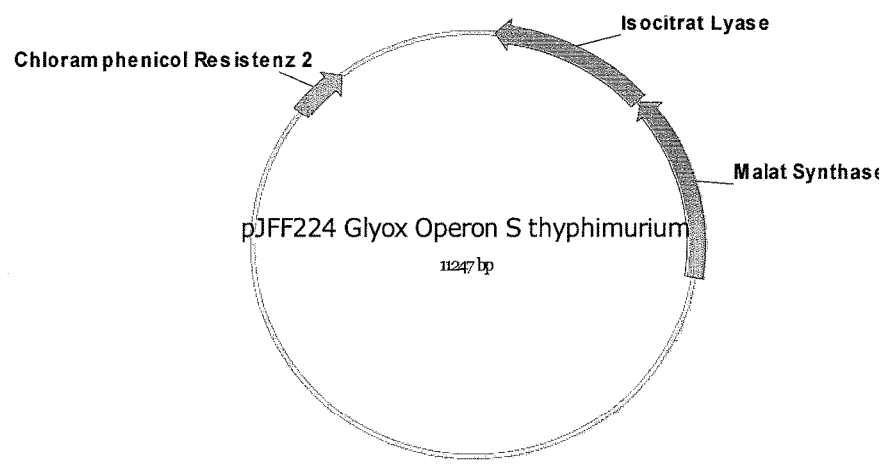
FIG. 5: A schematic map of the plasmid pJFF224 (icl/ms S.t.) for the expression of the glyoxylate shunt operon of *Salmonella typhimurium*.

In another embodiment the glyoxylate shunt operon from *Salmonella typhimurium* (*S. typhimurium*) LT2 ATCC 15277 is amplified by PCR cloned from chromosomal DNA of from *S. typhimurium* LT2 ATCC 15277 using the PfuTurbo™ DNA polymerase (Roche) and is inserted into the vector pJFF224. The expression of the genes in this construct is driven by the native promoter of the operon as well as by a T4 promoter located on the vector pJFF224. FIG. 5 shows a schematic map of the resulting plasmid termed pJFF224 (icl ms S.t). The strain DD1 (termed LU13843) was transformed with the plasmid pJFF224 (icl ms S.t.) as described above. A serum bottle experiment was performed and analyzed as described above. It can be found that upon overexpression of the glyoxylate shunt operon from *S. typhimurium* the succinic acid production was increased over the control. The yield of glucose converted to succinic was increased from 0.42 g SA/g glucose to 0.51 g SA/g glucose.

TABLE 6

Results after expression of the glyoxylate shunt operon from *S. typhimurium* LT2 in LU13843.

| Strain | succinic acid | lactic acid | formic acid | acetic acid | yield succinic acid g SA/g substrate |
|---|---|---|---|---|---|
| LU13843 pJFF224 | 15.1 | 10.1 | 6.8 | 7.5 | 0.42 |
| LU13843 pJFF224 (icl ms S. t.) | 18.1 | 6.5 | 6 | 8.1 | 0.51 |

Example 7

Strain Expression of the Glyoxylate Shunt Operon From *S. Typhimurium* LT2 in the Strain DD1 Delta LDH (LU15050)

The strain DD1 delta ldh (LU15050) was transformed with the plasmid pJFF224 (icl ms S.t.) as described above. A serum bottle experiment was performed and analyzed as described above. Cells were grown overnight on BHI agar plates with chloramphenicol, added to 4 µg/ml. Cells were scraped off the agar plate and inoculated with an OD 600 nm of 0.1. It can be found that upon overexpression of the glyoxylate shunt operon from *S. typhimurium* in LU15050 the succinic acid production was increased over the control. The yield of glucose converted to succinic was increased from 0.62 g SA/g glucose to 0.72 g SA/g glucose.

TABLE 7

Results after expression of the glyoxylate shunt operon from *S. typhimurium* LT2 in LU15050.

| | Succinic acid | Formic acid | Acetic acid | ethanol | yield succinic acid, SA/g substrate |
|---|---|---|---|---|---|
| LU15050 | 31.10 | 6.40 | 7.11 | 0.98 | 0.62 |
| LU15050 pJFF224 (icl ms S. t.) | 35.90 | 5.60 | 7.50 | 1.15 | 0.72 |

Example 8

Cloning and Expression of the Glyoxylate Shunt Operon From *Yersinia Molaretii* ATCC 43969

Figure 6:
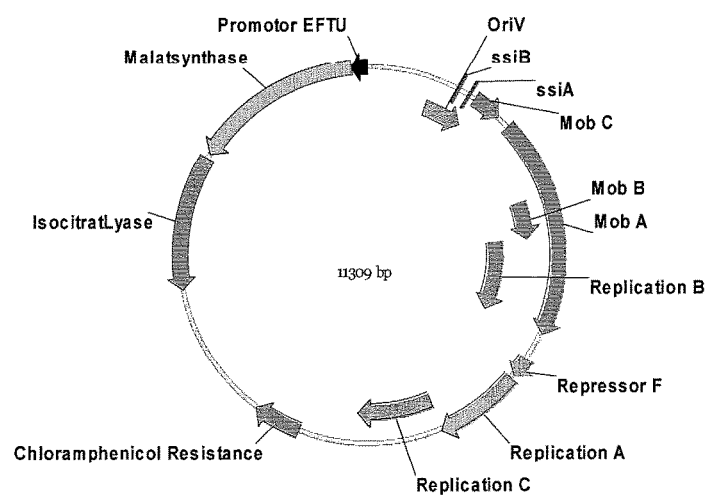
FIG. 6: A schematic map of the plasmid pJFF224 (icl ms Y.m.).

In another embodiment the glyoxylate shunt operon from *Yersinia molaretii* (*Y. molaretii*) ATCC 43969 is amplified by PCR cloned from chromosomal DNA of *Y. molaretii* ATCC 43969 using the PfuTurbo™ DNA polymerase (Roche) and is inserted into the vector pJFF224. The expression of the genes in this construct is driven by the native promoter of the operon as well as by a T4 promoter located on the vector pJFF224. FIG. 6 shows a schematic map of the resulting plasmid termed pJFF224 (icl ms Y.m.). The strain DD1 delta ldh (LU15050) was transformed with the plasmid pJFF224 (icl ms Y.m.) as described above. A serum bottle experiment using 48 g/l glucose was performed and analyzed as described above. Cells were grown overnight on BHI agar plates with chloramphenicol, added to 4 µg/ml. Cells were scraped off the agar plate and inoculated with an OD 600 nm of 0.1. It can be found that upon overexpression of the glyoxylate operon from *Y. molaretii* in LU15505 the succinic acid production was significantly increased over the control. The yield of glucose converted to succinic was increased from 0.60 g SA/g glucose for LU15050 to 0.69 g SA/g glucose for LU15050 pJFF224 (icl ms Y.m.).

TABLE 8

Results from expression of the glyoxylate operon from
Y. molaretii ATCC 43969 in LU 15050.

| | succinic acid | formic acid | acetic acid | yield succinic acid, g SA/g substrate |
|---|---|---|---|---|
| LU 15050 | 28.7 | 5.2 | 7.3 | 0.60 |
| LU 15050 pJFF224 (icl ms Y. m.) | 33.0 | 5.5 | 6.7 | 0.69 |

Example 9

Cloning and Expression of the Formate Dehydrogenase Gene From *Candida Boidinii*

Figure 7:
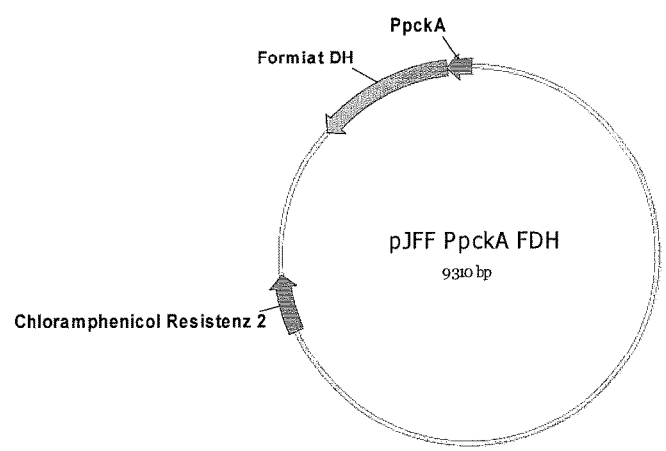
FIG. 7: A schematic map of the plasmid pJFF224 (PpckA fdh C.b.)

The formate dehydrogenase gene (fdh) from *Candida boidinii* (*C. boidinii*) ATCC 18810 was amplified by PCR from chromosomal DNA from *C. boidinii* ATCC 18810 using the PfuTurbo™ DNA polymerase (Roche). The gene was fused to the PpckA promoter from the strain DD1 and was inserted into the vector pJFF224. The expression of the genes in this construct is driven by the PpckA promoter as well as by a T4 promoter located on the vector pJFF224. FIG. 7 shows a schematic map of the resulting plasmid termed pJFF224 (PpckA fdh C.b.). The strains DD1 (LU13843) and DD1 delta ldh (LU 15050) were transformed with the plasmid pJFF224 pJFF224 (PpckA fdh C.b.) as described above.

The resulting strains were selected on agar containing 4 µg/ml chloramphenicol. The succinic acid productivity was analyzed as described above. It was found that upon overexpression of fdh the amount of succinic acid was increased from 27.5 to 30.3 g/l, while the amount of formate as a side product was reduced to either lower than 0.1 g/l or 0.16 g/l in LU 15050. The yield of succinic acid was increased from 0.57 to 0.63 in LU 13843 or from 0.67 to 0.68 for LU 15050.

TABLE 9

Results after expression of fdh from *C. boidinii* in
LU 13843 and LU 15050.

| strain | succinic acid | lactic acid | formic acid | acetic acid | yield succinic acid, g SA/g substrate |
|---|---|---|---|---|---|
| LU 13843 pJFF224 | 27.5 | 7.80 | 4.74 | 7.32 | 0.57 |
| LU 13843 pJFF224 (PpckA fdh C. b.) | 30.3 | 5.82 | — | 6.39 | 0.63 |
| LU 15050 pJFF224 | 32.40 | 0.26 | 4.51 | 7.19 | 0.67 |
| LU 15050 pJFF224 (PpckA fdh C. b.) | 32.61 | 0.25 | 0.16 | 6.59 | 0.68 |

Example 10

Simultaneous Over Expression of the Formate Dehydrogenase Gene From *C. Boidinii* and the Glyoxylate Shunt Operon From *Y. Molaretii*

The formate dehydrogenase gene from *C. boidinii* ATCC 18810 under the control of the PpckA promoter and the glyoxylate shunt operon from *Y. molaretii* under the control of the EFTU promoter from DD1 were inserted into the vector pJFF224 to yield pJFF224 (PpckA fdh C.b., PEFTU icl ms Y.m.). The expression of the genes in this construct is driven by the PpckA promoter, the PEFTU promoter as well as by a T4 promoter located on the vector pJFF224. FIG. 7 shows a schematic map of the resulting plasmid termed pJFF224 (PpckA fdh C.b., PEFTU icl ms Y.m.). The strains LU13843 and LU 15050 were transformed with the plasmid pJFF224 and pJFF224 (PpckA fdh C.b., PEFTU icl ms Y.m.) as described above.

The resulting strains were selected on agar containing 4 µg/ml chloramphenicol. The succinic acid productivity was analyzed as described above except that xylose was added as the carbon source instead of glucose. It was found that upon overexpression of fdh the amount of succinic acid was increased from 35.6 g/l to 36.4 g/l, while the amount of lactic acid as a side product was reduced from 2.1 g/l to 1.7 g/l in LU 13843.

The yield of succinic acid was increased from 0.75 in LU 13843 to 0.76 in LU 13843 pJFF224 (PpckA fdh C.b., PEFTU icl ms Y.m.).

TABLE 10

Results after expression of fdh from *C. boidinii* and the glyoxylate shunt
operon from *Y. molaretii* in LU 13843 after growth in xylose.

| strain | succinic acid | lactic acid | formic acid | acetic acid | yield succinic acid, g SA/g substrate |
|---|---|---|---|---|---|
| LU 13843 pJFF224 | 35.6 | 2.1 | 3.4 | 10.2 | 0.75 |
| LU 13843 pJFF224 (PpckA fdh C. b., PEFTU icl ms Y. m.) | 36.4 | 1.7 | 3.9 | 10.4 | 0.76 |

Example 11

Deletion of adhE Gene From DD1 and DD1 Mutant Strains

Figure 8:
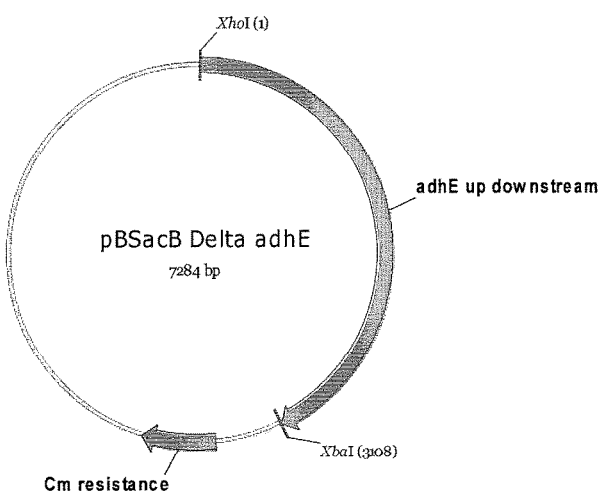
FIG. 8: A schematic map of the pSacB (delta adhE).

The adhE gene was identified on the chromosome of the DD1 genome by sequence analysis using the know adhE gene from *E. coli* and analyzing for homologues in DD1. A gene deletion fragment for the adhE gene is obtained through PCR amplification of 1500 bp covering the upstream region and the respective downstream region of the adhE gene from DD1 with forward and reverse primers carrying the restriction sequences for XhoI and XbaI. The fragment is purified and digested with XhoI and XbaI, as well as the vector which is additionally dephosphorylated. The ligated vector carrying the fragment of the DD1 genome with the adhE up- and downstream regions is propagated in *E. coli* and is used for the transformation of DD1. The strain LU15050 DD1 delta ldh is transformed as described above with the pSacB (delta adhE) and "Campbelled in" to yield a "Campbell in" strain. FIG. 8 shows a schematic map of the pSacB (delta adhE). Transformation and integration into the genome of LU15050 is confirmed by PCR yielding bands for the integrational event of the plasmid into the genome of LU15050. The "Campbell in" strain is then "Campbelled out" using agar plates containing sucrose as a counter selection medium, selecting for the loss (of function) of the sacB gene. Therefore, the "Campbell in" strains are incubated in 25-35 mL of non selective medium (BHI containing no antibiotic) at 37° C., 220 rpm over night. The overnight culture is then streaked onto freshly prepared BHI containing sucrose plates (10%, no antibiotics) and incubated overnight at 37° C. ("first sucrose transfer"). Single colony obtained from first transfer are again streaked onto freshly prepared BHI containing sucrose plates (10%) and are incubated overnight at 37° C. ("second sucrose transfer"). This procedure is repeated until a minimal completion of five transfers ("third, forth, fifth sucrose transfer") in sucrose. The term "first to fifth sucrose transfer" refers to the transfer of a strain after chromosomal integration of a vector containing a sacB levansucrase gene onto sucrose and growth medium containing agar plates for the purpose of selecting for strains with the loss of the sacB gene and the surrounding plasmid sequences. Single colony from the fifth transfer plates are inoculated onto 25-35 ml of non selective medium (BHI containing no antibiotic) and are incubated at 37° C., 220 rpm over night. The overnight culture was serially diluted and plated onto BHI plates to obtain isolated single colonies. The "Campbelled out" strains containing the deletion of the adhE gene are confirmed by chloramphenicol sensitivity. The deletion mutants among these strains are identified and confirmed by PCR analysis. This led to the adhe deletion mutant LU15050 delta adhE. LU15050 delta adhE is transformed with pJFF224 (PpckA fdh C.b.) expressing the formate dehydrogenase from *Candida boidinii* pJFF224 as a vector control. Resulting transformants are used for further experiments. After growth in serum bottles as described above the strains are found to contain significantly increased amounts of succinic acid if compared to the plasmid control not containing a fdh gene. Also the amount of side products such as ethanol is significantly reduced in the DD1 delta adhE strain over expressing a formate dehydrogenase.

Example 12

Figure 9:
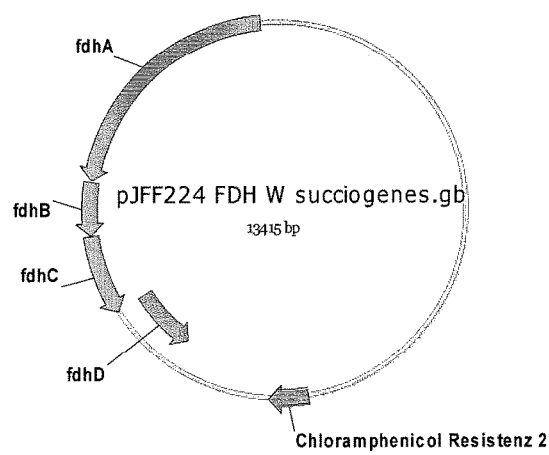
FIG. 9: A schematic map of the pJFF224 (fdh W.s.) for the expression of the *W. succiogenes* formate dehydrogenase (fdh W.s.).
Figure 10:
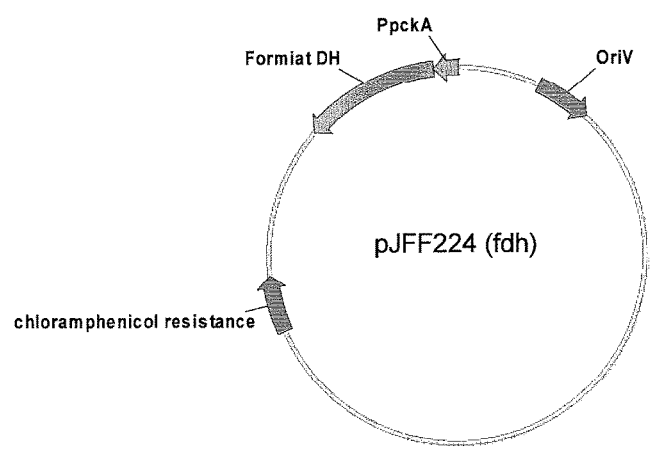
FIG. 10: A schematic map of an expression plasmid pJFF224 (fdh C.b.) for the expression of the *Candida boidinii* formate dehydrogenase (fdh C.b.).

Cloning and Expression of the *Wolinella succinogenes* fdh in DD1 and DD1 Mutant Strains In another embodiment of formate dehydrogenase operon encoding the genes: fdhA, fdhB, fdhC and fdhD from *Wolinella succinogenes* (*W. succinogenes*) DSMZ 1714 is amplified by PCR cloned from chromosomal DNA of *W. succinogenes* DSMZ 1714 using the PfuTurbo™ DNA polymerase (Roche) and is inserted into the vector pJFF224. The expression of the genes in this construct is driven by a promoter fragment amplified from the 5'-region of the phosphoenolypyruvate carboxykinase (pck) gene from DD1 and by a T4 promoter located on the vector. FIG. 9 shows a schematic map of the resulting plasmid termed pJFF224 (fdh W.s.).
The resulting plasmid is transformed into the strains LU 13843 and LU 15050 and DD1 delta (ldh adhE). The resulting strains selected for plasmid content by the addition of 4 μg/ml chloramphenicol are analyzed for succinic acid production in serum bottle experiments as described above. It is found that the expression of the formate dehydrogenase operon encoding the genes: fdhA, fdhB fdhC and fdhD from *Wolinella succinogenes* DSMZ 1714 increases the succinic acid yield as well as decreasing amount of the side product formate.

REFERENCES

Kim J M, Lee K H, Lee S Y, 2008, "Development of a markerless gene knock-out system for *Mannheimia succiniciproducens* using a temperature-sensitive plasmid." Ferris Microbiol Lett 278, 78-85.
Lee S J, Song H, Lee S Y, 2006, "Genome-based metabolic engineering of *Mannheimia succiniciproducens* for succinic acid production.", Appl Environ Microbiol 72, 1939-48.
(Lee S Y, 2005, "BTEC 18Genome-scale metabolic engineering of *Mannheimia succiniciproducens* for enhanced succinic acid production.", The 229th ACS National Meeting, in San Diego, Calif., March 13-17, 2005
Frey J, 1992, "Construction of a broad host range shuttle vector for gene cloning and expression in *Actinobacillus pleuropneumoniae* and other *pasteurellaceae*." Res Microbiol 143, 263-269.
Lee P C, Lee S Y, Hong S H, Chang H N, 2002, "Isolation and characterization of a new succinic acid-producing bacterium, *Mannheimia succiniciproducens* MBEL55E, from bovine rumen.", Appl Microbiol Biotechnol 58, 663-668.
Dharmadi Y, Murarka A, Gonzalez R, 2006, "Anaerobic fermentation of glycerol by *Escherichia coli*: a new platform for metabolic engineering." Biotechnol Bioeng 94, 821-829.
Lee P C, Lee W G, Lee S Y, Chang H N, 2001, "Succinic acid production with reduced by-product formation in the fermentation of *Anaerobiospirillum succiniciproducens* using glycerol as a carbon source.", Biotechnol Bioeng 72, 41-48.
Robertson E F, Reeves H C, 1987, "Purification and characterization of isocitrate lyase from *Escherichia coli*.", Curr Microbiol 14, 347-350.
Hoyt J C, Robertson E F, Berlyn K A, Reeves H C, 1988, "*Escherichia coli* isocitrate lyase: properties and comparisons.", Biochim Biophys Acta 966, 30-5.
MacKintosh C, Nimmo H G, 1988, "Purification and regulatory properties of isocitrate lyase from *Escherichia coli* ML308.", Biochem J 250, 25-31.
Watanabe S, Takada Y, Fukunaga N, 2001, "Purification and characterization of a cold-adapted isocitrate lyase and a malate synthase from *Colwellia maris*, a psychrophilic bacterium.", Biosci Biotechnol Biochem 65, 1095-1103.
Sundaram T K, Chell R M, Wilkinson A E, 1980, "Monomeric malate synthase from a thermophilic *Bacillus*. Molecular and kinetic characteristics.", Arch Biochem Biophys 1980 February; 199, 515-525.
Eggerer H and Klette A, 1967, "On the catalysis principle of malate synthase.", Eur J Biochem 1, 447-75.
Durchschlag H, Biedermann G, Eggerer H, 1981, "Large-scale purification and some properties of malate synthase from baker's yeast.", Eur J Biochem 114, 255-262.
Feng D F and Doolittle R F, 1987, "Progressive sequence alignment as a prerequisite to correct phylogenetic trees." J Mol Evol 25, 351-360.
Higgins D G and Sharp P M, 1989, "Fast and sensitive multiple sequence alignments on a microcomputer.", Comput Appl Biosci 5, 151-153.
Needleman S B and Wunsch C D, 1970, J Mol Biol 48, 443-453
Smith T F and Waterman M S, 1981, "Identification of Common Molecular Subsequences.", J Mol Biol 147, 195-197
Ferry J G, 1990, "Formate dehydrogenase", FEMS Microbiol Rev 7, 377-382.
Müller U, Willnow P, Ruschig U, Höpner T, 1978, "Formate dehydrogenase from *Pseudomonas oxalaticus*.", Eur J Biochem 83, 485-498.
Leenhouts K J, Kok J, Venema G, 1989, "Campbell-Like Integration of Heterologous Plasmid DNA into the Chromosome of *Lactococcus lactis* subsp. *lactis*.", Appl Env Microbiol 55, 394-400.

The invention claimed is:

1. A bacterial cell of the genus *Pasteurella* comprising a heterologous polypeptide having isocitrate lyase activity and a heterologous polypeptide having malate synthase activity, wherein the bacterial cell has increased succinic acid production relative to a corresponding control bacterial cell,
   wherein the heterologous polypeptide having isocitrate lyase activity is encoded by a nucleic acid selected from the group consisting of:
   a. a nucleic acid having the nucleotide sequence of SEQ ID NO: 1;
   b. a nucleic acid encoding the amino acid sequence of SEQ ID NO: 2;
   c. a nucleic acid which is at least 98% identical to the nucleic acid of a) or b); and
   d. a nucleic acid encoding a polypeptide comprising an amino acid sequence which is at least 98% identical to the amino acid sequence encoded by the nucleic acid of a) or b), and
   wherein the heterologous polypeptide having malate synthase activity is encoded by a nucleic acid selected from the group consisting of:
   a. a nucleic acid having the nucleotide sequence of SEQ ID NO: 3;
   b. a nucleic acid encoding the amino acid sequence of SEQ ID NO: 4;
   c. a nucleic acid which is at least 98% identical to the nucleic acid of a) or b); and
   d. a nucleic acid encoding a polypeptide comprising an amino acid sequence which is at least 98% identical to the amino acid sequence encoded by the nucleic acid of a) or b).

2. The bacterial cell of claim 1, wherein the bacterial cell further comprises a heterologous polypeptide having formate dehydrogenase activity.

3. The bacterial cell of claim 2, wherein the heterologous polypeptide having formate dehydrogenase activity is encoded by a nucleic acid selected from the group consisting of:
   a. a nucleic acid having the nucleotide sequence of SEQ ID NO: 5 or 18;
   b. a nucleic acid encoding the amino acid sequence of SEQ ID NO: 6;
   c. a nucleic acid which is at least 90% identical to the nucleic acid of a) or b); and
   d. a nucleic acid encoding a polypeptide comprising an amino acid sequence which is at least 90% identical to the amino acid sequence encoded by the nucleic acid of a) or b).

4. The bacterial cell of claim 1, wherein the bacterial cell has reduced lactate dehydrogenase activity relative to a corresponding wildtype bacterial cell.

5. A method for manufacturing succinic acid comprising
   i) cultivating the bacterial cell of claim 1 under suitable culture conditions; and
   ii) obtaining succinic acid from the cultured bacterial cells.

6. A bacterial cell of strain DD1 of the genus *Pasteurella* as deposited under DSM18541 with the DSMZ Germany comprising a heterologous polypeptide having isocitrate lyase activity and a heterologous polypeptide having malate synthase activity, wherein the bacterial cell has increased succinic acid production relative to a corresponding control bacterial cell,
   wherein the heterologous polypeptide having isocitrate lyase activity is encoded by a nucleic acid selected from the group consisting of:
   a. a nucleic acid having the nucleotide sequence of SEQ ID NO: 1;
   b. a nucleic acid encoding the amino acid sequence of SEQ ID NO: 2;
   c. a nucleic acid which is at least 90% identical to the nucleic acid of a) or b); and
   d. a nucleic acid encoding a polypeptide comprising an amino acid sequence which is at least 90% identical to the amino acid sequence encoded by the nucleic acid of a) or b), and
   wherein the heterologous polypeptide having malate synthase activity is encoded by a nucleic acid selected from the group consisting of:
   a. a nucleic acid having the nucleotide sequence of SEQ ID NO: 3;
   b. a nucleic acid encoding the amino acid sequence of SEQ ID NO: 4;
   c. a nucleic acid which is at least 90% identical to the nucleic acid of a) or b); and
   d. a nucleic acid encoding a polypeptide comprising an amino acid sequence which is at least 90% identical to the amino acid sequence encoded by the nucleic acid of a) or b).

7. The bacterial cell of claim 6, wherein the heterologous polypeptide having isocitrate lyase activity is encoded by a nucleic acid selected from the group consisting of:
   a. a nucleic acid having the nucleotide sequence of SEQ ID NO: 1;
   b. a nucleic acid encoding the amino acid sequence of SEQ ID NO: 2;
   c. a nucleic acid which is at least 95% identical to the nucleic acid of a) or b); and
   d. a nucleic acid encoding a polypeptide comprising an amino acid sequence which is at least 95% identical to the amino acid sequence encoded by the nucleic acid of a) or b), and
   wherein the heterologous polypeptide having malate synthase activity is encoded by a nucleic acid selected from the group consisting of:
   a. a nucleic acid having the nucleotide sequence of SEQ ID NO: 3;
   b. a nucleic acid encoding the amino acid sequence of SEQ ID NO: 4;
   c. a nucleic acid which is at least 95% identical to the nucleic acid of a) or b); and
   d. a nucleic acid encoding a polypeptide comprising an amino acid sequence which is at least 95% identical to the amino acid sequence encoded by the nucleic acid of a) or b).

8. The bacterial cell of claim 6, wherein the bacterial cell further comprises a heterologous polypeptide having formate dehydrogenase activity.

9. The bacterial cell of claim 8, wherein the heterologous polypeptide having formate dehydrogenase activity is encoded by a nucleic acid selected from the group consisting of:
   a. a nucleic acid having the nucleotide sequence of SEQ ID NO: 5 or 18;
   b. a nucleic acid encoding the amino acid sequence of SEQ ID NO: 6;
   c. a nucleic acid which is at least 90% identical to the nucleic acid of a) or b); and
   d. a nucleic acid encoding a polypeptide comprising an amino acid sequence which is at least 90% identical to the amino acid sequence encoded by the nucleic acid of a) or b).

10. The bacterial cell of claim 6, wherein the bacterial cell has reduced lactate dehydrogenase activity relative to a corresponding wildtype bacterial cell.

11. A method for manufacturing succinic acid comprising
   i) cultivating the bacterial cell of claim 6 under suitable culture conditions; and
   ii) obtaining succinic acid from the cultured bacterial cells.

12. An isolated polynucleotide comprising a first nucleic acid encoding a heterologous polypeptide having isocitrate lyase activity operably linked to heterologous regulatory sequences, wherein the polypeptide is encoded by:
   a. a nucleic acid having the nucleotide sequence of SEQ ID NO: 1;
   b. a nucleic acid encoding the amino acid sequence of SEQ ID NO: 2;
   c. a nucleic acid which is at least 98% identical to the nucleic acid of a) or b); or
   d. a nucleic acid encoding a polypeptide comprising an amino acid sequence which is at least 98% identical to the amino acid sequence encoded by the nucleic acid of a) or b).

13. The isolated polynucleotide of claim 12, further comprising a second nucleic acid encoding a polypeptide having malate synthase activity operably linked to heterologuous regulatory sequences, wherein the polypeptide having malate synthase activity is encoded by:
   a. a nucleic acid having the nucleotide sequence of SEQ ID NO: 3;
   b. a nucleic acid encoding the amino acid sequence of SEQ ID NO: 4;
   c. a nucleic acid which is at least 98% identical to the nucleic acid of a) or b); or
   d. a nucleic acid encoding a polypeptide comprising an amino acid sequence which is at least 98% identical to the amino acid sequence encoded by the nucleic acid of a) or b).

14. The isolated polynucleotide of claim 13, further comprising a third nucleic acid encoding a polypeptide having formate dehydrogenase activity, wherein the polypeptide having formate dehydrogenase activity is encoded by:
   a. a nucleic acid having the nucleotide sequence of SEQ ID NO: 5 or 18;
   b. a nucleic acid encoding the amino acid sequence of SEQ ID NO: 6;
   c. a nucleic acid which is at least 98% identical to the nucleic acid of a) or b); or
   d. a nucleic acid encoding a polypeptide comprising an amino acid sequence which is at least 98% identical to the amino acid sequence encoded by the nucleic acid of a) or b).

\* \* \* \* \*

SEQUENCE LISTING

<160> NUMBER OF SEQ ID NOS: 24

<210> SEQ ID NO 1
<211> LENGTH: 1308
<212> TYPE: DNA
<213> ORGANISM: Yersinia mollaretii

<400> SEQUENCE: 1

```
atgacaacct ctcgtactca acaaattcag cagttggaac aggaatggaa atcaccgcgc     60
tggaagggca tcacccgccc ctatagcgcc gaagaagtga tcaaactgcg cggttccgtt    120
aacccagaat gtacgctggc acagcacggc gcgaaaagat tgtgggagtt gctgcacggc    180
gaatcgcgta aaggctacat caactgtctg ggggcgctaa caggcggtca ggcattgcaa    240
caggcaaagg ccggtgttga agcgatttat ctgtcgggtt ggcaggtcgc cgccgatgcc    300
aataccgcct ccagcatgta tcccgatcaa tctctttacc cggtcgactc tgttccggcc    360
gtggttaagc gtattaataa cagcttccgc cgtgcagatc agattcagtg gtcgaataat    420
attgagccgg gcagcaaagg ctataccgac tatttcctgc cgattgtggc ggatgccgaa    480
gcgggttttg gcggcgtatt gaatgcgttt gaattgatga aagccatgat tgaagccggt    540
gctgcgggcg ttcactttga agatcaattg gcggcggtga agaaatgcgg ccatatgggc    600
ggcaaagttt tggtgccaac acaagaagcg attcagaagc tggttgctgc ccgcttagcc    660
gctgacgttc ttggcgtgcc aacactgctg attgcgcgca ctgatgctga tgctgcggat    720
ttgctgacct ctgattgcga cccttatgac agcgaattta ttgctggtga tcgtactgct    780
gagggcttct tccgcactca cgcgggcatt gagcaagcca tcagccgtgg tctggcctat    840
gccccttacg ccgacttggt gtggtgtgaa acctcgacgc cagatctggc gctggctaaa    900
cgctttgcag atgcggttca cgctaaattc cccggtaaat tattggctta taactgttcg    960
ccatcattta actggaaaaa gaacctgact gaccagcaga tcgccagctt ccaagatgac   1020
ctctccgcga tgggctacaa atatcaattt attaccttgg cgggcatcca cagtatgtgg   1080
ttcaacatgt tcgacttggc ccatgcttac gcgcaaggcg agggcatgaa gcactatgtt   1140
gagaaagtgc agcagccaga atttgcctcc gttgaacgcg gctacacctt tgcttcccat   1200
caacaagaag tgggcacggg ctattttgat aaagtcacca atatcattca gggcggcgag   1260
tcatcagtca ctgcactgac tggctcgacg gaagagcagc agttctaa                1308
```

<210> SEQ ID NO 2
<211> LENGTH: 435
<212> TYPE: PRT
<213> ORGANISM: Yersinia mollaretii

<400> SEQUENCE: 2

```
Met Thr Thr Ser Arg Thr Gln Gln Ile Gln Gln Leu Glu Gln Glu Trp
1               5                   10                  15

Lys Ser Pro Arg Trp Lys Gly Ile Thr Arg Pro Tyr Ser Ala Glu Glu
            20                  25                  30

Val Ile Lys Leu Arg Gly Ser Val Asn Pro Glu Cys Thr Leu Ala Gln
        35                  40                  45

His Gly Ala Lys Arg Leu Trp Glu Leu Leu His Gly Glu Ser Arg Lys
    50                  55                  60

Gly Tyr Ile Asn Cys Leu Gly Ala Leu Thr Gly Gly Gln Ala Leu Gln
65                  70                  75                  80

Gln Ala Lys Ala Gly Val Glu Ala Ile Tyr Leu Ser Gly Trp Gln Val
                85                  90                  95
```

```
Ala Ala Asp Ala Asn Thr Ala Ser Ser Met Tyr Pro Asp Gln Ser Leu
            100                 105                 110

Tyr Pro Val Asp Ser Val Pro Ala Val Val Lys Arg Ile Asn Asn Ser
            115                 120                 125

Phe Arg Arg Ala Asp Gln Ile Gln Trp Ser Asn Asn Ile Glu Pro Gly
130                 135                 140

Ser Lys Gly Tyr Thr Asp Tyr Phe Leu Pro Ile Val Ala Asp Ala Glu
145                 150                 155                 160

Ala Gly Phe Gly Gly Val Leu Asn Ala Phe Glu Leu Met Lys Ala Met
                165                 170                 175

Ile Glu Ala Gly Ala Ala Gly Val His Phe Glu Asp Gln Leu Ala Ala
            180                 185                 190

Val Lys Lys Cys Gly His Met Gly Gly Lys Val Leu Val Pro Thr Gln
            195                 200                 205

Glu Ala Ile Gln Lys Leu Val Ala Ala Arg Leu Ala Ala Asp Val Leu
210                 215                 220

Gly Val Pro Thr Leu Leu Ile Ala Arg Thr Asp Ala Asp Ala Ala Asp
225                 230                 235                 240

Leu Leu Thr Ser Asp Cys Asp Pro Tyr Asp Ser Glu Phe Ile Ala Gly
                245                 250                 255

Asp Arg Thr Ala Glu Gly Phe Phe Arg Thr His Ala Gly Ile Glu Gln
            260                 265                 270

Ala Ile Ser Arg Gly Leu Ala Tyr Ala Pro Tyr Ala Asp Leu Val Trp
            275                 280                 285

Cys Glu Thr Ser Thr Pro Asp Leu Ala Leu Ala Lys Arg Phe Ala Asp
290                 295                 300

Ala Val His Ala Lys Phe Pro Gly Lys Leu Leu Ala Tyr Asn Cys Ser
305                 310                 315                 320

Pro Ser Phe Asn Trp Lys Lys Asn Leu Thr Asp Gln Ile Ala Ser
                325                 330                 335

Phe Gln Asp Asp Leu Ser Ala Met Gly Tyr Lys Tyr Gln Phe Ile Thr
            340                 345                 350

Leu Ala Gly Ile His Ser Met Trp Phe Asn Met Phe Asp Leu Ala His
            355                 360                 365

Ala Tyr Ala Gln Gly Glu Gly Met Lys His Tyr Val Glu Lys Val Gln
370                 375                 380

Gln Pro Glu Phe Ala Ser Val Glu Arg Gly Tyr Thr Phe Ala Ser His
385                 390                 395                 400

Gln Gln Glu Val Gly Thr Gly Tyr Phe Asp Lys Val Thr Asn Ile Ile
                405                 410                 415

Gln Gly Gly Glu Ser Ser Val Thr Ala Leu Thr Gly Ser Thr Glu Glu
            420                 425                 430

Gln Gln Phe
        435

<210> SEQ ID NO 3
<211> LENGTH: 1632
<212> TYPE: DNA
<213> ORGANISM: Yersinia mollaretii

<400> SEQUENCE: 3
atgatcgtcg agagatgggg aaggggaagg ggaatgacac aacagatagt cggcacggag      60
ttagttttca cccagcattt taatgctgct gagcggcagg ttttgcccga tgaggccatc     120
```

| | |
|---|---|
| gaattttttgg cagaattggt ggcgaaattt gcagagccgc gtagcaaact ccttgctgca | 180 |
| cgggccgctt ggcaacaggc cattgaccaa ggcgcattgc ctgatttcat ttcggaaacc | 240 |
| aattccattc gtaatggtga ctggaaaatt caaagtattc ctgcggattt acgtgatcgt | 300 |
| cgcgtcgaga tcaccgggcc ggttgagcgc aaaatggtga ttaatgccct caatgcgaat | 360 |
| gtgaaagtct ttatggctga cttttgaggat cgctggcac ccagttggga taaggttatc | 420 |
| gaaggtcaga ttaatttgca cgatgcggtc aaaggcacaa tctcttacgc gaatgaatcc | 480 |
| ggtaagattt atcagctaaa acccaatcca gcggtgttga ttgctcgggt gcgtggtctg | 540 |
| cacttgccag aaaaacacgt gaagtggcag ggggaggata tccccggtgg cttattcgat | 600 |
| ttcgcgttgt atttctacca taactataag ttactgcttg ccaatggcag cggcccctat | 660 |
| ttctatctac ccaagatgca gtcttatcag gaagcggctt ggtggagtga tgttttcagc | 720 |
| tttaccgagc agcgtttcga tctgccgcaa ggcaccatta aggccacagt attaatcgag | 780 |
| acattgcctg cggtattcca gatggatgag atcctctacc atctgcgcca tcacattgtt | 840 |
| gccctgaatt gtggccgttg ggactacatt ttcagctata tcaaaacgct gaaaaatcac | 900 |
| agcgatcgcg tgctgcccga tcgccagtcg gtcacgatga cgaaacccct cctgagtgcc | 960 |
| tactctcgtt tactgatcaa aacctgccat aagcgcggtg ccttggcgat gggcggcatg | 1020 |
| gcggcccttta tcccgaacaa agatccagaa aaaatgcgc tggtcttaga taaagttcgc | 1080 |
| gctgacaaag agctggaagc cagcaacggc acgatggta catgggtcgc acaccccggt | 1140 |
| ctggccgata ccgtgatgga cgttttcaac aaagtactgg gcgatcgtcc aaaccaatta | 1200 |
| gaggtgagtc gcgcgcaaga taaaccaatc actgccgctg agttgctaga gccttgcacg | 1260 |
| ggtgagcgca ccgaagaggg gatgcgggcc aatatccggg tcgcagtgca atacatcgaa | 1320 |
| gcatggatat cgggcaatgg ctgtgtaccg atttatggcc tgatggaaga tgccgcgacg | 1380 |
| gctgagattt cccgtacttc tatctggcaa tggatacatc accagaaaag cctgagcaat | 1440 |
| ggtcagacgg tgaccaaaga gctgttccgt aacatgttga gtgaagaaat gcaggtcgtg | 1500 |
| aaacttgaac ttggcgcaga gcgttttgat ggcgggcggt ttgaagaagc cgcacgtctg | 1560 |
| atggagcgga ttcaacaca agacgagctt atcgactttc tgacgttgcc gggctacgca | 1620 |
| ttactcgcct ag | 1632 |

<210> SEQ ID NO 4
<211> LENGTH: 543
<212> TYPE: PRT
<213> ORGANISM: Yersinia mollaretii

<400> SEQUENCE: 4

Met Ile Val Glu Arg Trp Gly Arg Gly Arg Gly Met Thr Gln Gln Ile
1               5                   10                  15

Val Gly Thr Glu Leu Val Phe Thr Gln His Phe Asn Ala Ala Glu Arg
            20                  25                  30

Gln Val Leu Pro Asp Glu Ala Ile Glu Phe Leu Ala Glu Leu Val Ala
        35                  40                  45

Lys Phe Ala Glu Pro Arg Ser Lys Leu Leu Ala Arg Ala Ala Trp
    50                  55                  60

Gln Gln Ala Ile Asp Gln Gly Ala Leu Pro Asp Phe Ile Ser Glu Thr
65                  70                  75                  80

Asn Ser Ile Arg Asn Gly Asp Trp Lys Ile Gln Ser Ile Pro Ala Asp
                85                  90                  95

```
Leu Arg Asp Arg Arg Val Glu Ile Thr Gly Pro Val Glu Arg Lys Met
            100                 105                 110

Val Ile Asn Ala Leu Asn Ala Asn Val Lys Val Phe Met Ala Asp Phe
        115                 120                 125

Glu Asp Ser Leu Ala Pro Ser Trp Asp Lys Val Ile Glu Gly Gln Ile
    130                 135                 140

Asn Leu His Asp Ala Val Lys Gly Thr Ile Ser Tyr Ala Asn Glu Ser
145                 150                 155                 160

Gly Lys Ile Tyr Gln Leu Lys Pro Asn Pro Ala Val Leu Ile Ala Arg
                165                 170                 175

Val Arg Gly Leu His Leu Pro Glu Lys His Val Lys Trp Gln Gly Glu
        180                 185                 190

Asp Ile Pro Gly Gly Leu Phe Asp Phe Ala Leu Tyr Phe Tyr His Asn
    195                 200                 205

Tyr Lys Leu Leu Leu Ala Asn Gly Ser Gly Pro Tyr Phe Tyr Leu Pro
210                 215                 220

Lys Met Gln Ser Tyr Gln Glu Ala Ala Trp Trp Ser Asp Val Phe Ser
225                 230                 235                 240

Phe Thr Glu Gln Arg Phe Asp Leu Pro Gln Gly Thr Ile Lys Ala Thr
                245                 250                 255

Val Leu Ile Glu Thr Leu Pro Ala Val Phe Gln Met Asp Glu Ile Leu
        260                 265                 270

Tyr His Leu Arg His His Ile Val Ala Leu Asn Cys Gly Arg Trp Asp
    275                 280                 285

Tyr Ile Phe Ser Tyr Ile Lys Thr Leu Lys Asn His Ser Asp Arg Val
290                 295                 300

Leu Pro Asp Arg Gln Ser Val Thr Met Thr Lys Pro Phe Leu Ser Ala
305                 310                 315                 320

Tyr Ser Arg Leu Leu Ile Lys Thr Cys His Lys Arg Gly Ala Leu Ala
                325                 330                 335

Met Gly Gly Met Ala Ala Phe Ile Pro Asn Lys Asp Pro Glu Lys Asn
        340                 345                 350

Ala Leu Val Leu Asp Lys Val Arg Ala Asp Lys Glu Leu Glu Ala Ser
    355                 360                 365

Asn Gly His Asp Gly Thr Trp Val Ala His Pro Gly Leu Ala Asp Thr
370                 375                 380

Val Met Asp Val Phe Asn Lys Val Leu Gly Asp Arg Pro Asn Gln Leu
385                 390                 395                 400

Glu Val Ser Arg Ala Gln Asp Lys Pro Ile Thr Ala Ala Glu Leu Leu
                405                 410                 415

Glu Pro Cys Thr Gly Glu Arg Thr Glu Glu Gly Met Arg Ala Asn Ile
        420                 425                 430

Arg Val Ala Val Gln Tyr Ile Glu Ala Trp Ile Ser Gly Asn Gly Cys
    435                 440                 445

Val Pro Ile Tyr Gly Leu Met Glu Asp Ala Ala Thr Ala Glu Ile Ser
450                 455                 460

Arg Thr Ser Ile Trp Gln Trp Ile His His Gln Lys Ser Leu Ser Asn
465                 470                 475                 480

Gly Gln Thr Val Thr Lys Glu Leu Phe Arg Asn Met Leu Ser Glu Glu
                485                 490                 495

Met Gln Val Val Lys Leu Glu Leu Gly Ala Glu Arg Phe Asp Gly Gly
        500                 505                 510
```

```
Arg Phe Glu Glu Ala Ala Arg Leu Met Glu Arg Ile Thr Thr Gln Asp
        515                 520                 525

Glu Leu Ile Asp Phe Leu Thr Leu Pro Gly Tyr Ala Leu Leu Ala
    530                 535                 540

<210> SEQ ID NO 5
<211> LENGTH: 1092
<212> TYPE: DNA
<213> ORGANISM: Candida boidinii

<400> SEQUENCE: 5
atgaagatcg ttttagtctt atatgatgct ggtaagcacg ctgctgatga agaaaaatta      60
tatggttgta ctgaaaataa attaggtatt gctaattggt taaaagatca aggtcatgaa     120
ctaattacta cttctgataa agaaggtgaa acaagtgaat tggataaaca tatcccagat     180
gctgatatta tcatcaccac tcctttccat cctgcttata tcactaagga aagacttgac     240
aaggctaaga acttaaaatt agtcgttgtc gctggtgttg gttctgatca cattgattta     300
gattatatta atcaaacagg taagaaaatc tcagtcttgg aagttacagg ttctaatgtt     360
gtctctgttg ctgaacacgt tgtcatgacc atgcttgtct tggttagaaa tttcgttcca     420
gcacatgaac aaattattaa ccacgattgg gaggttgctg ctatcgctaa ggatgcttac     480
gatatcgaag gtaaaactat tgctaccatt ggtgctggta gaattggtta cagagtcttg     540
gaaagattac tccctttaa tccaaaagaa ttattatact acgattatca agctttacca     600
aaagaagctg aagaaaagt tggtgctaga gagttgaaaa tattgaaga attagttgct     660 caagctgata tcgttacagt taatgctcca ttacacgcag gtacaaaagg tttaattaat     720
aaggaattat tatctaaatt taaaaaaggt gcttggttag tcaataccgc aagaggtgct     780
atttgtgttg ctgaagatgt tgcagcagct ttagaatctg gtcaattaag aggttacggt     840
ggtgatgttt ggttcccaca accagctcca aaggatcacc catggagaga tatgagaaat     900
aaatatggtg ctggtaatgc catgactcct cactactctg gtactacttt agatgctcaa     960
acaagatacg ctgaaggtac taaaaatatc ttggaatcat tctttactgg taaatttgat    1020
tacagaccac aagatattat cttattaaat ggtgaatacg ttactaaagc ttacggtaaa    1080
cacgataaga aa                                                       1092

<210> SEQ ID NO 6
<211> LENGTH: 364
<212> TYPE: PRT
<213> ORGANISM: Candida boidinii

<400> SEQUENCE: 6

Met Lys Ile Val Leu Val Leu Tyr Asp Ala Gly Lys His Ala Ala Asp
1               5                   10                  15

Glu Glu Lys Leu Tyr Gly Cys Thr Glu Asn Lys Leu Gly Ile Ala Asn
            20                  25                  30

Trp Leu Lys Asp Gln Gly His Glu Leu Ile Thr Thr Ser Asp Lys Glu
        35                  40                  45

Gly Glu Thr Ser Glu Leu Asp Lys His Ile Pro Asp Ala Asp Ile Ile
    50                  55                  60

Ile Thr Thr Pro Phe His Pro Ala Tyr Ile Thr Lys Glu Arg Leu Asp
65                  70                  75                  80

Lys Ala Lys Asn Leu Lys Leu Val Val Val Ala Gly Val Gly Ser Asp
                85                  90                  95
```

His Ile Asp Leu Asp Tyr Ile Asn Gln Thr Gly Lys Lys Ile Ser Val
            100                 105                 110

Leu Glu Val Thr Gly Ser Asn Val Val Ser Val Ala Glu His Val Val
        115                 120                 125

Met Thr Met Leu Val Leu Val Arg Asn Phe Val Pro Ala His Glu Gln
    130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
            180                 185                 190

Tyr Tyr Asp Tyr Gln Ala Leu Pro Lys Glu Ala Glu Lys Val Gly
        195                 200                 205

Ala Arg Arg Val Glu Asn Ile Glu Glu Leu Val Ala Gln Ala Asp Ile
    210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Cys Val Ala Glu Asp Val Ala Ala Ala Leu Glu
            260                 265                 270

Ser Gly Gln Leu Arg Gly Tyr Gly Gly Asp Val Trp Phe Pro Gln Pro
        275                 280                 285

Ala Pro Lys Asp His Pro Trp Arg Asp Met Arg Asn Lys Tyr Gly Ala
    290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
            340                 345                 350

Tyr Val Thr Lys Ala Tyr Gly Lys His Asp Lys Lys
        355                 360

<210> SEQ ID NO 7
<211> LENGTH: 1541
<212> TYPE: DNA
<213> ORGANISM: Pasteurella DSM 18541

<400> SEQUENCE: 7
attgaagagt ttgatcatgg ctcagattga acgctggcgg caggcttaac acatgcaagt    60
cgaacggtag cgggaggaaa gcttgctttc tttgccgacg agtggcggac gggtgagtaa   120
tgcttgggga tctggcttat ggaggggat aacgacggga aactgtcgct aataccgcgt   180
aatatcttcg gattaaaggg tgggactttc gggccaccg ccataagatg agcccaagtg   240
ggattaggta gttggtgggg taaaggccta ccaagccgac gatctctagc tggtctgaga   300
ggatgaccag ccacactgga actgagacac ggtccagact cctacgggag gcagcagtgg   360
ggaatattgc acaatggggg gaaccctgat gcagccatgc cgcgtgaatg aagaaggcct   420
tcgggttgta aagttctttc ggtgacgagg aaggtgtttg ttttaatagg acaagcaatt   480
gacgttaatc acagaagaag caccggctaa ctccgtgcca gcagccgcgg taatacggag   540
ggtgcgagcg ttaatcggaa taactgggcg taaagggcat gcaggcggac ttttaagtga   600

```
gatgtgaaag ccccgggctt aacctgggaa ttgcatttca gactgggagt ctagagtact     660
ttagggaggg gtagaattcc acgtgtagcg gtgaaatgcg tagagatgtg gaggaatacc     720
gaaggcgaag gcagccccct tgggaagatac tgacgctcat atgcgaaagc gtggggagca   780
aacaggatta gataccctgg tagtccacgc ggtaaacgct gtcgatttgg ggattgggct    840
ttaggcctgg tgctcgtagc taacgtgata aatcgaccgc ctggggagta cggccgcaag    900
gttaaaactc aaatgaattg acgggggccc gcacaagcgg tggagcatgt ggtttaattc    960
gatgcaacgc gaagaacctt acctactctt gacatccaga gaatcctgta gagatacggg   1020
agtgccttcg ggagctctga gacaggtgct gcatggctgt cgtcagctcg tgttgtgaaa   1080
tgttgggtta agtcccgcaa cgagcgcaac ccttatcctt gttgccagc atgtaaagat    1140
gggaactcaa aggagactgc cggtgacaaa ccggaggaag gtgggatga cgtcaagtca    1200
tcatggccct tacgagtagg gctacacacg tgctacaatg gtgcatacag agggcggcga   1260
taccgcgagg tagagcgaat ctcagaaagt gcatcgtagt ccggattgga gtctgcaact   1320
cgactccatg aagtcggaat cgctagtaat cgcaaatcag aatgttgcgg tgaatacgtt   1380
cccgggcctt gtacacaccg cccgtcacac catgggagtg ggttgtacca gaagtagata   1440
gcttaacctt cggggggcgt ttaccacggt atgattcatg actggggtga agtcgtaaca   1500
aggtaaccgt aggggaacct gcggttggat cacctcctta c                      1541

<210> SEQ ID NO 8
<211> LENGTH: 2891
<212> TYPE: DNA
<213> ORGANISM: Pasteurella DSM 18541
<220> FEATURE:
<221> NAME/KEY: misc_feature
<222> LOCATION: (456)..(456)
<223> OTHER INFORMATION: n is a, c, g, or t
<400> SEQUENCE: 8
gttaagtgac taagcgtaca aggtggatgc cttggcaatc agaggcgaag aaggacgtgc     60
taatctgcga aaagcttggg tgagttgata agaagcgtct aacccaagat atccgaatgg   120
ggcaacccag tagatgaaga atctactatc aataaccgaa tccataggtt attgaggcaa    180
accgggagaa ctgaaacatc taagtacccc gaggaaaaga aatcaaccga gattacgtca    240
gtagcggcga gcgaaagcgt aagagccggc aagtgatagc atgaggatta gaggaatcgg   300
ctgggaagcc gggcggcaca gggtgatagc cccgtacttg aaaatcattg tgtggtactg   360
agcttgcgag aagtagggcg ggacacgaga atcctgtttt gaagaagggg ggaccatcct   420
ccaaggctaa atactcctga ttgaccgata gtgaanagta ctgtgaagga aaggcgaaaa    480
gaacccggt gaggggagtg aaatagaacc tgaaaccttg tacgtacaag cagtgggagc    540
ccgcgagggt gactgcgtac ctttttgtata atgggtcagc gacttatatt atgtagcgag    600
gttaaccgaa taggggagcc gaagggaaac cgagtcttaa ctgggcgtcg agttgcatga    660
tatagacccg aaacccggtg atctagccat gggcaggttg aaggttgggt aacactaact    720
ggaggaccga accgactaat gttgaaaaat tagcggatga cctgtggctg ggggtgaaag    780
gccaatcaaa ccgggagata gctggttctc cccgaaatct atttaggtag agccttatgt    840
gaataccttc gggggtagag cactgtttcg gctaggggc catcccggct taccaacccg     900
atgcaaactg cgaataccga agagtaatgc ataggagaca cacggcgggt gctaacgttc    960
gtcgtggaga gggaaacaac ccagaccgcc agctaaggtc ccaaagtttta tattaagtgg  1020
gaaacgaagt gggaaggctt agacagctag gatgttggct tagaagcagc catcatttaa  1080
```

| | |
|---|---|
| agaaagcgta atagctcact agtcgagtcg gcctgcgcgg aagatgtaac ggggctcaaa | 1140 |
| tatagcaccg aagctgcggc atcaggcgta agcctgttgg gtaggggagc gtcgtgtaag | 1200 |
| cggaagaagg tggttcgaga gggctgctgg acgtatcacg agtgcgaatg ctgacataag | 1260 |
| taacgataaa acgggtgaaa aacccgttcg ccggaagacc aagggttcct gtccaacgtt | 1320 |
| aatcggggca gggtgagtcg gcccctaagg cgaggctgaa gagcgtagtc gatgggaaac | 1380 |
| gggttaatat tcccgtactt gttataattg cgatgtgggg acggagtagg ttaggttatc | 1440 |
| gacctgttgg aaaaggtcgt ttaagttggt aggtggagcg tttaggcaaa tccggacgct | 1500 |
| tatcaacacc gagagatgat gacgaggcgc taaggtgccg aagtaaccga taccacactt | 1560 |
| ccaggaaaag ccactaagcg tcagattata ataaaccgta ctataaaccg acacaggtgg | 1620 |
| tcaggtagag aatactcagg cgcttgagag aactcgggtg aaggaactag gcaaaatagc | 1680 |
| accgtaactt cgggagaagg tgcgccggcg tagattgtag aggtataccc ttgaaggttg | 1740 |
| aaccggtcga agtgacccgc tggctgcaac tgtttattaa aaacacagca ctctgcaaac | 1800 |
| acgaaagtgg acgtataggg tgtgatgcct gcccggtgct ggaaggttaa ttgatggcgt | 1860 |
| tatcgcaaga gaagcgcctg atcgaagccc cagtaaacgg cggccgtaac tataacggtc | 1920 |
| ctaaggtagc gaaattcctt gtcgggtaag ttccgacctg cacgaatggc ataatgatgg | 1980 |
| ccaggctgtc tccacccgag actcagtgaa attgaaatcg ccgtgaagat gcggtgtacc | 2040 |
| cgcggctaga cggaaagacc ccgtgaacct ttactatagc ttgacactga accttgaatt | 2100 |
| ttgatgtgta ggataggtgg gaggctttga agcggtaacg ccagttatcg tggagccatc | 2160 |
| cttgaaatac caccctttaa cgtttgatgt tctaacgaag tgcccggaac gggtactcgg | 2220 |
| acagtgtctg gtgggtagtt tgactgggc ggtctcctcc caaagagtaa cggaggagca | 2280 |
| cgaaggtttg ctaatgacgg tcggacatcg tcaggttagt gcaatggtat aagcaagctt | 2340 |
| aactgcgaga cggacaagtc gagcaggtgc gaaagcaggt catagtgatc cggtggttct | 2400 |
| gaatggaagg gccatcgctc aacggataaa aggtactccg gggataacag gctgataccg | 2460 |
| cccaagagtt catatcgacg gcggtgtttg gcacctcgat gtcggctcat cacatcctgg | 2520 |
| ggctgaagta ggtcccaagg gtatggctgt tcgccattta aagtggtacg cgagctgggt | 2580 |
| ttaaaacgtc gtgagacagt ttggtcccta tctgccgtgg gcgttggaga attgagaggg | 2640 |
| gctgctccta gtacgagagg accggagtgg acgcatcact ggtgttccgg ttgtgtcgcc | 2700 |
| agacgcattg ccgggtagct acatgcggaa gagataagtg ctgaaagcat ctaagcacga | 2760 |
| aacttgcctc gagatgagtt ctcccagtat ttaatactgt aagggttgtt ggagacgacg | 2820 |
| acgtagatag gccgggtgtg taagcgttgc gagacgttga gctaaccggt actaattgcc | 2880 |
| cgagaggctt a | 2891 |

<210> SEQ ID NO 9
<211> LENGTH: 4285
<212> TYPE: DNA
<213> ORGANISM: Artificial Sequence
<220> FEATURE:
<223> OTHER INFORMATION: vector

<400> SEQUENCE: 9

| | |
|---|---|
| tcgagaggcc tgacgtcggg cccggtacca cgcgtcatat gactagttcg gacctaggga | 60 |
| tatcgtcgac atcgatgctc ttctgcgtta attaacaatt gggatcctct agactccata | 120 |
| ggccgctttc ctggctttgc ttccagatgt atgctctcct ccggagagta ccgtgacttt | 180 |

-continued

| | |
|---|---|
| attttcggca caaatacagg ggtcgatgga taaatacggc gatagttttcc tgacggatga | 240 |
| tccgtatgta ccggcggaag acaagctgca aacctgtcag atggagattg atttaatggc | 300 |
| ggatgtgctg agagcaccgc cccgtgaatc cgcagaactg atccgctatg tgtttgcgga | 360 |
| tgattggccg gaataaataa agccgggctt aatacagatt aagcccgtat agggtattat | 420 |
| tactgaatac caaacagctt acggaggacg gaatgttacc cattgagaca accagactgc | 480 |
| cttctgatta ttaatatttt tcactattaa tcagaaggaa taaccatgaa ttttacccgg | 540 |
| attgacctga atacctggaa tcgcagggaa cactttgccc tttatcgtca gcagattaaa | 600 |
| tgcggattca gcctgaccac caaactcgat attaccgctt tgcgtaccgc actggcggag | 660 |
| acaggttata agttttatcc gctgatgatt tacctgatct cccgggctgt taatcagttt | 720 |
| ccggagttcc ggatggcact gaaagacaat gaacttattt actgggacca gtcagacccg | 780 |
| gtctttactg tctttcataa agaaaccgaa acattctctg cactgtcctg ccgttatttt | 840 |
| ccggatctca gtgagtttat ggcaggttat aatgcggtaa cggcagaata tcagcatgat | 900 |
| accagattgt ttccgcaggg aaatttaccg gagaatcacc tgaatatatc atcattaccg | 960 |
| tgggtgagtt ttgacgggat ttaacctgaa catcaccgga aatgatgatt attttgcccc | 1020 |
| ggttttacg atggcaaagt ttcagcagga aggtgaccgc gtattattac ctgtttctgt | 1080 |
| acaggttcat catgcagtct gtgatggctt tcatgcagca cggtttatta atacacttca | 1140 |
| gctgatgtgt gataacatac tgaaataaat taattaattc tgtatttaag ccaccgtatc | 1200 |
| cggcaggaat ggtggctttt tttttatatt ttaaccgtaa tctgtaattt cgtttcagac | 1260 |
| tggttcagga tgagctcgct tggactcctg ttgatagatc cagtaatgac ctcagaactc | 1320 |
| catctggatt tgttcagaac gctcggttgc cgccgggcgt tttttattgg tgagaatcca | 1380 |
| agcactagcg gcgcgccggc cggcccggtg tgaaataccg cacagatgcg taaggagaaa | 1440 |
| ataccgcatc aggcgctctt ccgcttcctc gctcactgac tcgctgcgct cggtcgttcg | 1500 |
| gctgcggcga gcggtatcag ctcactcaaa ggcggtaata cggttatcca cagaatcagg | 1560 |
| ggataacgca ggaaagaaca tgtgagcaaa aggccagcaa aaggccagga accgtaaaaa | 1620 |
| ggccgcgttg ctggcgtttt tccataggct ccgcccccct gacgagcatc acaaaaatcg | 1680 |
| acgctcaagt cagaggtggc gaaacccgac aggactataa agataccagg cgtttccccc | 1740 |
| tggaagctcc ctcgtgcgct ctcctgttcc gaccctgccg cttaccggat acctgtccgc | 1800 |
| cttttctccct tcgggaagcg tggcgctttc tcatagctca cgctgtaggt atctcagttc | 1860 |
| ggtgtaggtc gttcgctcca agctgggctg tgtgcacgaa ccccccgttc agcccgaccg | 1920 |
| ctgcgcctta tccggtaact atcgtcttga gtccaacccg gtaagacacg acttatcgcc | 1980 |
| actggcagca gccactggta acaggattag cagagcgagg tatgtaggcg gtgctacaga | 2040 |
| gttcttgaag tggtggccta actacggcta cactagaagg acagtatttg gtatctgcgc | 2100 |
| tctgctgaag ccagttacct tcggaaaaag agttggtagc tcttgatccg gcaaacaaac | 2160 |
| caccgctggt agcggtggtt ttttgtttg caagcagcag attacgcgca gaaaaaaagg | 2220 |
| atctcaagaa gatcctttga tcttttctac ggggtctgac gctcagtgga acgaaaactc | 2280 |
| acgttaaggg attttggtca tgagattatc aaaaaggatc ttcacctaga tccttttaaa | 2340 |
| ggccggccgc ggccgccatc ggcattttct tttgcgtttt tatttgttaa ctgttaattg | 2400 |
| tccttgttca aggatgctgt ctttgacaac agatgttttc ttgcctttga tgttcagcag | 2460 |
| gaagctcggc gcaaacgttg attgtttgtc tgcgtagaat cctctgtttg tcatatagct | 2520 |
| tgtaatcacg acattgtttc ctttcgcttg aggtacagcg aagtgtgagt aagtaaaggt | 2580 |

-continued

```
tacatcgtta ggatcaagat ccattttaa cacaaggcca gttttgttca gcggcttgta      2640
tgggccagtt aaagaattag aaacataacc aagcatgtaa atatcgttag acgtaatgcc      2700
gtcaatcgtc atttttgatc cgcgggagtc agtgaacagg taccatttgc cgttcatttt      2760
aaagacgttc gcgcgttcaa tttcatctgt tactgtgtta gatgcaatca gcggtttcat      2820
cacttttttc agtgtgtaat catcgtttag ctcaatcata ccgagagcgc cgtttgctaa      2880
ctcagccgtg cgttttttat cgctttgcag aagttttga ctttcttgac ggaagaatga      2940
tgtgcttttg ccatagtatg ctttgttaaa taaagattct tcgccttggt agccatcttc      3000
agttccagtg tttgcttcaa atactaagta tttgtggcct ttatcttcta cgtagtgagg      3060
atctctcagc gtatggttgt cgcctgagct gtagttgcct tcatcgatga actgctgtac      3120
attttgatac gttttccgt caccgtcaaa gattgattta taatcctcta caccgttgat       3180
gttcaaagag ctgtctgatg ctgatacgtt aacttgtgca gttgtcagtg tttgtttgcc      3240
gtaatgttta ccggagaaat cagtgtagaa taaacggatt tttccgtcag atgtaaatgt      3300
ggctgaacct gaccattctt gtgtttggtc ttttaggata gaatcatttg catcgaattt      3360
gtcgctgtct ttaaagacgc ggccagcgtt tttccagctg tcaatagaag tttcgccgac      3420
tttttgatag aacatgtaaa tcgatgtgtc atccgcattt ttaggatctc cggctaatgc      3480
aaagacgatg tggtagccgt gatagtttgc gacagtgccg tcagcgtttt gtaatggcca      3540
gctgtcccaa acgtccaggc ttttgcaga agagatattt ttaattgtgg acgaatcaaa       3600
ttcagaaact tgatattttt cattttttg ctgttcaggg atttgcagca tatcatggcg       3660
tgtaatatgg gaaatgccgt atgtttcctt atatggcttt tggttcgttt ctttcgcaaa      3720
cgcttgagtt gcgcctcctg ccagcagtgc ggtagtaaag gttaatactg ttgcttgttt      3780
tgcaaacttt ttgatgttca tcgttcatgt ctccttttt atgtactgtg ttagcggtct       3840
gcttcttcca gccctcctgt ttgaagatgg caagttagtt acgcacaata aaaaagacc       3900 taaaatatgt aaggggtgac gccaaagtat acactttgcc ctttacacat tttaggtctt      3960
gcctgcttta tcagtaacaa acccgcgcga tttactttc gacctcattc tattagactc       4020
tcgtttggat tgcaactggt ctattttcct cttttgtttg atagaaaatc ataaaaggat      4080
ttgcagacta cgggcctaaa gaactaaaaa atctatctgt ttcttttcat tctctgtatt      4140
ttttatagtt tctgttgcat gggcataaag ttgccttttt aatcacaatt cagaaaatat      4200
cataatatct catttcacta ataatagtg aacggcaggt atatgtgatg ggttaaaaag       4260
gatcggcggc cgctcgattt aaatc                                             4285
```

<210> SEQ ID NO 10
<211> LENGTH: 7112
<212> TYPE: DNA
<213> ORGANISM: artificial
<220> FEATURE:
<223> OTHER INFORMATION: vector

<400> SEQUENCE: 10

```
tcgagaggcc tgacgtcggg cccggtacca cgcgtcatat gactagttcg gacctaggga      60
tatcgtcgac atcgatgctc ttctgcgtta attaacaatt gggatcctct agacccgggg     120
attccaacct gaagactggc tcggtatgac cgaacccgtc aatattccgg gaaccagcac      180
tcaatatgct aactggcggc gccgtttaac cgcaaatata gaggatattt ttgccgatac      240
ggatattcaa catctgttaa aagaggtgaa tgctattcgt aaggaataat tttgttgcga      300
```

```
acgcaatgtg attttaacgg gtgccggata tggcacccct atcaaaacga cgaatattat    360
agacctctta cgatgacgca tctttcccca gatacgcagg attagacgga tgatgttacg    420
gaatatcccg tccctgtgcg gcaacataaa ccttaatcca ttcttcctca gtgaaggaaa    480
ttcgtaacgc atccgccgcg cttttttaccc gttcaatttt accggacccc ataaccggca    540
taatttttgc cggatgcgcc aataaccagg cataagccaa tgtatctaaa cgggtttctc    600
ctttcgtttc accgatttcg agtaatgttt tttgcaccgc ccgactgttc tcatcctgat    660
tgaataaacg accgccggca gtggcgacc  atgccatcgg ttgaatacgt ttttccagta    720
aaaaatccag ggtaccgtca tcaaaagcct gacgatgaag aggcgaaatc tcaatttgat    780
tagtgattaa cggctgattc acataagatt gcaacatggc gaacttagcc ggcgtatagt    840
tagataccc  gaaataacgt actttyccgg tttgataaag ttcatcaaaa gcccgcgcga    900
tttgttcggg atccgcacag ggagaaagwc ggtgaatcag caatacatct aaatagtcgc    960
attgcagttt ttcaatggaa cgttgcgccg accacataat atggcggtag ctgttgtcat   1020
agtgatggga ttttatatcg ggtaattctt cattaggata caaaatcccg catttggtca   1080
ccaaagtaag ctgtgcgcgc aaggatttat ccagcgccag cgcccgtccg aattccgcct   1140
cggaagtaaa agccccgtaa caagcggcat gatccagcgt atcaacgcct aattctaatc   1200
cttgcttaac gaatgtaagc aattcctgcg gcgatttccg ccagcttttt aaccgccaga   1260
atccttgaat taagcgactg aatgttaaat cgggagccaa ttgaatgtgt tgcataaaac   1320
ctccaaataa attgaatcaa acagacttaa gtataaatct ttaaagaaaa agtgcggtag   1380
aaaaatatgg attttccgca taaaaaaagc gtacccgatt aggtacgcta ttaaaaatat   1440
aagcggcgct attctactct cttatggatc tcagtcaaga aaggatccgg caaccrccga   1500
acaaatggag rcgaaraaat tgaaaagacg aggaaatcag cgcgttaaaa attcccgaaa   1560
acccaccgca cttttttattg gaatttgcta accttaaaag tgcggtcaaa agttaaaaa    1620
ttttaagatt gcaattccaa cggattctta cccgctttac gcaaagcctg atgttcttta   1680
ataatcgcca taaaggctg  tccgaagcgc tgccatttga tggcgccgac accgttgatt   1740
tgcagcattt ccactttgct ggtcggctga tacaacgaca tttcctgcaa ggtcgcgtca   1800
ctgaacacaa tataaggcgg aatgttttct ttgtcggcaa tctgtttgcg caggaaacgc   1860
aggcgggcaa ataaatcttt gtcgtagttg gttaccgcat tgcgttgcgg agcctgtacc   1920
atggtaatgg aagataatct cggcatggcc agttccaaag acacttcgcc gcgcagcacg   1980
ggacgcgcgc tttcggtgag ctgtaatctg gtccccatgc cgaaatcgct gatgatttgt   2040
tgcacaaagc ccaaatgaat cagctgacga attaccgatt gccagtattc tttgctttta   2100
tctttgccaa ttccgtagac tttcaactca tcatgttgat tttctttat  tttctgattc   2160
tgcaaaccgc gcattacgcc gattacgtat tgcgtgccga acgttgccc  ggtgcgataa   2220
atggtcgaaa ggattttctg cgcgtctaat aatccgtcat attttttcgg cggatcgagg   2280
cagatatcac agttattaca tggcgtttgg cggttttcgc cgaataatt  taacagcact   2340
aaacgacggc aggtctggct ttcggcaaat tcgccgatgg cttccagctt atgccgttta   2400
atatcccgtt gcgggctttc cggctcttcc aataaaattt tatgcaacca ggcataatcc   2460
gccggctcgt aaaacagtac cgcttccgcc ggcaggtcgt cccgcccgc  gcgccggtt    2520
tcctgataat acgcctcaat gctgcgagat aaatcaaaat gcgccacaaa acgcacatta   2580
gatttgttga tccccatacc aaaagcaatg gtcgccacca ccacttgaat attatcccgt   2640
tgaaacgcct gttgcaccgc ttcccgctgc gacggctcca tgcccgcatg ataagcggct   2700
```

```
gcggaaatgc ctctttcctt cagggcttcc gcaatgcgct ccactttgct acggctgttg    2760
caatagacga taccgcttt accttttgc gccgccacaa aattgtataa ttgctccatc    2820
ggtttgaatt tttccaccaa ggtataacga atattcgggc ggtcaaaact acctacatac    2880
aagtgcggtt cgttcaggct gacccgggat ttaaatcgct agcgggctgc taaaggaagc    2940
ggaacacgta gaaagccagt ccgcagaaac ggtgctgacc ccggatgaat gtcagctact    3000
gggctatctg gacaagggaa aacgaagcg caaagagaaa gcaggtagct tgcagtgggc    3060
ttacatggcg atagctagac tgggcggttt tatggacagc aagcgaaccg gaattgccag    3120
ctggggcgcc ctctggtaag gttgggaagc cctgcaaagt aaactggatg gctttcttgc    3180
cgccaaggat ctgatggcgc aggggatcaa gatctgatca agagacagga tgaggatcgt    3240
ttcgcatgat tgaacaagat ggattgcacg caggttctcc ggccgcttgg gtggagaggc    3300
tattcggcta tgactgggca caacagacaa tcggctgctc tgatgccgcc gtgttccggc    3360
tgtcagcgca ggggcgcccg gttcttttg tcaagaccga cctgtccggt gccctgaatg    3420
aactgcagga cgaggcagcg cggctatcgt ggctggccac gacgggcgtt ccttgcgcag    3480
ctgtgctcga cgttgtcact gaagcgggaa gggactggct gctattgggc gaagtgccgg    3540
ggcaggatct cctgtcatct caccttgctc ctgccgagaa agtatccatc atggctgatg    3600
caatgcggcg gctgcatacg cttgatccgg ctacctgccc attcgaccac caagcgaaac    3660
atcgcatcga gcgagcacgt actcggatgg aagccggtct tgtcgatcag gatgatctgg    3720
acgaagagca tcaggggctc gcgccagccg aactgttcgc caggctcaag gcgcgcatgc    3780
ccgacggcga ggatctcgtc gtgacccatg gcgatgcctg cttgccgaat atcatggtgg    3840 aaaatgccg cttttctgga ttcatcgact gtggccggct gggtgtggcg gaccgctatc    3900
aggacatagc gttggctacc cgtgatattg ctgaagagct tggcggcgaa tgggctgacc    3960
gcttcctcgt gctttacggt atcgccgctc ccgattcgca gcgcatcgcc ttctatcgcc    4020
ttcttgacga gttcttctga gcgggactct ggggttcgaa atgaccgacc aagcgacgcc    4080
caacctgcca tcacgagatt tcgattccac cgccgccttc tatgaaaggt tgggcttcgg    4140
aatcgttttc cgggacgccg gctggatgat cctccagcgc ggggatctca tgctggagtt    4200
cttcgcccac gctagcggcg cgccggccgg cccggtgtga ataccgcac agatgcgtaa    4260 ggagaaaata ccgcatcagg cgctcttccg cttcctcgct cactgactcg ctgcgctcgg    4320
tcgttcggct gcggcgagcg gtatcagctc actcaaaggc ggtaatacgg ttatccacag    4380
aatcagggga taacgcagga aagaacatgt gagcaaaagg ccagcaaaag gccaggaacc    4440
gtaaaaaggc cgcgttgctg gcgtttttcc ataggctccg cccccctgac gagcatcaca    4500
aaaatcgacg ctcaagtcag aggtggcgaa acccgacagg actataaaga taccaggcgt    4560
ttccccctgg aagctccctc gtgcgctctc ctgttccgac cctgccgctt accggatacc    4620
tgtccgcctt tctcccttcg ggaagcgtgg cgctttctca tagctcacgc tgtaggtatc    4680
tcagttcggt gtaggtcgtt cgctccaagc tgggctgtgt gcacgaaccc cccgttcagc    4740
ccgaccgctg cgccttatcc ggtaactatc gtcttgagtc aacccggta agacacgact    4800 tatcgccact ggcagcagcc actggtaaca ggattagcag agcgaggtat gtaggcggtg    4860
ctacagagtt cttgaagtgg tggcctaact acggctacac tagaaggaca gtatttggta    4920
tctgcgctct gctgaagcca gttaccttcg gaaaaagagt tggtagctct tgatccggca    4980
aacaaaccac cgctggtagc ggtggttttt tgtttgcaa gcagcagatt acgcgcagaa    5040
```

```
aaaaaggatc tcaagaagat cctttgatct tttctacggg gtctgacgct cagtggaacg    5100
aaaactcacg ttaagggatt ttggtcatga gattatcaaa aaggatcttc acctagatcc    5160
ttttaaaggc cggccgcggc cgccatcggc attttctttt gcgtttttat ttgttaactg    5220
ttaattgtcc ttgttcaagg atgctgtctt tgacaacaga tgttttcttg cctttgatgt    5280
tcagcaggaa gctcggcgca aacgttgatt gtttgtctgc gtagaatcct ctgtttgtca    5340
tatagcttgt aatcacgaca ttgttttcct tcgcttgagg tacagcgaag tgtgagtaag    5400
taaaggttac atcgttagga tcaagatcca ttttttaacac aaggccagtt ttgttcagcg    5460
gcttgtatgg gccagttaaa gaattagaaa cataaccaag catgtaaata tcgttagacg    5520
taatgccgtc aatcgtcatt tttgatccgc gggagtcagt gaacaggtac catttgccgt    5580
tcattttaaa gacgttcgcg cgttcaattt catctgttac tgtgttagat gcaatcagcg    5640
gtttcatcac ttttttcagt gtgtaatcat cgtttagctc aatcataccg agagcgccgt    5700
ttgctaactc agccgtgcgt tttttatcgc tttgcagaag ttttttgactt tcttgacgga    5760 agaatgatgt gcttttgcca tagtatgctt tgttaaataa agattcttcg ccttggtagc    5820
catcttcagt tccagtgttt gcttcaaata ctaagtattt gtggccttta tcttctacgt    5880
agtgaggatc tctcagcgta tggttgtcgc ctgagctgta gttgccttca tcgatgaact    5940
gctgtacatt tgatacgtt tttccgtcac cgtcaaagat tgatttataa tcctctacac    6000
cgttgatgtt caaagagctg tctgatgctg atacgttaac ttgtgcagtt gtcagtgttt    6060
gtttgccgta atgtttaccg gagaaatcag tgtagaataa acggatttt ccgtcagatg    6120 taaatgtggc tgaacctgac cattcttgtg tttggtcttt taggatagaa tcatttgcat    6180
cgaatttgtc gctgtctta aagacgcggc cagcgttttt ccagctgtca atagaagttt    6240
cgccgacttt tgatagaac atgtaaatcg atgtgtcatc cgcatttta ggatctccgg    6300 ctaatgcaaa gacgatgtgg tagccgtgat agtttgcgac agtgccgtca gcgttttgta    6360
atggccagct gtcccaaacg tccaggcctt tgcagaaga gatattttta attgtggacg    6420
aatcaaattc agaaacttga tatttttcat tttttttgctg ttcagggatt tgcagcatat    6480 catgcgtgt aatatgggaa atgccgtatg tttccttata tggcttttgg ttcgtttctt    6540
tcgcaaacgc ttgagttgcg cctcctgcca gcagtgcggt agtaaaggtt aatactgttg    6600
cttgttttgc aaacttttg atgttcatcg ttcatgtctc ctttttttatg tactgtgtta    6660 gcggtctgct tcttccagcc ctcctgtttg aagatggcaa gttagttacg cacaataaaa    6720
aaagacctaa aatatgtaag gggtgacgcc aaagtataca ctttgcccct tacacatttt    6780
aggtcttgcc tgctttatca gtaacaaacc cgcgcgattt acttttcgac ctcattctat    6840
tagactctcg tttggattgc aactggtcta ttttcctctt ttgtttgata gaaaatcata    6900
aaaggatttg cagactacgg gcctaaagaa ctaaaaaatc tatctgtttc ttttcattct    6960
ctgtattttt tatagtttct gttgcatggg cataaagttg ccttttttaat cacaattcag    7020 aaaatatcat aatatctcat ttcactaaat aatagtgaac ggcaggtata tgtgatgggt    7080
taaaaaggat cggcggccgc tcgatttaaa tc                                   7112
```

<210> SEQ ID NO 11
<211> LENGTH: 7161
<212> TYPE: DNA
<213> ORGANISM: artificial
<220> FEATURE:
<223> OTHER INFORMATION: vector

<400> SEQUENCE: 11

```
tcgagaggcc tgacgtcggg cccggtacca cgcgtcatat gactagttcg gacctaggga     60
tgggatcgag ctcttttcct tgccgacaag gcggaagctt taggggaaat tcccgtaggt    120
gccgtattgg tggatgaacg gggcaatatc attggtgaag gctggaacct ctctattgtg    180
aactcggatc ccaccgccca tgccgaaatt attgcgttgc gtaacgccgc gcagaaaatc    240
caaaattacc gcctgctcaa taccacttta tacgtgactt tagaaccctg caccatgtgc    300 gccgcgcga ttttacacag ccgaatcaaa cgcttggtat tcggggcgtc cgattacaaa    360
accggtgcgg tgggttccag atttcatttt tttgaggatt ataaaatgaa tcatggggtt    420
gagatcacaa gcggtgtctt ataggatcaa tgcagtcaga agttaagccg ctttttccaa    480
aagcgcaggg aacagaaaaa acaacaaaaa gctaccgcac ttttacaaca cccccggctt    540
aactcctctg aaaatagtg acaaaaaaac cgtcataatg tttacgacgg ttttttttatt    600 tcttctaata tgtcacatta agcccgtagc ctgcaagcaa ccccttaaca tgctccatta    660
attcttttgt cggcggtttt acatcttcaa gctcgtattt atcgccgagt acttcccatt    720
tatgggcgcc tagacggtga taggtaata attccacttt ttcgatattc ttcatatctt    780
taatgaaatt ccccagcatg tgcaaatctt cgtcactatc tgtataaccc ggcactacaa    840
catggcggat ccaggtacgc tgatttcgat ccgctaaata ttttgcgaat tcgagcactc    900
ttttattcgg cacgccaatc aggctttcgt gaacccgttc attcatttct ttcaggtcaa    960
gcaacacaag atccgtgtca tcaatcaatt catcaataat atgatcatga tgacggacga   1020
aaccgttggt atccaagcaa gtattaattc cttctttatg gcaggctctg aaccagtccc   1080
gtacaaattc cgcctgtaaa atagcttcac cgccggaagc ggtaactccg ccgcccgagg   1140
cgttcataaa atggcgatag gtcaccactt cttcattaa ttcttcaacg gaaatttctt   1200
taccgccgtg caaatcccag gtgtctctgt tatggcaata tttacaacgc attaagcagc   1260
cttgtaaaaa taaataaag cggattcccg gcccgtcaac tgtcccgcag gtttcaaatg   1320
aatgaattcg tcctaaaacc gacataatat gcccttaaat aatcaacaaa atatagcaag   1380
aagattatag caaagaattt cgttttttttc agagaatagt caaatcttcg caaaaaacta   1440
ccgcactttt atccgcttta atcaggggaa ttaaaacaaa aaaattccgc ctattgaggc   1500
ggaatttatt aagcaataag acaaactctc aattttaata cttccttctt ttctagtatt   1560
gataagattg aaaccttgca aggatgacgg cggatttgcc gtcactctca cccaactaat   1620
gtggacgact ggtaaaccat tgcattagac caatgcaaac accaccaccg acgatgttac   1680
ctaaagtaac aggaattaaa ttttttaatta ctaaatggta catatctaaa tttgcaaact   1740
gctcggcatt taaacccgtt gcctgccaga attccggcga tgcgaaattt gcaattacca   1800
tgcccatagg gatcataaac atatttgcta cgcagtgttc aaagcctgaa gcgacaaaya   1860
acccgatcgg caggatcata ataaaagctt tatccgttag agtyttgccg gcataggcca   1920
tccaaacggc aatacatacc ataatgttgc aaagaatacc taaacagaag gcttcaaycc   1980
aggtatgttc tattttatgt tgtgccgtat ttaaaatggt taatccccac tgaccgtttg   2040
ccgccatgat ctgaccggaa aaccaaatta atgcaacaat aaataaaccg ccgacaaaat   2100
taccgaarta aaccacaatc cagttacgta acatctgaat tgttgtaatt ttactctcaa   2160
agcgggcaat agtcgataaa gttgatgaag taaatagttc acagccgcaa accgccacca   2220
taattacccc gagagagaac accaaaccgc cgaccagttt agttaatccc caaggcgctc   2280
ccgcagaggc tgtttgagtt gttgtataaa aaacgaatgc aagagcaata aacataccgg   2340
```

```
cagagatcgc cgataaaaat gaataggctt gttttttcgt agctttataa acgccgacgt    2400
ctaacccggt ttgagccatc tcggttggcg aagccatcca agccaattta aaatcttccg    2460
atttcattga gctttcctta gtaataaaac tactcggaaa tgagtagaac tgccttaaag    2520
cataaatgat agattaaaaa atccaaaatt gttgaatatt atttaacggg gggattataa    2580
aagattcata aattagataa tagctaattt gagtgatcca tatcacccttt tacagatttt   2640
ttgacctaaa tcaaaattac ccaaatagag taataatacc attataaagg gtgtggatttt  2700
attcctttgg tttacgagat aaattgctat ttaagctgat ttctgataaa aagtgcggta   2760
gattttttccc aaaaataagg aaacacaaaa tggcagaaga aacaattttc agtaaaatta  2820
ttcgtaaaga aattcccgcc gacattatat atcaagacga tcttgtcacc gcatttcgcg   2880
atattgcgcc gcaggcaaaa actcatattt taattattcc gaataaattg attccgacag   2940
taaacgacgt aaccgcccat cgtcgacatc gatgctcttc tgcgttaatt aacaattggg   3000
atcctctaga ctttgcttcc agatgtatgc tctcctccgg agagtaccgt gactttattt   3060
tcggcacaaa tacaggggtc gatggataaa tacgcgata gttttcctgac ggatgatccg   3120
tatgtaccgg cggaagacaa gctgcaaacc tgtcagatgg agattgattt aatggcggat   3180
gtgctgagag caccgccccg tgaatccgca gaactgatcc gctatgtgtt tgcggatgat   3240
tggccggaat aaataaagcc gggcttaata cagattaagc ccgtataggg tattattact   3300
gaataccaaa cagcttacgg aggacggaat gttacccatt gagacaacca gactgccttc   3360
tgattattaa tattttttcac tattaatcag aaggaataac catgaatttt acccggattg   3420
acctgaatac ctggaatcgc agggaacact ttgcccttta tcgtcagcag attaaatgcg   3480
gattcagcct gaccaccaaa ctcgatatta ccgctttgcg taccgcactg gcggagacag   3540
gttataagtt ttatccgctg atgatttacc tgatctcccg ggctgttaat cagtttccgg   3600
agttccggat ggcactgaaa gacaatgaac ttatttactg ggaccagtca gacccggtct   3660
ttactgtctt tcataaagaa accgaaacat tctctgcact gtcctgccgt tattttccgg   3720
atctcagtga gtttatggca ggttataatg cggtaacggc agaatatcag catgatacca   3780
gattgttttcc gcagggaaat ttaccggaga atcacctgaa tatatcatca ttaccgtggg   3840
tgagttttga cgggatttaa cctgaacatc accggaaatg atgattattt tgccccggtt   3900
tttacgatgg caaagtttca gcaggaaggt gaccgcgtat tattacctgt ttctgtacag   3960
gttcatcatg cagtctgtga tggctttcat gcagcacggt ttattaatac acttcagctg   4020
atgtgtgata acatactgaa ataaattaat taattctgta tttaagccac cgtatccggc   4080
aggaatggtg gctttttttt tatattttaa ccgtaatctg taatttcgtt tcagactggt   4140
tcaggatgag ctcgcttgga ctcctgttga tagatccagt aatgacctca gaactccatc   4200
tggatttgtt cagaacgctc ggttgccgcc gggcgttttt tattggtgag aatccaagca   4260
ctagcggcgc gccggccggc ccggtgtgaa ataccgcaca gatgcgtaag gagaaaatac   4320
cgcatcaggc gctcttccgc ttcctcgctc actgactcgc tgcgctcggt cgttcggctg   4380
cggcgagcgg tatcagctca ctcaaaggcg gtaatacggt tatccacaga atcaggggat   4440
aacgcaggaa agaacatgtg agcaaaaggc cagcaaaagg ccaggaaccg taaaaaggcc   4500
gcgttgctgg cgttttttcca taggctccgc cccctgacg agcatcacaa aaatcgacgc   4560
tcaagtcaga ggtggcgaaa cccgacagga ctataaagat accaggcgtt tccccctgga   4620
agctccctcg tgcgctctcc tgttccgacc ctgccgctta ccggatacct gtccgccttt   4680
ctcccttcgg gaagcgtggc gctttctcat agctcacgct gtaggtatct cagttcggtg   4740
```

```
taggtcgttc gctccaagct gggctgtgtg cacgaacccc ccgttcagcc cgaccgctgc    4800
gccttatccg gtaactatcg tcttgagtcc aacccggtaa gacacgactt atcgccactg    4860
gcagcagcca ctggtaacag gattagcaga gcgaggtatg taggcggtgc tacagagttc    4920
ttgaagtggt ggcctaacta cggctacact agaaggacag tatttggtat ctgcgctctg    4980
ctgaagccag ttaccttcgg aaaaagagtt ggtagctctt gatccggcaa acaaaccacc    5040
gctggtagcg tggtttttt tgtttgcaag cagcagatta cgcgcagaaa aaaggatct    5100 caagaagatc ctttgatctt ttctacgggg tctgacgctc agtggaacga aaactcacgt    5160
taagggattt tggtcatgag attatcaaaa aggatcttca cctagatcct tttaaaggcc    5220
ggccgcggcc gccatcggca ttttcttttg cgttttatt tgttaactgt taattgtcct    5280
tgttcaagga tgctgtcttt gacaacagat gttttcttgc ctttgatgtt cagcaggaag    5340
ctcggcgcaa acgttgattg tttgtctgcg tagaatcctc tgtttgtcat atagcttgta    5400
atcacgacat tgtttccttt cgcttgaggt acagcgaagt gtgagtaagt aaaggttaca    5460
tcgttaggat caagatccat ttttaacaca aggccagttt tgttcagcgg cttgtatggg    5520
ccagttaaag aattagaaac ataaccaagc atgtaaatat cgttagacgt aatgccgtca    5580
atcgtcattt ttgatccgcg ggagtcagtg aacaggtacc atttgccgtt cattttaaag    5640
acgttcgcgc gttcaatttc atctgttact gtgttagatg caatcagcgg tttcatcact    5700
tttttcagtg tgtaatcatc gtttagctca atcataccga gagcgccgtt tgctaactca    5760
gccgtgcgtt tttatcgct ttgcagaagt ttttgactttc cttgacggaa gaatgatgtg    5820
cttttgccat agtatgcttt gttaaataaa gattcttcgc cttggtagcc atcttcagtt    5880
ccagtgtttg cttcaaatac taagtatttg tggcctttat cttctacgta gtgaggatct    5940
ctcagcgtat ggttgtcgcc tgagctgtag ttgccttcat cgatgaactg ctgtacattt    6000
tgatacgttt ttccgtcacc gtcaaagatt gatttataat cctctacacc gttgatgttc    6060
aaagagctgt ctgatgctga tacgttaact tgtgcagttg tcagtgtttg tttgccgtaa    6120
tgtttaccgg agaaatcagt gtagaataaa cggatttttc cgtcagatgt aaatgtggct    6180
gaacctgacc attcttgtgt ttggtctttt aggatagaat catttgcatc gaatttgtcg    6240
ctgtctttaa agacgcggcc agcgtttttc cagctgtcaa tagaagtttc gccgactttt    6300
tgatagaaca tgtaaatcga tgtgtcatcc gcatttttag gatctccggc taatgcaaag    6360
acgatgtggt agccgtgata gtttgcgaca gtgccgtcag cgttttgtaa tggccagctg    6420
tcccaaacgt ccaggccttt tgcagaagag atatttttaa ttgtggacga atcaaattca    6480
gaaacttgat attttttcatt tttttgctgt tcagggattt gcagcatatc atggcgtgta    6540
atatgggaaa tgccgtatgt ttccttatat ggctttggt tcgttctttt cgcaaacgct    6600
tgagttgcgc ctcctgccag cagtgcggta gtaaaggtta atactgttgc ttgttttgca    6660 aacttttga tgttcatcgt tcatgtctcc tttttatgt actgtgttag cggtctgctt    6720
cttccagccc tcctgtttga agatggcaag ttagttacgc acaataaaaa aagacctaaa    6780
atatgtaagg ggtgacgcca agtatacac tttgcccttt acacatttta ggtcttgcct    6840
gctttatcag taacaaaccc gcgcgattta cttttcgacc tcattctatt agactctcgt    6900
ttggattgca actggtctat tttcctcttt tgtttgatag aaaatcataa aaggatttgc    6960
agactacggg cctaaagaac taaaaaatct atctgtttct tttcattctc tgtatttttt    7020
atagtttctg ttgcatgggc ataaagttgc cttttaatc acaattcaga aaatatcata    7080
```

```
atatctcatt tcactaaata atagtgaacg gcaggtatat gtgatgggtt aaaaaggatc   7140
ggcggccgct cgatttaaat c                                             7161

<210> SEQ ID NO 12
<211> LENGTH: 11309
<212> TYPE: DNA
<213> ORGANISM: Yersinia mollaretii

<400> SEQUENCE: 12
gatccccagt agatttacgt ttaaacattt ttatttcctt tttaatttaa tttaattaac     60
agttggtgct atgacacttt acctcatagc tggcataatt cgcaatactc tgggtcttcg    120
agaggtatcc aacctgagtt gaaatacttt accatcgatt tagcagttgt atcagttata    180
tttatattac ctttaactct tcgccatcca ggagttttac cgtacagatt agaggataat    240
aataacacat aattctcgta agcaatatga gataatttcc aagactctat attagctcgt    300
gatgttttcc aaggtctaaa atcgtcacgg ttcatataat tagccaatct catatgctct    360
ctaacttccg atgataagct gtcaaacatg agaattaacg atctgataga gaagggtttg    420
ctcgggtcgg tggctctggt aacgaccagt atcccgatcc cggctggccg tcctggccgc    480
cacatgaggc atgttccgcg tccttgcaat actgtgttta catacagtct atcgcttagc    540
ggaaagttct tttaccctca gccgaaatgc ctgccgttgc tagacattgc cagccagtgc    600
ccgtcactcc cgtactaact gtcacgaacc cctgcaataa ctgtcacgcc cccctgcaat    660
aactgtcacg aacccctgca ataactgtca cgcccccaaa cctgcaaacc cagcaggggc    720
gggggctggc ggggtgttgg aaaaatccat ccatgattat ctaagaataa tccactaggc    780
gcggttatca gcgcccttgt ggggcgctgc tgcccttgcc caatatgccc ggccagaggc    840
cggatagctg gtctattcgc tgcgctaggc tacacaccgc cccaccgctg cgcggcaggg    900
ggaaaggcgg gcaaagcccg ctaaacccca caccaaaccc cgcagaaata cgctgggagc    960
gcttttagcc gctttagcgg cctttccccc tacccgaagg gtgggggcgc gtgtgcagcc   1020
ccgcagggcc tgtctcggtc gatcattcag cccggctcat ccttctggcg tggcggcaga   1080
ccgaacaagg cgcggtcgtg gtcgcgttca aggtacgcat ccattgccgc catgagccga   1140
tcctccggcc actcgctgct gttcaccttg gccaaaatca tggcccccac cagcaccttg   1200
cgccttgttt cgttcttgcg ctattgctgc tgttcccttg cccgcacccg ctgaatttcg   1260
gcattgattc gcgctcgttg ttcttcgagc ttggccagcc gatccgccgc cttgttgctc   1320
cccttaacca tcttgacacc ccattgttaa tgtgctgtct cgtaggctat catggaggca   1380
cagcggcggc aatcccgacc ctactttgta ggggagggcc attgcatgga gccgaaaagc   1440
aaaagcaaca gcgaggcagc atggcgattt atcaccttac ggcgaaaacc ggcagcaggt   1500
cgggcggcca atcggccagg gccaaggccg actacatcca gcgcgaaggc aagtatgccc   1560
gcgacatgga tgaagtcttg cacgccgaat ccgggcacat gccggagttc gtcgagcggc   1620
ccgccgacta ctgggatgct gccgacctgt atgaacgcgc caatgggcgg ctgttcaagg   1680
aggtcgaatt tgccctgccg gtcgagctga ccctcgacca gcagaaggcg ctggcgtccg   1740
agttcgccca gcacctgacc ggtgccgagc gcctgccgta tacgctggcc atccatgccg   1800
gtggcggcga gaacccgcac tgccacctga tgatctccga gcggatcaat gacggcatcg   1860
agcggcccgc cgctcagtgg ttcaagcggt acaacggcaa gaccccggag aagggcgggg   1920
cacagaagac cgaagcgctc aagcccaagg catggcttga gcagacccgc gaggcatggg   1980
ccgaccatgc caaccgggca ttagagcggg ctggccacga cgcccgcatt gaccacagaa   2040
```

```
cacttgaggc gcagggcatc gagcgcctgc ccggtgttca cctggggccg aacgtggtgg    2100
agatggaagg ccggggcatc cgcaccgacc gggcagacgt ggccctgaac atcgacaccg    2160
ccaacgccca gatcatcgac ttacaggaat accgggaggc aatagaccat gaacgcaatc    2220
gacagagtga agaaatccag aggcatcaac gagttagcgg agcagatcga accgctggcc    2280
cagagcatgg cgacactggc cgacgaagcc cggcaggtca tgagccagac ccagcaggcc    2340
agcgaggcga aggcggcgga gtggctgaaa gcccagcgcc agacaggggc ggcatgggtg    2400
gagctggcca aagagttgcg ggaggtagcc gccgaggtga gcagcgccgc gcagagcgcc    2460
cggagcgcgt cgcgggggtg gcactggaag ctatggctaa ccgtgatgct ggcttccatg    2520
atgcctacgg tggtgctgct gatcgcatcg ttgctcttgc tcgacctgac gccactgaca    2580
accgaggacg gctcgatctg gctgcgcttg gtggcccgat gaagaacgac aggactttgc    2640
aggccatagg ccgacagctc aaggccatgg gctgtgagcg cttcgatatc ggcgtcaggg    2700
acgccaccac cggccagatg atgaaccggg aatggtcagc cgccgaagtg ctccagaaca    2760
cgccatggct caagcggatg aatgcccagg caatgacgt gtatatcagg cccgccgagc    2820
aggagcggca tggtctggtg ctggtggacg acctcagcga gtttgacctg gatgacatga    2880
aagccgaggg ccggggagcct gccctggtag tggaaaccag cccgaagaac tatcaggcat    2940
gggtcaaggt ggccgacgcc gcaggcggtg aacttcgggg gcagattgcc cggacgctgg    3000
ccagcgagta cgacgccgac ccggccagcg ccgacagccg ccactatggc cgcttggcgg    3060
gcttcaccaa ccgcaaggac aagcacacca cccgcgccgg ttatcagccg tgggtgctgc    3120
tgcgtgaatc caagggcaag accgccaccg ctggcccggc gctggtgcag caggctggcc    3180
agcagatcga gcaggcccag cggcagcagg agaaggcccg caggctggcc agcctcgaac    3240
tgcccgagcg gcagcttagc cgccaccggc gcacggcgct ggacgagtac cgcagcgaga    3300
tggccgggct ggtcaagcgc ttcggtgatg acctcagcaa gtgcgacttt atcgccgcgc    3360
agaagctggc cagccggggc cgcagtgccg aggaaatcgg caaggccatg gccgaggcca    3420
gcccagcgct ggcagagcgc aagcccggcc acgaagcgga ttacatcgag cgcaccgtca    3480
gcaaggtcat gggtctgccc agcgtccagc ttgcgcgggc cgagctggca cgggcaccgg    3540
caccccgcca gcgaggcatg gacaggggcg ggccagattt cagcatgtag tgcttgcgtt    3600
ggtactcacg cctgttatac tatgagtact cacgcacaga agggggtttt atggaatacg    3660
aaaaaagcgc ttcagggtcg gtctacctga tcaaaagtga caagggctat tggttgcccg    3720
gtggctttgg ttatacgtca aacaaggcg aggctggccg cttttcagtc gctgatatgg    3780
ccagccttaa ccttgacggc tgcaccttgt ccttgttccg cgaagacaag cctttcggcc    3840
ccggcaagtt tctcggtgac tgatatgaaa gaccaaaagg acaagcagac cggcgacctg    3900
ctggccagcc ctgacgctgt acgccaagcg cgatatgccg agcgcatgaa ggccaaaggg    3960
atgcgtcagc gcaagttctg gctgaccgac gacgaatacg aggcgctgcg cgagtgcctg    4020
gaagaactca gagcggcgca gggcgggggt agtgaccccg ccagcgccta accaccaact    4080
gcctgcaaag gaggcaatca atggctaccc ataagcctat caatattctg gaggcgttcg    4140
cagcagcgcc gccaccgctg gactacgttt tgcccaacat ggtggccggt acggtcgggg    4200
cgctggtgtc gcccggtggt gccggtaaat ccatgctggc cctgcaactg gccgcacaga    4260
ttgcaggcgg gccggatctg ctggaggtgg gcgaactgcc caccgcccg gtgatctacc    4320 tgccccgcga agacccgccc accgccattc atcaccgcct gcacgccctt ggggcgcacc    4380
```

```
tcagcgccga ggaacggcaa gccgtggctg acggcctgct gatccagccg ctgatcggca    4440
gcctgcccaa catcatggcc ccggagtggt tcgacggcct caagcgcgcc gccgagggcc    4500
gccgcctgat ggtgctggac acgctgcgcc ggttccacat cgaggaagaa aacgccagcg    4560
gccccatggc ccaggtcatc ggtcgcatgg aggccatcgc cgccgatacc gggtgctcta    4620
tcgtgttcct gcaccatgcc agcaagggcg cggccatgat gggcgcaggc gaccagcagc    4680
aggccagccg gggcagctcg gtactggtcg ataacatccg ctggcagtcc tacctgtcga    4740
gcatgaccag cgccgaggcc gaggaatggg gtgtggacga cgaccagcgc cggttcttcg    4800
tccgcttcgg tgtgagcaag gccaactatg gcgcaccgtt cgctgatcgg tggttcaggc    4860
ggcatgacgg cggggtgctc aagcccgccg tgctggagag gcagcgcaag agcaagggggg    4920
tgccccgtgg tgaagcctaa gaacaagcac agcctcagcc acgtccggca cgacccggcg    4980
cactgtctgg cccccggcct gttccgtgcc ctcaagcggg gcgagcgcaa gcgcagcaag    5040
ctggacgtga cgtatgacta cggcgacggc aagcggatcg agttcagcgg cccggagccg    5100
ctgggcgctg atgatctgcg catcctgcaa gggctggtgg ccatggctgg gcctaatggc    5160
ctagtgcttg gcccggaacc caagaccgaa ggcggacggc agctccggct gttcctggaa    5220
cccaagtggg aggccgtcac cgctgatgcc atggtggtca aggtagcta tcgggcgctg    5280
gcaaaggaaa tcggggcaga ggtcgatagt ggtgggcgc tcaagcacat acaggactgc    5340
atcgagcgcc tttggaaggt atccatcatc gcccagaatg ccgcaagcg gcaggggttt    5400
cggctgctgt cggagtacgc cagcgacgag gcggacgggc gcctgtacgt ggccctgaac    5460
cccttgatcg cgcaggccgt catgggtggc ggccagcatg tgcgcatcag catggacgag    5520
gtgcgggcgc tggacagcga aaccgcccgc ctgctgcacc agcggctgtg tggctggatc    5580
gaccccggca aaaccggcaa ggcttccata gataccttgt gcggctatgt ctggccgtca    5640
gaggccagtg gttcgaccat gcgcaagcgc cgccagcggg tgcgcgaggc gttgccggag    5700
ctggtcgcgc tgggctggac ggtaaccgag ttcgcggcgg gcaagtacga catcacccgg    5760
cccaaggcgg caggctgacc ccccccactc tattgtaaac aagacatttt ttatctttta    5820
tattcaatgg cttatttcc tgctaattgg taataccatg aaaatacca tgctcagaaa    5880
aggcttaaca atattttgaa aaattgccta ctgagcgctg ccgcacagct ccataggccg    5940
cttttcctggc tttgcttcca gatgtatgct ctcctccgga gagtaccgtg actttattt    6000
cggcacaaat acaggggtcg atggataaat acggcgatag tttcctgacg gatgatccgt    6060
atgtaccggc ggaagacaag ctgcaaacct gtcagatgga gattgattta atggcggatg    6120
tgctgagagc accgccccgt gaatccgcag aactgatccg ctatgtgttt gcggatgatt    6180
ggccggaata aataaagccg ggcttaatac agattaagcc cgtataggggt attattactg    6240
aataccaaac agcttacgga ggacggaatg ttacccattg agacaaccag actgccttct    6300
gattattaat atttttcact attaatcaga aggaataacc atgaatttta cccgattga    6360
cctgaatacc tggaatcgca gggaacactt tgcccttat cgtcagcaga ttaaatgcgg    6420
attcagcctg accaccaaac tcgatattac cgctttgcgt accgcactgg cggagacagg    6480
ttataagttt tatccgctga tgatttacct gatctcccgg gctgttaatc agtttccgga    6540
gttccggatg gcactgaaag acaatgaact tatttactgg gaccagtcag accggtctt    6600
tactgtcttt cataaagaaa ccgaaacatt ctctgcactg tcctgccgtt attttccgga    6660
tctcagtgag tttatggcag gttataatgc ggtaacggca gaatatcagc atgataccag    6720
attgtttccg cagggaaatt taccggagaa tcacctgaat atatcatcat taccgtgggt    6780
```

```
gagttttgac gggatttaac ctgaacatca ccggaaatga tgattatttt gccccggttt    6840
ttacgatggc aaagtttcag caggaaggtg accgcgtatt attacctgtt tctgtacagg    6900
ttcatcatgc agtctgtgat ggctttcatg cagcacggtt tattaataca cttcagctga    6960
tgtgtgataa catactgaaa taaattaatt aattctgtat ttaagccacc gtatccggca    7020
ggaatggtgg cttttttttt atattttaac cgtaatctgt aatttcgttt cagactggtt    7080
caggatcact gtacgataat gcccccgcag tttggtaata cccttaataa aaagaaaca    7140 gcaaagactg acagcaataa taataaagta agcagtaaca ataatattaa caacaccaga    7200
tgcagttata ataatagtat ttaagacacc agaaagactg ctgcgacagt cattttgaac    7260
aacaccaaaa tgccgtaaag gcagtagtaa caacaccagt gaaaacatca cgatagcata    7320
gtgatatgcc tgagtgtgtg taattaaaca ataaataaac cgccatatat aacagaagat    7380
agtattctga atggcatgct tttctgttca gtataaacat atcatcccgg ttggtataag    7440
gatgatatat aataagttaa gctgaacaca tatttatttt ggttttattt tacaaataaa    7500
gtaagacgat ccgttaagtc aaagcggggt atatttatta taccctgctt ttttatttgt    7560
ccgccgggcg cggataatgg atcagattat gcagtgtcac aatggcctta ccgggattgg    7620
cgtaagcgtg cgggatatcc gcatggaagc gcagggattc cccggcagaa acggtgtgcc    7680
actcatcccc cagccgcagt tgtaatgcgc cttccagtac aatgcatgt tctctggttc    7740 tgaaatccat ccctgtcggt gttgcttatg cagtctggtc gggactcggc gtcgtcataa    7800
ttacagccat tgcctggttg cttcatgggc aaaagcttta tgcttgtaaa ccgttttgtg    7860
aaaaaatttt taaaataaaa aaggggacct ctagggtccc caattaatta gtaatataat    7920
ctattaaagg tcattcaaaa ggtcatccac cggatccggg cccccctcg aggtcgacgg    7980 tatcgataag cttgatatcg aattcccata ttgtgcatcg aatccctgca aaattgtctg    8040
agcgattaat tgttctaatt ttaccgccat gctcaccccc cgccatacgg aacagagcct    8100
gcatcagcag gctccagata aaacataaac tcattaatca gtggcttaga actgctgctc    8160
ttccgtcgag ccagtcagtg cagtgactga tgactcgccg ccctgaatga tattggtgac    8220
tttatcaaaa tagcccgtgc ccacttcttg ttgatgggaa gcaaaggtgt agccgcgttc    8280
aacggaggca aattctggct gctgcacttt ctcaacatag tgcttcatgc cctcgccttg    8340
cgcgtaagca tgggccaagt cgaacatgtt gaaccacata ctgtggatgc cgccaaggt    8400 aataaattga tatttgtagc ccatcgcgga gaggtcatct tggaagctgg cgatctgctg    8460
gtcagtcagg ttcttttttcc agttaaatga tggcgaacag ttataagcca ataatttacc    8520
ggggaattta gcgtgaaccg catctgcaaa gcgtttagcc agcgccagat ctggcgtcga    8580
ggtttcacac cacaccaagt cggcgtaagg gcataggcc agaccacggc tgatggcttg    8640
ctcaatgccc gcgtgagtgc ggaagaagcc ctcagcagta cgatcaccag caataaattc    8700
gctgtcataa gggtcgcaat cagaggtcag caaatccgca gcatcagcat cagtgcgcgc    8760
aatcagcagt gttggcacgc caagaacgtc agcggctaag cgggcagcaa ccagcttctg    8820
aatcgcttct tgtgttggca ccaaaacttt gccgcccata tggccgcatt tcttcaccgc    8880
cgccaattga tcttcaaagt gaacgcccgc agcaccggct tcaatcatgg ctttcatcaa    8940
ttcaaacgca ttcaatacgc cgccaaaacc cgcttcggca tccgccacaa tcggcaggaa    9000
atagtcggta tagcctttgc tgcccggctc aatattattc gaccactgaa tctgatctgc    9060
acggcggaag ctgttattaa tacgcttaac cacggccgga acagagtcga ccgggtaaag    9120
```

```
agattgatcg ggatacatgc tggaggcggt attggcatcg gcggcgacct gccaacccga      9180
cagataaatc gcttcaacac cggcctttgc ctgttgcaat gcctgaccgc ctgttagcgc      9240
ccccagacag ttgatgtagc ctttacgcga ttcgccgtgc agcaactccc acaatctttt      9300
cgcgccgtgc tgtgccagcg tacattctgg gttaacggaa ccgcgcagtt tgatcacttc      9360
ttcggcgcta taggggcggg tgatgccctt ccagcgcggt gatttccatt cctgttccaa      9420
ctgctgaatt tgttgagtac gagaggttgt catggcgata ttccttatta cttattttg     9480
tagggttaaa taactggcct aggcgagtaa tgcgtagccc ggcaacgtca gaaagtcgat      9540
aagctcgtct tgtgttgtaa tccgctccat cagacgtgcg gcttcttcaa accgcccgcc      9600
atcaaaacgc tctgcgccaa gttcaagttt cacgacctgc atttcttcac tcaacatgtt      9660
acggaacagc tctttggtca ccgtctgacc attgctcagg cttttctggt gatgtatcca      9720
tgccagata gaagtacggg aaatctcagc cgtcgcggca tcttccatca ggccataaat      9780
cggtacacag ccattgcccg atatccatgc ttcgatgtat tgcactgcga cccggatatt      9840
ggcccgcatc ccctcttcgg tgcgctcacc cgtgcaaggc tctagcaact cagcggcagt      9900
gattggttta tcttgcgcgc gactcacctc taattggttt ggacgatcgc ccagtacttt      9960
gttgaaaacg tccatcacgg tatcggccag accggggtgt gcgacccatg taccatcgtg     10020
gccgttgctg gcttccagct ctttgtcagc gcgaacttta tctaagacca gcgcatttt     10080
ttctggatct ttgttcggga taaaggccgc catgccgccc atcgcaaggg caccgcgctt     10140
atggcaggtt ttgatcagta acgagagta ggcactcagg aagggtttcg tcatcgtgac     10200
cgactggcga tcgggcagca cgcgatcgct gtgattttc agcgttttga tatagctgaa     10260
aatgtagtcc caacggccac aattcagggc aacaatgtga tggcgcagat ggtagaggat     10320
ctcatccatc tggaataccg caggcaatgt ctcgattaat actgtggcct taatggtgcc     10380
ttgcggcaga tcgaaacgct gctcggtaaa gctgaaaaca tcactccacc aagccgcttc     10440
ctgataagac tgcatcttgg gtagatagaa ataggggccg ctgccattgg caagcagtaa     10500
cttatagtta tggtagaaat acaacgcgaa atcgaataag ccaccgggga tatcctcccc     10560
ctgccacttc acgtgttttt ctggcaagtg cagaccacgc acccgagcaa tcaacaccgc     10620
tggattgggt tttagctgat aaatcttacc ggattcattc gcgtaagaga ttgtgccttt     10680
gaccgcatcg tgcaaattaa tctgaccttc gataaccttta tcccaactgg gtgccagcga     10740
atcctcaaag tcagccataa agactttcac attcgcattg agggcattaa tcaccatttt     10800
gcgctcaacc ggcccggtga tctcgacgcg acgatcacgt aaatccgcag gaatactttg     10860
aatttttccag tcaccattac gaatggaatt ggtttccgaa atgaaatcag gcaatgcgcc     10920
ttggtcaatg gcctgttgcc aagcggcccg tgcagcaagg agtttgctac gcggctctgc     10980
aaatttcgcc accaattctg ccaaaaattc gatggcctca tcgggcaaaa cctgccgctc     11040
agcagcatta aaatgctggg tgaaaactaa ctccgtgccg actatctgtt gtgtcattcc     11100
ccttccccctt ccccatctct cgacgatcat ttttcagttt ccttttgtta ttccccaaaa     11160
gtgcggtgca aatttgggga gttttagtta attaaaaaaa ttatttttta cgagcttcga     11220
ttactgcagc agcaacactt gttggcgctt cagcatattt taacggttcc attgagtatg     11280
atgctctaga gcggccgcca ccgcggtgg                                       11309
```

<210> SEQ ID NO 13  
<211> LENGTH: 11247  
<212> TYPE: DNA  
<213> ORGANISM: Salmonella typhimurium

<400> SEQUENCE: 13

```
gatcccaccg cggtggcggc cgctctagag ggttccctca tccggcacca cgtcatgccg      60
gatggcgcgt tcgcttatcc ggcctacgct atctgtaggc ccggtaagcg cagcgccacc     120
gggcatcaat caaaactgcg cttcttcggt ggaacccgtt aacgcggtaa cggatgacgc     180
gccgccctga ataatggtgg tgactttgtc gaagtaacca gtacccactt cctgctggtg     240
ggaaacaaag gtgtagccat ctttcgccgc ggcgaactcg ggttgttgaa ccttctcaac     300
atagtgcttc atgccctcgc cctgcgcgta tgcatgcgcc aggtcgaaca tgttgaacca     360
catgctgtgg atgcccgcca gggtaataaa ctggtatttg taacccatgt ccgacaactg     420
ctgctggaag ctggcaatgg tcttgtcgtc cagattcttc tgccagttga aggatggtga     480
acagttatag gccagcagtt tgcccggata cttcgcgtgg atagcatcgg caaaacgacg     540
cgccagttcg agatccggcg tagaggtttc gcaccatacc agatcggcat acggggcata     600
cgccagaccg cggctgatcg cctgctcaat gcccgcatgg gtgcggtaga aaccttcgct     660
ggtgcgttcg ccggtaataa aaccgctgtc atagggatcg cagtcggagg tgatcagatc     720
tgccgcatcc gcatcggtac gcgcaatcac cagcgtcggg acgcccatca catcagcggc     780
cagacgcgca gcaaccagtt tctgaatcgc ctcctgcgtg gggaccagca ccttgccgcc     840
catatggccg catttcttca ccgacgccag ctgatcttcg aagtgaacgg ccgctgcacc     900
ggcttcaatc atcgatttca tcagttcgaa ggcattcaga acgccgccaa aaccggcttc     960
cgcatcagca acgatcggca ggaagtaatc cacatagcgc ggatcgttgg gttcaatacc    1020
ggatgcccac tggatctgat ctgcacgacg aaaagtgttg ttgatccgat ccactaccgc    1080
cggaacagag tttgccgggt acaacgattg atccggatac atgctggatg ccaggttggc    1140
atctgccgcc acctgccagc ctgaaagata aatcgcctca ataccggctt cgcctgctg     1200
caacgcctga ccgccggtca gcgcgccaag gctgttgata tagccttttt tcgcttcacc    1260
gtgcaacagc cgccacattt tcgcggcgcc gagctgcgcc agcgtgcatt ccgggttaac    1320
cgagccgcgt aatttcacca cctcctccgc gctgtacggg cgggtgatgc cttcccagcg    1380
cggttgtgtc cactctttct gtaattcttc gatttgttga gtacgggttt tcatgtgcag    1440
atgctccata ttgttatgtg gtgaattaag ccagtaagcg atagcccggc agggtgagga    1500
agtcgattaa gtcatctgag gtggtgattt gctccatcag acgtgcgca tcgtcgaagc     1560
gcccgctgct gtagcggtgc tcgcccagtt cgtcctggat tacccgcatc tcttccgcca    1620
acatttcgcg gaaaagcgtt ttcgttacgg gttttccatt gctcagtgtt ttctcatggt    1680
gaatccactg ccagatagag gttcgtgaga tttccgccgt cgcggcatcc tccatcagac    1740
cgtaaatcgg tacacagcca ttgccggaga tccacgcttc aatgtactgc actgccacgc    1800
gaatattggc gcgcattccc gcttctgtgc gttcgccttc acatggctcc agtaactgtt    1860
cagcggtaat cggcgcatct tcatcacggg taatgaacag ctgattttg tgctcgccca    1920
gtacctcgtt aaagacggcc attgcggtat ccgccaaccc aggatgcgca atccacgtgc    1980
cgtcgtggcc gttgttcgct tccagcgctt tatccgcttt cactttggca aggacctgat    2040
tgttgcgttc aacgtctttg ctcgggataa acgccgccat accgcccatc gcgaacgcgc    2100
cgcgcttgtg gcaggttttg atcagcaggc gcgagtaggc gctcagaaac ggtttgtcca    2160
tcgttaccac ctgcctgtcc ggcaaaacgc gatccgggtg attttcaac gttttgatat     2220
agctgaaaat ataatcccag cgaccacagt tgagaccgac gatatgatca cgcagcgcat    2280
```

```
gaagaatctc atccatctgg aaaacagccg gcagcgtttc aatcaacagg gtcgctttga    2340
tcgtaccgcg cggcaggtta aagcggtctt cggcgtagct gaacacttcg ctccaccagg    2400
ctgcctcctg ccaggcttgc gttttcggca ggtaaaaata cgggccgcta cctttagcga    2460
gcagcgcttt atagttgtgg aaaaagtaca gagcaaaatc aaacaggctg ccgggaatgg    2520 cttcccccccg ccaggtaaca tgttttcctg gcagatgtag accacgtaca cgacaaatca    2580
atacggccgg atcgggcttg agctgataga ttttccggc ttcgttggta tagctaatgg    2640
tgccgttcac cgcatcacgc aggttgattt gaccatcaat aactttattc cagtccggcg    2700
ccagcgagtc ttcaaaatcc gccataaaca ctttcacatt tgcgttcagg cattaatca    2760 ccatttacg ttcaaccggc ccggtaattt ctactcggcg atcctgtaaa tccgccggaa    2820
taccacgaat ctgccaatta ctttctctaa tggaagtggt ttccgaaata aaatcaggca    2880
acttaccgtt atcaatatcc tgctgttgct ggatacgggc agccaggagt ttattgcgtt    2940
ttggcgtaaa acgggtgact aactccgtca aaaactcgac tgcttcagcg gtcaggactt    3000
gcttttccag ctcgccttgc ggcctggtaa aggttaattc atcagttgtg gttgcctgtg    3060
gattcatcat gcagctcctc gttgttgatc cagatacatc cccaatgcga acgaaggatc    3120
actgtgcact tttcgttcaa cacaactaag actactcaat taaatttcaa aatcaaaaac    3180
aatttccatt tttaatttaa ttatgcatta acctattgat aacaatataa attaaattta    3240
attacatgat gaggtgcgtt tcggaaagac gtcaggcctc tcgagggggg gcccggatcc    3300
ccagtagatt tacgtttaaa cattttatt tccttttttaa tttaatttaa ttaacagttg    3360
gtgctatgac actttacctc atagctggca taattcgcaa tactctgggt cttcgagagg    3420
tatccaacct gagttgaaat actttaccat cgatttagca gttgtatcag ttatatttat    3480 attacctta actcttcgcc atccaggagt tttaccgtac agattagagg ataataataa    3540
cacataattc tcgtaagcaa tatgagataa tttccaagac tctatattag ctcgtgatgt    3600
tttccaaggt ctaaaatcgt cacggttcat ataattagcc aatctcatat gctctctaac    3660
ttccgatgat aagctgtcaa acatgagaat taacgatctg atagagaagg gtttgctcgg    3720
gtcggtggct ctggtaacga ccagtatccc gatcccggct ggccgtcctg gccgccacat    3780
gaggcatgtt ccgcgtcctt gcaatactgt gtttacatac agtctatcgc ttagcggaaa    3840
gttcttttac cctcagccga aatgcctgcc gttgctagac attgccagcc agtgcccgtc    3900
actcccgtac taactgtcac gaacccctgc aataactgtc acgccccct gcaataactg    3960 tcacgaaccc ctgcaataac tgtcacgccc caaacctgc aaacccagca ggggcggggg    4020 ctggcgggt gttggaaaaa tccatccatg attatctaag aataatccac taggcgcggt    4080
tatcagcgcc cttgtggggc gctgctgccc ttgcccaata tgcccggcca gaggccggat    4140
agctggtcta ttcgctgcgc taggctacac accgccccac cgctgcgcgg caggggaaa    4200 ggcgggcaaa gcccgctaaa ccccacacca accccgcag aaatacgctg ggagcgcttt    4260
tagccgcttt agcggccttt cccctaccc gaagggtggg ggcgcgtgtg cagccccgca    4320
gggcctgtct cggtcgatca ttcagcccgg ctcatccttc tggcgtggcg gcagaccgaa    4380
caaggcgcgg tcgtggtcgc gttcaaggta cgcatccatt gccgccatga gccgatcctc    4440
cggccactcg ctgctgttca ccttggccaa aatcatggcc cccaccagca ccttgcgcct    4500
tgtttcgttc ttgcgctatt gctgctgttc ccttgcccgc accgctgaa tttcggcatt    4560 gattcgcgct cgttgttctt cgagcttggc cagccgatcc gccgcttgt tgctccccctt    4620 aaccatcttg acaccccatt gttaatgtgc tgtctcgtag gctatcatgg aggcacagcg    4680
```

```
gcggcaatcc cgaccctact ttgtagggga gggccattgc atggagccga aaagcaaaag   4740
caacagcgag gcagcatggc gatttatcac cttacggcga aaaccggcag caggtcgggc   4800
ggccaatcgg ccagggccaa ggccgactac atccagcgcg aaggcaagta tgcccgcgac   4860
atggatgaag tcttgcacgc cgaatccggg cacatgccgg agttcgtcga gcggcccgcc   4920
gactactggg atgctgccga cctgtatgaa cgcgccaatg gcggctgtt caaggaggtc   4980 gaatttgccc tgccggtcga gctgaccctc gaccagcaga aggcgctggc gtccgagttc   5040
gcccagcacc tgaccggtgc cgagcgcctg ccgtatacgc tggccatcca tgccggtggc   5100
ggcgagaacc cgcactgcca cctgatgatc tccgagcgga tcaatgacgg catcgagcgg   5160
cccgccgctc agtggttcaa gcggtacaac ggcaagaccc cggagaaggg cggggcacag   5220
aagaccgaag cgctcaagcc caaggcatgg cttgagcaga cccgcgaggc atgggccgac   5280
catgccaacc gggcattaga gcgggctggc cacgacgccc gcattgacca cagaacactt   5340
gaggcgcagg gcatcgagcg cctgcccggt gttcacctgg ggccgaacgt ggtggagatg   5400
gaaggccggg gcatccgcac cgaccgggca gacgtggccc tgaacatcga caccgccaac   5460
gcccagatca tcgacttaca ggaataccgg gaggcaatag accatgaacg caatcgacag   5520
agtgaagaaa tccagaggca tcaacgagtt agcggagcag atcgaaccgc tggcccagag   5580
catggcgaca ctggccgacg aagcccggca ggtcatgagc cagacccagc aggcagcga   5640 ggcgcaggcg gcggagtggc tgaaagccca gcgccagaca ggggcggcat gggtggagct   5700
ggccaaagag ttgcgggagg tagccgccga ggtgagcagc gccgcgcaga gcgcccggag   5760
cgcgtcgcgg gggtggcact ggaagctatg gctaaccgtg atgctggctt ccatgatgcc   5820
tacggtggtg ctgctgatcg catcgttgct cttgctcgac ctgacgccac tgacaaccga   5880
ggacggctcg atctggctgc gcttggtggc ccgatgaaga acgacaggac tttgcaggcc   5940
ataggccgac agctcaaggc catgggctgt gagcgcttcg atatcggcgt cagggacgcc   6000
accaccggcc agatgatgaa ccgggaatgg tcagccgccg aagtgctcca gaacacgcca   6060
tggctcaagc ggatgaatgc ccagggcaat gacgtgtata tcaggcccgc cgagcaggag   6120
cggcatggtc tggtgctggt ggacgacctc agcgagtttg acctggatga catgaaagcc   6180
gagggccggg agcctgccct ggtagtggaa accagcccga agaactatca ggcatgggtc   6240
aaggtggccg acgccgcagg cggtgaactt cgggggcaga ttgcccggac gctggccagc   6300
gagtacgacg ccgacccggc cagcgccgac agccgccact atggccgctt ggcgggcttc   6360
accaaccgca aggacaagca caccaccgc gccggttatc agccgtgggt gctgctgcgt   6420
gaatccaagg gcaagaccgc caccgctggc ccggcgctgg tgcagcaggc tggccagcag   6480
atcgagcagg cccagcggca gcaggagaag gcccgcaggc tggccagcct cgaactgccc   6540
gagcggcagc ttagccgcca ccggcgcacg gcgctggacg agtaccgcag cgagatggcc   6600
gggctggtca gcgcttcgg tgatgacctc agcaagtgcg actttatcgc cgcgcagaag   6660
ctggccagcc ggggccgcag tgccgaggaa atcggcaagg ccatggccga ggccagccca   6720
gcgctggcag agcgcaagcc cggccacgaa gcggattaca tcgagcgcac cgtcagcaag   6780
gtcatgggtc tgcccagcgt ccagcttgcg cgggccgagc tggcacgggc accggcaccc   6840
cgccagcgag gcatggacag gggcgggcca gatttcagca tgtagtgctt cgttggtac   6900 tcacgcctgt tatactatga gtactcacgc acagaagggg gttttatgga atacgaaaaa   6960
agcgcttcag ggtcggtcta cctgatcaaa agtgacaagg gctattggtt gcccggtggc   7020
```

```
tttggttata cgtcaaacaa ggccgaggct ggccgctttt cagtcgctga tatggccagc    7080
cttaaccttg acggctgcac cttgtccttg ttccgcgaag acaagccttt cggcccggc     7140 aagtttctcg gtgactgata tgaaagacca aaaggacaag cagaccggcg acctgctggc   7200
cagccctgac gctgtacgcc aagcgcgata tgccgagcgc atgaaggcca agggatgcg    7260 tcagcgcaag ttctggctga ccgacgacga atacgaggcg ctgcgcgagt gcctggaaga   7320
actcagagcg gcgcagggcg ggggtagtga ccccgccagc gcctaaccac caactgcctg   7380
caaaggaggc aatcaatggc tacccataag cctatcaata ttctggaggc gttcgcagca   7440
gcgccgccac cgctggacta cgttttgccc aacatggtgg ccggtacggt cggggcgctg   7500
gtgtcgcccg gtggtgccgg taaatccatg ctggccctgc aactggccgc acagattgca   7560
ggcgggccgg atctgctgga ggtgggcgaa ctgcccaccg gcccggtgat ctacctgccc   7620
gccgaagacc cgcccaccgc cattcatcac cgcctgcacg cccttgggc gcacctcagc    7680 gccgaggaac ggcaagccgt ggctgacggc ctgctgatcc agccgctgat cggcagcctg   7740
cccaacatca tggccccgga gtggttcgac ggcctcaagc gcgccgccga gggccgccgc   7800
ctgatggtgc tggacacgct gcgccggttc cacatcgagg aagaaaacgc cagcggcccc   7860
atggcccagg tcatcggtcg catggaggcc atcgccgccg ataccgggtg ctctatcgtg   7920
ttcctgcacc atgccagcaa gggcgcggcc atgatgggcg caggcgacca gcagcaggcc   7980
agccggggca gctcggtact ggtcgataac atccgctggc agtcctacct gtcgagcatg   8040
accagcgccg aggccgagga atggggtgtg gacgacgacc agcgccggtt cttcgtccgc   8100
ttcggtgtga gcaaggccaa ctatggcgca ccgttcgctg atcggtggtt caggcggcat   8160
gacggcgggg tgctcaagcc cgccgtgctg gagaggcagc gcaagagcaa ggggtgccc    8220 cgtggtgaag cctaagaaca agcacagcct cagccacgtc cggcacgacc cggcgcactg   8280
tctggccccc ggcctgttcc gtgccctcaa gcggggcgag cgcaagcgca gcaagctgga   8340
cgtgacgtat gactacggcg acggcaagcg gatcgagttc agcggccggg agccgctggg   8400
cgctgatgat ctgcgcatcc tgcaagggct ggtggccatg gctgggccta atggcctagt   8460
gcttggcccg gaacccaaga ccgaaggcgg acggcagctc cggctgttcc tggaacccaa   8520
gtgggaggcc gtcaccgctg atgccatggt ggtcaaaggt agctatcggg cgctggcaaa   8580
ggaaatcggg gcagaggtcg atagtggtgg ggcgctcaag cacatacagg actgcatcga   8640
gcgcctttgg aaggtatcca tcatcgccca gaatggccgc aagcggcagg ggtttcggct   8700
gctgtcggag tacgccagcg acgaggcgga cgggcgcctg tacgtggccc tgaaccccctt   8760 gatcgcgcag gccgtcatgg gtggcggcca gcatgtgcgc atcagcatgg acgaggtgcg   8820
ggcgctggac agcgaaaccg cccgcctgct gcaccagcgg ctgtgtggct ggatcgaccc   8880
cggcaaaacc ggcaaggctt ccatagatac cttgtgcggc tatgtctggc cgtcagaggc   8940
cagtggttcg accatgcgca agcgccgcca gcgggtgcgc gaggcgttgc cggagctggt   9000
cgcgctgggc tggacggtaa ccgagttcgc ggcgggcaag tacgacatca cccggcccaa   9060
ggcggcaggc tgaccccccc cactctattg taaacaagac atttttttatc ttttatattc    9120 aatggcttat tttcctgcta attggtaata ccatgaaaaa taccatgctc agaaaaggct   9180
taacaatatt ttgaaaaatt gcctactgag cgctgccgca cagctccata ggccgctttc   9240 ctggcttttgc ttccagatgt atgctctcct ccggagagta ccgtgacttt atttttcggca   9300 caaatacagg ggtcgatgga taaatacggc gatagttttcc tgacggatga tccgtatgta   9360
ccggcggaag acaagctgca aacctgtcag atggagattg atttaatggc ggatgtgctg   9420
```

| | |
|---|---|
| agagcaccgc cccgtgaatc cgcagaactg atccgctatg tgtttgcgga tgattggccg | 9480 |
| gaataaataa agccgggctt aatacagatt aagcccgtat agggtattat tactgaatac | 9540 |
| caaacagctt acggaggacg gaatgttacc cattgagaca accagactgc cttctgatta | 9600 |
| ttaatatttt tcactattaa tcagaaggaa taaccatgaa ttttacccgg attgacctga | 9660 |
| atacctggaa tcgcagggaa cactttgccc tttatcgtca gcagattaaa tgcggattca | 9720 |
| gcctgaccac caaactcgat attaccgctt tgcgtaccgc actggcggag acaggttata | 9780 |
| agttttatcc gctgatgatt tacctgatct cccgggctgt taatcagttt ccggagttcc | 9840 |
| ggatggcact gaaagacaat gaacttattt actgggacca gtcagacccg gtctttactg | 9900 |
| tctttcataa agaaaccgaa acattctctg cactgtcctg ccgttatttt ccggatctca | 9960 |
| gtgagtttat ggcaggttat aatgcggtaa cggcagaata tcagcatgat accagattgt | 10020 |
| ttccgcaggg aaatttaccg gagaatcacc tgaatatatc atcattaccg tgggtgagtt | 10080 |
| ttgacgggat ttaacctgaa catcaccgga atgatgatt attttgcccc ggttttacg | 10140 |
| atggcaaagt ttcagcagga aggtgaccgc gtattattac ctgtttctgt acaggttcat | 10200 |
| catgcagtct gtgatggctt tcatgcagca cggtttatta atacacttca gctgatgtgt | 10260 |
| gataacatac tgaaataaat taattaattc tgtatttaag ccaccgtatc cggcaggaat | 10320 |
| ggtggctttt tttttatatt ttaaccgtaa tctgtaattt cgtttcagac tggttcagga | 10380 |
| tcactgtacg ataatgcccc cgcagtttgg taatacccct aataaaaaag aaacagcaaa | 10440 |
| gactgacagc aataataata aagtaagcag taacaataat attaacaaca ccagatgcag | 10500 |
| ttataataat agtatttaag acaccagaaa gactgctgcg acagtcattt tgaacaacac | 10560 |
| caaaatgccg taaaggcagt agtaacaaca ccagtgaaaa catcacgata gcatagtgat | 10620 |
| atgcctgagt gtgtgtaatt aaacaataaa taaaccgcca tatataacag aagatagtat | 10680 |
| tctgaatggc atgcttttct gttcagtata aacatatcat cccggttggt ataaggatga | 10740 |
| tatataataa gttaagctga acacatattt attttggttt tattttacaa ataaagtaag | 10800 |
| acgatccgtt aagtcaaagc ggggtatatt tattataccc tgcttttta tttgtccgcc | 10860 |
| gggcgcggat aatggatcag attatgcagt gtcacaatgg ccttaccggg attggcgtaa | 10920 |
| gcgtgcggga tatccgcatg gaagcgcagg gattccccgg cagaaacggt gtgccactca | 10980 |
| tcccccagcc gcagttgtaa tgcgccttcc agtacaatga catgttctct ggttctgaaa | 11040 |
| tccatccctg tcggtgttgc ttatgcagtc tggtcgggac tcggcgtcgt cataattaca | 11100 |
| gccattgcct ggttgcttca tgggcaaaag ctttatgctt gtaaaccgtt ttgtgaaaaa | 11160 |
| attttttaaaa taaaaaaggg gacctctagg gtccccaatt aattagtaat ataatctatt | 11220 |
| aaaggtcatt caaaaggtca tccaccg | 11247 |

<210> SEQ ID NO 14
<211> LENGTH: 9310
<212> TYPE: DNA
<213> ORGANISM: Candida boidinii

<400> SEQUENCE: 14

| | |
|---|---|
| ctagttctag agcggccgcc accgcggtgg atccccagta gatttacgtt taaacatttt | 60 |
| tatttccttt ttaatttaat ttaattaaca gttggtgcta tgacacttta cctcatagct | 120 |
| ggcataattc gcaatactct gggtcttcga gaggtatcca acctgagttg aaatacttta | 180 |
| ccatcgattt agcagttgta tcagttatat ttatattacc tttaactctt cgccatccag | 240 |

```
gagttttacc gtacagatta gaggataata ataacacata attctcgtaa gcaatatgag      300
ataatttcca agactctata ttagctcgtg atgttttcca aggtctaaaa tcgtcacggt      360
tcatataatt agccaatctc atatgctctc taacttccga tgataagctg tcaaacatga      420
gaattaacga tctgatagag aagggttttgc tcgggtcggt ggctctggta acgaccagta    480
tcccgatccc ggctggccgt cctggccgcc acatgaggca tgttccgcgt ccttgcaata     540
ctgtgtttac atacagtcta tcgcttagcg gaaagttctt ttaccctcag ccgaaatgcc     600
tgccgttgct agacattgcc agccagtgcc cgtcactccc gtactaactg tcacgaaccc     660
ctgcaataac tgtcacgccc ccctgcaata actgtcacga acccctgcaa taactgtcac    720
gcccccaaac ctgcaaaccc agcaggggcg ggggctggcg gggtgttgga aaaatccatc     780
catgattatc taagaataat ccactaggcg cggttatcag cgcccttgtg gggcgctgct    840
gcccttgccc aatatgcccg gccagaggcc ggatagctgg tctattcgct gcgctaggct    900
acacaccgcc ccaccgctgc gcggcagggg gaaaggcggg caaagcccgc taaaccccac    960
accaaacccc gcagaaatac gctgggagcg cttttagccg ctttagcggc cttttcccct    1020
acccgaaggg tggggcgcg tgtgcagccc cgcagggcct gtctcggtcg atcattcagc     1080
ccggctcatc cttctggcgt ggcggcagac cgaacaaggc gcggtcgtgg tcgcgttcaa    1140
ggtacgcatc cattgccgcc atgagccgat cctccggcca ctcgctgctg ttcaccttgg    1200
ccaaaatcat ggccccacc agcaccttgc gccttgtttc gttcttgcgc tattgctgct    1260
gttcccttgc ccgcacccgc tgaatttcgg cattgattcg cgctcgttgt tcttcgagct    1320
tggccagccg atccgccgcc ttgttgctcc ccttaaccat cttgacaccc cattgttaat    1380
gtgctgtctc gtaggctatc atggaggcac agcggcggca atcccgaccc tactttgtag    1440
gggagggcca ttgcatggag ccgaaaagca aaagcaacag cgaggcagca tggcgattta    1500
tcaccttacg gcgaaaaccg gcagcaggtc gggcggccaa tcggccaggg ccaaggccga    1560
ctacatccag cgcgaaggca agtatgcccg cgacatggat gaagtcttgc acgccgaatc    1620
cgggcacatg ccggagttcg tcgagcggcc cgccgactac tgggatgctg ccgacctgta    1680
tgaacgcgcc aatgggcggc tgttcaagga ggtcgaattt gccctgccgg tcgagctgac    1740
cctcgaccag cagaaggcgc tggcgtccga gttcgcccag cacctgaccg gtgccgagcg    1800
cctgccgtat acgctggcca tccatgccgg tggcggcgag aacccgcact gccacctgat    1860
gatctccgag cggatcaatg acggcatcga gcggcccgcc gctcagtggt tcaagcggta    1920
caacggcaag accccggaga agggcgggc acagaagacc gaagcgctca gcccaaggc     1980 atggcttgag cagacccgcg aggcatgggc cgaccatgcc aaccgggcat tagagcgggc    2040
tggccacgac gcccgcattg accacagaac acttgaggcg cagggcatcg agcgcctgcc    2100
cggtgttcac ctggggccga acgtggtgga gatggaaggc cggggcatcc gcaccgaccg    2160
ggcagacgtg gccctgaaca tcgacaccgc caacgcccag atcatcgact acaggaata    2220 ccgggaggca atagaccatg aacgcaatcg acagagtgaa gaaatccaga ggcatcaacg    2280
agttagcgga gcagatcgaa ccgctggccc agagcatggc gacactggcc gacgaagccc    2340
ggcaggtcat gagccagacc cagcaggcca gcgaggcgca ggcggcggag tggctgaaag    2400
cccagcgcca gacaggggcg gcatgggtgg agctggccaa agagttgcgg gaggtagccg    2460
ccgaggtgag cagcgccgcg cagagcgccc ggagcgcgtc gcggggtgg cactggaagc    2520 tatggctaac cgtgatgctg gcttccatga tgcctacggt ggtgctgctg atcgcatcgt    2580
tgctcttgct cgacctgacg ccactgacaa ccgaggacgg ctcgatctgg ctgcgcttgg    2640
```

```
tggcccgatg aagaacgaca ggactttgca ggccataggc cgacagctca aggccatggg   2700
ctgtgagcgc ttcgatatcg gcgtcaggga cgccaccacc ggccagatga tgaacccggga  2760 atggtcagcc gccgaagtgc tccagaacac gccatggctc aagcggatga atgcccaggg  2820
caatgacgtg tatatcaggc ccgccgagca ggagcggcat ggtctggtgc tggtggacga  2880
cctcagcgag tttgacctgg atgacatgaa agccgagggc cgggagcctg ccctggtagt  2940
ggaaaccagc ccgaagaact atcaggcatg ggtcaaggtg ccgacgccg caggcggtga   3000 acttcggggg cagattgccc ggacgctggc cagcgagtac gacgccgacc cggccagcgc  3060
cgacagccgc cactatggcc gcttggcggg cttcaccaac cgcaaggaca agcacaccac  3120
ccgcgccggt tatcagccgt gggtgctgct gcgtgaatcc aagggcaaga ccgccaccgc  3180
tggcccggcg ctggtgcagc aggctggcca gcagatcgag caggcccagc ggcagcagga  3240
gaaggcccgc aggctggcca gcctcgaact gcccgagcgg cagcttagcc gccaccggcg  3300
cacgcgcctg gacgagtacc gcagcgagat ggccgggctg gtcaagcgct tcggtgatga  3360
cctcagcaag tgcgacttta tcgccgcgca gaagctggcc agccggggcc gcagtgccga  3420
ggaaatcggc aaggccatgg ccgaggccag cccagcgctg gcagagcgca agcccggcca  3480
cgaagcggat tacatcgagc gcaccgtcag caaggtcatg ggtctgccca gcgtccagct  3540
tgcgcgggcc gagctggcac gggcaccggc accccgccag cgaggcatgg acaggggcgg  3600
gccagatttc agcatgtagt gcttgcgttg gtactcacgc ctgttatact atgagtactc  3660
acgcacagaa gggggtttta tggaatacga aaaaagcgct tcagggtcgg tctacctgat  3720
caaaagtgac aagggctatt ggttgcccgg tggctttggt tatacgtcaa acaaggccga  3780
ggctggccgc ttttcagtcg ctgatatggc cagccttaac cttgacggct gcaccttgtc  3840
cttgttccgc gaagacaagc ctttcggccc cggcaagttt ctcggtgact gatatgaaag  3900
accaaaagga caagcagacc ggcgacctgc tggccagccc tgacgctgta cgccaagcgc  3960
gatatgccga gcgcatgaag gccaaaggga tgcgtcagcg caagttctgg ctgaccgacg  4020
acgaatacga ggcgctgcgc gagtgcctgg aagaactcag agcggcgcag ggcggggta   4080 gtgaccccgc cagcgcctaa ccaccaactg cctgcaaagg aggcaatcaa tggctaccca  4140
taagcctatc aatattctgg aggcgttcgc agcagcgccg ccaccgctgg actacgtttt  4200
gcccaacatg tgtgccggta cggtcggggc gctggtgtcg cccggtggtg ccggtaaatc  4260
catgctggcc ctgcaactgg ccgcacagat tgcaggcggg ccggatctgc tggaggtggg  4320
cgaactgccc accggcccgg tgatctacct gcccgccgaa gacccgccca ccgccattca  4380
tcaccgcctg cacgcccttg gggcgcacct cagcgccgag gaacggcaag ccgtggctga  4440
cggcctgctg atccagccgc tgatcggcag cctgcccaac atcatggccc ggagtggtt   4500 cgacggcctc aagcgcgccg ccgagggccg ccgcctgatg gtgctggaca cgctgcgccg  4560
gttccacatc gaggaagaaa acgcagcgg ccccatggcc caggtcatcg gtcgcatgga   4620
ggccatcgcc gccgatacc ggtgctctat cgtgttcctg caccatgcca gcaagggcgc   4680
ggccatgatg ggcgcaggcg accagcagca ggccagccgg ggcagctcgg tactggtcga  4740
taacatccgc tggcagtcct acctgtcgag catgaccagc gccgaggccg aggaatgggg  4800
tgtggacgac gaccagcgcc ggttcttcgt ccgcttcggt gtgagcaagg ccaactatgg  4860
cgcaccgttc gctgatcggt ggttcaggcg gcatgacggc ggggtgctca gcccgccgt   4920 gctggagagg cagcgcaaga gcaagggggt gccccgtggt gaagcctaag aacaagcaca  4980
```

```
gcctcagcca cgtccggcac gacccggcgc actgtctggc ccccggcctg ttccgtgccc   5040
tcaagcgggg cgagcgcaag cgcagcaagc tggacgtgac gtatgactac ggcgacggca   5100
agcggatcga gttcagcggc ccggagccgc tgggcgctga tgatctgcgc atcctgcaag   5160
ggctggtggc catggctggg cctaatggcc tagtgcttgg cccggaaccc aagaccgaag   5220
gcggacggca gctccggctg ttcctggaac ccaagtggga ggccgtcacc gctgatgcca   5280
tggtggtcaa aggtagctat cgggcgctgg caaaggaaat cggggcagag gtcgatagtg   5340
gtggggcgct caagcacata caggactgca tcgagcgcct ttggaaggta tccatcatcg   5400
cccagaatgg ccgcaagcgg caggggtttc ggctgctgtc ggagtacgcc agcgacgagg   5460
cggacgggcg cctgtacgtg gccctgaacc ccttgatcgc gcaggccgtc atgggtggcg   5520
gccagcatgt gcgcatcagc atggacgagg tgcgggcgct ggacagcgaa accgcccgcc   5580
tgctgcacca gcggctgtgt ggctggatcg accccggcaa aaccggcaag gcttccatag   5640
ataccttgtg cggctatgtc tggccgtcag aggccagtgg ttcgaccatg cgcaagcgcc   5700
gccagcgggt gcgcgaggcg ttgccggagc tggtcgcgct gggctggacg gtaaccgagt   5760
tcgcggcggg caagtacgac atcacccggc ccaaggcggc aggctgaccc ccccactct   5820 attgtaaaca agacattttt tatcttttat attcaatggc ttattttcct gctaattggt   5880
aataccatga aaataccat gctcagaaaa ggcttaacaa tattttgaaa aattgcctac   5940
tgagcgctgc cgcacagctc cataggccgc tttcctggct ttgcttccag atgtatgctc   6000
tcctccggag agtaccgtga ctttatttt ggcacaaata caggggtcga tggataaata   6060
cggcgatagt ttcctgacgg atgatccgta tgtaccggcg gaagacaagc tgcaaacctg   6120
tcagatggag attgatttaa tggcggatgt gctgagagca ccgccccgtg aatccgcaga   6180
actgatccgc tatgtgtttg cggatgattg gccggaataa ataaagccgg gcttaataca   6240
gattaagccc gtatagggta ttattactga ataccaaaca gcttacggag gacggaatgt   6300
tacccattga gacaaccaga ctgccttctg attattaata ttttcacta ttaatcagaa   6360 ggaataacca tgaattttac ccggattgac ctgaataacct ggaatcgcag ggaacactt   6420 gcccttatc gtcagcagat taaatgcgga ttcagcctga ccaccaaact cgatattacc   6480
gctttgcgta ccgcactggc ggagacaggt tataagtttt atccgctgat gatttacctg   6540
atctcccggg ctgttaatca gtttccggag ttccggatgg cactgaaaga caatgaactt   6600
atttactggg accagtcaga cccggtcttt actgtctttc ataaagaaac cgaaacattc   6660
tctgcactgt cctgccgtta ttttccggat ctcagtgagt ttatggcagg ttataatgcg   6720
gtaacggcag aatatcagca tgataccaga ttgtttccgc agggaaattt accggagaat   6780
cacctgaata tatcatcatt accgtggggtg agttttgacg ggatttaacc tgaacatcac   6840
cggaaatgat gattatttg ccccggtttt tacgatggca agtttcagc aggaaggtga   6900 ccgcgtatta ttacctgtttt ctgtacaggt tcatcatgca gtctgtgatg gctttcatgc   6960
agcacggttt attaatacac ttcagctgat gtgtgataac atactgaaat aaattaatta   7020
attctgtatt taagccaccg tatccggcag gaatggtggc tttttttta tattttaacc   7080 gtaatctgta atttcgttttc agactggttc aggatcactg tacgataatg cccccgcagt   7140
ttggtaatac ccttaataaa aagaaacag caaagactga cagcaataat aataaagtaa   7200
gcagtaacaa taatattaac aacaccagat gcagttataa aatagtatt taagacacca   7260 gaaagactgc tgcgacagtc attttgaaca acaccaaaat gccgtaaagg cagtagtaac   7320
aacaccagtg aaaacatcac gatagcatag tgatatgcct gagtgtgtgt aattaaacaa   7380
```

-continued

```
taaataaacc gccatatata acagaagata gtattctgaa tggcatgctt ttctgttcag    7440
tataaacata tcatcccggt tggtataagg atgatatata ataagttaag ctgaacacat    7500
atttattttg gttttatttt acaaataaag taagacgatc cgttaagtca aagcggggta    7560
tatttattat accctgcttt tttatttgtc cgccgggcgc ggataatgga tcagattatg    7620
cagtgtcaca atggccttac cgggattggc gtaagcgtgc gggatatccg catggaagcg    7680
cagggattcc ccggcagaaa cggtgtgcca ctcatccccc agccgcagtt gtaatgcgcc    7740
ttccagtaca atgacatgtt ctctggttct gaaatccatc cctgtcggtg ttgcttatgc    7800
agtctggtcg ggactcggcg tcgtcataat tacagccatt gcctggttgc ttcatgggca    7860
aaagctttat gcttgtaaac cgttttgtga aaaattttt aaataaaaa aggggacctc    7920
tagggtcccc aattaattag taatataatc tattaaaggt cattcaaaag gtcatccacc    7980
gggggccccc cctcgagagg cctgacgtcg ggcccggtac cacgcgttta tttcttatcg    8040
tgtttaccgt aagctttagt aacgtattca ccatttaata agataatatc ttgtggtctg    8100
taatcaaatt taccagtaaa gaatgattcc aagatatttt tagtaccttc agcgtatctt    8160
gtttgagcat ctaaagtagt accagagtag tgaggagtca tggcattacc agcaccatat    8220
ttatttctca tatctctcca tgggtgatcc tttggagctg gttgtgggaa ccaaacatca    8280
ccaccgtaac ctcttaattg accagattct aaagctgctg caacatcttc agcaacacaa    8340
atagcacctc ttgcggtatt gactaaccaa gcaccttttt taaatttaga taataattcc    8400
ttattaatta aaccttttgt acctgcgtgt aatggagcat taactgtaac gatatcagct    8460
tgagcaacta attcttcaat attttcaact cttctagcac caactttttc ttcagcttct    8520
tttggtaaag cttgataatc gtagtataat aattcttttg gattaaaagg gagtaatctt    8580
tccaagactc tgtaaccaat tctaccagca ccaatggtag caatagtttt accttcgata    8640
tcgtaagcat ccttagcgat agcagcaacc tcccaatcgt ggttaataat tgttcatgt    8700
gctggaacga aatttctaac caagacaagc atggtcatga caacgtgttc agcaacagag    8760
acaacattag aacctgtaac ttccaagact gagattttct tacctgtttg attaatataa    8820
tctaaatcaa tgtgatcaga accaacacca gcgacaacga ctaattttaa gttcttagcc    8880
ttgtcaagtc tttccttagt gatataagca ggatggaaag gagtggtgat gataatatca    8940
gcatctggga tatgtttatc caattcactt gtttcacctt ctttatcaga agtagtaatt    9000
agttcatgac cttgatcttt taaccaatta gcaataccta atttattttc agtacaacca    9060
tataatttt cttcatcagc agcgtgctta ccagcatcat ataagactaa aacgatcttc    9120
atacatcacc tcataaaata aattaaaaaa taataaaaac taatgtttcg cattatagga    9180
caaaagatac ctaaaaaatg ttatctagat caaattattg gaaaatatat gaaataatt    9240
tttgtttaaa aagcgaacga cattagtatt tttcataaaa atacgtacat tgttatccgt    9300
cgctatttaa                                                          9310
```

<210> SEQ ID NO 15
<211> LENGTH: 11309
<212> TYPE: DNA
<213> ORGANISM: Yersinia mollaretii
<400> SEQUENCE: 15

```
gatccccagt agatttacgt ttaaacattt ttatttcctt tttaatttaa tttaattaac      60
agttggtgct atgacacttt acctcatagc tggcataatt cgcaatactc tgggtcttcg     120
```

```
agaggtatcc aacctgagtt gaaatacttt accatcgatt tagcagttgt atcagttata    180
tttatattac ctttaactct tcgccatcca ggagttttac cgtacagatt agaggataat    240
aataacacat aattctcgta agcaatatga gataatttcc aagactctat attagctcgt    300
gatgttttcc aaggtctaaa atcgtcacgg ttcatataat tagccaatct catatgctct    360
ctaacttccg atgataagct gtcaaacatg agaattaacg atctgataga aagggtttg     420
ctcgggtcgg tggctctggt aacgaccagt atcccgatcc cggctggccg tcctggccgc    480
cacatgaggc atgttccgcg tccttgcaat actgtgttta catacagtct atcgcttagc    540
ggaaagttct tttaccctca gccgaaatgc ctgccgttgc tagacattgc cagccagtgc    600
ccgtcactcc cgtactaact gtcacgaacc cctgcaataa ctgtcacgcc ccctgcaat     660
aactgtcacg aaccctgca ataactgtca cgcccccaaa cctgcaaacc cagcaggggc     720
ggggctggc ggggtgttgg aaaaatccat ccatgattat ctaagaataa tccactaggc     780
gcggttatca gcgcccttgt ggggcgctgc tgcccttgcc caatatgccc ggccagaggc    840
cggatagctg gtctattcgc tgcgctaggc tacacaccgc cccaccgctg cgcggcaggg    900
ggaaaggcgg gcaaagcccg ctaaacccca caccaaaccc cgcagaaata cgctgggagc    960
gcttttagcc gctttagcgg cctttccccc tacccgaagg gtgggggcgc gtgtgcagcc    1020
ccgcagggcc tgtctcggtc gatcattcag cccggctcat ccttctggcg tggcggcaga    1080
ccgaacaagg cgcggtcgtg gtcgcgttca aggtacgcat ccattgccgc catgagccga    1140
tcctccggcc actcgctgct gttcaccttg gccaaaatca tggcccccac cagcaccttg    1200
cgccttgttt cgttcttgcg ctattgctgc tgttcccttg cccgcacccg ctgaatttcg    1260
gcattgattc gcgctcgttg ttcttcgagc ttggccagcc gatccgccgc cttgttgctc    1320
cccttaacca tcttgacacc ccattgttaa tgtgctgtct cgtaggctat catggaggca    1380
cagcggcggc aatcccgacc ctactttgta ggggagggcc attgcatgga gccgaaaagc    1440
aaaagcaaca gcgaggcagc atggcgattt atcaccttac ggcgaaaacc ggcagcaggt    1500
cgggcggcca atcggccagg gccaaggccg actacatcca gcgcgaaggc aagtatgccc    1560
gcgacatgga tgaagtcttg cacgccgaat ccgggcacat gccggagttc gtcgagcggc    1620
ccgccgacta ctgggatgct gccgacctgt atgaacgcgc caatgggcgg ctgttcaagg    1680
aggtcgaatt tgccctgccg gtcgagctga ccctcgacca gcagaaggcg ctggcgtccg    1740
agttcgccca gcacctgacc ggtgccgagc gcctgccgta tacgctggcc atccatgccg    1800
gtggcggcga gaacccgcac tgccacctga tgatctccga gcggatcaat gacggcatcg    1860
agcggcccgc cgctcagtgg ttcaagcggt acaacggcaa gaccccggag aagggcgggg    1920
cacagaagac cgaagcgctc aagcccaagg catggcttga gcagaccgcg aggcatgggg    1980
ccgaccatgc caaccgggca ttagagcggg ctggccacga cgcccgcatt gaccacagaa    2040
cacttgaggc gcaggcatc gagcgcctgc ccggtgttca cctggggccg aacgtggtgg    2100
agatggaagg ccgggcatc cgcaccgacc gggcagacgt ggccctgaac atcgacaccg    2160
ccaacgccca gatcatcgac ttacaggaat accgggaggc aatagaccat gaacgcaatc    2220
gacagagtga gaaatccag aggcatcaac gagttagcgg agcagatcga accgctggcc    2280
cagagcatgg cgacactggc cgacgaagcc cggcaggtca tgagccagac ccagcaggcc    2340
agcgaggcgc aggcggcgga gtggctgaaa gcccagcgcc agacaggggc ggcatgggtg    2400
gagctggcca aagagttgcg ggaggtagcc gccgaggtga gcagccgc gcagagcgcc     2460
cggagcgcgt cgcgggggtg gcactggaag ctatggctaa ccgtgatgct ggcttccatg    2520
```

```
atgcctacgg tggtgctgct gatcgcatcg ttgctcttgc tcgacctgac gccactgaca   2580
accgaggacg gctcgatctg gctgcgcttg gtggcccgat gaagaacgac aggactttgc   2640
aggccatagg ccgacagctc aaggccatgg gctgtgagcg cttcgatatc ggcgtcaggg   2700
acgccaccac cggccagatg atgaaccggg aatggtcagc cgccgaagtg ctccagaaca   2760
cgccatggct caagcggatg aatgcccagg gcaatgacgt gtatatcagg cccgccgagc   2820
aggagcggca tggtctggtg ctggtggacg acctcagcga gtttgacctg gatgacatga   2880
aagccgaggg ccgggagcct gccctggtag tggaaaccag cccgaagaac tatcaggcat   2940
gggtcaaggt ggccgacgcc gcaggcggtg aacttcgggg gcagattgcc cggacgctgg   3000
ccagcgagta cgacgccgac ccggccagcg ccgacagccg ccactatggc cgcttggcgg   3060
gcttcaccaa ccgcaaggac aagcacacca cccgcgccgg ttatcagccg tgggtgctgc   3120
tgcgtgaatc caagggcaag accgccaccg ctggcccggc gctggtgcag caggctggcc   3180
agcagatcga gcaggcccag cggcagcagg agaaggcccg caggctggcc agcctcgaac   3240
tgcccgagcg gcagcttagc cgccaccggc gcacggcgct ggacgagtac cgcagcgaga   3300
tggccgggct ggtcaagcgc ttcggtgatg acctcagcaa gtgcgacttt atcgccgcgc   3360
agaagctggc cagccggggc cgcagtgccg aggaaatcgg caaggccatg gccgaggcca   3420
gcccagcgct ggcagagcgc aagcccggcc acgaagcgga ttacatcgag cgcaccgtca   3480
gcaaggtcat gggtctgccc agcgtccagc ttgcgcgggc cgagctggca cgggcaccgg   3540
caccccgcca gcgaggcatg gacaggggcg ggccagattt cagcatgtag tgcttgcgtt   3600
ggtactcacg cctgttatac tatgagtact cacgcacaga agggggtttt atggaatacg   3660
aaaaaagcgc ttcagggtcg gtctacctga tcaaaagtga caagggctat tggttgcccg   3720
gtggctttgg ttatacgtca aacaaggccg aggctggccg cttttcagtc gctgatatgg   3780
ccagccttaa ccttgacggc tgcaccttgt ccttgttccg cgaagacaag cctttcggcc   3840
ccggcaagtt tctcggtgac tgatatgaaa gaccaaaagg acaagcagac cggcgacctg   3900
ctggccagcc ctgacgctgt acgccaagcg cgatatgccg agcgcatgaa ggccaaaggg   3960
atgcgtcagc gcaagttctg gctgaccgac gacgaatacg aggcgctgcg cgagtgcctg   4020
gaagaactca gagcggcgca gggcgggggt agtgaccccg ccagcgccta accaccaact   4080
gcctgcaaag gaggcaatca atggctaccc ataagcctat caatattctg gaggcgttcg   4140
cagcagcgcc gccaccgctg gactacgttt tgcccaacat ggtggccggt acggtcgggg   4200
cgctggtgtc gcccggtggt gccggtaaat ccatgctggc cctgcaactg gccgcacaga   4260
ttgcaggcgg gccggatctg ctggaggtgg gcgaactgcc caccggcccg gtgatctacc   4320
tgcccgccga agaccgcccc accgccattc atcaccgcct gcacgccctt ggggcgcacc   4380
tcagcgccga ggaacggcaa gccgtggctg acggcctgct gatccagccg ctgatcggca   4440
gcctgcccaa catcatggcc ccggagtggt tcgacgcct caagcgcgcc gccgagggcc   4500
gccgcctgat ggtgctggac acgctgcgcc ggttccacat cgaggaagaa aacgccagcg   4560
gccccatggc ccaggtcatc ggtcgcatgg aggccatcgc cgccgatacc gggtgctcta   4620
tcgtgttcct gcaccatgcc agcaagggcg cggccatgat gggcgcaggc gaccagcagc   4680
aggccagccg gggcagctcg gtactggtcg ataacatccg ctggcagtcc tacctgtcga   4740
gcatgaccag cgccgaggcc gaggaatggg gtgtggacga cgaccagcgc cggttcttcg   4800
tccgcttcgg tgtgagcaag gccaactatg gcgcaccgtt cgctgatcgg tggttcaggc   4860
```

```
ggcatgacgg cggggtgctc aagcccgccg tgctggagag gcagcgcaag agcaaggggg    4920
tgccccgtgg tgaagcctaa gaacaagcac agcctcagcc acgtccggca cgacccggcg    4980
cactgtctgg cccccggcct gttccgtgcc ctcaagcggg gcgagcgcaa gcgcagcaag    5040
ctggacgtga cgtatgacta cggcgacggc aagcggatcg agttcagcgg cccggagccg    5100
ctgggcgctg atgatctgcg catcctgcaa gggctggtgg ccatggctgg gcctaatggc    5160
ctagtgcttg gcccggaacc caagaccgaa ggcggacggc agctccggct gttcctggaa    5220
cccaagtggg aggccgtcac cgctgatgcc atggtggtca aaggtagcta tcgggcgctg    5280
gcaaaggaaa tcggggcaga ggtcgatagt ggtggggcgc tcaagcacat acaggactgc    5340
atcgagcgcc tttggaaggt atccatcatc gcccagaatg gccgcaagcg gcagggtttt    5400
cggctgctgt cggagtacgc cagcgacgag gcggacgggc gcctgtacgt ggccctgaac    5460
cccttgatcg cgcaggccgt catgggtggc ggccagcatg tgcgcatcag catggacgag    5520
gtgcgggcgc tggacagcga aaccgcccgc ctgctgcacc agcggctgtg tggctggatc    5580
gaccccggca aaaccggcaa ggcttccata gataccttgt gcggctatgt ctggccgtca    5640
gaggccagtg gttcgaccat gcgcaagcgc cgccagcggg tgcgcgaggc gttgccggag    5700
ctggtcgcgc tgggctggac ggtaaccgag ttcgcggcgg gcaagtacga catcacccgg    5760
cccaaggcgg caggctgacc cccccactc tattgtaaac aagacatttt ttatctttta    5820
tattcaatgg cttattttcc tgctaattgg taataccatg aaaatacca tgctcagaaa    5880 aggcttaaca atattttgaa aaattgccta ctgagcgctg ccgcacagct ccataggccg    5940
ctttcctggc tttgcttcca gatgtatgct ctcctccgga gagtaccgtg actttatttt    6000
cggcacaaat acaggggtcg atggataaat acggcgatag tttcctgacg gatgatccgt    6060
atgtaccggc ggaagacaag ctgcaaacct gtcagatgga gattgattta atggcggatg    6120
tgctgagagc accgccccgt gaatccgcag aactgatccg ctatgtgttt gcggatgatt    6180
ggccggaata aataaagccg gcttaatac agattaagcc cgtatagggt attattactg    6240
aataccaaac agcttacgga ggacggaatg ttacccattg agacaaccag actgccttct    6300
gattattaat attttcact attaatcaga aggaataacc atgaattta cccggattga    6360 cctgaatacc tggaatcgca gggaacactt tgcccttat cgtcagcaga ttaaatgcgg    6420
attcagcctg accaccaaac tcgatattac cgctttgcgt accgcactgg cggagacagg    6480
ttataagttt tatccgctga tgatttacct gatctcccgg gctgttaatc agtttccgga    6540
gttccggatg gcactgaaag acaatgaact tatttactgg gaccagtcag accggtctt    6600 tactgtcttt cataaagaaa ccgaaacatt ctctgcactg tcctgccgtt attttccgga    6660
tctcagtgag tttatggcag gttataatgc ggtaacggca gaatatcagc atgataccag    6720
attgtttccg cagggaaatt taccggagaa tcacctgaat atatcatcat taccgtgggt    6780
gagttttgac gggatttaac ctgaacatca ccggaaatga tgattatttt gccccggttt    6840
ttacgatggc aaagtttcag caggaaggtg accgcgtatt attacctgtt tctgtacagg    6900
ttcatcatgc agtctgtgat ggctttcatg cagcacggtt tattaataca cttcagctga    6960
tgtgtgataa catactgaaa taaattaatt aattctgtat ttaagccacc gtatccggca    7020
ggaatggtgg cttttttttt atattttaac cgtaatctgt aatttcgttt cagactggtt    7080
caggatcact gtacgataat gccccgcag tttggtaata cccttaataa aaagaaaca    7140 gcaaagactg acagcaataa taataagta agcagtaaca ataatattaa caacaccaga    7200
tgcagttata ataatagtat ttaagacacc agaaagactg ctgcgacagt cattttgaac    7260
```

```
aacaccaaaa tgccgtaaag gcagtagtaa caacaccagt gaaaacatca cgatagcata   7320
gtgatatgcc tgagtgtgtg taattaaaca ataaataaac cgccatatat aacagaagat   7380
agtattctga atggcatgct tttctgttca gtataaacat atcatcccgg ttggtataag   7440
gatgatatat aataagttaa gctgaacaca tatttatttt ggttttattt tacaaataaa   7500
gtaagacgat ccgttaagtc aaagcggggt atatttatta taccctgctt ttttatttgt   7560
ccgccgggcg cggataatgg atcagattat gcagtgtcac aatggcctta ccgggattgg   7620
cgtaagcgtg cgggatatcc gcatggaagc gcagggattc cccggcagaa acggtgtgcc   7680
actcatcccc cagccgcagt tgtaatgcgc cttccagtac aatgacatgt tctctggttc   7740
tgaaatccat ccctgtcggt gttgcttatg cagtctggtc gggactcggc gtcgtcataa   7800
ttacagccat tgcctggttg cttcatgggc aaaagcttta tgcttgtaaa ccgttttgtg   7860
aaaaaatttt taaaataaaa aaggggacct ctagggtccc caattaatta gtaatataat   7920
ctattaaagg tcattcaaaa ggtcatccac cggatccggg ccccccctcg aggtcgacgg   7980
tatcgataag cttgatatcg aattcccata ttgtgcatcg aatccctgca aaattgtctg   8040
agcgattaat tgttctaatt ttaccgccat gctcaccccc cgccatacgg aacagagcct   8100
gcatcagcag gctccagata aaacataaac tcattaatca gtggcttaga actgctgctc   8160
ttccgtcgag ccagtcagtg cagtgactga tgactcgccg ccctgaatga tattggtgac   8220
tttatcaaaa tagcccgtgc ccacttcttg ttgatgggaa gcaaaggtgt agccgcgttc   8280
aacggaggca aattctggct gctgcacttt ctcaacatag tgcttcatgc cctcgccttg   8340
cgcgtaagca tgggccaagt cgaacatgtt gaaccacata ctgtggatgc cgccaaggt   8400 aataaattga tatttgtagc ccatcgcgga gaggtcatct tggaagctgg cgatctgctg   8460
gtcagtcagg ttcttttttcc agttaaatga tggcgaacag ttataagcca ataatttacc   8520
ggggaattta gcgtgaaccg catctgcaaa gcgtttagcc agcgccagat ctggcgtcga   8580
ggtttcacac cacaccaagt cggcgtaagg ggcataggcc agaccacggc tgatggcttg   8640
ctcaatgccc gcgtgagtgc ggaagaagcc ctcagcagta cgatcaccag caataaattc   8700
gctgtcataa gggtcgcaat cagaggtcag caaatccgca gcatcagcat cagtgcgcgc   8760
aatcagcagt gttggcacgc caagaacgtc agcggctaag cgggcagcaa ccagcttctg   8820
aatcgcttct tgtgttggca ccaaaacttt gccgcccata tggccgcatt tcttcaccgc   8880
cgccaattga tcttcaaagt gaacgcccgc agcaccggct tcaatcatgg ctttcatcaa   8940
ttcaaacgca ttcaatacgc cgccaaaacc cgcttcggca tccgcacaa tcggcaggaa   9000 atagtcggta tagcctttgc tgcccggctc aatattattc gaccactgaa tctgatctgc   9060
acggcggaag ctgttattaa tacgcttaac cacggccgga acagagtcga ccgggtaaag   9120
agattgatcg ggatacatgc tggaggcggt attggcatcg gcggcgacct gccaacccga   9180
cagataaatc gcttcaacac cggcctttgc ctgttgcaat gcctgaccgc tgttagcgc   9240 ccccagacag ttgatgtagc ctttacgcga ttcgccgtgc agcaactccc acaatctttt   9300
cgcgccgtgc tgtgccagcg tacattctgg gttaacggaa ccgcgcagtt tgatcacttc   9360
ttcggcgcta taggggcggg tgatgccctt ccagcgcggt gatttccatt cctgttccaa   9420
ctgctgaatt tgttgagtac gagaggttgt catggcgata ttccttatta cttattttg   9480 tagggttaaa taactggcct aggcgagtaa tgcgtagccc ggcaacgtca gaaagtcgat   9540
aagctcgtct tgtgttgtaa tccgctccat cagacgtgcg gcttcttcaa accgcccgcc   9600
```

| | |
|---|---|
| atcaaaacgc tctgcgccaa gttcaagttt cacgacctgc atttcttcac tcaacatgtt | 9660 |
| acggaacagc tctttggtca ccgtctgacc attgctcagg cttttctggt gatgtatcca | 9720 |
| ttgccagata gaagtacggg aaatctcagc cgtcgcggca tcttccatca ggccataaat | 9780 |
| cggtacacag ccattgcccg atatccatgc ttcgatgtat tgcactgcga cccggatatt | 9840 |
| ggcccgcatc ccctcttcgg tgcgctcacc cgtgcaaggc tctagcaact cagcggcagt | 9900 |
| gattggttta tcttgcgcgc gactcacctc taattggttt ggacgatcgc ccagtacttt | 9960 |
| gttgaaaacg tccatcacgg tatcggccag accggggtgt gcgacccatg taccatcgtg | 10020 |
| gccgttgctg gcttccagct cttgtcagc gcgaacttta tctaagacca gcgcattttt | 10080 |
| ttctggatct ttgttcggga taaaggccgc catgccgccc atcgccaagg caccgcgctt | 10140 |
| atggcaggtt ttgatcagta acgagagta ggcactcagg aagggtttcg tcatcgtgac | 10200 |
| cgactggcga tcgggcagca cgcgatcgct gtgattttc agcgttttga tatagctgaa | 10260 |
| aatgtagtcc caacgccac aattcagggc aacaatgtga tggcgcagat ggtagaggat | 10320 |
| ctcatccatc tggaataccg caggcaatgt ctcgattaat actgtggcct taatggtgcc | 10380 |
| ttgcggcaga tcgaaacgct gctcggtaaa gctgaaaaca tcactccacc aagccgcttc | 10440 |
| ctgataagac tgcatcttgg gtagataaa ataggggccg ctgccattgg caagcagtaa | 10500 |
| cttatagtta tggtagaaat acaacgcgaa atcgaataag ccaccgggga tatcctcccc | 10560 |
| ctgccacttc acgtgttttt ctggcaagtg cagaccacgc acccgagcaa tcaacaccgc | 10620 |
| tggattgggt tttagctgat aaatcttacc ggattcattc gcgtaagaga ttgtgccttt | 10680 |
| gaccgcatcg tgcaaattaa tctgaccttc gataaccta tcccaactgg gtgccagcga | 10740 |
| atcctcaaag tcagccataa agactttcac attcgcattg agggcattaa tcaccatttt | 10800 |
| gcgctcaacc ggcccggtga tctcgacgcg acgatcacgt aaatccgcag gaatactttg | 10860 |
| aattttccag tcaccattac gaatggaatt ggtttccgaa atgaaatcag gcaatgcgcc | 10920 |
| ttggtcaatg gcctgttgcc aagcggcccg tgcagcaagg agtttgctac gcggctctgc | 10980 |
| aaatttcgcc accaattctg ccaaaaattc gatggcctca tcgggcaaaa cctgccgctc | 11040 |
| agcagcatta aaatgctggg tgaaaactaa ctccgtgccg actatctgtt gtgtcattcc | 11100 |
| ccttccccctt ccccatctct cgacgatcat ttttcagttt ccttttgtta ttccccaaaa | 11160 |
| gtgcggtgca aatttgggga gttttagtta attaaaaaaa ttatttttta cgagcttcga | 11220 |
| ttactgcagc agcaacactt gttggcgctt cagcatattt taacggttcc attgagtatg | 11280 |
| atgctctaga gcggccgcca ccgcggtgg | 11309 |

<210> SEQ ID NO 16
<211> LENGTH: 2628
<212> TYPE: DNA
<213> ORGANISM: Pasteurella DSM 18541

<400> SEQUENCE: 16

| | |
|---|---|
| atgattatga gtaacgctgt tgaaaacaca gtaagccccg ctcaagcgga ggtgaactca | 60 |
| ctggttgaga aaggtttagt ggcactggag caattccgcc aactaaatca ggaacaggtg | 120 |
| gactacattg tagcgaaagc ttctgttgcc gctttagacc aacatggagc attggcgcta | 180 |
| catgcgttag aggaaaccgg gcgcggcgtg ttcgaggaca aagccactaa aaacctgttt | 240 |
| gcctgcgaac atgtagtgaa caaaatgcga cattggaaaa ccgccgggat tatcagtgac | 300 |
| gacgatgtca caggtatcac cgaaattgcc gatccggtgg gagtggtctg cggcattaca | 360 |
| cctaccacta atcctacttc cacggctatc ttcaaatcac tgatcgcttt aaaaacccgc | 420 |

```
aatcctattg ttttcgcttt ccaccttcc gcccaacagt cttccgctca tgccgcacaa    480
attgtgcgcg atgccgcggt agccgccggt gcgccggaaa actgtattca atggattgca    540
caaccctcta tggaaggaac taatgcgtta atgaaccatc cgggtattgc caccattctg    600
gctaccggcg gtaacgctat ggtgcaggcc gcttattcat gcggcaagcc ggcgttggga    660
gtcggtgccg gaaatgtacc cgcttatgtg gaaaaatccg ccgatattaa acaggcaact    720
cacgatatcg tgatgtcgaa atcctttgat aacggtatgg tatgcgcttc agagcaagcc    780
gctattgccg atgcggaaat ttatgacgaa ttcgtcaacg aattaaaatc ctacggtgtg    840
tatttcgtca ataaaaaaga aaaaacttta ttggaagaat ttatgttcgg tgtaaaagct    900
aacggtgcaa attgcgccgg tgcgaaacta acgccgacg tggtaggtaa atccgcatac    960
tggattgctc aacaagcggg ctttgaagtg ccgaaaaaaa ccaatattct tgccgcagaa    1020
tgtaaagaag tcagcccgaa agaacccttta acccgggaaa aattatcacc ggtgcttgcc    1080
gttttaaaat cccgttctac cgaagaggga ttaacgcttg ccgaagccat ggtggaattt    1140
aacggtttag gacactccgc ggcaattcac accaaagatg cggcgcttgc caaacgcttc    1200
ggcgagcgcg ttaaagccat tcgcgttatc tggaattcgc cttctacctt cggcggtatc    1260
ggcgacgttt ataacgcttt cctgccttca ttaaccctgg gttgcggttc ttacggcaaa    1320
aattccgtca gcaacaatgt cagcgccatg aacttagtaa atatcaaacg tgtgggaaga    1380
cggagaaata atatgcaatg gtttaaagta ccttcaaaaa tctatttga acgggattca    1440 attcaatatt tacaatccgt accggatatg cgacgagtag ttatcgtaac cgaccgcact    1500
atggtggatc ttgggtttgt acaaaaaatc gcccatcagt tggaatcccg tcgcgatccg    1560
gtttcttacc agttatttgc cgatgtagaa ccggatccga gtattcaaac cgtgcgccgc    1620
ggtgtggatt taatccgtaa tttcaaaccg gacactatta tcgcgcttgg cggcggttcc    1680
gccatggatg cggcaaaagt gatgtggtta ttctatgaac aaccggaaat tgacttccgt    1740
gatttggttc aaaaattcat ggatattcgt aaacgtgcct ttaaatttcc atcattggga    1800
aaaaaagccc gctatatcgg cattccgacc acatccggta cgggttcgga agtgaccccg    1860
tttgcggtga ttaccgaagg taacaaaaaa tatccgattg cggactattc gctaacgccg    1920
actatcgctt tagtggatcc ggcattagtt atgacggtac ccgcccatgt agcggcggat    1980
acgggattag acgtattaac tcatgccacc gaagcttatg tttccgtact ggccaacgat    2040
tataccgacg gtcttgcttt acaggcgatt aaactggtat tccggtattt ggaaaaatcc    2100
gtaaaagaaa atgatccgga ggcaagagaa aagatgcata atgcgtccac cattgcgggt    2160
atggcgtttg ccaatgcatt cttaggtatg aatcattccc ttgcgcataa acttggcggc    2220
catttccata cgcctcacgg gcgcactaat gcgatcttaa tgccgcacgt gatccgttat    2280
aacggtacta aaccgacgaa aaccgccaca tggccgaaat acaactatta caaagcggac    2340
gaaaaatatc aggatatcgc ccgtttatta ggcttacctg cggcgacccc ggaagagggc    2400
gtgaaatctt atgccaaagc ggtttacgat ttagcggtac gttgcggtat taaaatgtcc    2460
ttcaaagaac agggactgga agaacaggcc tggatggacg cccgccatga aattgcattg    2520
cttgcctatg aagaccaatg ttcgccggca aatccgcgat taccgattgt ggcggacatg    2580
gaagaaattc tcactaacgc ctactatggt tatgacgaaa gcaaatac    2628
```

<210> SEQ ID NO 17
<211> LENGTH: 876
<212> TYPE: PRT

<213> ORGANISM: Pasteurella DSM 18541

<400> SEQUENCE: 17

```
Met Ile Met Ser Asn Ala Val Glu Asn Thr Val Ser Pro Ala Gln Ala
1               5                   10                  15

Glu Val Asn Ser Leu Val Glu Lys Gly Leu Val Ala Leu Glu Gln Phe
            20                  25                  30

Arg Gln Leu Asn Gln Glu Gln Val Asp Tyr Ile Val Ala Lys Ala Ser
        35                  40                  45

Val Ala Ala Leu Asp Gln His Gly Ala Leu Ala Leu His Ala Leu Glu
    50                  55                  60

Glu Thr Gly Arg Gly Val Phe Glu Asp Lys Ala Thr Lys Asn Leu Phe
65                  70                  75                  80

Ala Cys Glu His Val Val Asn Lys Met Arg His Trp Lys Thr Ala Gly
                85                  90                  95

Ile Ile Ser Asp Asp Asp Val Thr Gly Ile Thr Glu Ile Ala Asp Pro
            100                 105                 110

Val Gly Val Val Cys Gly Ile Thr Pro Thr Thr Asn Pro Thr Ser Thr
        115                 120                 125

Ala Ile Phe Lys Ser Leu Ile Ala Leu Lys Thr Arg Asn Pro Ile Val
    130                 135                 140

Phe Ala Phe His Pro Ser Ala Gln Gln Ser Ser Ala His Ala Ala Gln
145                 150                 155                 160

Ile Val Arg Asp Ala Ala Val Ala Ala Gly Ala Pro Glu Asn Cys Ile
                165                 170                 175

Gln Trp Ile Ala Gln Pro Ser Met Glu Gly Thr Asn Ala Leu Met Asn
            180                 185                 190

His Pro Gly Ile Ala Thr Ile Leu Ala Thr Gly Gly Asn Ala Met Val
        195                 200                 205

Gln Ala Ala Tyr Ser Cys Gly Lys Pro Ala Leu Gly Val Gly Ala Gly
    210                 215                 220

Asn Val Pro Ala Tyr Val Glu Lys Ser Ala Asp Ile Lys Gln Ala Thr
225                 230                 235                 240

His Asp Ile Val Met Ser Lys Ser Phe Asp Asn Gly Met Val Cys Ala
                245                 250                 255

Ser Glu Gln Ala Ala Ile Ala Asp Ala Glu Ile Tyr Asp Glu Phe Val
            260                 265                 270

Asn Glu Leu Lys Ser Tyr Gly Val Tyr Phe Val Asn Lys Lys Glu Lys
        275                 280                 285

Thr Leu Leu Glu Glu Phe Met Phe Gly Val Lys Ala Asn Gly Ala Asn
    290                 295                 300

Cys Ala Gly Ala Lys Leu Asn Ala Asp Val Val Gly Lys Ser Ala Tyr
305                 310                 315                 320

Trp Ile Ala Gln Gln Ala Gly Phe Glu Val Pro Lys Lys Thr Asn Ile
                325                 330                 335

Leu Ala Ala Glu Cys Lys Glu Val Ser Pro Lys Glu Pro Leu Thr Arg
            340                 345                 350

Glu Lys Leu Ser Pro Val Leu Ala Val Leu Lys Ser Arg Ser Thr Glu
        355                 360                 365

Glu Gly Leu Thr Leu Ala Glu Ala Met Val Glu Phe Asn Gly Leu Gly
    370                 375                 380

His Ser Ala Ala Ile His Thr Lys Asp Ala Ala Leu Ala Lys Arg Phe
385                 390                 395                 400
```

```
Gly Glu Arg Val Lys Ala Ile Arg Val Ile Trp Asn Ser Pro Ser Thr
                405                 410                 415
Phe Gly Gly Ile Gly Asp Val Tyr Asn Ala Phe Leu Pro Ser Leu Thr
            420                 425                 430
Leu Gly Cys Gly Ser Tyr Gly Lys Asn Ser Val Ser Asn Asn Val Ser
        435                 440                 445
Ala Met Asn Leu Val Asn Ile Lys Arg Val Gly Arg Arg Asn Asn
    450                 455                 460
Met Gln Trp Phe Lys Val Pro Ser Lys Ile Tyr Phe Glu Arg Asp Ser
465                 470                 475                 480
Ile Gln Tyr Leu Gln Ser Val Pro Asp Met Arg Arg Val Val Ile Val
                485                 490                 495
Thr Asp Arg Thr Met Val Asp Leu Gly Phe Val Gln Lys Ile Ala His
            500                 505                 510
Gln Leu Glu Ser Arg Arg Asp Pro Val Ser Tyr Gln Leu Phe Ala Asp
        515                 520                 525
Val Glu Pro Asp Pro Ser Ile Gln Thr Val Arg Arg Gly Val Asp Leu
    530                 535                 540
Ile Arg Asn Phe Lys Pro Asp Thr Ile Ile Ala Leu Gly Gly Gly Ser
545                 550                 555                 560
Ala Met Asp Ala Ala Lys Val Met Trp Leu Phe Tyr Glu Gln Pro Glu
                565                 570                 575
Ile Asp Phe Arg Asp Leu Val Gln Lys Phe Met Asp Ile Arg Lys Arg
            580                 585                 590
Ala Phe Lys Phe Pro Ser Leu Gly Lys Lys Ala Arg Tyr Ile Gly Ile
        595                 600                 605
Pro Thr Thr Ser Gly Thr Gly Ser Glu Val Thr Pro Phe Ala Val Ile
    610                 615                 620
Thr Glu Gly Asn Lys Lys Tyr Pro Ile Ala Asp Tyr Ser Leu Thr Pro
625                 630                 635                 640
Thr Ile Ala Leu Val Asp Pro Ala Leu Val Met Thr Val Pro Ala His
                645                 650                 655
Val Ala Ala Asp Thr Gly Leu Asp Val Leu Thr His Ala Thr Glu Ala
            660                 665                 670
Tyr Val Ser Val Leu Ala Asn Asp Tyr Thr Asp Gly Leu Ala Leu Gln
        675                 680                 685
Ala Ile Lys Leu Val Phe Arg Tyr Leu Glu Lys Ser Val Lys Glu Asn
    690                 695                 700
Asp Pro Glu Ala Arg Glu Lys Met His Asn Ala Ser Thr Ile Ala Gly
705                 710                 715                 720
Met Ala Phe Ala Asn Ala Phe Leu Gly Met His Ser Leu Ala His
                725                 730                 735
Lys Leu Gly Gly His Phe His Thr Pro His Gly Arg Thr Asn Ala Ile
            740                 745                 750
Leu Met Pro His Val Ile Arg Tyr Asn Gly Thr Lys Pro Thr Lys Thr
        755                 760                 765
Ala Thr Trp Pro Lys Tyr Asn Tyr Tyr Lys Ala Asp Glu Lys Tyr Gln
    770                 775                 780
Asp Ile Ala Arg Leu Leu Gly Leu Pro Ala Ala Thr Pro Glu Glu Gly
785                 790                 795                 800
Val Lys Ser Tyr Ala Lys Ala Val Tyr Asp Leu Ala Val Arg Cys Gly
                805                 810                 815
```

```
Ile Lys Met Ser Phe Lys Glu Gln Gly Leu Glu Gln Ala Trp Met
            820                 825                 830

Asp Ala Arg His Glu Ile Ala Leu Leu Ala Tyr Glu Asp Gln Cys Ser
        835                 840                 845

Pro Ala Asn Pro Arg Leu Pro Ile Val Ala Asp Met Glu Glu Ile Leu
    850                 855                 860

Thr Asn Ala Tyr Tyr Gly Tyr Asp Glu Ser Lys Tyr
865                 870                 875

<210> SEQ ID NO 18
<211> LENGTH: 7284
<212> TYPE: DNA
<213> ORGANISM: artificial
<220> FEATURE:
<223> OTHER INFORMATION: integrational plasmid

<400> SEQUENCE: 18
```

| | | | | | |
|---|---|---|---|---|---|
| tcgagataaa | ttcgcggaac | cggcgcaggc | tcacctggct | gttgcgatcg | ataggtacgt | 60 |
| tgattatggt | gttgattaca | tctcttgtac | ctggcacatt | tgccgtttta | tcaatttcac | 120 |
| tgctcacctc | gttttgtgcg | ttcacgttga | ttacaatgat | gtttttttaat | tgattctttta | 180 |
| ccgcttcctg | atacatacct | tcctgacccg | caacatcata | aatatcaatt | aagccggaca | 240 |
| gtcctaaatt | atccgttaaa | ccgccgtcca | ccaaatgaat | aaaagggcgt | tctttgctgt | 300 |
| tttgatataa | agacaaggta | ttttttaatt | cttccagatt | ttttgatttt | tgcgcatcat | 360 |
| tgctgatatt | ttggctgatt | tgaattaatt | ccggtatatc | gaaatggcag | ttgccgccgt | 420 |
| tgttgtttaa | agtcaacggg | ctgaacagca | acggtaccga | acttgatgcg | gcgacggcac | 480 |
| gggaaatttc | cattttactt | aagtcaatac | aaagaccgtc | gaaaaattct | tgcgtaaagg | 540 |
| ttatttttg | tcctaaattc | atatccgtcg | cactcactac | gacaaacggt | cctttacgtt | 600 |
| ttcgctcaag | atcaccgaag | gtagcgcctt | tgtataatgt | ttgatccagc | tgttcctgta | 660 |
| ataagtcgcc | gcgaccgaat | tgaggggagg | ttattcgcgg | taaattggaa | agggataaaa | 720 |
| cctgactgat | aatttcccgc | tggaaatttt | ttttaggaa | gttttcttca | aatttaggca | 780 |
| ccgcatcccg | cccgtatagg | aataataag | tggctaaaac | ggatccgccg | gatacgccgt | 840 |
| ataccaaatc | cacattatca | attagggttg | taccttttgc | cgtcgggcgc | acggcggcgt | 900 |
| ttttaaattc | ctctaacacg | ccgtagccca | aacttgccgc | ccggctgccg | ccgcccgaaa | 960 |
| acattaaaat | aatcaaattg | ccgtcgggtt | gctgaatggc | atttctcatt | cgatacccttt | 1020 |
| gcttagcgtt | cacatggctg | atggtatcaa | cgggctgata | agtcactaag | gtacaagctg | 1080 |
| acaacaacaa | aacagtcaaa | ccggcgaaaa | tattttttag | catcatagtt | gtaacggata | 1140 |
| aatctaaatt | tttatttata | gaaaagaaa | ataatatgct | acatcgtact | atattaattt | 1200 |
| tatcctgcgt | tcatatctta | tcagaaggca | aaccgctttt | tctatgcaag | gaaaatttta | 1260 |
| taaatgacta | atgtactcaa | ataatgaaga | aagataaaca | aacattttt | catgagaaaa | 1320 |
| ttcttatgaa | ttctaagcct | cggtaattcc | tattggtatt | tatttttgaa | accgattacc | 1380 |
| ttttaaatta | aaatttttta | tttgatttaa | atcaatttaa | tcgcattatt | aatcccattt | 1440 |
| cataactcca | aagtagtaaa | attcgcacca | gtaaccaaat | ttaaatatta | aacaacttta | 1500 |
| ggagaataat | ttgtaaaatt | cttaaaaatc | gtaccgcact | ttttctaaaa | gtgcggtatt | 1560 |
| tttttgattg | tttttatccg | tctaaagggt | aaaatcaacg | ggatttattg | atattaaagg | 1620 |
| aaacaattat | ggcaacaact | attcatacag | aaaacgcgcc | cgcagcaatc | ggtccttatg | 1680 |
| ttcaagcggt | agatttaggc | aatttagtgc | tgacttcggg | gcaaattccg | gtgaatccgg | 1740 |

```
caaccggcga agtgccggcg gatattagcg cacaagcccg ccaatcttta gaaaacgtta   1800
aagcgattat cgaacaggca gggttaaccg tggcggatat tgtaaaaact acggttttg    1860
ttaaggattt aaacgatttt gccaccgtaa atgcggaata cgaacgtttt ttcaaagaga   1920
atgaccatcc gaatttccct gctcgctcat gcgttgaagt ggcgcgttta ccgaaagacg   1980
tcggcttgga aattgaagct attgcggtgc gcaaataagg ctgggttaag cgcttattta   2040
tacaaaagtg cggtcaaaaa atccgttttt tgtaaaagaa aaggcatagt tttattgacc   2100
gtgcctttt gctatttgat gatttatttg cgcaacttca cttcttgtac cgcatggtcg    2160
gcacctttgc gtaaaattaa atttgcccgt tcacgggtcg gcaaaatatt ttgccgtaaa   2220
tttaagccgt taatagtatt ccaaatatta gcggcggttt caaccgcttc ttctttagag   2280
agttttgcat aatctttaaa ataggaattc ggatcggtaa acgcgctttc acggaatttc   2340
aaaaagcggc gaatatacca ttcctttaat aaggcttcat cggcgtccac ataaacggaa   2400
aaatcaacaa aatcggagac aaaagtctgt tccgctttgc gcgaaccggt ttgtaatacg   2460
tttaaacctt ccaatataag aatatccggg cgatctacct tgttaaattt atcggggata   2520
atatcatagg tcaaatgcga ataaatcggc gccgacacgt tcggtttgcc ggattttacg   2580
tccgccagaa atttgattaa tttgggcgta tcgtaagaga cggggaagcc ttttttatgc   2640
aataaattt cttttttta ttttttctaaa ggatagagaa aaccgtcggt ggtaatcaaa    2700
tccactttgc gattttcagg ccagttagac agtaaagact gcaaaatacg cgcggaagtg   2760
cttttcccga ccgaaacgct gccggcaata ctgataatat aaggtacatt ggcgttggta   2820
ttgccgagaa aacggttcat tacggtctgg cgacgtaaat tttcttcaat ataataatta   2880
attaaacgcg caagaggcag gtaaatggtg ctgacttctt ccaacgataa ttcttcgtta   2940
aaaccgagta aaggctttaa atcttgttct gtcagttta aaggcacgga tttccgcaat    3000
tccgcccatt gtttacgggt aaatgtcaaa aacgggctga atttctctga aactgacgat   3060
tggcttcta tgttcacggc tcattctaat gttaagaaag taaaaatcta gactccatag    3120
gccgctttcc tggctttgct tccagatgta tgctctcctc cggagagtac cgtgacttta   3180
ttttcggcac aaatacaggg gtcgatggat aaatacggcg atagtttcct gacggatgat   3240
ccgtatgtac cggcggaaga caagctgcaa acctgtcaga tggagattga tttaatggcg   3300
gatgtgctga gagcaccgcc ccgtgaatcc gcagaactga tccgctatgt gtttgcggat   3360
gattggccgg aataaataaa gccgggctta atacagatta agcccgtata gggtattatt   3420
actgaatacc aaacagctta cggaggacgg aatgttaccc attgagacaa ccagactgcc   3480
ttctgattat taatatttt cactattaat cagaaggaat aaccatgaat tttacccgga    3540
ttgacctgaa tacctggaat cgcagggaac actttgccct ttatcgtcag cagattaaat   3600
gcggattcag cctgaccacc aaactcgata ttaccgcttt gcgtaccgca ctggcggaga   3660
caggttataa gttttatccg ctgatgattt acctgatctc ccgggctgtt aatcagtttc   3720
cggagttccg gatggcactg aaagacaatg aacttattta ctgggaccag tcagacccgg   3780
tctttactgt ctttcataaa gaaaccgaaa cattctctgc actgtcctgc cgttattttc   3840
cggatctcag tgagtttatg gcaggttata atgcggtaac ggcagaatat cagcatgata   3900
ccagattgtt tccgcaggga aatttaccgg agaatcacct gaatatatca tcattaccgt   3960
gggtgagttt tgacgggatt taacctgaac atcaccggaa atgatgatta ttttgccccg   4020
gttttttacga tggcaaagtt tcagcaggaa ggtgaccgcg tattattacc tgtttctgta   4080
```

```
caggttcatc atgcagtctg tgatggcttt catgcagcac ggtttattaa tacacttcag    4140
ctgatgtgtg ataacatact gaaataaatt aattaattct gtatttaagc caccgtatcc    4200
ggcaggaatg gtggcttttt ttttatattt taaccgtaat ctgtaatttc gtttcagact    4260
ggttcaggat gagctcgctt ggactcctgt tgatagatcc agtaatgacc tcagaactcc    4320
atctggattt gttcagaacg ctcggttgcc gccgggcgtt ttttattggt gagaatccaa    4380
gcactagcgg cgcgccggcc ggcccggtgt gaaataccgc acagatgcgt aaggagaaaa    4440
taccgcatca ggcgctcttc cgcttcctcg ctcactgact cgctgcgctc ggtcgttcgg    4500
ctgcggcgag cggtatcagc tcactcaaag gcggtaatac ggttatccac agaatcaggg    4560
gataacgcag gaaagaacat gtgagcaaaa ggccagcaaa aggccaggaa ccgtaaaaag    4620
gccgcgttgc tggcgttttt ccataggctc cgcccccctg acgagcatca caaaaatcga    4680
cgctcaagtc agaggtggcg aaacccgaca ggactataaa gataccaggc gtttccccct    4740
ggaagctccc tcgtgcgctc tcctgttccg accctgccgc ttaccggata cctgtccgcc    4800
tttctccctt cgggaagcgt ggcgctttct catagctcac gctgtaggta tctcagttcg    4860
gtgtaggtcg ttcgctccaa gctgggctgt gtgcacgaac cccccgttca gcccgaccgc    4920
tgcgccttat ccggtaacta tcgtcttgag tccaacccgg taagacacga cttatcgcca    4980
ctggcagcag ccactggtaa caggattagc agagcgaggt atgtaggcgg tgctacagag    5040
ttcttgaagt ggtggcctaa ctacggctac actagaagga cagtatttgg tatctgcgct    5100
ctgctgaagc cagttacctt cggaaaaaga gttggtagct cttgatccgg caaacaaacc    5160
accgctggta gcggtggttt ttttgtttgc aagcagcaga ttacgcgcag aaaaaaagga    5220
tctcaagaag atcctttgat cttttctacg gggtctgacg ctcagtggaa cgaaaactca    5280
cgttaaggga ttttggtcat gagattatca aaaaggatct tcacctagat ccttttaaag    5340
gccggccgcg gccgccatcg gcattttctt ttgcgttttt atttgttaac tgttaattgt    5400
ccttgttcaa ggatgctgtc tttgacaaca gatgttttct tgcctttgat gttcagcagg    5460
aagctcggcg caaacgttga ttgtttgtct gcgtagaatc ctctgtttgt catatagctt    5520
gtaatcacga cattgtttcc tttcgcttga ggtacagcga agtgtgagta agtaaaggtt    5580
acatcgttag gatcaagatc catttttaac acaaggccag ttttgttcag cggcttgtat    5640
gggccagtta agaattaga aacataacca agcatgtaaa tatcgttaga cgtaatgccg    5700
tcaatcgtca ttttttgatcc gcgggagtca gtgaacaggt accatttgcc gttcatttta    5760
aagacgttcg cgcgttcaat ttcatctgtt actgtgttag atgcaatcag cggtttcatc    5820
acttttttca gtgtgtaatc atcgtttagc tcaatcatac cgagagcgcc gtttgctaac    5880
tcagccgtgc gttttttatc gctttgcaga agttttttgac tttcttgacg gaagaatgat    5940
gtgcttttgc catagtatgc tttgttaaat aaagattctt cgccttggta gccatcttca    6000
gttccagtgt ttgcttcaaa tactaagtat ttgtggcctt tatcttctac gtagtgagga    6060
tctctcagcg tatggttgtc gcctgagctg tagttgcctt catcgatgaa ctgctgtaca    6120
ttttgatacg ttttccgtc accgtcaaag attgatttat aatcctctac accgttgatg    6180
ttcaaagagc tgtctgatgc tgatacgtta acttgtgcag ttgtcagtgt ttgtttgccg    6240
taatgtttac cggagaaatc agtgtagaat aaacggattt ttccgtcaga tgtaaatgtg    6300
gctgaacctg accattcttg tgtttggtct tttaggatag aatcatttgc atcgaatttg    6360
tcgctgtctt taaagacgcg gccagcgttt ttccagctgt caatagaagt ttcgccgact    6420
ttttgataga acatgtaaat cgatgtgtca tccgcatttt taggatctcc ggctaatgca    6480
```

```
aagacgatgt ggtagccgtg atagtttgcg acagtgccgt cagcgttttg taatggccag    6540
ctgtcccaaa cgtccaggcc ttttgcagaa gagatatttt taattgtgga cgaatcaaat    6600
tcagaaactt gatattttc attttttgc tgttcaggga tttgcagcat atcatggcgt      6660
gtaatatggg aaatgccgta tgtttcctta tatggctttt ggttcgtttc tttcgcaaac    6720
gcttgagttg cgcctcctgc cagcagtgcg gtagtaaagg ttaatactgt tgcttgtttt    6780
gcaaactttt tgatgttcat cgttcatgtc tccttttta tgtactgtgt tagcggtctg     6840
cttcttccag ccctcctgtt tgaagatggc aagttagtta cgcacaataa aaaaagacct    6900
aaaatatgta aggggtgacg ccaaagtata cactttgccc tttacacatt ttaggtcttg    6960
cctgctttat cagtaacaaa cccgcgcgat ttacttttcg acctcattct attagactct    7020
cgtttggatt gcaactggtc tattttcctc ttttgtttga tagaaaatca taaaaggatt    7080
tgcagactac gggcctaaag aactaaaaaa tctatctgtt tcttttcatt ctctgtattt    7140
tttatagttt ctgttgcatg ggcataaagt tgccttttta atcacaattc agaaaatatc    7200
ataatatctc atttcactaa ataatagtga acggcaggta tatgtgatgg gttaaaaagg    7260
atcggcggcc gctcgattta aatc                                           7284

<210> SEQ ID NO 19
<211> LENGTH: 5210
<212> TYPE: DNA
<213> ORGANISM: Wolinella succinogenes

<400> SEQUENCE: 19
atgagtgaag cgttaagcgg acgcgggaac gatcgaagaa agttcctaaa gatgtcggct      60
ttagcaggag tcgcaggcgt gagtcaagcg gttggctccg accaaagcaa agtgcttaga    120
cctgcaacaa aacaagagtt aatcgaaaaa tacccagtgt ccaaaaaggt aaaaacgatt    180
tgcacctatt gctcggtcgg atgtggaatt atagcggaag tggtcgatgg tgtatgggta    240
cgccaagagg tcgctcaaga tcaccccatt agtcaagggg gtcactgctg caagggcgcc    300
gatatgattg ataaggctcg aagcgaaaca agacttcgat accccattga aaagttggc     360 ggaaaatggc gtaaaacttc atgggatagc gccatggata agattgccaa gcagcttcag    420
gatctcaccc aaaatatgg ccctgatagc gtcatgttca ttggcggctc caagtgttcg     480
attgaacaat cctattattt tagaaagttt gccgcctttt ttggcaccaa caatctcgat    540
accatcgcac gaatctgcca tgccccaaca gttgctggag tctccaatac ccttggatat    600
ggcggtatga ccaatcactt ggcagacatg atgcactcca aggcgatttt tatcattggt    660
ggaaatcccg cagtgaatca ccctgtaggc atggtgcata tcttgcgcgc taaagaggca    720
ggagcaaaaa tcatcgttgt ggatccccac ttcagtcgaa cagcaactaa agccgatcac    780
tatgtgagat tgcgcaatgg cacggatgtc gccttcatgt atgggatgat tcgccatatt    840
gtaaaaaatg gactagaaga taagaatttt attcgacaac gcctatttgg ctacgaagag    900
attcttaaag agtgcgaaca gtacaccct gaagtggtcg aagaggtcac aggcgtgccc     960
gcccaacaac ttattgagat cacggagatc ttcgctaaag ccaagcctgc ttcactgatc    1020
tgggggatgg gtctcaccca gcacaccaca ggtacaagca cactcgttt ggccccctatt    1080 ttacagatga ttcttggaaa cattggcaaa cgaggtggag gcactaacgt tttacgaggt    1140
catgacaatg tccaaggcgc gacggacatg ggcaacctag ccgacagtct tcctggctat    1200
tatgggttag acaaaaatgc atggaatcac ttctgtggaa tctggaaagt ggatttcgaa    1260
```

```
gcaatgcaaa aacgctttaa gacccctgat atgatgcata aaaaaggttt cagtgtatcc      1320
acatggagat atggggtgac tgaagaggag aacatccccc acaatgcagg cactaaactt      1380
cgatccttga ttgtcgtggg aagcggaatc tctacgatcg cacgcgtgga taccaccaaa      1440
gacgctctag acaagatgga tttagtcgtc ttttttgatc cctatttcaa tgatgcagcc      1500
gccctcacca accgaaaaga taatctctat atccttcctg ccgccacaca gatggagacc      1560
agcggaagag tcgcagcgac gaatcgaagc tatcagtggc gatccatggt tatgaagcca      1620
ctctttgagt gtcgacctga cgaagagatt ctctttgatt tagctaagcg acttggattc      1680
tatgaggagt acactcgctc tttgggggat ggcaaaggaa actttgtatg cccgatgat       1740 gcgactagag aggtggccaa ggctatacga actgtcggct tccaaggcag aactccagaa      1800
cgactcaagg ctcatgcaga aaactggcat atgtttgata agttcaccct cagaggaaag      1860
ggcggccccg tcaaggcga  atactatggt cttccttggc cttgctggag cgaaaagcat      1920
cctggaacac caaatctatg ggatgacagc atccctgtaa tggatggagg tcttggcttt      1980
agggttcgat ggggtgatgt gtcacccaca ggagaaagtt tgttggccag ccaggacagc      2040
tctttgcccg gctcaaaatt caagggcggt catagcatga tcaccgataa aaatgtcgaa      2100
gctatcactg gaatcgccct caccgaagag gaaaaagcca agtggcagg caagacatgg       2160 gcgactgaca ccaccaatat cttggttgaa aaagcactcg ccgcaggtct ctcccctatg      2220
ggtaatggta gagctagagc gattgtttgg gagtggacgg atcagattcc taaacaccgt      2280
gaacccatct acacaattcg acacgatctc attagccaat atccaacctt caagacaag     2340 cccaaccact ttagggcaaa tattcgctat gagagccgcc aaaaagagaa agattggacc      2400
aaagagttcc cgcttaatat gctttctgga cgactagtag cacagtttgg cacaggcaca      2460
gagacaagat cagctcatta cctcgccgag gttcagcctg atgtttgt  ggagattcat       2520 cccgaaacag ccacggattt aggcgtgaag catggtgaca tggtttgggt gcacggcacc      2580 aatgggcaa agattctcgt gaaagcgaga catagctaca aggtcaacaa acaagtgtt        2640 ttcctccccc agaatttcgg aggaatgtat caaggagagt cactggttcc gtatcatatt      2700
gcaggcacag agcctatgt tattggtgaa tcatgcaata ccatcacaag tgatgcatac       2760
gacatcaaca ccagtactcc tgaaaccaag tgcggcctct gccgcatcga aaaagcgtag      2820
ggggtgaagc atggaaagtc aagctagagt caagttctat tgtgatgagg ctagatgtat      2880
tgattgtcat ggatgtgatg tggcttgtaa agaggcccat caccttcctg tgggagtcaa      2940
ccgaagaaga gtggtgaccc tcaatgaagg tcttgtaggc aaagagaaat ccctctctat      3000
tgcctgcatg cactgctctg atgccccttg tgctcaggtc tgcccagtgg actgcttcta      3060
tgttcgagcc gatgggattg tattgcatga caaagagaag tgcattggat gcggttactg      3120
cctctatgcc tgcccctttg gtgctcctca attccccaag agtggaatct ttggttcaag      3180
aggacctatg gataagtgca ccttctgtgc tggaggtcct gaagagactc acagcgagaa      3240
ggagtataag ctctatggac agaatcgtat cgctgagggc aaagtccctg tatgtgcagc      3300
gatgtgctcc accaaggcac tcctagcagg agattctgat agcatctcgc tcatcattcg      3360
tgagagagtg ctcaagcgag gcagtggaac agccagtgtt ccttacacct ggtcacaagc      3420
ctacaaggat taagaatgaa aaagcctcta ttgcccctcc tctcccttct gggagccttg      3480
ggggcacaag cttctgagaa tctcaaggag cccttggatt tcagctacaa cacccaaatc      3540
tatgaaaagc ccatgattga ggcaatcccc acttggggaa gtgagggat tctaggtctt       3600 ggagagattg gaggaatagg aggattagga gagctcttca ccttcttgca aagtggttac      3660
```

```
tttgctctta tcttcctagc gatcatcatc gctatccctt tggtcttcct aggtcactat   3720
atggtgattg gacccaagcg attctctcat gaggggaaga agatcaaggt ctttaacacc   3780
ttcaacatca tggtgcactg gattgcaggg attcccttg tgcttctttg catcacagga    3840
cttctgatgg tctttggaga tgccctaggg ggtggagctt ttattcgatt cgctagagat   3900
gtgcatggat tagccacgat catctttgcg atctttggtc ccctcatgtt catcatgtgg   3960
gtgaagcacg ctctctttaa gatgtatgac atcgactgga tgctcattct tggagggtat   4020
ctaagcaagg tgaagagacc tattcctgca ggcaaattca atgcgggtca agatgtgg    4080
ttctgggtct gcacgatggg aggattcttc atggtctata gtggctatgt gatgttcttc   4140
caagagggca atattgagac cctaagactc atggcgatct gcacaatgt agtggggttt    4200
gctgtggtgg ctctccttat gactcacatc tatatggcag cctttgcgat tgagggtgca   4260
ttgcactcca tcctagatgg tcatatgggt gaagaggagg tagcgattct tcatagtttc   4320
tactataaag agttgcaggc ggaggggaaa gtatgagaca caccgataga tttgttaaaa   4380
aggtggtgat tgaacgaatc ggcgatcaga gagtgctcgc cgaggaggaa gatgtggtga   4440
tcaaagagga gagaatctct ctctatctta tggcaccaa gcttatgtcc atgatgtctc    4500
ttccttccga tcaagatgct catgcggtgg gcttcttgat gagtgagggg gtgattgaga   4560
agatcgaaga cttaaagagt gttcaaatct cttctgatgg gagctctgtc tatgtagagg   4620
ctctcatcaa ccatgagaac atcaccaatc tcttcaaaga gaagacactc acttcaggtt   4680
gttgtgtcgg agtgacgggg aatcttgaag gcaatgtcct aagaaagttc atcgctactc   4740
ccatgcagat ttctttggag agaatctggg aagggatgga agagtttgag atgagcagcc   4800
atctctttca tgagacaggc tgcgttcata aagcctccct tctcttagaa gatggaagca   4860
agatcacggc tgaggatatt ggtcgtcata atgcaattga aaggtgatg ggtaaagcca    4920
ggctagggag aatagataca gagaaggctg tgctagtggt gagcggaaga ctctccatgg   4980
agatggtggt taaagctgtc atgcacaaca ttcccatgat tgtctctagg gcagcagcaa   5040
cctttcttgg aatcaagaca gcccaagagc taggggtgac tctagtgggc tttgctagag   5100
gggagaagat gaatatctac acccattctg gtcgagtgga cttgagggct tgcaagagga   5160
aaagagggt gactcttcac gctccaaatc aatctagctc tcttcttcgt              5210
```

<210> SEQ ID NO 20
<211> LENGTH: 13415
<212> TYPE: DNA
<213> ORGANISM: Wolinella succinogenes

<400> SEQUENCE: 20

```
tcgaggggg gcccggatcc ccagtagatt tacgtttaaa cattttatt tccttttaa      60
tttaattta ttaacagttg gtgctatgac actttacctc atagctggca taattcgcaa   120
tactctgggt cttcgagagg tatccaacct gagttgaaat actttaccat cgatttagca   180
gttgtatcag ttatatttat attacccttta actcttcgcc atccaggagt tttaccgtac  240
agattagagg ataataataa cacataattc tcgtaagcaa tatgagataa tttccaagac   300
tctatattag ctcgtgatgt tttccaaggt ctaaaatcgt cacggttcat ataattagcc   360
aatctcatat gctctctaac ttccgatgat aagctgtcaa acatgagaat taacgatctg   420
atagagaagg gtttgctcgg gtcggtggct ctggtaacga ccagtatccc gatcccggct   480
ggccgtcctg gccgccacat gaggcatgtt ccgcgtcctt gcaatactgt gtttacatac   540
```

-continued

| | |
|---|---|
| agtctatcgc ttagcggaaa gttcttttac cctcagccga aatgcctgcc gttgctagac | 600 |
| attgccagcc agtgcccgtc actcccgtac taactgtcac gaaccctgc aataactgtc | 660 |
| acgccccct gcaataactg tcacgaaccc ctgcaataac tgtcacgccc ccaaacctgc | 720 |
| aaacccagca ggggcggggg ctggcggggt gttggaaaaa tccatccatg attatctaag | 780 |
| aataatccac taggcgcggt tatcagcgcc cttgtggggc gctgctgccc ttgcccaata | 840 |
| tgcccggcca gaggccggat agctggtcta ttcgctgcgc taggctacac accgccccac | 900 |
| cgctgcgcgg caggggaaa gcgggcaaa gcccgctaaa ccccacacca aaccccgcag | 960 |
| aaatacgctg ggagcgcttt tagccgcttt agcggccttt cccctaccc gaagggtggg | 1020 |
| ggcgcgtgtg cagccccgca gggcctgtct cggtcgatca ttcagcccgg ctcatccttc | 1080 |
| tggcgtggcg gcagaccgaa caaggcgcgg tcgtggtcgc gttcaaggta cgcatccatt | 1140 |
| gccgccatga gccgatcctc cggccactcg ctgctgttca ccttggccaa aatcatggcc | 1200 |
| cccaccagca ccttgcgcct tgtttcgttc ttgcgctatt gctgctgttc ccttgcccgc | 1260 |
| acccgctgaa tttcggcatt gattcgcgct cgttgttctt cgagcttggc cagccgatcc | 1320 |
| gccgccttgt tgctccccctt aaccatcttg acaccccatt gttaatgtgc tgtctcgtag | 1380 |
| gctatcatgg aggcacagcg gcggcaatcc cgaccctact ttgtagggga gggccattgc | 1440 |
| atggagccga aaagcaaaag caacagcgag gcagcatggc gatttatcac cttacggcga | 1500 |
| aaaccggcag caggtcgggc ggccaatcgg ccagggccaa ggccgactac atccagcgcg | 1560 |
| aaggcaagta tgcccgcgac atggatgaag tcttgcacgc cgaatccggg cacatgccgg | 1620 |
| agttcgtcga gcggcccgcc gactactggg atgctgccga cctgtatgaa cgcgccaatg | 1680 |
| ggcggctgtt caaggaggtc gaatttgccc tgccggtcga gctgaccctc gaccagcaga | 1740 |
| aggcgctggc gtccgagttc gcccagcacc tgaccggtgc cgagcgcctg ccgtatacgc | 1800 |
| tggccatcca tgccggtggc ggcgagaacc cgcactgcca cctgatgatc tccgagcgga | 1860 |
| tcaatgacgg catcgagcgg cccgccgctc agtggttcaa gcggtacaac ggcaagaccc | 1920 |
| cggagaaggg cggggcacag aagaccgaag cgctcaagcc caaggcatgg cttgagcaga | 1980 |
| cccgcgaggc atgggccgac catgccaacc gggcattaga gcgggctggc cacgacgccc | 2040 |
| gcattgacca cagaacactt gaggcgcagg gcatcgagcg cctgcccggt gttcacctgg | 2100 |
| ggccgaacgt ggtggagatg gaaggccggg gcatccgcac cgaccgggca gacgtggccc | 2160 |
| tgaacatcga caccgccaac gcccagatca tcgacttaca ggaataccgg gaggcaatag | 2220 |
| accatgaacg caatcgacag agtgaagaaa tccagaggca tcaacgagtt agcggagcag | 2280 |
| atcgaaccgc tggcccagag catggcgaca ctggccgacg aagcccggca ggtcatgagc | 2340 |
| cagacccagc aggccagcga ggcgcaggcg cggagtggc tgaaagccca cgccagaca | 2400 |
| ggggcggcat gggtggagct ggccaaagag ttgcgggagg tagccgccga ggtgagcagc | 2460 |
| gccgcgcaga gcgcccggag cgcgtcgcgg gggtggcact ggaagctatg ctaaccgtg | 2520 |
| atgctggctt ccatgatgcc tacgtggtg ctgctgatcg catcgttgct cttgctcgac | 2580 |
| ctgacgccac tgacaaccga ggacggctcg atctggctgc gcttggtggc ccgatgaaga | 2640 |
| acgacaggac tttgcaggcc ataggccgac agctcaaggc catgggctgt gagcgcttcg | 2700 |
| atatcggcgt cagggacgcc accaccggcc agatgatgaa ccgggaatgg tcagccgccg | 2760 |
| aagtgctcca gaacacgcca tggctcaagc ggatgaatgc ccagggcaat gacgtgtata | 2820 |
| tcaggcccgc cgagcaggag cggcatggtc tggtgctggt ggacgacctc agcgagtttg | 2880 |
| acctggatga catgaaagcc gagggccggg agcctgccct ggtagtggaa accagcccga | 2940 |

```
agaactatca ggcatgggtc aaggtggccg acgccgcagg cggtgaactt cgggggcaga    3000
ttgcccggac gctggccagc gagtacgacg ccgacccggc cagcgccgac agccgccact    3060
atggccgctt ggcgggcttc accaaccgca aggacaagca caccacccgc gccggttatc    3120
agccgtgggt gctgctgcgt gaatccaagg gcaagaccgc caccgctggc ccggcgctgg    3180
tgcagcaggc tggccagcag atcgagcagg cccagcggca gcaggagaag gcccgcaggc    3240
tggccagcct cgaactgccc gagcggcagc ttagccgcca ccggcgcacg cgctggacg     3300
agtaccgcag cgagatggcc gggctggtca agcgcttcgg tgatgacctc agcaagtgcg    3360
actttatcgc cgcgcagaag ctggccagcc ggggccgcag tgccgaggaa atcggcaagg    3420
ccatggccga ggccagccca cgcctggcag agcgcaagcc cggccacgaa gcggattaca    3480
tcgagcgcac cgtcagcaag gtcatgggtc tgcccagcgt ccagcttgcg cgggccgagc    3540
tggcacgggc accggcaccc cgccagcgag gcatggacag gggcggggcca gatttcagca    3600
tgtagtgctt gcgttggtac tcacgcctgt tatactatga gtactcacgc acagaagggg    3660
gttttatgga atacgaaaaa agcgcttcag ggtcggtcta cctgatcaaa agtgacaagg    3720
gctattggtt gcccggtggc tttggttata cgtcaaacaa ggccgaggct ggccgctttt    3780
cagtcgctga tatggccagc cttaaccttg acggctgcac cttgtccttg ttccgcgaag    3840
acaagccttt cggccccggc aagtttctcg gtgactgata tgaaagacca aaaggacaag    3900
cagaccggcg acctgctggc cagccctgac gctgtacgcc aagcgcgata tgccgagcgc    3960
atgaaggcca aagggatgcg tcagcgcaag ttctggctga ccgacgacga atacgaggcg    4020
ctgcgcgagt gcctggaaga actcagagcg cgcagggcg ggggtagtga ccccgccagc     4080
gcctaaccac caactgcctg caaaggaggc aatcaatggc tacccataag cctatcaata    4140
ttctggaggc gttcgcagca gcgccgccac cgctggacta cgttttgccc aacatggtgg    4200
ccggtacggt cggggcgctg gtgtcgcccg gtggtgccgg taaatccatg ctggccctgc    4260
aactggccgc acagattgca ggcgggccgg atctgctgga ggtgggcgaa ctgcccaccg    4320
gcccggtgat ctacctgccc gccgaagacc cgcccaccgc cattcatcac cgcctgcacg    4380
cccttggggc gcacctcagc gccgaggaac ggcaagccgt ggctgacggc ctgctgatcc    4440
agccgctgat cggcagcctg cccaacatca tggccccgga gtggttcgac ggcctcaagc    4500
gcgccgccga gggccgccgc ctgatggtgc tggacacgct cgccggttc  cacatcgagg    4560
aagaaaacgc cagcggcccc atggcccagg tcatcggtcg catggaggcc atcgccgccg    4620
ataccgggtg ctctatcgtg ttcctgcacc atgccagcaa gggcgcggcc atgatgggcg    4680
caggcgacca gcagcaggcc agccggggca gctcggtact ggtcgataac atccgctggc    4740
agtcctacct gtcgagcatg accagcgccg aggccgagga tggggtgtg gacgacgacc     4800
agcgccggtt cttcgtccgc ttcggtgtga gcaaggccaa ctatggcgca ccgttcgctg    4860
atcggtggtt caggcggcat gacgcgggg tgctcaagcc cgccgtgctg agagaggcagc     4920
gcaagagcaa gggggtgccc cgtggtgaag cctaagaaca agcacagcct cagccacgtc    4980
cggcacgacc cggcgcactg tctggccccc ggcctgttcc gtgccctcaa gcggggcgag    5040
cgcaagcgca gcaagctgga cgtgacgtat gactacggcg acggcaagcg gatcgagttc    5100
agcggcccgg agccgctggg cgctgatgat ctgcgcatcc tgcaagggct ggtggccatg    5160
gctgggccta atggcctagt gcttggcccg gaacccaaga ccgaaggcgg acggcagctc    5220
cggctgttcc tggaacccaa gtgggaggcc gtcaccgctg atgccatggt ggtcaaaggt    5280
```

```
agctatcggg cgctggcaaa ggaaatcggg gcagaggtcg atagtggtgg ggcgctcaag   5340
cacatacagg actgcatcga gcgcctttgg aaggtatcca tcatcgccca gaatggccgc   5400
aagcggcagg ggtttcggct gctgtcggag tacgccagcg acgaggcgga cgggcgcctg   5460
tacgtggccc tgaacccctt gatcgcgcag gccgtcatgg gtggcggcca gcatgtgcgc   5520
atcagcatgg acgaggtgcg ggcgctggac agcgaaaccg cccgcctgct gcaccagcgg   5580
ctgtgtggct ggatcgaccc cggcaaaacc ggcaaggctt ccatagatac cttgtgcggc   5640
tatgtctggc cgtcagaggc cagtggttcg accatgcgca agcgccgcca gcgggtgcgc   5700
gaggcgttgc cggagctggt cgcgctgggc tggacggtaa ccgagttcgc ggcgggcaag   5760
tacgacatca cccggcccaa ggcggcaggc tgacccccccc cactctattg taaacaagac   5820
attttttatc ttttatattc aatggcttat tttcctgcta attggtaata ccatgaaaaa   5880
taccatgctc agaaaaggct taacaatatt ttgaaaaatt gcctactgag cgctgccgca   5940
cagctccata ggccgctttc ctggctttgc ttccagatgt atgctctcct ccggagagta   6000
ccgtgacttt attttcggca caaatacagg ggtcgatgga taaatacggc gatagtttcc   6060
tgacggatga tccgtatgta ccggcggaag acaagctgca aacctgtcag atggagattg   6120
atttaatggc ggatgtgctg agagcaccgc cccgtgaatc cgcagaactg atccgctatg   6180
tgtttgcgga tgattggccg gaataaaataa agccgggctt aatacagatt aagcccgtat   6240
agggtattat tactgaatac caaacagctt acggaggacg gaatgttacc cattgagaca   6300
accagactgc cttctgatta ttaatatttt tcactattaa tcagaaggaa taaccatgaa   6360
ttttacccgg attgacctga atacctggaa tcgcagggaa cactttgccc tttatcgtca   6420
gcagattaaa tgcggattca gcctgaccac caaactcgat attaccgctt gcgtaccgc   6480 actggcggag acaggttata agttttatcc gctgatgatt tacctgatct cccgggctgt   6540
taatcagttt ccggagttcc ggatggcact gaaagacaat gaacttattt actgggacca   6600
gtcagacccg gtctttactg tcttcataa agaaaccgaa acattctctg cactgtcctg   6660
ccgttatttt ccggatctca gtgagtttat ggcaggttat aatgcggtaa cggcagaata   6720
tcagcatgat accagattgt ttccgcaggg aaatttaccg gagaatcacc tgaatatatc   6780
atcattaccg tgggtgagtt ttgacgggat ttaacctgaa catcaccgga aatgatgatt   6840
attttgcccc ggttttttacg atggcaaagt ttcagcagga aggtgaccgc gtattattac   6900
ctgtttctgt acaggttcat catgcagtct gtgatggctt tcatgcagca cggtttatta   6960
atacacttca gctgatgtgt gataacatac tgaaataaat taattaattc tgtatttaag   7020
ccaccgtatc cggcaggaat ggtggctttt tttttatatt ttaaccgtaa tctgtaattt   7080
cgtttcagac tggttcagga tcactgtacg ataatgcccc cgcagtttgg taatacccct   7140
aataaaaaag aaacagcaaa gactgacagc aataataata agtaagcag taacaataat   7200 attaacaaca ccagatgcag ttataataat agtatttaag acaccagaaa gactgctgcg   7260
acagtcattt tgaacaacac caaaatgccg taaaggcagt agtaacaaca ccagtgaaaa   7320
catcacgata gcatagtgat atgcctgagt gtgtgtaatt aaacaataaa taaaccgcca   7380
tatataacag aagatagtat tctgaatggc atgcttttct gttcagtata acatatcat    7440 cccggttggt ataaggatga tatataataa gttaagctga acacatattt attttggttt   7500
tattttacaa ataaagtaag acgatccgtt aagtcaaagc ggggtatatt tattataccc   7560 tgcttttta tttgtccgcc gggcgcggat aatggatcag attatgcagt gtcacaatgg   7620
ccttaccggg attggcgtaa gcgtgcggga tatccgcatg gaagcgcagg gattccccgg   7680
```

```
cagaaacggt gtgccactca tcccccagcc gcagttgtaa tgcgccttcc agtacaatga    7740
catgttctct ggttctgaaa tccatccctg tcggtgttgc ttatgcagtc tggtcgggac    7800
tcggcgtcgt cataattaca gccattgcct ggttgcttca tgggcaaaag ctttatgctt    7860 gtaaccgtt  ttgtgaaaaa attttaaaa  taaaaaggg  gacctctagg  gtccccaatt    7920
aattagtaat ataatctatt aaaggtcatt caaaggtca  tccaccggat cccaccgcgg    7980
tggcggccgt ctaacgaaga agagagctag attgatttgg agcgtgaaga gtcaccctc    8040 ttttcctctt gcaagccctc aagtccactc gaccagaatg ggtgtagata ttcatcttct    8100
cccctctagc aaagcccact agagtcaccc ctagctcttg ggctgtcttg attccaagaa    8160
aggttgctgc tgccctagag acaatcatgg gaatgttgtg catgacagct ttaaccacca    8220
tctccatgga gagtcttccg ctcaccacta gcacagcctt ctctgtatct attctcccta    8280
gcctggcttt acccatcacc ttatcaattg cattatgacg accaatatcc tcagccgtga    8340
tcttgcttcc atcttctaag agaagggagg ctttatgaac gcagcctgtc tcatgaaaga    8400
gatggctgct catctcaaac tcttccatcc cttcccagat tctctccaaa gaaatctgca    8460
tgggagtagc gatgaacttt cttaggacat tgccttcaag attccccgtc actccgacac    8520
aacaacctga agtgagtgtc ttctctttga agagattggt gatgttctca tggttgatga    8580
gagcctctac atagacagag ctcccatcag aagagatttg aacactcttt aagtcttcga    8640
tcttctcaat caccccctca ctcatcaaga agcccaccgc atgagcatct tgatcggaag    8700
gaagagacat catggacata agcttggtgc cattaagata gagagagatt ctctcctctt    8760
tgatcaccac atcttcctcc tcggcgagca ctctctgatc gccgattcgt tcaatcacca    8820
cctttttaac aaatctatcg gtgtgtctca tactttcccc tccgcctgca actctttata    8880
gtagaaacta tgaagaatcg ctacctcctc ttcacccata tgaccatcta ggatggagtg    8940
caatgcaccc tcaatcgcaa aggctgccat atagatgtga gtcataagga gagccaccac    9000
agcaaacccc actacattgt gcaagatcgc catgagtctt agggtctcaa tattgccctc    9060
ttggaagaac atcacatagc cactatagac catgaagaat cctcccatcg tgcagaccca    9120
gaaccacatc ttctgacccg cattgaattt gcctgcagga ataggtctct tcaccttgct    9180 tagatacct  ccaagaatga gcatccagtc gatgtcatac atcttaaaga gagcgtgctt    9240
cacccacatg atgaacatga ggggaccaaa gatcgcaaag atgatcgtgg ctaatccatg    9300
cacatctcta gcgaatcgaa taaaagctcc acccctagg  gcatctccaa agaccatcag    9360
aagtcctgtg atgcaaagaa gcacaaaggg aatccctgca atccagtgca ccatgatgtt    9420
gaaggtgtta aagaccttga tcttcttccc ctcatgagag aatcgcttgg gtccaatcac    9480
catatagtga cctaggaaga ccaaagggat agcgatgatg atcgctagga agataagagc    9540
aaagtaacca ctttgcaaga aggtgaagag ctctcctaat cctcctattc ctccaatctc    9600
tccaagacct agaatccctc cacttcccca agtggggatt gcctcaatca tgggctttcc    9660
atagatttgg gtgttgtagc tgaaatccaa gggctccttg agattctcag aagcttgtgc    9720
ccccaaggct cccagaaggg agaggagggg caatagaggc ttttcattc  ttaatccttg    9780 taggcttgtg accaggtgta aggaacactg gctgttccac tgcctcgctt gagcactctc    9840
tcacgaatga tgagcgagat gctatcagaa tctcctgcta ggagtgcctt ggtggagcac    9900
atcgctgcac atacagggac tttgccctca gcgatacgat tctgtccata gagcttatac    9960
tccttctcgc tgtgagtctc ttcaggacct ccagcacaga aggtgcactt atccataggt   10020
```

```
cctcttgaac caaagattcc actcttgggg aattgaggag caccaaaggg gcaggcatag   10080
aggcagtaac cgcatccaat gcacttctct ttgtcatgca atacaatccc atcggctcga   10140
acatagaagc agtccactgg gcagacctga gcacaagggg catcagagca gtgcatgcag   10200
gcaatagaga gggatttctc tttgcctaca agaccttcat tgagggtcac cactcttctt   10260
cggttgactc ccacaggaag gtgatgggcc tctttacaag ccacatcaca tccatgacaa   10320
tcaatacatc tagcctcatc acaatagaac ttgactctag cttgactttc catgcttcac   10380
cccctacgct ttttcgatgc ggcagaggcc gcacttggtt tcaggagtac tggtgttgat   10440
gtcgtatgca tcacttgtga tggtattgca tgattcacca ataacataag gctctgtgcc   10500
tgcaatatga tacggaacca gtgactctcc ttgatacatt cctccgaaat tctgggggag   10560
gaaaacactt gttttgttga ccttgtagct atgtctcgct ttcacgagaa tctttgcccc   10620
attggtgccg tgcacccaaa ccatgtcacc atgcttcacg cctaaatccg tggctgtttc   10680
gggatgaatc tccacaaaca tctcaggctg aacctcggcg aggtaatgag ctgatcttgt   10740
ctctgtgcct gtgccaaact gtgctactag tcgtccagaa agcatattaa gcgggaactc   10800
tttggtccaa tctttctctt tttggcggct ctcatagcga atatttgccc taaagtggtt   10860
gggcttgtct ttgaaggttg gatattggct aatgagatcg tgtcgaattg tgtagatggg   10920
ttcacggtgt ttaggaatct gatccgtcca ctcccaaaca atcgctctag ctctaccatt   10980
acccataggg gagagacctg cggcgagtgc ttttcaacc aagatattgg tggtgtcagt   11040
cgcccatgtc ttgcctgcca ctttggcttt ttcctcttcg gtgagggcga ttccagtgat   11100
agcttcgaca ttttttatcgg tgatcatgct atgaccgccc ttgaattttg agccgggcaa   11160
agagctgtcc tggctggcca acaaactttc tcctgtgggt gacacatcac cccatcgaac   11220
cctaaagcca agacctccat ccattacagg gatgctgtca tcccatagat ttggtgttcc   11280
aggatgcttt tcgctccagc aaggccaagg aagaccatag tattcgcctt tgacggggcc   11340
gccctttcct ctgagggtga acttatcaaa catatgccag ttttctgcat gagccttgag   11400
tcgttctgga gttctgcctt ggaagccgac agttcgtata gccttggcca cctctctagt   11460
cgcatcatcg ggcctacaaa agtttccttt gccatccccc aaagagcgag tgtactcctc   11520
atagaatcca agtcgcttag ctaaatcaaa gagaatctct tcgtcaggtc gacactcaaa   11580
gagtggcttc ataaccatgg atcgccactg atagcttcga ttcgtcgctg cgactcttcc   11640
gctggtctcc atctgtgtgg cggcaggaag gatatagaga ttatcttttc ggttggtgag   11700
ggcggctgca tcattgaaat agggatcaaa aaagacgact aaatccatct tgtctagagc   11760
gtctttggtg gtatccacgc gtgcgatcgt agagattccg cttcccacga caatcaagga   11820
tcgaagttta gtgcctgcat tgtgggggat gttctcctct tcagtcaccc catatctcca   11880
tgtggataca ctgaaacctt ttttatgcat catatcaggg gtcttaaagc gttttttgcat   11940 tgcttcgaaa tccactttcc agattccaca gaagtgattc catgcatttt tgtctaaccc   12000
ataatagcca ggaagactgt cggctaggtt gcccatgtcc gtcgcgcctt ggacattgtc   12060
atgacctcgt aaaacgttag tgcctccacc tcgtttgcca atgtttccaa gaatcatctg   12120
taaaataggg gccaaacgag tgttgcttgt acctgtggtg tgctgggtga gacccatccc   12180
ccagatcagt gaagcaggct tggctttagc gaagatctcc gtgatctcaa taagttgttg   12240
ggcgggcacg cctgtgacct cttcgaccac ttcaggggtg tactgttcgc actctttaag   12300
aatctcttcg tagccaaata ggcgttgtcg aataaattct ttatcttcta gtccattttt   12360
tacaatatgg cgaatcatcc catacatgaa ggcgacatcc gtgccattgc gcaatctcac   12420
```

-continued

```
atagtgatcg gctttagttg ctgttcgact gaagtgggga tccacaacga tgattttgc    12480 tcctgcctct ttagcgcgca agatatgcac catgcctaca gggtgattca ctgcgggatt    12540
tccaccaatg ataaaaatcg ccttggagtg catcatgtct gccaagtgat tggtcatacc    12600
gccatatcca agggtattgg agactccagc aactgttggg gcatggcaga ttcgtgcgat    12660
ggtatcgaga ttgttggtgc caaaaaggc ggcaaacttt ctaaaataat aggattgttc     12720
aatcgaacac ttggagccgc caatgaacat gacgctatca gggccatatt tttgggtgag    12780
atcctgaagc tgcttggcaa tcttatccat ggcgctatcc catgaagttt tacgccattt    12840
tccgccaact ttctcaatgg ggtatcgaag tcttgtttcg cttcgagcct tatcaatcat    12900
atcggcgccc ttgcagcagt gacccccttg actaatgggg tgatcttgag cgacctcttg    12960
gcgtacccat acaccatcga ccacttccgc tataattcca catccgaccg agcaataggt    13020
gcaaatcgtt tttaccttttt tggacactgg gtattttcg attaactctt gttttgttgc    13080
aggtctaagc actttgcttt ggtcggagcc aaccgcttga ctcacgcctg cgactcctgc    13140
taaagccgac atctttagga actttcttcg atcgttcccg cgtccgctta acgcttcact    13200
catacatcac ctcataaaat aaattaaaaa ataataaaaa ctaatgtttc gcattatagg    13260
acaaaagata cctaaaaaat gttatctaga tcaaattatt ggaaaatata tgaaaataat    13320
ttttgtttaa aaagcgaacg acattagtat ttttcataaa aatacgtaca ttgttatccg    13380
tcgctattta ggtaccgggc ccgacgtcag gcctc                               13415
```

<210> SEQ ID NO 21
<211> LENGTH: 1026
<212> TYPE: DNA
<213> ORGANISM: Pasteurella DSM 18541

<400> SEQUENCE: 21

```
ttgacaaaat cagtatgttt aaataaggag ctaactatga agttgccgt ttacagtact     60 aaaaattatg atcgcaaaca tctggatttg gcgaataaaa aatttaattt tgagcttcat    120
ttctttgatt ttttacttga tgaacaaacc gcgaaaatgg cggagggcgc cgatgccgtc    180 tgtatttttcg tcaatgatga tgcgagccgc ccggtgttaa caaagttggc gcaaatcgga    240
gtgaaaatta tcgctttacg ttgtgccggt tttaataatg tggatttgga ggcggcaaaa    300
gagctgggat taaaagtcgt acgggtgcct gcgtattcgc cggaagccgt tgccgagcat    360
gcgatcggat taatgctgac tttaaaccgc cgtatccata aggcttatca gcgtacccgc    420
gatgcgaatt tttctctgga aggattggtc ggttttaata tgttcggcaa aaccgccgga    480
gtgattggta cgggaaaaat cggcttggcg gctattcgca ttttaaaagg cttcggtatg    540
gacgttctgg cgtttgatcc ttttaaaaat ccggcggcgg aagcgttggg cgcaaaatat    600
gtcggtttag acgagcttta tgcaaaatcc catgttatca ctttgcattg cccggctacg    660
gcggataatt atcatttatt aaatgaagcg cttttaata aaatgcgcga cggtgtaatg    720
attattaata ccagccgcgg cgttttaatt gacagccggg cggcaatcga agcgttaaaa    780
cggcagaaaa tcggcgctct cggtatggat gtttatgaaa atgaacggga ttttgtttttc    840 gaggataaat ctaacgatgt tattacggat gatgtattcc gtcgcctttc ttcctgtcat    900 aatgtgctt tttaccggtca tcaggcgttt ttaacggaag aagcgctgaa taatatcgcc    960
gatgtgactt tatcgaatat tcaggcggtt tccaaaaatg caacgtgcga aaatagcgtt    1020
gaaggc                                                              1026
```

<210> SEQ ID NO 22
<211> LENGTH: 342
<212> TYPE: PRT
<213> ORGANISM: Pasteurella DSM 18541

<400> SEQUENCE: 22

```
Met Thr Lys Ser Val Cys Leu Asn Lys Glu Leu Thr Met Lys Val Ala
1               5                   10                  15

Val Tyr Ser Thr Lys Asn Tyr Asp Arg Lys His Leu Asp Leu Ala Asn
            20                  25                  30

Lys Lys Phe Asn Phe Glu Leu His Phe Phe Asp Phe Leu Leu Asp Glu
        35                  40                  45

Gln Thr Ala Lys Met Ala Glu Gly Ala Asp Ala Val Cys Ile Phe Val
    50                  55                  60

Asn Asp Asp Ala Ser Arg Pro Val Leu Thr Lys Leu Ala Gln Ile Gly
65                  70                  75                  80

Val Lys Ile Ile Ala Leu Arg Cys Ala Gly Phe Asn Asn Val Asp Leu
                85                  90                  95

Glu Ala Ala Lys Glu Leu Gly Leu Lys Val Arg Val Pro Ala Tyr
            100                 105                 110

Ser Pro Glu Ala Val Ala Glu His Ala Ile Gly Leu Met Leu Thr Leu
        115                 120                 125

Asn Arg Arg Ile His Lys Ala Tyr Gln Arg Thr Arg Asp Ala Asn Phe
    130                 135                 140

Ser Leu Glu Gly Leu Val Gly Phe Asn Met Phe Gly Lys Thr Ala Gly
145                 150                 155                 160

Val Ile Gly Thr Gly Lys Ile Gly Leu Ala Ala Ile Arg Ile Leu Lys
                165                 170                 175

Gly Phe Gly Met Asp Val Leu Ala Phe Asp Pro Phe Lys Asn Pro Ala
            180                 185                 190

Ala Glu Ala Leu Gly Ala Lys Tyr Val Gly Leu Asp Glu Leu Tyr Ala
        195                 200                 205

Lys Ser His Val Ile Thr Leu His Cys Pro Ala Thr Ala Asp Asn Tyr
    210                 215                 220

His Leu Leu Asn Glu Ala Ala Phe Asn Lys Met Arg Asp Gly Val Met
225                 230                 235                 240

Ile Ile Asn Thr Ser Arg Gly Val Leu Ile Asp Ser Arg Ala Ala Ile
                245                 250                 255

Glu Ala Leu Lys Arg Gln Lys Ile Gly Ala Leu Gly Met Asp Val Tyr
            260                 265                 270

Glu Asn Glu Arg Asp Leu Phe Phe Glu Asp Lys Ser Asn Asp Val Ile
        275                 280                 285

Thr Asp Asp Val Phe Arg Arg Leu Ser Ser Cys His Asn Val Leu Phe
    290                 295                 300

Thr Gly His Gln Ala Phe Leu Thr Glu Glu Ala Leu Asn Asn Ile Ala
305                 310                 315                 320

Asp Val Thr Leu Ser Asn Ile Gln Ala Val Ser Lys Asn Ala Thr Cys
                325                 330                 335

Glu Asn Ser Val Glu Gly
            340
```

<210> SEQ ID NO 23
<211> LENGTH: 2310
<212> TYPE: DNA
<213> ORGANISM: Pasteurella DSM 18541

<400> SEQUENCE: 23

```
atggctgaat taacagaagc tcaaaaaaaa gcatgggaag gattcgttcc cggtgaatgg      60
caaaacggcg taaatttacg tgactttatc caaaaaaact atactccgta tgaaggtgac     120
gaatcattct tagctgatgc gactcctgca accagcgagt tgtggaacag cgtgatggaa     180
ggcatcaaaa tcgaaaacaa aactcacgca cctttagatt tcgacgaaca tactccgtca     240
actatcactt ctcacaagcc tggttatatc aataaagatt tagaaaaaat cgttggtctt     300
caaacagacg ctccgttaaa acgtgcaatt atgccgtacg gcggtatcaa aatgatcaaa     360
ggttcttgcg aagtttacgg tcgtaaatta gatccgcaag tagaatttat tttcaccgaa     420
tatcgtaaaa cccataacca aggcgtattc gacgtttata cgccggatat tttacgctgc     480
cgtaaatcag gcgtgttaac cggtttaccg gatgcttacg gtcgtggtcg tattatcggt     540
gactaccgtc gtttagcggt atacggtatt gattacctga tgaaagataa aaaagcccaa     600
ttcgattcat tacaaccgcg tttggaagcg ggcgaagaca ttcaggcaac tatccaatta     660
cgtgaagaaa ttgccgaaca cacccgcgct ttaggcaaaa tcaaagaaat ggcggcatct     720
tacggttacg acatttccgg ccctgcgaca aacgcacagg aagcaatcca atggacatat     780
tttgcttatc tggcagcggt taaatcacaa aacggtgcgg caatgtcatt cggtcgtacg     840
tctacattct tagatatcta tatcgaacgt gacttaaaac gcggtttaat cactgaacaa     900
caggcgcagg aattaatgga ccacttagta atgaaattac gtatggttcg tttcttacgt     960
acgccggaat acgatcaatt attctcaggc gacccgatgt gggcaaccga aactatcgcc    1020
ggtatgggct tagacggtcg tccgttggta actaaaaaca gcttccgcgt attacatact    1080
ttatacacta tgggtacttc tccggaacca aacttaacta ttctttggtc cgaacaatta    1140
cctgaagcgt tcaaacgttt ctgtgcgaaa gtatctattg atacttcctc cgtacaatac    1200
gaaaatgatg acttaatgcg tcctgacttc aacaacgatg actatgcaat cgcatgctgc    1260
gtatcaccga tggtcgtagg taaacaaatg caattcttcg gtgcgcgcgc aaacttagct    1320
aaaactatgt tatacgcaat taacggcggt atcgatgaga aaaatggtat gcaagtcggt    1380
cctaaaactg cgccgattac agacgaagta ttgaatttcg ataccgtaat cgaacgtatg    1440
gacagtttca tggactggtt ggcgactcaa tatgtaaccg cattgaacat catccacttc    1500
atgcacgata aatatgcata tgaagcggca ttgatggcgt tccacgatcg cgacgtattc    1560
cgtacaatgg cttgcggtat cgcgggtctt tccgtggctg cggactcatt atccgcaatc    1620
aaatatgcga aagttaaacc gattcgcggc gacatcaaag ataaagacgg taatgtcgtg    1680
gcctcgaatg ttgctatcga cttcgaaatt gaaggcgaat atccgcaatt cggtaacaat    1740
gatccgcgtg ttgatgattt agcggtagac ttagttgaac gtttcatgaa aaaagttcaa    1800
aaacacaaaa cttaccgcaa cgcaactccg acacaatcta tcctgactat cacttctaac    1860
gtggtatacg gtaagaaaac cggtaatact ccggacggtc gtcgagcagg cgcgccattc    1920
ggaccgggtg caaacccaat gcacggtcgt gaccaaaaag gtgcggttgc ttcacttact    1980
tctgtggcta aacttccgtt cgcttacgcg aaagacggta tttcatatac cttctctatc    2040
gtaccgaacg cattaggtaa agatgacgaa gcgcaaaaac gcaaccttgc cggtttaatg    2100
gacggttatt tccatcatga agcgacagtg aaggcggtc aacacttgaa tgttaacgtt    2160
cttaaccgtg aaatgttgtt agacgcgatg gaaaatccgg aaaaatacc gcaattaacc    2220
attcgtgttt caggttacgc ggttcgtttc aactcattaa ctaaagagca acaacaagac    2280
```
gtcatcactc gtacgtttac acaatcaatg     2310

<210> SEQ ID NO 24
<211> LENGTH: 770
<212> TYPE: PRT
<213> ORGANISM: Pasteurella DSM 18541

<400> SEQUENCE: 24

```
Met Ala Glu Leu Thr Glu Ala Gln Lys Lys Ala Trp Glu Gly Phe Val
1               5                   10                  15

Pro Gly Glu Trp Gln Asn Gly Val Asn Leu Arg Asp Phe Ile Gln Lys
            20                  25                  30

Asn Tyr Thr Pro Tyr Glu Gly Asp Glu Ser Phe Leu Ala Asp Ala Thr
        35                  40                  45

Pro Ala Thr Ser Glu Leu Trp Asn Ser Val Met Glu Gly Ile Lys Ile
    50                  55                  60

Glu Asn Lys Thr His Ala Pro Leu Asp Phe Asp Glu His Thr Pro Ser
65                  70                  75                  80

Thr Ile Thr Ser His Lys Pro Gly Tyr Ile Asn Lys Asp Leu Glu Lys
                85                  90                  95

Ile Val Gly Leu Gln Thr Asp Ala Pro Leu Lys Arg Ala Ile Met Pro
            100                 105                 110

Tyr Gly Gly Ile Lys Met Ile Lys Gly Ser Cys Glu Val Tyr Gly Arg
        115                 120                 125

Lys Leu Asp Pro Gln Val Glu Phe Ile Phe Thr Glu Tyr Arg Lys Thr
130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Leu Ala Val Tyr Gly Ile Asp Tyr
            180                 185                 190

Leu Met Lys Asp Lys Lys Ala Gln Phe Asp Ser Leu Gln Pro Arg Leu
        195                 200                 205

Glu Ala Gly Glu Asp Ile Gln Ala Thr Ile Gln Leu Arg Glu Glu Ile
    210                 215                 220

Ala Glu Gln His Arg Ala Leu Gly Lys Ile Lys Glu Met Ala Ala Ser
225                 230                 235                 240

Tyr Gly Tyr Asp Ile Ser Gly Pro Ala Thr Asn Ala Gln Glu Ala Ile
                245                 250                 255

Gln Trp Thr Tyr Phe Ala Tyr Leu Ala Ala Val Lys Ser Gln Asn Gly
            260                 265                 270

Ala Ala Met Ser Phe Gly Arg Thr Ser Thr Phe Leu Asp Ile Tyr Ile
        275                 280                 285

Glu Arg Asp Leu Lys Arg Gly Leu Ile Thr Glu Gln Gln Ala Gln Glu
    290                 295                 300

Leu Met Asp His Leu Val Met Lys Leu Arg Met Val Arg Phe Leu Arg
305                 310                 315                 320

Thr Pro Glu Tyr Asp Gln Leu Phe Ser Gly Asp Pro Met Trp Ala Thr
                325                 330                 335

Glu Thr Ile Ala Gly Met Gly Leu Asp Gly Arg Pro Leu Val Thr Lys
            340                 345                 350

Asn Ser Phe Arg Val Leu His Thr Leu Tyr Thr Met Gly Thr Ser Pro
        355                 360                 365
```

```
Glu Pro Asn Leu Thr Ile Leu Trp Ser Glu Gln Leu Pro Glu Ala Phe
    370                 375                 380
Lys Arg Phe Cys Ala Lys Val Ser Ile Asp Thr Ser Ser Val Gln Tyr
385                 390                 395                 400
Glu Asn Asp Asp Leu Met Arg Pro Asp Phe Asn Asn Asp Asp Tyr Ala
                405                 410                 415
Ile Ala Cys Cys Val Ser Pro Met Val Val Gly Lys Gln Met Gln Phe
                420                 425                 430
Phe Gly Ala Arg Ala Asn Leu Ala Lys Thr Met Leu Tyr Ala Ile Asn
            435                 440                 445
Gly Gly Ile Asp Glu Lys Asn Gly Met Gln Val Gly Pro Lys Thr Ala
450                 455                 460
Pro Ile Thr Asp Glu Val Leu Asn Phe Asp Thr Val Ile Glu Arg Met
465                 470                 475                 480
Asp Ser Phe Met Asp Trp Leu Ala Thr Gln Tyr Val Thr Ala Leu Asn
                485                 490                 495
Ile Ile His Phe Met His Asp Lys Tyr Ala Tyr Glu Ala Ala Leu Met
            500                 505                 510
Ala Phe His Asp Arg Asp Val Phe Arg Thr Met Ala Cys Gly Ile Ala
            515                 520                 525
Gly Leu Ser Val Ala Ala Asp Ser Leu Ser Ala Ile Lys Tyr Ala Lys
530                 535                 540
Val Lys Pro Ile Arg Gly Asp Ile Lys Asp Lys Asp Gly Asn Val Val
545                 550                 555                 560
Ala Ser Asn Val Ala Ile Asp Phe Glu Ile Glu Gly Glu Tyr Pro Gln
                565                 570                 575
Phe Gly Asn Asn Asp Pro Arg Val Asp Asp Leu Ala Val Asp Leu Val
            580                 585                 590
Glu Arg Phe Met Lys Lys Val Gln Lys His Lys Thr Tyr Arg Asn Ala
            595                 600                 605
Thr Pro Thr Gln Ser Ile Leu Thr Ile Thr Ser Asn Val Val Tyr Gly
            610                 615                 620
Lys Lys Thr Gly Asn Thr Pro Asp Gly Arg Arg Ala Gly Ala Pro Phe
625                 630                 635                 640
Gly Pro Gly Ala Asn Pro Met His Gly Arg Asp Gln Lys Gly Ala Val
                645                 650                 655
Ala Ser Leu Thr Ser Val Ala Lys Leu Pro Phe Ala Tyr Ala Lys Asp
            660                 665                 670
Gly Ile Ser Tyr Thr Phe Ser Ile Val Pro Asn Ala Leu Gly Lys Asp
            675                 680                 685
Asp Glu Ala Gln Lys Arg Asn Leu Ala Gly Leu Met Asp Gly Tyr Phe
            690                 695                 700
His His Glu Ala Thr Val Glu Gly Gly Gln His Leu Asn Val Asn Val
705                 710                 715                 720
Leu Asn Arg Glu Met Leu Leu Asp Ala Met Glu Asn Pro Glu Lys Tyr
                725                 730                 735
Pro Gln Leu Thr Ile Arg Val Ser Gly Tyr Ala Val Arg Phe Asn Ser
                740                 745                 750
Leu Thr Lys Glu Gln Gln Gln Asp Val Ile Thr Arg Thr Phe Thr Gln
            755                 760                 765
Ser Met
    770
```